US008785454B2

(12) United States Patent
Ren et al.

(10) Patent No.: US 8,785,454 B2
(45) Date of Patent: Jul. 22, 2014

(54) HETEROCYCLIC COMPOUNDS AND USES THEREOF

(75) Inventors: Pingda Ren, San Diego, CA (US); Yi Liu, San Diego, CA (US); Liansheng Li, San Diego, CA (US); Troy Edward Wilson, San Marino, CA (US)

(73) Assignee: Intellikine LLC, La Jolla, CA (US)

( * ) Notice: Subject to any disclaimer, the term of this patent is extended or adjusted under 35 U.S.C. 154(b) by 0 days.

(21) Appl. No.: 13/289,540

(22) Filed: Nov. 4, 2011

(65) Prior Publication Data

US 2012/0329776 A1 Dec. 27, 2012

Related U.S. Application Data

(63) Continuation of application No. PCT/US2010/033939, filed on May 6, 2010.

(60) Provisional application No. 61/176,449, filed on May 7, 2009.

(51) Int. Cl.
*A61K 31/52* (2006.01)
*C07D 473/00* (2006.01)

(52) U.S. Cl.
USPC ..................................... 514/263.21; 544/264

(58) Field of Classification Search
USPC .......................................................... 544/277
See application file for complete search history.

(56) References Cited

U.S. PATENT DOCUMENTS

| | | | |
|---|---|---|---|
| 4,547,508 A | 10/1985 | Konz et al. | |
| 4,656,159 A | 4/1987 | McPherson et al. | |
| 4,704,381 A | 11/1987 | Schaumann et al. | |
| 4,795,627 A | 1/1989 | Fisher et al. | |
| 5,240,941 A | 8/1993 | Bruneau | |
| 5,294,612 A | 3/1994 | Bacon et al. | |
| 5,310,731 A | 5/1994 | Olsson et al. | |
| 5,364,862 A | 11/1994 | Spada et al. | |
| 5,420,419 A | 5/1995 | Wood | |
| 5,428,125 A | 6/1995 | Hefner, Jr. et al. | |
| 5,442,039 A | 8/1995 | Hefner, Jr. et al. | |
| 5,504,103 A | 4/1996 | Bonjouklian et al. | |
| 5,506,347 A | 4/1996 | Erion et al. | |
| 5,561,134 A | 10/1996 | Spada et al. | |
| 5,563,257 A | 10/1996 | Zilch et al. | |
| 5,593,997 A | 1/1997 | Dow et al. | |
| 5,646,128 A | 7/1997 | Firestein et al. | |
| 5,652,366 A | 7/1997 | Spada et al. | |
| 5,654,307 A | 8/1997 | Bridges et al. | |
| 5,665,721 A | 9/1997 | Bhagwat et al. | |
| 5,674,998 A | 10/1997 | Boyer et al. | |
| 5,686,455 A | 11/1997 | Adams et al. | |
| 5,736,554 A | 4/1998 | Spada et al. | |
| 5,747,235 A | 5/1998 | Farid et al. | |
| 5,756,711 A | 5/1998 | Zilch et al. | |
| 5,763,596 A | 6/1998 | Boyer et al. | |
| 5,763,597 A | 6/1998 | Ugarkar et al. | |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |

(Continued)

FOREIGN PATENT DOCUMENTS

| | | |
|---|---|---|
| CA | 1338379 C | 6/1996 |
| CN | 101602768 A | 12/2009 |

(Continued)

OTHER PUBLICATIONS

"Report of the Expert Committee on the diagnosis and classification of diabetes mellitus", Diabetes Care, 1992, vol. 2, Suppl. 1, pp. S5-S19.

(Continued)

*Primary Examiner* — Golam M M Shameem
*Assistant Examiner* — Laura Daniel
(74) *Attorney, Agent, or Firm* — Jones Day

(57) ABSTRACT

Heterocyclic entities that modulate PI3 kinase activity, pharmaceutical compositions containing the isoquinolone entities, and methods of using these chemical entities for treating diseases and conditions associated with PI3 kinase activity are described herein.

39 Claims, No Drawings

(56) References Cited

U.S. PATENT DOCUMENTS

| | | |
|---|---|---|
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,495,002 B2 * | 2/2009 | Langkopf et al. .......... 514/263.2 |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,106,146 B2 | 1/2012 | Benz et al. |
| 8,193,182 B2 | 6/2012 | Ren et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043959 A1 * | 3/2004 | Bloom et al. .................. 514/46 |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |

(56) References Cited

U.S. PATENT DOCUMENTS

| | | |
|---|---|---|
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 * | 12/2006 | Wu ............................... 514/46 |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0275561 A1 * | 11/2011 | Graefe-Mody et al. ....... 514/6.5 |
| 2011/0281866 A1 | 11/2011 | Ren et al. |
| 2011/0301144 A1 | 12/2011 | Knight et al. |
| 2012/0059000 A1 | 3/2012 | Ren et al. |
| 2012/0065154 A1 | 3/2012 | Tanaka et al. |
| 2012/0122838 A1 | 5/2012 | Ren et al. |
| 2012/0149701 A1 | 6/2012 | Ren et al. |
| 2012/0184568 A1 | 7/2012 | Ren et al. |
| 2012/0202784 A1 | 8/2012 | Aronov et al. |
| 2012/0245169 A1 | 9/2012 | Ren et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0053362 A1 | 2/2013 | Castro et al. |

FOREIGN PATENT DOCUMENTS

| | | | |
|---|---|---|---|
| DE | 2139107 | 2/1973 | |
| DE | 2139107 A1 * | 2/1973 | ............. C07D 57/38 |
| EP | 773023 A1 | 5/1997 | |
| EP | 1020445 B1 | 7/2000 | |
| GB | 812366 A | 4/1959 | |
| GB | 937725 A | 9/1963 | |
| JP | 61109797 A | 5/1986 | |
| JP | 5256693 A | 10/1993 | |
| JP | 08295667 A | 11/1996 | |
| JP | 09143163 A | 6/1997 | |
| JP | 10206995 A | 8/1998 | |
| JP | 2000072773 A | 3/2000 | |
| JP | 2002131859 A | 5/2002 | |
| JP | 2003073357 A | 3/2003 | |
| JP | 2004161716 A | 6/2004 | |
| WO | 8301446 A1 | 4/1983 | |
| WO | 9117161 A1 | 11/1991 | |
| WO | 9214733 A1 | 9/1992 | |
| WO | 9316091 A1 | 8/1993 | |
| WO | 9316092 A1 | 8/1993 | |
| WO | 9318035 A1 | 9/1993 | |
| WO | 9319767 A1 | 10/1993 | |
| WO | 9322443 A1 | 11/1993 | |
| WO | 9413677 A1 | 6/1994 | |
| WO | 9417803 A1 | 8/1994 | |
| WO | 9429436 A1 | 12/1994 | |
| WO | 9510628 A2 | 4/1995 | |
| WO | 9512588 A1 | 5/1995 | |
| WO | 9529673 A1 | 11/1995 | |
| WO | 9532984 A1 | 12/1995 | |
| WO | 9510628 A3 | 9/1996 | |
| WO | 9640706 A1 | 12/1996 | |
| WO | 9728133 A1 | 8/1997 | |
| WO | 9728161 A1 | 8/1997 | |
| WO | 9841525 A1 | 9/1998 | |
| WO | 9852611 A1 | 11/1998 | |
| WO | 9857952 A1 | 12/1998 | |
| WO | 0017202 A1 | 3/2000 | |
| WO | 0102369 A2 | 1/2001 | |
| WO | 0116114 A2 | 3/2001 | |
| WO | 0119829 A2 | 3/2001 | |
| WO | 0125238 A2 | 4/2001 | |
| WO | 0131063 A1 | 5/2001 | |
| WO | 0138584 A2 | 5/2001 | |
| WO | 0116114 A3 | 8/2001 | |

(56) References Cited

FOREIGN PATENT DOCUMENTS

| | | |
|---|---|---|
| WO | 0155140 A1 | 8/2001 |
| WO | 0156988 A1 | 8/2001 |
| WO | 0119829 A3 | 9/2001 |
| WO | 0125238 A3 | 10/2001 |
| WO | 0138584 A3 | 10/2001 |
| WO | 0181346 A2 | 11/2001 |
| WO | 0206192 A1 | 1/2002 |
| WO | 0181346 A3 | 3/2002 |
| WO | 0102369 A3 | 4/2002 |
| WO | 0230944 A2 | 4/2002 |
| WO | 02057425 A2 | 7/2002 |
| WO | 02076986 A1 | 10/2002 |
| WO | 02080926 A1 | 10/2002 |
| WO | 02083143 A1 | 10/2002 |
| WO | 02088025 A1 | 11/2002 |
| WO | 02090334 A1 | 11/2002 |
| WO | 0230944 A3 | 1/2003 |
| WO | 03000187 A2 | 1/2003 |
| WO | 03016275 A1 | 2/2003 |
| WO | 03/024969 A1 | 3/2003 |
| WO | 03020880 A2 | 3/2003 |
| WO | 03028341 A2 | 4/2003 |
| WO | 03035075 A1 | 5/2003 |
| WO | 03059884 A1 | 7/2003 |
| WO | 03020880 A3 | 10/2003 |
| WO | 03082341 A1 | 10/2003 |
| WO | 03106426 A1 | 12/2003 |
| WO | 2004006906 A2 | 1/2004 |
| WO | 2004006906 A3 | 1/2004 |
| WO | 2004039774 A3 | 1/2004 |
| WO | 03000187 A3 | 3/2004 |
| WO | 2004018058 A2 | 3/2004 |
| WO | 2004031177 A1 | 4/2004 |
| WO | 2004039774 A2 | 5/2004 |
| WO | 2004018058 A3 | 7/2004 |
| WO | WO 2004/058717 A1 | 7/2004 |
| WO | 2004087053 A2 | 10/2004 |
| WO | 2004111014 A1 | 12/2004 |
| WO | 2005002585 A1 | 1/2005 |
| WO | 2005007085 A2 | 1/2005 |
| WO | 2005012323 A2 | 2/2005 |
| WO | 2005016348 A1 | 2/2005 |
| WO | 2005016349 A1 | 2/2005 |
| WO | 2005016528 A2 | 2/2005 |
| WO | 2005021533 A1 | 3/2005 |
| WO | 0257425 A3 | 4/2005 |
| WO | 2005012323 A3 | 5/2005 |
| WO | 2005016528 A3 | 5/2005 |
| WO | 2005044181 A2 | 5/2005 |
| WO | 2005047289 A1 | 5/2005 |
| WO | 2005061460 A1 | 7/2005 |
| WO | 2005063258 A1 | 7/2005 |
| WO | 2005067901 A2 | 7/2005 |
| WO | 2005074603 A2 | 8/2005 |
| WO | 2005007085 A3 | 9/2005 |
| WO | 05097800 A1 | 10/2005 |
| WO | 2005097800 A1 | 10/2005 |
| WO | 2005105760 A1 | 11/2005 |
| WO | 2005067901 A3 | 12/2005 |
| WO | 2005112935 A1 | 12/2005 |
| WO | 2005113556 A1 | 12/2005 |
| WO | 2005117889 A1 | 12/2005 |
| WO | 2005120511 A1 | 12/2005 |
| WO | 2005044181 A3 | 3/2006 |
| WO | 2006030032 A1 | 3/2006 |
| WO | 2006038865 A1 | 4/2006 |
| WO | 2006050501 A2 | 5/2006 |
| WO | 2006050946 A1 | 5/2006 |
| WO | 2006068760 A2 | 6/2006 |
| WO | 2004087053 A3 | 8/2006 |
| WO | 2006089106 A2 | 8/2006 |
| WO | 2006108107 A1 | 10/2006 |
| WO | 2006112666 A1 | 10/2006 |
| WO | 2005074603 A3 | 11/2006 |
| WO | 2006114064 A2 | 11/2006 |
| WO | 2006114065 A2 | 11/2006 |
| WO | 2006068760 A3 | 12/2006 |
| WO | 2006089106 A3 | 12/2006 |
| WO | 2007002293 A2 | 1/2007 |
| WO | 2007006547 A1 | 1/2007 |
| WO | 2007020046 A1 | 2/2007 |
| WO | 2007002293 A3 | 3/2007 |
| WO | 2007025090 A2 | 3/2007 |
| WO | 2006050501 A3 | 5/2007 |
| WO | 2007061737 A2 | 5/2007 |
| WO | 2006114064 A3 | 6/2007 |
| WO | 2006114065 A3 | 6/2007 |
| WO | 2007025090 A3 | 6/2007 |
| WO | 2007075554 A2 | 7/2007 |
| WO | 2007079164 A2 | 7/2007 |
| WO | 2007079164 A3 | 9/2007 |
| WO | 2007103308 A2 | 9/2007 |
| WO | 2007112005 A2 | 10/2007 |
| WO | 2007114926 A2 | 10/2007 |
| WO | 2007121453 A2 | 10/2007 |
| WO | 2007121920 A2 | 11/2007 |
| WO | 2007121924 A2 | 11/2007 |
| WO | 2007124854 A1 | 11/2007 |
| WO | 2007125310 A2 | 11/2007 |
| WO | 2007125315 A2 | 11/2007 |
| WO | 2007126841 A2 | 11/2007 |
| WO | 2007134828 A1 | 11/2007 |
| WO | 2007135380 A2 | 11/2007 |
| WO | 2007135398 A1 | 11/2007 |
| WO | 2007061737 A3 | 12/2007 |
| WO | 2007125315 A3 | 12/2007 |
| WO | 2007121920 A3 | 1/2008 |
| WO | 2008012326 A1 | 1/2008 |
| WO | WO 2008/001236 A2 | 1/2008 |
| WO | 2007103308 A3 | 2/2008 |
| WO | 2007112005 A3 | 2/2008 |
| WO | 2007125310 A3 | 3/2008 |
| WO | 2008025755 A1 | 3/2008 |
| WO | 2008047821 A1 | 4/2008 |
| WO | 2008063625 A2 | 5/2008 |
| WO | 2008064018 A1 | 5/2008 |
| WO | 2007121453 A3 | 7/2008 |
| WO | 2008079028 A1 | 7/2008 |
| WO | 2008082487 A2 | 7/2008 |
| WO | 2008094737 A2 | 8/2008 |
| WO | 2007121924 A3 | 9/2008 |
| WO | 2008112715 A2 | 9/2008 |
| WO | 2007114926 A3 | 10/2008 |
| WO | 2008118454 A2 | 10/2008 |
| WO | 2008118455 A1 | 10/2008 |
| WO | 2008118468 A1 | 10/2008 |
| WO | 2008125014 A1 | 10/2008 |
| WO | 2008125207 A1 | 10/2008 |
| WO | 2008127226 A2 | 10/2008 |
| WO | 2007126841 A3 | 11/2008 |
| WO | 2008112715 A2 | 11/2008 |
| WO | 2008118454 A3 | 11/2008 |
| WO | 2008136457 A1 | 11/2008 |
| WO | 2008082487 A3 | 12/2008 |
| WO | 2008127226 A3 | 12/2008 |
| WO | 2009000412 A1 | 12/2008 |
| WO | 2009004621 A1 | 1/2009 |
| WO | 2009010925 A2 | 1/2009 |
| WO | 2009023718 A2 | 2/2009 |
| WO | 2008094737 A3 | 3/2009 |
| WO | 2009023718 A3 | 4/2009 |
| WO | 2009044707 A1 | 4/2009 |
| WO | 2009050506 A2 | 4/2009 |
| WO | 2009064802 A2 | 5/2009 |
| WO | 2009010925 A3 | 7/2009 |
| WO | 2009064802 A3 | 7/2009 |
| WO | 2009088986 A1 | 7/2009 |
| WO | 2009088990 A1 | 7/2009 |
| WO | 2009100406 A2 | 8/2009 |
| WO | 2009117157 A1 | 9/2009 |
| WO | 2009050506 A3 | 11/2009 |
| WO | 2009100406 A3 | 11/2009 |
| WO | 2010006086 A2 | 1/2010 |
| WO | 2010009207 A1 | 1/2010 |

(56) References Cited

FOREIGN PATENT DOCUMENTS

| WO | 2010019210 A2 | 2/2010 |
|---|---|---|
| WO | 2010036380 A1 | 4/2010 |
| WO | 2010039534 A2 | 4/2010 |
| WO | 2010019210 A3 | 5/2010 |
| WO | 2010039534 A3 | 8/2010 |
| WO | 2011146882 A1 | 11/2011 |
| WO | WO 2012/064973 A2 | 5/2012 |

OTHER PUBLICATIONS

Abdel-Mohsen. Synthesis, Reactions and Antimicrobial Activity of 2-Amino-4-(8-quinolinol-5-yl)-1-(p-tolyl)-pyrrole-3-carbonitrile. Bull. Korean Chem. Soc. 2005;26(5):719-728.

Abe et al., "T cell receptor-mediated recognition of self-ligand induces signaling in immature thymocytes before negative selection", J. Exp. Med., Aug. 1992, vol. 176, pp. 459-468.

Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan., 14: 1390-1395 (1975).

Anderson et al., "Paradoxical inhibition of T-cell function in response to CTLA-4 blockade; heterogeneity within the human T-cell population", Nature, 2000, vol. 6, No. 2, pp. 211-214.

Andrews et al., "Effects of the 11b-hydroxysteroid dehydrogenase inhibitor carbenoxolone on insulin sensitive in men with type 2 diabetes", J. Clin. Endocrinol. Metab., 2003, vol. 88, No. 1, pp. 285-291.

Arcaro et al., "Wortmannin is a potent phosphatidylinositol 3-kinase inhibitor: the role of phosphatidylinositol 3,4,5-triphosphate in neutrophil responses", Biochem. J., Dec. 1, 1993, vol. 296, Pt. 2, pp. 297-301.

Arnold et al., "Pyrrolo[2,3-d]pyrimidines containing an extended 5-substituent as potent and selective inhibitors of Ick I", Bioorg. and Med. Chem. Lett., 2000, vol. 10, pp. 2167-2170.

Augustine et al., "Interleukin 2- and polyomavirus middle T antigen-induced modification of phosphatidylinositol 3- kinase activity in activated T lymphocytes", Molecular and Cellular Biology, 1991, vol. 11, No. 9, pp. 4431-4440.

Baggiolini et al., "Inhibition of the phagocytosis-induced respiratory burst by the fungal metabolite wortmannin and some analogues", Experimental Cell Research, 1987, vol. 169, pp. 408-418.

Ballell et al. "New Thiopyrazolo[3,4-d] pryimidine derivatives as anti-mycobacterial agents". Bioorganic and Medicinal Chemistry Letters. vol. 17. Dec. 22, 2006. pp. 1736-1740.

Banker et al., Modern Pharmaceutics, 1996, pp. 451-593, 3ed, Marcel Dekker, New York.

Barf et al., "Arylsulfonamidothiazoles as a new class of potential antidiabetic drugs. Discovery of potent and selective inhibitors of the 11b-hydroxysteroid dehydrogenase Type 1", J. Med. Chem., 2002, vol. 45, No. 18, pp. 3813-3815.

Barnes et al., "Efficacy and Safety of Inhaled Corticosteroids in Asthma—Report of a Workshop Held in Eze, France Oct. 1992". Am. Rev. Resir. Dis., 1993, vol. 148, pp. S1-S26.

BASOTEST®, "Test Kit for the Quantitative Determination of the Degranulation of Basophilic Granulocytes in Heparinized Human Whole Blood", Retreived from the Internet Nov. 29, 2011.

Beeram et al. Akt-Induced Endocrine Therapy Resistance is Reversed by Inhibition of mTOR Signaling. Ann Oncol. Aug. 2007. 18(8):1323-8.

Bell et al., "Glucokinase mutations insulin secretion, and diabetes mellitus", Annu. Reb. Physiol., 1996, vol. 58, pp. 171-186.

Bhat et al., "Pyraszolopyrimidine nucleosides. 12. Synthesis and biological activity of certain pyrazolo[3,4-d] pyrimidine nucleosides related to adenosine", J. Med. Chem., 1981, vol. 24, No. 10, pp. 1165-1172.

Bishop et al., "Generation of monospecific nanomolar tyrosine kinase inhbitors via a chemical genetic approach", Journal of the American Chemical Society, 1999, vol. 121, No. 4, pp. 627-631, Washington, DC.

Bochner et al. "Immunological aspects of allergic asthma". Annual review of Immunology 1994—Annual Reviews, pp. 295-335.

Bohren et al., "Expression, crystallization and preliminary crystallographic analysis of human carbonyl reductase", J. Mol. Biol., 1994, vol. 224, pp. 659-664.

Campora et al., "Binuclear complexes of nickel bridged by hydrocarbon ligands. Isocyanide insertion chemistry and amide formation by intramolecular coupling of acyl and imidoyl functionalities", Organometallics, Jan. 1992, vol. 11, No. 1, pp. 11-13.

Campora et al., "Isocyanide insertion chemistry. Synthesis and structural characterization of bridging imidoyl complexes of nickel and amide formation by intramolecular coupling of acyl and imidoyl functionalities", Organometallics, Oct. 1993, vol. 12, No. 10, pp. 4025-4031.

Chaisuparat et al., "Dual inhibition of P13Ka and mTOR as an alternative treatment for Kaposi's Sarcoma", Cancer Research, 2008, vol. 68, pp. 8361-8368.

Chappelow et al., "Neovascular age-related macular degeneration: potential therapies", Drugs, 2008, vol. 68, No. 8, pp. 1029-1036.

Closse et al., "2,3-dihydrobenzofuran-2-ones: a new class of highly potent antiinflammatory agents", J. Med. Chem., 1981, vol. 24, pp. 1465-1471.

Cox et al., "Human colorectal cancer cells efficiently conjugate the cyclopentenone prostaglandin, prostaglandin J2 to glutathione", Biochem. Biophys. Acta., 2002, vol. 1584, pp. 37-45.

Davies et al., "The human T3y chain is phosphorylated at Serine 126 in response to T lymphocyte activation", The Journal of Biological Chemistry, 1987, vol. 262, No. 23, pp. 10918-10921.

Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide", Synthetic Communications, Sep. 1997, vol. 27, No. 17, pp. 2961-2969.

Diederich et al., "In search for specific inhibitors of human 11b-hydroxysteroid-dehydrogenases (11bHSDs): chenodeoxycholic acid selectively inhibits 11b-HSD-I", Eur. J. Endocrinol., 2000, vol. 142, pp. 200-207.

Dijksman et al., "271.1: 2-dihydro-2-thianaphthalene derivatives. Part I. Preperation and reactions of 1 : 2-dihydro-1-keto-2-thianaphthalenes", J. Chem. Soc., vol. 1951, pp. 1213-1218.

Ding et al., "A combinatorial scaffold approach toward kinase-directed heterocycle libraries", J. Am. Chem. Soc., 2002, vol. 124, No. 8, pp. 1594-1596.

Ding et al., "A concise and traceless linker strategy toward combinatorial libraries of 2,6,9-substituted purines", J. Org. Chem., 2001, vol. 66, pp. 8273-8276.

Ding et al., "Resin-capture and release strategy toward combinatorial libraries of 2,6,9-substituted purines", J. Comb. Chem., 2002, vol. 4, pp. 183-186.

Donati et al., "Emerging therapies for neovascular age-related macular degeneration: state of art", Ophthalmologica, 2007, vol. 221, pp. 366-377.

European Examination Report for EP 07873406.8 dated Sep. 14, 2011.

European Seach Report dated Feb. 4, 2011, for EP Application No. 05857011.0.

European Seach Report dated Oct. 28, 2011, for EP Application No. 09700784.3.

European Search Report and Search Opinion for EP 09700424.6 dated Oct. 26, 2011.

European Search Report for EP 07873406.8 dated Mar. 1, 2010.

Examination Report for GB Application No. GB0819947.3 dated Oct. 27, 2010.

Extended European Search Report for EP 09816603 dated Mar. 19, 2012.

Extended European Search Report from Eureopean Application No. 09700784.3 dated Oct. 28, 2011.

Fajans et al., "Maturity onset diabetes of the young (MODY)", Diabet. Med., 1996, vol. 13, pp. S90-S95.

Feinstein et al., "Regulation of the action of hydrocotisone in airway epithelial cells by 11b-hydroxysteroid dehydrogenase", Am. J. Resp. Cell. Mol. Biol., 1999, vol. 21, pp. 403-408.

(56) References Cited

OTHER PUBLICATIONS

Feldman et al. Active-Site Inhibitors of mTOR Target Rapamycin-Resistant Outputs of mTORC1 and mTORC2. PLoS Biol. Feb. 10, 2009. 7(2):371-383.
Fingl et al., "General principles", The Pharmacological Basis of Therapeutics, 1975, Ch. 1, pp. 1-46, Fifth edition.
Forrest et al., "Carbonyl Reductase", Chem. Biol. Interact., 2000, vol. 129, pp. 21-40.
Forrest et al., "Induction of a human carbonyl reductase gene located on chromosome 21", Biochem. Biophys. Acta., 1990, vol. 1048, pp. 149-155.
Franzen, "The Suzuki, the Heck, and the Stille reaction—three versative methods for the introduction of new C—C bonds on solid support", Can. J. Chem., 2000, vol. 78, pp. 957-962.
International Search Report and Written Opinion for PCT/US2012/20831 dated May 2, 2012.
Berndt et al., "The P110 Structure: Mechanisms for selectivity and potency of new P1(3)K Inhibitors", Nat Chem Biol. Feb. 2010;6(2):117-24.
International Search Report & Written Opinion for PCT/US2011/60212 dated Jun. 1, 2012.
International Search Report & Written Opinion issued after Submission of Request for Additional Search for PCT/US2011/60212 dated Jul. 6, 2012.
Bansal, N., et al., "The Molecular Biology of Endometrial Cancers and the Implications for Pathogenesis, Classification, and Targeted Therapies," Cancer Control, 16(1):8-13 (2009).
Billottet, C., et al., "A Selective Inhibitor of the p110d Isoform of PI 3-Kinase Inhibits AML Cell Proliferation and Survival and Increases the Cytotoxic Effects of VP16," Oncogene, 25:6648-6659 (2006).
Billottet, C., et al., "Inhibition of Class 1 Phosphoinositide 3-Kinase Activity Impairs Proliferation and Triggers Apoptosis in Acute Promyelocytic Leukemia without Affecting Atra-Induced Differentiation," Cancer Res. 69(3):1027-36 (2009).
Chapuis, N., et al., "Dual Inhibition of P13K and mTORC1/2 Signaling by NVP-BEZ235 as a New Therapeutic Strategy for Acute Myeloid Leukemia," Clin. Cancer Res., 16(22):5424-35 (2010).
Chen, J.S., et al., "Characterization of Structurally Distinct, Isoform-Selective Phosphoinositide 3'-Kinase Inhibitors in Combination with Radiation in the Treatment of Glioblastoma," Mol. Cancer Ther., 7(4):841-50 (2008).
Courtney, K.D., et al., "The PI3K Pathway As Drug Target in Human Cancer," J. of Clinical Oncology, 28 (6):1075-1083 (2010).
Brzezianska, E., et al., "A Minireview: The Role of MAPK/ERK and PI3K/Akt Pathways in Thyroid Follicular Cell-Derived Neoplasm," Frontiers in Bioscience, 16:422-439 (2011).
Flinn, I.W., et al., "Preliminary Evidence of Clinical Activity in a Phase I Study of CAL-101, a Selective Inhibitor of the p110δ Isoform of Phosphatidylinositol 3-Kinase (P13K), in Patients with Select Hematologic Malignancies," J. Clin. Oncol. 27:156s (Suppl: Abstr 3543) (2009).
Vara, J.A.F., et al., "P13K/Akt Signalling Pathway and Cancer," Cancer Treat. Rev. 30(2):193-204 (2004).
Furukawa, T., "Molecular Targeting Therapy for Pancreatic Cancer: Current Knowledge and Perspectives from Bench to Bedside," J. Gastroenterol., 43:905-911 (2008).
Haluska, F., et al., "The RTK/RAS/BRAF/P13K Pathways in Melanoma: Biology, Small Molecule Inhibitors, and Potential Applications," Semin. Oncol., 34(6):546-54 (2007).
Herman, S.E.M., et al., "Phosphatidylinositol 3-Kinase-d Inhibitor CAL-101 Shows Promising Preclinical Activity in Chronic Lymphocytic Leukemia by Antagonizing Intrinsic and Extrinsic Cellular Survival Signals," Blood, 116 (12):2078-88 (2010).
Herman, S.E.M., et al., "The Role of Phosphatidylinositol 3-Kinase-d in the Immunomodulatory Effects of Lenalidomide in Chronic Lymphocytic Leukemia," Blood, 117(16):4323-7 (2011).
Herrera, V.A., et al., "The Dual P13K/mTOR Inhibitor BEZ235 Is Effective in Lung Cancer Cell Lines," Anticancer Research, 31:849-854 (2011).

Ikeda, H., et al., "P13K/p110d is a Novel Therapeutic Target in Multiple Myeloma," Blood, 116(9):1460-8 (2010).
Khwaja, A., "P13K as a Target for Therapy in Haematological Malignancies," Curr Top Microbiol immunol., 347:169-88 (2010).
Kong, D. and Yamori, T., "Advances in Development of Phosphatidylinositol 3-Kinase Inhibitors," Curr. Med. Chem., 16:2839-2854 (2009).
Markman, B., et al., "Status of PI3K Inhibition and Biomarker Development in Cancer Therapeutics," Ann. Oncol., 21 (4):683-91 (2010).
Mazzoletti, M. and Broggini, M., "PI3K/AKT/mTOR Inhibitors in Ovarian Cancer," Curr. Med. Chem., 17:4433-4447 (2010).
Meadows, S.A., et al., "CAL-101, a Potent Selective Inhibitor of the p110d Isoform of Phosphatidylinositol 3-Kinase, Attenuates Pathway Signaling, Induces Apoptosis, and Oversomces Signals From the Microenvironment in Cellular Models of Hodgkin Lymphoma," Blood (ASH Annual Meeting Abstracts), 116:Abstract 3926 (2010).
Porta, C. and Figlin, R.A., "Phsophatidylinositol-3-Kinase/Akt Signaling Pathway and Kidney Cancer, and the Therapeutic Potential of Phosphatidylinositol-3-Kinase/Akt Inhibitors," J. Urol., 182(6):2569-77 (2009).
Saif, M.W. and Chu, E., "Biology of Colorectal Cancer," Cancer J., 16(3):196-201 (2010).
Salmena, L., et al. "Tenets of PTEN Tumor Suppression," Cell, 133:403-414(2008).
Sarker, D., et al., "Targeting the PI3K/AKT Pathway for the Treatment of Prostate Cancer," Clin. Cancer Res., 15 (15):4799-805 (2009).
Shapiro, G., et al., "Phase I Dose-Escalation Study of XL147, A PI3K Inhibitor Administered Orally to Patients with Solid Tumors," J. Clin. Oncol., 27:146x (Suppl Abstr 3500) (2009).
Torbett, N.E., et al., "A Chemical Screen in Diverse Breast Cancer Cell Lines Reveals Genetic Enhancers and Suppressors of Sensitvity to PI3K Isoform-Selective Inhibition," Biochem. J., 415:97-100 (2008).
Vogt, P.K., et al., "Phosphoinositide 3-Kinase: From Viral Oncoprotein to Drug Target," Virology, 344:131-138 (2006).
Vogt, P.K., et al., "Phosphatidylinositol 3-Kinase: The Oncoprotein," Curr. Top. Microbiol. Immunol., 347:79-104 (2010).
Wagner, A.J., et al., "A First-in-Human Phase I Study to Evaluate the Pan-PI3K Inhibitor GDC-0941 Administered QD or BID in Patients with Advanced Solid Tumors," J. Clin. Oncol., 27:146s (Suppl, Abstr 3501) (2009).
Ward, S., et al., "Therapeutic Potential of Phosphoinositide 3-Kinase Inhibitors," Chem. & Biol., 10:207-213 (2003).
Zhao, L. and Vogt, P.K., "Class I PI3K in Oncogenic Cellular Transformation," Oncogene, 27:5486-5496 (2008).
Jimeno, A., et al., "Phase I Trial of PX-866, a Novel Phosphoinositide-3-Kinase (PI-3K) Inhibitor," J. Clin. Oncol., 27:15s (Suppl Abstr 3542) (2009).
International Preliminary Report on Patentability for PCT/US2009/000038 dated Jul. 6, 2010.
European Search Report for EP 07 754 845.1, dated Sep. 20, 2011.
International Preliminary Report on Patentability for PCT/US2010/002020 dated Jan. 26, 2012.
International Preliminary Report on Patentability for PCT/US2009/005380 dated Apr. 7, 2011.
Abrahamian et al. "Immunological and Clinical Profile of Adult Patients with Selective Immunoglobulin Subclass Deficiency: Response to Intravenous Immunoglobulin Therapy". Clinical & Experimental Immunology. The Journal of Translational Immunology vol. 159, pp. 344-350 (2009).
Bartholomeusz et al. "Targeting the PI3K Signaling Pathway in Cancer Therapy". Expert Opin. Ther. Targets (2012). pp. 121-130.
International Search Report and Written Opinion, International Application No. PCT/US10/33939, date of mailing Nov. 5, 2010.
Ward et al., "Ligation of CD28 receptor by B7 induces formation of D-3 phosphoinositides in T lymphocytes independently of T cell receptor/CD3 activation", Eur. J. Immunol., 1993, vol. 23, pp. 2572-2577.
Ward et al., "Regulation of D-3 phosphoinositides during T cell activation via the T cell antigen receptor/CD3 complex and CD2 antigens", Eur. J. Immunol., 1992, vol. 22, pp. 45-49.

(56) References Cited

OTHER PUBLICATIONS

Ward et al., "Regulation of phosphoinositide kinases in T cells", J. Biol. Chem., Nov. 25, 1992, vol. 267, No. 33, pp. 23862-23869.
White et al., "11b-hydroxysteroid dehyrdogenase and the syndrome of apparent mineralocorticoid excess", Endocr. Rev., 1997, vol. 18, No. 1, pp. 135-156.
Widler et al., "7-alkyl- and 7-Cycloalky1-5-aryl-pyrrolo[2,3-d]pyrimidines—potent inhibitors of the tyrosine kinase c-Src", Bioorganis and Medicinal Chemistry Letters, 2001, vol. 11, No. 6, pp. 849-852.
Wiesinger et al., "Antiinflammatory activity of the new mold metabolite 11-desacetoxy-wortmannin and some of its derivatives", Experientia, 1974, vol. 30, pp. 135-136.
Wolff, Burger's Medicinal Chemistry, 5ed, 1995, Part 1, pp. 975-977, John Wiley & Sons.
Woscholski et al., "A comparison of demthoxyviridin and wortmannin as inhibitors of phosphatidylinositol 3-kinase", FEBS letters, 1994, vol. 342, pp. 109-114.
Yaguchi et al., "Antitumor activity of ZSTK474, a new phosphatidylinositol 3-kinase inhibitor", J. Natl. Cancer Inst., 2006, vol. 98, No. 8, pp. 545-556.
Yang et al., "A novel activation pathway for mature thymocytes", J Exp. Med., Oct. 1988, vol. 168, pp. 1457-1486.
Yano et al., "Inhibition of histamine secretion by wortmannin through the blockade of phosphatidylinositol 3-kinase in RBL-2H3 cells", J. Biol. Chem., Dec. 5, 1993, vol. 268, No. 34, pp. 25846-25856.
Yoshida et al., "Quercetin arrests human leukemic T-cells in late G1 phase of the cell cycle", 1992, vol. 52, pp. 6676-6681.
Mayer et al., "Small molecule inhibitor of mitotic spindle bipolarity identified in a pheontype-cased screen", Science, 1999, vol. 286, pp. 971-974.
Mellinghoff et al., "TORward AKTually useful mouse models", Nature Medicine, 2004, vol. 10, pp. 579-580.
Miyaura et al., "Palladium-catalyzed cross-coupling reactions of organoboron compounds", Chem Rev., 1995, vol. 95, No. 7, pp. 2457-2483.
Modi et al., "Isoquinolones; part IV—synthesis of methyl, 3-formyl & other 3-substituted N-arylisoquinolones", Indian J. Chem., 1979, vol. 18B, pp. 304-306.
Moon et al., "A novel microtubule destabilizing entity from orthogonal synthesis of triazine library and zebrafish embryo screening", J. Am. Chem. Soc., 2002, vol. 124, pp. 11608-11609.
Mosmann et al., "The expanding universe of T-cell subsets: Th1, Th2 and more", Immunology Today, 1996, pp. 138-146.
Nakanishi et al., "Cloning and sequence analysis of a cDNA encoding tetrameric corbonyl reductase of pig lung", Biochem. Biophys. Acta, 1993, vol. 194, No. 3, pp. 1311-1316.
Nemazanyi et al., "3-Amino-4aryl-1(2H)-isoquinolones", Chemistry of Heterocyclic Compounds, Mar. 1991, vol. 27, No. 3, pp. 307-308.
Niswender et al., "Protein engineering of protein kinase a catalytic subunits results in the acquisition of novel inhibitor sensitivity", The Journal of Biological Chemistry, 2002, vol. 277, No. 32, pp. 28916-28922.
Nobel et al., "Purification of full-length recombinant human and rat type 1 11b-hydroxysteroid dehydrogenases with retained oxidoreductase activities", Protein Expr. Purif., 2002, vol. 26, pp. 349-356.
Nunes et al., "Signalling Through CD28 T-Cell Activation Pathway Involves an Inositol Phospholipid-Specific Phospholipase C Activity". Biochem. J., 1993, vol. 293, pp. 835-842.
O'Shea et al., "Activaiton of human peripheral blood T lymphocytes by pharmacological induction of protein-tyrosine phosphorylation", Proc. Natl. Acad. Sci. USA, Nov. 1992, vol. 89, pp. 10306-10310.
Oda et al., "PIK3CA cooperates with other phosphatidylinositol 3'-kinase pathway mutations to effect oncogenic transformation", Cancer Research, 2008, vol. 68, pp. 8127.
Okada et al., "Essential role of phosphatidylinositol 3-kinase in insulin-induced glucose transport and antilipolysis in rat adipocytes", J. Biol. Chem., Feb. 4, 1994, vol. 269, No. 5, pp. 3568-3573.

Okada et al., "Blockage of chemotactic peptide-induced stimulation of neutrophils by wortmannin as a result of selective inhibition of phosphatidylinositol 3-kinase", J. Biol. Chem., Feb. 4, 1994, vol. 269, No. 5, pp. 3568-3573.
Oppermann et al., "Forms and functions of human SDR enzymes", Chem. Biol. Interact., 2001, vol. 130-132, No. 1-3, pp. 699-705.
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one", Chem. Pharm. Bull., Jun. 25, 1984, vol. 32, No. 6, pp. 2160-2164.
Ozol et al., "Autoxidative transformations of 2-substituted 3-alkyl-4-hydroxy-1-oxo-1, 2-dihydroisoquinolines", Chemistry of Heterocyclic Compounds, Jun. 1978 vol. 14, No. 6, pp. 644-648.
Patel et al., "Immunopathological aspects of age-related macular degeneration", Seminars in Immunopathology, 2008, vol. 30, No. 2, pp. 97-110.
Persson, "Glucocorticoids for asthma—early contributions", Pulm. Pharmacol., 1989, vol. 2, pp. 163-166.
Pietrie et al., "Novel biotinylated adenylate analogue derived from pyrazolo[3,4-d]pyrimidine for labeling DNA probes", Bioconj. Chem., 1991, vol. 2, No. 6, pp. 441-446.
Prasad et al., "Phosphatidylinositol (PI) 3-kinase and PI 4-kinase binding to the CD4-p56lck complex: the p56lck SH3 domain binds to PI 3-kinase but not PI 4-kinase", Molecular and Cellular Biology, Dec. 1993, vol. 13, No. 12, pp. 7708-7717.
Prasad et al., "Src-homology 3 domain of protein kinase p59fyn mediates binding phosphatidylinositol 3-kinase in T cells", Proc. Natl. Acad. Sci. USA, Aug. 1993, vol. 90, pp. 7366-7370.
Prasad et al., "T-cell antigen CD28 interacts with the lipid kinase phosphatidylinositol 2-kinase by a cytoplasmic Tyr (P)-Met-Xaa-Met motif", Proc. Natl. Acad. Sci. USA, 1994, vol. 91, pp. 2834-2838.
Pudlo et al., "Synthesis, antiproliferative, and antiviral activity of certain 4-substituted and 4,5 disubstituted 7-[1,3-dihydroxy-2-propoxy)methyl]pyrrolo[2,3-d]pyrimidines", J. Med. Chem., 1990, vol. 33, pp. 1984-1992.
Pérez-Blas et al., "Impaired T cell signal transduction through CD28 in a patient with idiopathic thrombocytopenia", Clin. Exp. Immunol., 1991, vol. 85, pp. 424-428.
Reif et al., "Divergent regulation of phosphatidylinositol 3-kinase P85a and P85b isoforms upon T cell activation", The Journal of Biological Chemistry, 1993, vol. 268, pp. No. 15, pp. 10780-10788.
Robertson, "Eicosanoids and human disease", Harrison's Principles of Internal Medicine, Isselbacher K.J. et al. (eds.), 1994, vol. 1, pp. 431-435, McGraw-Hill, New York City.
Romero et al., "Cloning and expression of the bovine 11b-hydroxysteroid dehydrogenase type-2", J. Steroid Biochem. Mol. Biol., 2000, vol. 72, pp. 231-237.
Rott et al., "Recent development in the use of biologics in psoriasis and autoimmune disorders. The role of autoantibodies", BMJ, Mar. 26, 2005, vol. 330, No. 7493, pp. 716-720.
Schwartz et al., "Quercetin inhibition of the induction and function of cytotoxic T lymphocytes", Immunopharmacology, 1982, vol. 4, pp. 125-138.
Schwartz, "A cell culture model for T lymphocyte clonal anergy", Science, Jun. 15, 1990, vol. 248, pp. 1349-1356.
Shibasaki et al., "Different properties of monomer and heterodimer forms of phosphatidylinositol 3-kinase", Biochem. J., 1993, vol. 289, pp. 227-231.
Singer et al., "Optimization of in situ hybridization using isotopic and non-isotopic detection methods", Biotechniques, 1986, vol. 4, No. 3, pp. 230-250.
Soldan et al., "Induction of daunorubicin carbonyl reducing enzymes in sensitive and resistant pancrease carcinoma cells", Biochem. Pharmacol., 1996, vol. 51, pp. 117-123.
Stanoeva et al., "Homophthalic anhydrides and their application to the synthesis of heterocyclic compounds (review)", Chemistry of Heterocyclic Compounds, Dec. 1984, vol. 20, No. 12, pp. 1305-1315.
Supplementary European Examination Report EP 07754845.1 dated Sep. 20, 2011.
Supplementary European Search Report dated Feb. 24, 2010, for EP Application No. 07754845, 4 pages.

(56) References Cited

OTHER PUBLICATIONS

Sykes et al., "Treatment of severe autoimmune disease by stem-cell transplantation", Nature, Jun. 2, 2005, vol. 35, No. 7042, pp. 620-627.
Takeuchi et al. "Synergistic Augmentation of Rapamycin-Induced Autophagy in Malignant Glioma Cells by Phosphatidylinositol 3-Kinase/Protein Kinase B Inhibitors". Cancer Res. 65(8):3336-46. Apr. 15, 2005.
Tanaka et al., "An unbiased cell morphology-based screen for new, biologically active small molecules", PLoS Biology, 2005, vol. 3, No. 5, pp. 0764-0776.
Truitt et al., "Stimulation of CD28 triggers an association between CD 28 and phosphatidylinositol 3-kinase in Jurkat T cells", J. Exp. Med., Mar. 1994, vol. 179, pp. 1071-1076.
U.S. Publication of U.S. Appl. No. 13/016,957, filed Jan. 28, 2011.
Ugarkar et al., "Adenosine kinase inhibitors. 2. Synthesis, enzyme inhibition, and antiseizure activity of diaryltubercidin analogues", J. Med. Chem., 2000, vol. 43, pp. 2894-2805.
Vandenberghe et al., "Antibody and B7/BB1-mediated ligation of the CD28 receptor induces tyrosine phosphorylation in human T cells", J. Exp. Med., Apr. 1992, vol. 175, pp. 951-960.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6): 1229-1233 (2002).
Vasilevsky et al., "Unexpected results in the heterocyclization of 5-acetylenylpyrazole-4-carboxylic acid hydrazides under the influence of CuCI: formatin of a diazepinone and dehydrodimerization into the corresponding bis(pyrazolo [4,3-d] [1,2] diazepinone)", Tetrahedron Letters, Jan., 46(26): 4457-4459 (2005).
Vlahos et al., "A specific inhibitor of phosphatidylinositol 3-kinase, 2-(4-morpholinyl)-8-phenyl-4H-1-benzopyran-4-one (LY294002)", The Journal of Biological Chemistry, 1994, vol. 269, No. 7, pp. 5241-5248.
Ward et al., "Inhibition of CD28-mediated T cell costimulation by the phosphoinisitide 3-kinase inhibitor wortmannin", Eur. J. Immunol., 1995, vol. 25, pp. 526-532.
Funder et al., "Mineralocorticoid action: target tissue specificity is enzyme, not receptor, mediated", Science, 1998, vol. 242, pp. 583-585.
Garber et al., "Diversity of gene expression in adenocarcinoma of the lung", Proc. Natl. Acad. Sci. USA, 2001, vol. 98, No. 24, pp. 13784-13789.
Gillespie et al. "Antagonists of the Human Adenosine A2A Receptor. Part 3. Design and Synthesis of Pyrazolo [3,4d] Pyrimidines, Pyrrolo [2, 3-d] Pyrimidines, and 6-arylpurines". Bioorganic and Medicinal Chemistry Letters. vol. 18, No. 9. Mar. 30, 2008. pp. 2924-2929.
Gonzalez et al., "Protection against daunorubicin cytotoxicity by expression of a cloned human carbonyl reductase cDNA in K562 leukemia cells", Cancer Res., 1995, vol. 55, pp. 4646-4650.
Graber et al., "The protein tyrosine kinase inhibitor herbimycin A, but not Genistein, specifically inhibits signal transduciton by the T cell antigen receptor", International Immunology, 1992, vol. 4, No. 1, pp. 1201-1210.
Graupera et al., "Angiogenesis selectively requires the p110 isoform of P13K to control endothelial cell migration", Nature, 2008, vol. 453, pp. 662-666.
Gunther et al., "Acute pathological effects on rats of orally administered wortmannin-containing preparations and purified wortmannin from *Fusarium oxysporum*", Fd. Chem. Toxic., 1989, vol. 27, No. 3, pp. 173-179.
Haase et al., "Detection of viral nucleic acids by in situ hybridization", Methods in Virology, 1984, vol. 7, pp. 189-226.
Hanefeld et al., "One-pot synthesis of tetrasubstituted pyrazoles proof of regiochemistry", J. Chem. Soc. Perkin Trans., 1996, vol. 1, pp. 1545-1552.
Harada et al., "Novel role of phosphatidylinositol 3-kinase in CD28-mediated costimulation", J. Biol. Chem., 2001, vol. 276, No. 12, pp. 9003-9008.
Harding et al., "CD28-mediated signalling co-stimulates murine T cells and prevents induction of anergy in T-cell clones", Nature, Apr. 16, 1992, vol. 356, pp. 607-609.
Hellwinkel et al., "Heterocyclensynthesen mit MF/Al2O3-basensystemen; 2-arylbenzofurane and 2,3-diarylisochinolin-1(2H)-one", Synthesis, 1995, vol. 1995, No. 9, pp. 1135-1141.
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 1, 2011.
International Preliminary Report on Patentability and Written Opinion for PCT/US2009/060985 dated Apr. 19, 2011.
International Preliminary Report on Patentability from International Application No. PCT/US2009/000042 issued Jul. 6, 2010.
International Search Report and Written Opinion for PCT/US2009/005380 dated Nov. 20, 2009.
International Search Report and Written Opinion for PCT/US2009/049969 dated Mar. 15, 2010.
International Search Report dated Aug. 22, 2011for PCT Application No. PCT/US2011/37412.
International Search Report dated Aug. 27, 2008 for International Applicaiton No. PCT/US07/08395, 4 pages.
International Search Report dated Mar. 11, 2009 for PCT Application No. US2009/00038.
International Search Report dated Mar. 23, 2009 for PCT/US2009/00042.
International Search Report dated Oct. 2, 2006, for International Application No. PCT/US05/042524, 7 pages.
International Search Report dated Oct. 26, 2011, for International Application No. PCT/US09/00038.
International Search Report dated Sep. 25, 2008, for International Application No. PCT/US2007/08355.
International Search Report for PCT/US2009/060985 dated Jun. 28, 2010.
International Search Report for PCT/US2010/02020 dated Nov. 2, 2010.
Ishiyama et al., "A stoichiometric aromatic C-H borylation catalyzed by iridium(I)/2,2'-bipyridine complexes at room temperature", Angew. Chem. Int. Ed., 2002, vol. 41, No. 16, pp. 3056-3058.
Ishiyama et al., "Mild iridium-catalyzed borylation of arenes. High turnover numbers, room temperature reactions, and isolation of a potential intermediate", J. Am. Chem. Soc., 2002, vol. 124, No. 3, pp. 390-391.
J.C.S. Perkin I, 1975, 1390-1395.
Johnson et al., "Accessory cell-derived signals required for T cell activation", Immunologic Research, 1993, pp. 48-64.
June et al., "Inhibition of tyrosine phosphorylation prevents T-cell receptor mediated signal transduction", Proc. Natl. Acad. Sci. USA, 1990, vol. 87, pp. 7722-7726.
Kajita et al., "Nickel-catalyzed decarbonylative addition of phthalimides to alkynes", J. Am. Chem. Soc., May 14, 2008, vol. 130, No. 19, pp. 6058-6059.
Kallberg et al., "Short-chain dehydrogenase/reductase (SDR) relationships: a large family with eight clusters common to human, animal, and plant genomes", Protein Sci., 2002, vol. 11, pp. 636-641.
Kallberg et al., "Short-Chain Dehydrogenases/Reductases (SDRs)— Coenzyme-Based Functional Assignments in Completed Genomes". Eur. J. Biochem., 2002, vol. 269, pp. 4409-4417.
Kim et al. "Activation and Function of the mTORC1 Pathway in Mast Cells". J Immunol. Apr. 1, 2008; 180(7):4586-95.
Knight et al., "A pharmacological map of the P13-K family defines a role for p110a in insulin signaling", Cell, 2006, vol. 125, pp. 733-747.
Kost et al., "Recyclization of 3-Alkyl- and 1,3-Dialkylisoquinolinium Salts to Naphthylamines", Chemistry of Heterocyclic Compounds, Jan., 16(9): 965-970 (1981).
Kraybill et al., "Inhibitor scaffolds as new allele specific kinase substrates", Journal of the American Chemical Society, Oct. 16, 2002, vol. 124, No. 41, pp. 12118-12128, American Chemical Society, Washington, DC, US.

(56) References Cited

OTHER PUBLICATIONS

Kreutzberger et al. 5-Substituierte 4-Aminopyrimidine durch Aminomethinylierung von Acetonitrilen. Liebigs Ann. Chem. 1977: pp. 537-544.
Kumar et al., "Keten Dithioacetals. Part 11. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine derivatives", Journal of the Chemical Society, Perkin Transactions 1, Chemical Society, Letchworth, Jan., 8: 857-862 (1978).
Kundu et al., "Palladium-catalysed heteroannualation with terminal alkynes; a highly regio-and stereoselective synthesis of (Z)-3-aryl(alykl)idene isoindolin-1-ones1", Tetrahedron, Jun. 30, 2000, vol. 56, No. 27, pp. 4777-4792.
Kwok et al., "The anti-inflammatory natural product parthenolide from the medicinal herb feverfew directly binds to and inhibits IkB kinase", Chem. Biol., 2001, vol. 8, pp. 759-766.
Ledbetter et al., "Crosslinking of surface antigens cause mobilization of intracellular ionized calcium in T lymphocytes", Proc. Natl. Acad. Sci. USA, Mar. 1987, vol. 84, pp. 1384-1388.
Lee et al., "All roads lead to mTOR integrating inflammation and tumor angiogenesis", Cell Cycle, 2007, vol. 6, No. 24, pp. 3011-3014.
Ley et al., "The T cell receptor/CD3 complex and CD2 stimulate the tyrosine phosphorylation of indistinguishable patterns of polypeptides in the human T leukemic cell line Jurkat", Eur. J. Immunol., 1991, vol. 21, pp. 2203-2209.
Liu et al., "Costimulation of T-cell growth", Current Biology, 1992, pp. 265-270.
Majumder et al., "mTOR inhibition reverses Akt-dependent prostate intraepithelial neoplasia through regulation of apoptic and HIF-1-dependent pathways", Nature Medicine, 2004, vol. 10, pp. 594-601.
Abraham, T., "Thermally induced intramolecular cycloaddition reaction of N-phenyl-2-phenylethynlbenzamide potential cure reaction for thermosetting polymers," *J. Polym. Sci. Polym. Chem. Ed.* 20(7):1953-1957 (1982).
Bhatt et al., "Dual inhibition of PI3K and mTOR inhibits autocrine and paracrine proliferative loops in PI3K/Akt/mTOR-addicted lymphomas," *Blood* 115(22):4455-4463.
Blunden et al., "Mycotoxins in food," *Medical Laboratory Sciences* 48:271-282 (1991).
Bone et al., "Phosphoinositide 3-kinase signalling regulates early development and developmental haemopoiesis," *J. Cell. Sci.* 120(Pt 10):1752-1762 (2007).
Buitenhuis et al., "The role of the P13k-PKB signaling module in regulation of hematopoiesis," *Cell Cycle* 8(4):560-566 (2009).
Burger et al., "High-level expression of the T-cell chemokines CCL3 and CCL4 by chronic lymphocytic leukemia B cells in nurselike cell cocultures and after BCR stimulation," *Blood* 113(13) 3050-3058 (2009).
Burger et al., "Phosphoinositide 3'-kinase delta: turning off BCR signaling in Chronic Lymphocytic Leukemia," *Oncotarget* 2:737-738 (2011).
Burger, "Inhibiting B-Cell Receptor Signaling Pathways in Chronic Lymphocytic Leukemia," *Curr. Mematol. Malig. Rep.* 7:26-33 (2012).
Byrd et al., "Translating PI3K-Delta Inhibitors to the Clinic in Chronic Lymphocytic Leukemia: The Story of CAL-101 (GS1101)," *ASCO Program Proceedings*, pp. 691-694. (2012).
Camps et al., "Blockade of PI3Kγ suppresses joint inflammation and damage in mouse models of rheumatoid arthritis," Nat. Med. 11(9):936-943 (2005).
Chang et al., "The Bruton tyrosine kinase inhibitor PCI-32765 ameliorates autoimmune arthritits by inhibition of multiple effector cells," *Arthritis Research & Therapy* 13:R115 (2011).
Chawla. et. al., "Challenges in Polymorphism of Pharmaceuticals," *Current Research & Information on Pharmaceutical Science* 5(1):9-12 (2004).
Cheson et al., "Bendamustine: rebirth of an old drug," *J. Clin. Oncol.* 27(9):1492-1501 (2009).

Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," *Cancer Res.* 70(20):8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," *Cancer Res.* 69(8): 3520-3528 (2009).
Cho et al., "A Novel Synthesis of Benzo[c] phenanthridine Skeleton and Biological Evaluation of Isoquinoline Derivatives," *Chem. Pharm. Bull. (Tokyo)* 47(6):900-902 (1999).
Cushing et al., "PI3Kδ and PI3Kγ as Targets for Autoimmune and Inflammatory Diseases," *J. Med. Chem.* 55:8559-8581 (2012).
Dai et al., "Distinct Roles of Phosphoinositide-3 Kinase and Phospholipase Cγ2 in B-Cell Receptor-Mediated Signal Transduction," *Mol. Cell. Biol.* 26(1):88-99 (2006).
Davids et al., "Decreased mitochondrial apoptotic priming underlies stroma-mediated treatment resistance in chronic lymphocytic leukemia," *Blood* 120(17):3501-3509 (2012).
Davis et al., "Chronic active B-cell-receptor signaling in diffuse large B-cell lymphoma," *Nature* 463:88-92 (2010).
De Weers et al., "The Bruton's tyrosine kinase gene is expressed throughout B cell differentiation, from early precursor B cell stages preceding immunoglobulin gene rearrangement up to mature B cell stages," *Eur. J. Immunol.* 23:3109-3114 (1993).
Gunther et al., "Immunosuppressive effects of dietary wortmannin on rats and mice," *Immunopharmacol. Immunotoxicol.* 11(4):559-570 (1989).
Hasselblom et al., "High immunohistochemical expression of p-AKT predicts inferior survival in patients with diffuse large B-cell lymphoma treated with immunochemotherapy," *Brit. J. Haematol.* 149:560-568 (2010).
Haylock-Jacobs et al., "PI3Kδ drives the pathogenesis of experimental autoimmune encephalomyelitis by inhibiting effector T cell apoptosis and promoting Th17 differentiation," *J. Autoimmun.* 36:278-287 (2011).
Herishanu et al., "The lymph node microenvironment promotes B-cell receptor signaling, Nf-κB activation, and tumor proliferation in chronic lymphocytic leukemia," *Blood* 117(2):563-574 (2011).
Hickey et al., "BCR-ABL Regulates Phosphatidylinositol 3-Kinase-p110γ Transcription and Activation and Is Required for Proliferation and Drug Resistance," *J. Biol. Chem.* 281(5):2441-2450 (2006).
Hirsch et al., "CALming Down T Cell Acute Leukemia," *Cancer Cell* 21: 449-450 (2012).
Hirsch et al., "Central Role for G Protein-Coupled Phosphoinositide 3-Kinase γ in Inflammation," *Science* 287:1049-1053 (2000).
Hoellenriegel and Burger, "Phosphoinositide 3'-kinase delta: turning off BCR signaling in Chronic Lymphocytic Leukemia," *Oncotarget* 2(10):737-738 (2011).
Hoellenriegel et al., "The phosphoinositide 3'-kinase delta inhibitor, CAL-101, inhibits B-cell receptor signaling and chemokine networks in chronic lymphocytic leukemia," *Blood* 118(13):3603-3612 (2011).
Hoellenriegel, J. et al., "Phosphoinositide 3'-kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Honigberg et al., "The Bruton tyrosine kinase inhibitor PCI-32765 blocks B-Cell activation and is efficacious in models of autoimmune disease and B-cell malignancy," *PNAS* 107(29):13075-13080 (2010).
International Search Report and Written Opinion for PCT/US2012/047190 dated Oct. 2, 2012.
International Search Report for PCT/US1995/005213 dated Aug. 21, 1995.
June et al., "Evidence for the involvement of three distinct signals in the induction of IL-2 gene expression in human T lymphocytes," *J. Immunol.* 143(1):153-161 (1989).
June et al., "Role of the CD28 receptor in T-cell activation," *Immunol. Today* 11(6):211-216 (1990).
June, "Signal transduction in T cells," *Curr. Opin. Immunol.* 3(3):287-293 (1991).

(56) References Cited

OTHER PUBLICATIONS

Kang et al., "Oncogenic transformation induced by the p110β, -γ, and -δ isoforms of class I phosphoinositide 3-kinase," *PNAS* 103(5):1289-1294 (2006).
Karpeiskii et al., "Pyridoxal-5'-Derivatives of Nucleobases," *Bioorganicheskaya Khimiya* 11(8):1097-1104 (1985).
Kumar et al., "Keten Dithioacetals. Part II. Reaction of 3-Cyano-4-methylthio-2(1H)-pyridones with Hydrazine and Guanidine: Synthesis of Novel Substituted and Fused Pyrazolo[4,3-c]pyridine and Pyrido[4,3-d]pyrimidine derivatives," *J.C.S. Perkin 1* 857-862 (1978).
Kurtova et al., "Diverse marrow stromal cells protect CLL cells from spontaneous and drug-induced apoptosis: development of a reliable and reproducible system to assess stromal cell adhesion-mediated drug resistance," *Blood* 114(20): 4441-4450 (2009).
Lannutti et al., "CAL-101 a p110δ selective phosphatidylinositol-3-kinase inhibitor for the treatment of B-cell malignancies, inhibits PI3K signaling and cellular viability," *Blood* 117(2):591-594 (2011).
Ledbetter et al., "CD28 ligation in T-cell activation: evidence for two signal transduction pathways," *Blood* 75(7):1531-1539 (1990).
Lee et al., "The CD28 Signal Transduction Pathway in T cell Activation", Advances in Regulation of Cell Growth, vol. 2, pp. 141-160, New York: Raven Press, Ltd. (1991).
Li et al., "Roles of PLC-β2 and -β3 and PI3Kγ in Chemoattractant-Mediated Signal Transduction," *Science* 287:1046-1049 (2000).
Lu et al., "CD28-induced T cell activation. Evidence for a protein-tyrosine kinase signal transduction pathway," *J. Immunol.* 149(1):24-29 (1992).
Martelli et al., "The emerging role of the phosphatidylinositol 3-kinase/Akt/mammalian target of rapamycin signaling network in normal myelopoiesis and leukemogenesis," *Biochim. Biophys. Acta.* 803:991-1002 (2010).
Martinez et al., "The Molecular Signature of Mantle Cell Lymphoma Reveals Multiple Signals Favoring Cell Survival," *Cancer Res.* 63:8226-8232 (2003).
Martin-Sanchez et al., "PI3K Inhibition As a Potential Therapeutic Strategy Peripheral T-Cell Lymphomas," *Blood (ASH Annual Meeting Abstracts)* 118: Abstract 3493 (2011).
Mattes et al., "DNA sequence selectivity of guanine-N7 alkylation by nitrogen mustards," *Nucleic Acids Res.* 14(7):2971-2987 (1986).
Maxwell et al., "Attenuation of phosphoinositide 3-kinase δ signaling restrains autoimmune disease," *J. Autoimmun.* 38:381-391 (2012).
Merida et al., "IL-2 binding activates a tyrosine-phosphorylated phosphatidylinositol-3-kinase," *J. Immunol.* 147(7):2202-2207 (1991).
Newman et al., "Solid state analysis of the active pharmaceutical ingredient in drug products," *Drug Discov. Today* 8(19):898-905 (2003).
Nisitani et al., "Posttranscriptional regulation of Bruton's tyrosine kinase expression in antigen receptor-stimulated splenic B cells," *PNAS* 97(6):2737-2742 (2000).
Norman, "Selective PI3K-delta Inhibitors, A Review of the Patent Literature," *Expert Opinion on Therapeutic Patents* 21(11):1773-1790 (2011).
Pighi et al., "Phospho-proteomic analysis of mantle cell lymphoma cells suggests a pro-survival role of B-cell receptor signaling," *Cell Oncol. (Dordr)* 34(2):141-153 (2011).
Polak et al., "The PI3K/PKB signaling module as key regulator of hematopoiesis: implications for therapeutic strategies in leukemia," *Blood* 119(4):911-923 (2012).
Puri and Gold, "Selective inhibitors of phosphoinositide 3-kinase delta: modulators of B-cell function with potential for treating autoimmune inflammatory disease and B-cell malignancies," *Front. Immunol.* 3:256 (2012).
Quiroga et al., "B-cell antigen receptor signaling enhances chronic lymphocytic leukemia cell migration and survival: specific targeting with a novel spleen tyrosine kinase inhibitor, R406," *Blood* 114(5):1029-1037 (2009).
Rizzatti et al., "Gene expression profiling of mantle cell lymphoma cells reveals aberrant expression of genes from the PI3K-AKT, WNT and TGFβ signaling pathways," *Brit. J. Haematol.* 130:516-526 (2005).
Roller et al., "Blockade of Phosphatidylinositol 3-Kinase (PI3K)δ or PI3Kγ Reduces IL-17 and Ameliorates Imiquimod-Induced Psoriasis-like Dermatitis," *J. Immunol.* 189:4612-4620 (2012).
Rommel et al., "PI3Kδ and PI3Kγ: partners in crime in inflammation in rheumatoid arthritis and beyond?" *Nat. Rev. Immunol.* 7:191-201 (2007).
Rudelius et al., "Constitutive activation of Akt contributes to the pathogenesis and survival of mantle cell lymphoma," *Blood* 108(5):1668-1676 (2006).
Sasaki et al., "Function of PI3Kγ in Thymocyte Development, T Cell Activation, and Neutrophil Migration," *Science* 287:1040-1046 (2000).
Sinclair et al., "Phosphatidylinositol-3 Kinase Delta (PI3Kδ) Inhibitor AMG 319 Is a Potent, Selective and Orally Bioavailable Small Molecule Inhibitor That Suppresses PI3K-Mediated Signaling and Viability in Neoplastic B Cells," *Blood (ASH Annual Meeting Abstracts)* 118: Abstract 4964 (2011).
Smith et al., "Expression of Bruton's Agammaglobulinemia Tyrosine Kinase Gene, BTK, Is Selectively Down-Regulated in T Lymphocytes and Plasma Cells," *J. Immunol.* 152:557-565 (1994).
Soond et al., "PI3K p110δ regulates T-cell cytokine production during primary and secondary immune responses in mice and humans," *Blood* 115(11):2203-2213 (2010).
Srinivasan et al., "PI3 Kinase Signals BCR-Dependent Mature B Cell Survival," *Cell* 139:573-586 (2009).
Subramaniam et al., "Targeting Nonclassical Oncogenes for Therapy in T-ALL," *Cancer Cell* 21:459-472 (2012).
Sujobert et al., "Essential role for the p110δ isoform in phosphoinositide 3-kinase activation and cell proliferation in acute myeloid leukemia," *Blood* 106(3):1063-1066 (2005).
Supplementary European Search Report for EP Application No. 10800175.1 dated Nov. 7, 2012.
Thompson et al., "Identification of distinct populations of PI-3 kinase activity following T-cell activation," *Oncogene* 7(4):719-725 (1992).
Tyukavkina et al., Bioorganicheskaya Khimiya, Moskva, DROFA, pp. 83-85 (2004).
Uddin et al., "Role of phosphatidylinositol 3'-kinase/AKT pathway in diffuse large B-cell lymphoma survival," *Blood* 108(13):4178-4186 (2006).
Vippagunta et al., "Crystalline Solids," *Adv. Drug Deliv. Rev.* 48(1):3-26 (2001).
Vitali et al., "Immunotherapy in rheumatoid arthritis: a review," *Int. J. Artif. Organs* 16 Suppl 5:196-200 (1993).
Wahlstrom et al., "Aberrant MAPK and PI3K Signaling Contribute to Chemotherapy Resistance in T Cell Acute Lymphobalstic Leukemia by Altering the Balance of Apoptosis Mediators," *Blood (ASH Annual Meeting Abstracts)* 118: Abstract 3490 (2011).
Wu et al., "Decreased immunological responses by wortmannin-containing rice culture of *Fusarium oxysporum* and by purified wortmannin in avian species," *Immunopharmacol. Immunotoxicol.* 14(4):913-923 (1992).
Wu et al., "Wortmannin (a mycotoxin) inhibited immune responses in chickens," *Poult. Sci.* 71 Suppl 1:13 (1992).
Basotest (R), "Test Kit for the Quantitative Determination of the Degranulation of Basophillic Granulocytes in Heparinized Human Whole Blood," [www.biocarta.com/TDS/10/0500.pdf], Retrieved from the Internet on Nov. 29, 2011.

* cited by examiner

HETEROCYCLIC COMPOUNDS AND USES THEREOF

The present application is a continuation of International Patent Application No. PCT/US2010/033939 filed on May 6, 2010, which claims the benefit of U.S. Provisional Application Ser. No. 61/176,449, filed on May 7, 2009, each of which is hereby incorporated by reference in its entirety.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, ably, serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3% OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the pathways of Akt/PDK1, mTOR, the Tec family kinases, and the Rho family GTPases. The class II and III PI3-Ks play a key role in intracellular trafficking through the synthesis of PI(3)P and $PI(3,4)P_2$.

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, auto-immune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). Akt possesses a plckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

Dysregulation of signaling pathways mediated by many other kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

As such, kinases particularly lipid kinases such as PI3Ks and protein kinases such as mTor are prime targets for drug development. The present invention addresses a need in the art by providing a new class of kinase inhibitors.

SUMMARY OF THE INVENTION

The present invention provides a compound of Formula I:

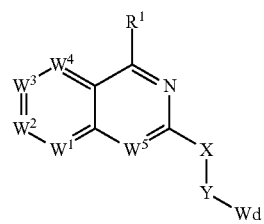

Formula I or its pharmaceutically acceptable salts thereof, wherein:
$W^1$ is N or $CR^5$, $W^2$ is N or $CR^6$, $W^3$ is N or $CR^7$, $W^4$ is N or $CR^8$, wherein no more than two N are adjacent;
$W^5$ is N or $CR^4$;
$R^1$ is $-(L)_n-R^1$;
L is —S—, —N($R^2$)—, —C($R^3$)$_2$—, or —O—;
n is 0 or 1;

$R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

X is absent or is —$(CH(R^{10}))_z$ and z is an integer of 1, 2, 3, or 4;

Y is absent, —O—, —S—, —S(═O)—, —S(═O)$_2$—, —N($R^9$)—, —C(═O)—(CHR$^{10}$)$_z$—, —C(═O)—, —N($R^9$)—C(═O)—, or —N($R^9$)—C(═O)NH—, —N($R^9$)C($R^{10}$)$_2$—, or —C(═O)—(CHR$^{10}$)$_z$—;

each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;

each instance of $R^3$ and $R^{10}$ is independently hydrogen, alkyl, aryl, heteroaryl or halo; and $W_d$ is heterocycloalkyl, aryl, cycloalkyl, or heteroaryl.

In a first aspect, the invention provides a compound of Formula I-A:

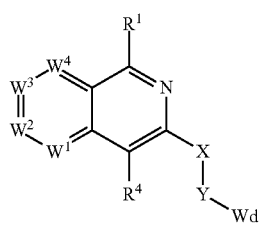

Formula I-A or its pharmaceutically acceptable salts thereof, wherein $W^1$ is N or $CR^5$, $W^2$ is N or $CR^6$, $W^3$ is N or $CR^7$, $W^4$ is N or $CR^8$, wherein no more than two N atoms are adjacent; $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —$(CH(R^{10}))_z$ and z is an integer of 1, 2, 3, or 4; Y is absent, —O—, —S—, —S(═O)—, —S(═O)$_2$—, —N($R^9$)—, —C(═O)—(CHR$^{10}$)$_z$, —C(═O)—, —N($R^9$)—C(═O)—, or —N($R^9$)—C(═O)NH—, —N($R^9$)C($R^{10}$)$_2$—, or —C(═O)—(CHR$^{10}$)$_2$; each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ is independently hydrogen, alkyl, aryl, heteroaryl or halo; and $W_d$ is heterocycloalkyl, aryl, cycloalkyl, or heteroaryl.

In a second aspect, the invention also provides a compound of Formula I-B:

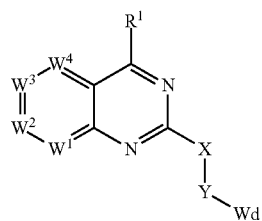

Formula I-B or its pharmaceutically acceptable salts thereof, wherein $W^1$ is N or $CR^5$, $W^2$ is N or $CR^6$, $W^3$ is N or $CR^7$, $W^4$ is N or $CR^8$, wherein no more than two N atoms are adjacent; $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —$(CH(R^{10}))_z$ and z is an integer of 1, 2, 3, or 4; Y is absent, —O—, —S—, —S(═O)—, —S(═O)$_2$—, —N($R^9$)—, —C(═O)—(CHR$^{10}$)$_z$—, —C(═O)—, —N($R^9$)—C(═O)—, or —N($R^9$)—C(═O)NH—, —N($R^9$)C($R^{10}$)$_2$—, or —C(═O)—(CHR$^{10}$)$_z$—; each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ is independently hydrogen, alkyl, aryl, heteroaryl or halo; and $W_d$ is heterocycloalkyl, aryl, cycloalkyl, or heteroaryl.

In a third aspect, the invention provides a composition comprising a pharmaceutically acceptable excipient and a compound of Formula I-A or Formula I-B. In some embodiments, the composition is a liquid, solid, semi-solid, gel, or an aerosol form.

In a fourth aspect, the invention provides a method for inhibiting a phosphatidyl inositol-3 kinase (PI3 kinase), comprising: contacting the PI3 kinase with an effective amount of a compound of Formula I-A or Formula I-B. In some embodiments, the PI3 kinase is PI3 kinase delta or PI3 kinase gamma. The step of contacting may further comprise contacting a cell that expresses said PI3 kinase. In some embodiments, the method further comprises administering a second therapeutic agent to the cell.

In a fifth aspect, the invention provides a method for treating a condition associated with PI3 kinase, comprising administering to a subject in need thereof an effective amount of the compound of Formula I-A or Formula I-B. In some embodiments, the condition associated with PI3 kinase is selected from the group consisting of asthma, emphysema, bronchitis, psoriasis, allergy, anaphylaxis, rheumatoid arthritis, graft versus host disease, lupus erythematosus, psoriasis, restenosis, benign prostatic hypertrophy, diabetes, pancreatitis, proliferative glomerulonephritis, diabetes-induced renal disease, inflammatory bowel disease, atherosclerosis, eczema, scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments of the compound of Formula I-A or Formula I-B, $W^1$ is N, $W^2$ is $CR^6$, $W^3$ is $CR^7$, $W^4$ is $CR^8$; $W^1$ is $CR^5$, $W^2$ is N, $W^3$ is $CR^7$, $W^4$ is $CR^8$; $W^1$ is $CR^5$, $W^2$ is $CR^6$, $W^3$ is N, $W^4$ is $CR^8$; $W^1$ is N, $W^2$ is $CR^6$, $W^3$ is N, $W^4$ is $CR^8$; $W^1$ is N, $W^2$ is N, $W^3$ is $CR^7$, $W^4$ is $CR^8$; $W^1$ is N, $W^2$ is $CR^6$, $W^3$ is $CR^7$, $W^4$ is N; $W^1$ is $CR^5$, $W^2$ is N, $W^3$ is N, $W^4$ is $CR^8$; $W^1$ is $CR^5$, $W^2$ is N, $W^3$ is $CR^7$, $W^4$ is N; $W^1$ is $CR^5$, $W^2$ is $CR^6$, $W^3$ is N, $W^4$ is N; or $W^1$ is $CR^5$, $W^2$ is $CR^6$, $W^3$ is $CR^7$, $W^4$ is $CR^8$.

In other embodiments of the compound of Formula I-A or Formula I-B, n is 0 and $R^{1'}$ is hydrogen, amino, alkoxy, alkyl, heterocycloalkyl, aryl, or NR'R" wherein R' and R" are taken together with nitrogen to form a cyclic moiety. In yet other embodiments, n is 1 and $R^{1'}$ is amino, alkoxy, alkyl, or NR'R" wherein R' and R" are taken together with nitrogen to form a cyclic moiety. In yet other embodiments of the compound of Formula I-A or Formula I-B, n is 1 and $R^{1'}$ is alkyl which is substituted with heterocycloalkyl or NR'R" wherein R' and R" are taken together with nitrogen to form a cyclic moiety.

The invention also provides a compound of Formula I-A or Formula I-B wherein $R^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety. In some embodiments, $R^8$ is hydrogen or alkyl. In yet other embodiments, $R^8$ is alkyl substituted with one or more fluoro.

In other embodiments, the compound of Formula I-A or Formula I-B is a compound of Formula XV-A or XV-B:

Formula XV-A

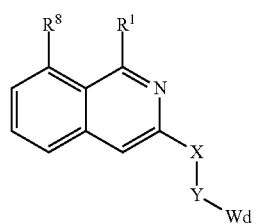

Formula XV-B

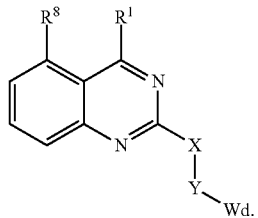

In some embodiments of the compound of Formula I-A or Formula I-B, X is —$CH_2$—, —$CH(CH_3)$—, —$CH(C_6H_5)$- or $CH(CH_2CH_3)$—. In various embodiments, when X is —CH($CH_3$)— or $CH(CH_2CH_3)$—, X has either a predominately (S) stereochemical configuration or a predominately (R) stereochemical configuration.

In various embodiments of the compound of Formula I-A or Formula I-B, Y is absent, —O—, —$N(R^9)$—, $N(R^9)$ $C(R^{10})_2$—, or —$S(=O)_2$—. In some embodiments, $R^9$ and $R^{10}$ are independently hydrogen, methyl or ethyl. In other embodiments, when $R^1$ is alkyl, X is —$CH(R^{10})_z$—, z is 1, and Y is —$N(R^9)$—, then $R^9$ is —NH—. In yet other embodiments, Y is $N(CH_2CH_3)CH_2$— or $N(CH_3)CH_2$—.

In some embodiments of the compound of Formula I-A or Formula I-B, X—Y is —$CH_2$—$N(CH_3)$, or —$CH_2$—N ($CH_2CH_3$).

The invention provides a compound of Formula I-A or Formula I-B wherein $W_d$ is a monocyclic or polycyclic heteroaryl which is unsubstituted or substituted with one or more substituents selected from the group consisting of alkyl, alkynyl, alkenyl, halo, aryl, heteroaryl, heterocycloalkyl, cycloalkyl, cyano, amino, carboxylic acid, hydroxy, alkoxy, acyloxy, alkoxycarbonyl, and amido. In some embodiments, $W_d$ is a bicyclic heteroaryl. In other embodiments, $W_d$ is a pyrazolopyrimidine or a purine. In further embodiments of the compound of Formula I-B, when $W_d$ is purine, and X—Y is —$(CH(R^{10}))N(R_9)$—, then $R_9$ is hydrogen In some embodiments of the compound of Formula I-A or Formula I-B, $W_d$ is one of the following formulae:

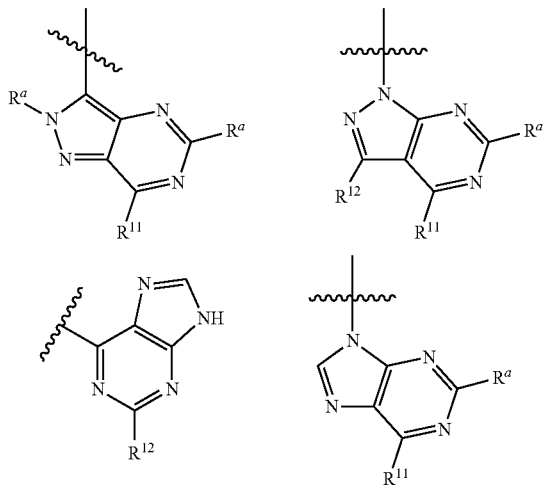

wherein each instance of $R^a$ is independently hydrogen or alkyl; $R^{11}$ is H, alkyl, halo, amino, amido, hydroxy, or alkoxy, and $R^{12}$ is H, alkyl, cyano, alkynyl, alkenyl, halo, aryl, heteroaryl, heterocycloalkyl, cycloalkyl, amino, carboxylic acid, alkoxycarbonyl, or amido. In other embodiments, $W_d$ has a structure of Formula XIII:

Formula XIII

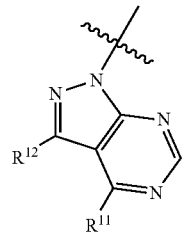

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido. In yet other embodiments, $W_d$ has a structure of Formula XIV:

Formula XIV

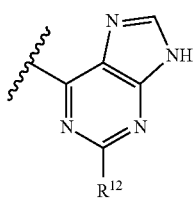

wherein $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido. In some embodiments, $R^{11}$ is amino. In other embodiments $R^{12}$ is a monocyclic heteroaryl, a bicyclic heteroaryl, or a heterocycloalkyl. Alternatively, $R^{12}$ is hydrogen.

In various embodiments of the invention, the compound of Formula I-A has a structure of Formula XVI-A, Formula XVIII-A, Formula XIX-A, or Formula XX-A:

Formula XVI-A

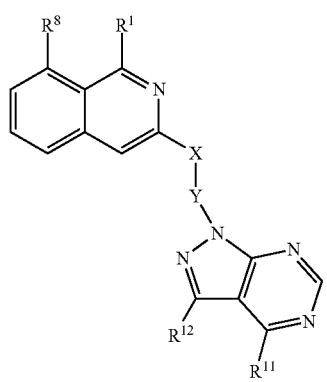

Formula XVIII-A

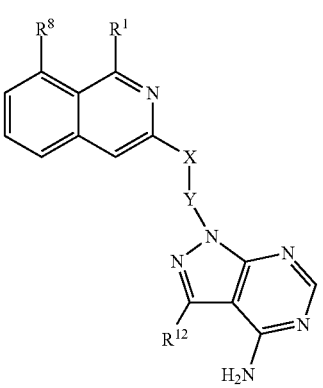

Formula XIX-A

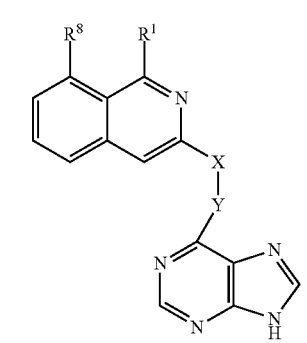

Formula XX-A

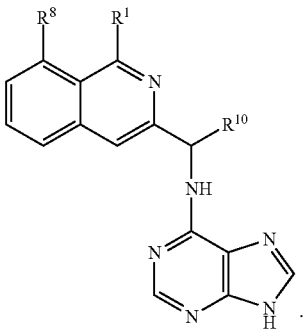

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

"Treatment", "treating", "palliating" and "ameliorating", as used herein, are used interchangeably. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and "Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target.

The term "B-ALL" as used herein refers to B-cell Acute Lymphoblastic Leukemia.

"Subject" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionucleotides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

Unless otherwise stated, structures depicted herein are also meant to include compounds which differ only in the presence of one or more isotopically enriched atoms. For example, compounds having the present structures wherein hydrogen is replaced by deuterium or tritium, or wherein carbon atom is replaced by $^{13}$C— or $^{14}$C-enriched carbon, are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PIKK=Phosphoinositide Kinase Like Kinase; AIDS=Acquired Immuno Deficiency Syndrome; TLC=Thin Layer Chromatography; MeOH=Methanol; and CHCl$_3$=Chloroform.

Abbreviations used herein have their conventional meaning within the chemical and biological arts.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, $N(R^a)C(O)N(R^a)_2$, $N(R^a)C(NR^a)N(R^a)_2$, —$N(R^a)S(O)_tR^a$ (where t is 1 or 2), —$S(O)_tOR^a$ where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one triple bond, having from two to ten carbon atoms (i.e. $C_2$-$C_{10}$ alkynyl). Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$,—OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxaldehyde" refers to a —(C═O)H radical.

"Carboxyl" refers to a —(C═O)H radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. $C_2$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, $N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —$N(R^a)_2$, —$C(O)OR^a$, —$C(O)OR^a$, —$OC(O)N(R^a)_2$, —$C(O)N(R^a)_2$, —$N(R^a)C(O)OR^a$, —$N(R^a)C(O)R^a$, $N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group. In some embodiments, $C_1$-$C_4$ alkoxy, is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, $SR^a$, —OC(O)—$R^a$, —N$(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_tR^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein "R" is alkyl, aryl, heteroaryl, heteroalkyl, or heterocycloalkyl, which are as described herein. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e. three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N$(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2-S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N$(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N$(R^a)_2$ group has two $R^a$ other than hydrogen they can be combined with the nitrogen atom to form a 4-, 5-, 6-, or 7-membered ring. For example, —N$(R^a)_2$ is meant to include, but not be limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N$(R^a)_2$, —C(O)$R^a$, —C(O)O$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties may be optionally substituted as defined herein.

The term "substituted amino" also refers to N-oxides of the groups —NHR$^a$, and NR$^a$R$^a$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The R$_2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3.sup.rd Ed., John Wiley & Sons, New York, N.Y., 1999, which is incorporated herein by reference in its entirety.

"Aromatic" or "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —N$(R^a)_2$, —C(O)$R^a$, —C(O)$R^a$, —OC(O)N$(R^a)_2$, —C(O)N$(R^a)_2$, —N$(R^a)$C(O)O$R^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_t$O$R^a$ (where t is 1 or 2), —S(O)$_t$N$(R^a)_2$ (where t is 1 or 2), or PO$_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl—radical wherein the arylalkyl moiety is attached via the alkyl portion of the moiety. Aryl and alkyl are as disclosed herein and are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, $N(R^a)C(O)OR^a$, $N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers "to an -(heteroalkyl)aryl radical where heteroalkyl and aryl are as disclosed herein and which are optionally substituted by one or more of the substituents described as suitable substituents for heteroalkyl and aryl respectively.

"Heteroaryl" or, alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzo[i]ranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)R$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as pyridinyl N-oxides.

"Heteroarylalkyl" refers to a moiety having a heteroaryl moiety, as described herein, connected to an alkyl moiety, as described herein, wherein the connection to the remainder of the molecule is through the alkyl group. Heteroaryl and alkyl are as disclosed herein and are optionally substituted by one or more of the substituents described as suitable substituents for heteroaryl and alkyl respectively.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C$_5$-C$_{10}$ heterocycloalkyl. In some embodiments, it is a C$_4$-C$_{10}$ heterocycloalkyl. In some embodiments, it is a C$_3$-C$_{10}$ heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Heterocycloalkyloxy" refers to a (heterocycloalkyl)-O— moiety, where the heterocycloalkyl moiety is attached via a carbon atom to oxygen, wherein the oxygen functions as a linker to attach the moiety to a compound. The heterocycloalkyl is as described herein and is optionally substituted by one or more substituents described herein as suitable for heterocycloalkyl.

"Isomers" are different compounds that have the same molecular formula. "Stereoisomers" are isomers that differ only in the way the atoms are arranged in space. "Enantiomers" are a pair of stereoisomers that are non-superimposable minor images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not minor-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Nitro" refers to the NO$_2$ radical.

"Oxa" refers to the —O— radical.

"Oxo" refers to the =O radical.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

A "leaving group or atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

"Solvate" refers to a compound (e.g., a compound selected from Formula I or a pharmaceutically acceptable salt thereof) in physical association with one or more molecules of a pharmaceutically acceptable solvent. It will be understood that "a compound of Formula I" encompass the compound of Formula I and solvates of the compound, as well as mixtures thereof.

"Substituted" means that the referenced group may be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves may be substituted, for example, a cycloakyl substituent may have a halide substituted at one or more ring carbons, and the like. The protecting groups that may form the protective derivatives of the above substituents are known to those of skill in the art and may be found in references such as Greene and Wuts, above.

"Sulfonyl" refers to the groups: $-S(O_2)-H$, $-S(O_2)$-(optionally substituted alkyl), $-S(O_2)$-(optionally substituted amino), $-S(O_2)$-(optionally substituted aryl), $-S(O_2)$-(optionally substituted heteroaryl), and $-S(O_2)$-(optionally substituted heterocycloalkyl).

"Sulfonamidyl" or "sulfonamido" refers to a $-S(=O)_2-$NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the $-S(=O)_2$—NRR radical may be taken together with the nitrogen to which it is attached to form a 4-, 5-, 6-, or 7-membered ring. In some embodiments, it is a sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, heteroaryl respectively "Sulfoxyl" refers to a $-S(=O)_2OH$ radical.

"Sulfonate" refers to a $-S(=O)_2-OR$ radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl respectively.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

Compounds of the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Solvent," "organic solvent," and "inert solvent" each means a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. In addition, if the compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, the present invention provides various compounds that are useful as antagonists for one or more lipid kinases and/or protein kinases.

In one aspect, the present invention provides a compound of Formula I:

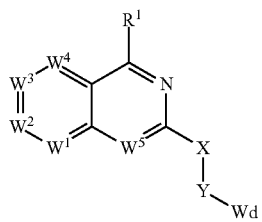

Formula I or its pharmaceutically acceptable salts thereof, wherein:
$W^1$ is N or $CR^5$, $W^2$ is N or $CR^6$, $W^3$ is N or $CR^7$, $W^4$ is N or $CR^8$, wherein no more than two N are adjacent;
$W^5$ is N or $CR^4$;
$R^1$ is -(L)$_n$-$R^{1'}$;
L is —S—, —N($R^2$)—, —C($R^3$)$_2$—, or —O—;
n is 0 or 1;
$R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
$R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;
X is absent or is —(CH($R^{10}$))$_z$ and z is an integer of 1, 2, 3, or 4;
Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, or —N($R^9$)—C(=O)NH—, —N($R^9$)C($R^{10}$)$_2$—, or —C(=O)—(CHR$^{10}$)$_z$;

each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;
each instance of $R^3$ and $R^{10}$ is independently hydrogen, alkyl, aryl, heteroaryl or halo; and
$W_d$ is heterocycloalkyl, aryl, cycloalkyl, or heteroaryl.

In some embodiments, the compound of Formula I exists as a tautomer, and such tautomers are contemplated by the present invention.

The invention also provides compounds of Formula I having a structure of Formula I-A or Formula I-B:

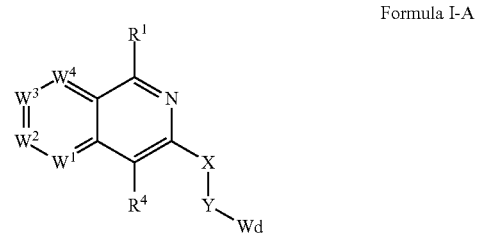

Formula I-A

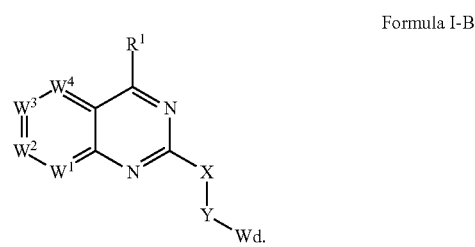

Formula I-B

In some embodiments of the compound of Formula I, $W^1$ is $CR^5$, $W^2$ is $CR^6$, $W^3$ is $CR^7$, $W^4$ is $CR^8$ (Formula II-A or Formula II-B); $W^1$ is N, $W^2$ is $CR^6$, $W^3$ is $CR^7$, $W^4$ is $CR^8$ (Formula III-A or Formula III-B); $W^1$ is $CR^5$, $W^2$ is N, $W^3$ is $CR^7$, $W^4$ is $CR^8$ (Formula IV-A or Formula IV-B); $W^1$ is $CR^5$, $W^2$ is $CR^6$, $W^3$ is N, $W^4$ is $CR^8$ (Formula V-A or Formula V-B); $W^1$ is $CR^5$, $W^2$ is $CR^6$, $W^3$ is $CR^7$, $W^4$ is N (Formula VI-A or Formula VI-B); $W^1$ is N, $W^2$ is $CR^6$, $W^3$ is N, $W^4$ is $CR^8$ (Formula VII-A or Formula VII-B); $W^1$ is N, $W^2$ is $CR^6$, $W^3$ is N, $W^4$ is $CR^8$ (Formula VIII-A or Formula VIII-B); $W^1$ is N, $W^2$ is $CR^6$, $W^3$ is $CR^7$, $W^4$ is N (Formula IX-A or Formula IX-B); $W^1$ is $CR^5$, $W^2$ is N, $W^3$ is N, $W^4$ is $CR^8$ (Formula X-A or Formula X-B); $W^1$ is $CR^5$, $W^2$ is N, $W^3$ is $CR^7$, $W^4$ is N (Formula XI-A or Formula XI-B); or $W^1$ is $CR^5$, $W^2$ is $CR^6$, $W^3$ is N, $W^4$ is N (Formula XII-A or Formula XII-B); all of which are shown below.

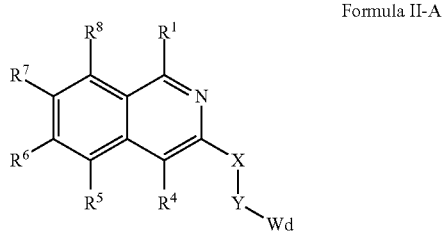

Formula II-A

-continued
Formula II-B
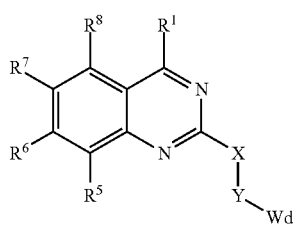
Formula III-A
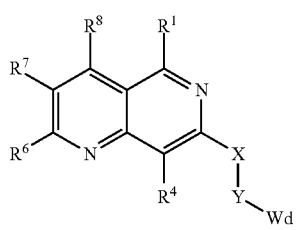
Formula IV-A
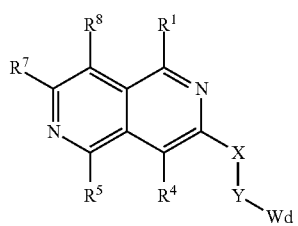
Formula V-A
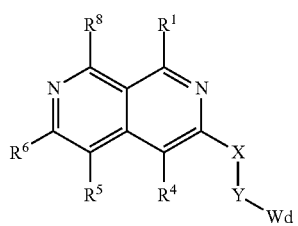
Formula VI-A
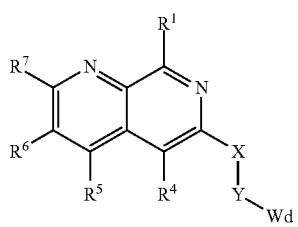
Formula VII-A
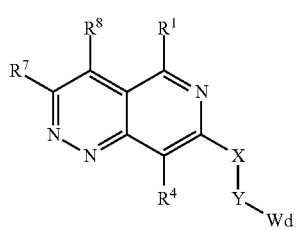
Formula VIII-A
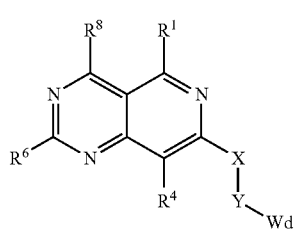
-continued
Formula IX-A
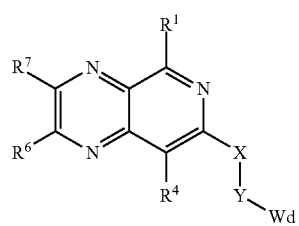
Formula X-A
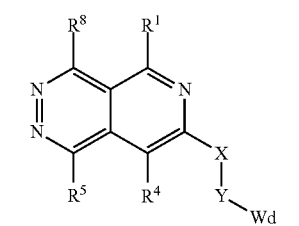
Formula XI-A
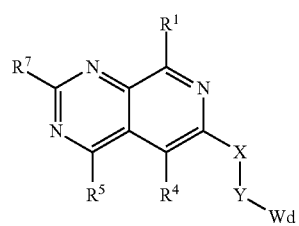
Formula XII-A
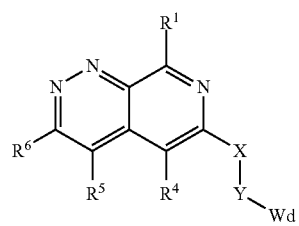
Formula III-B
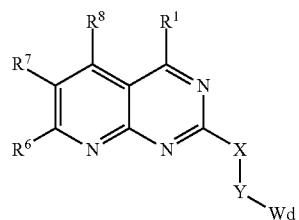
Formula IV-B
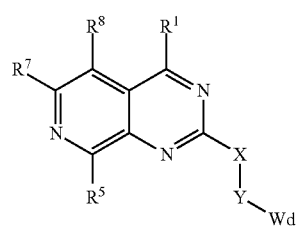
Formula V-B
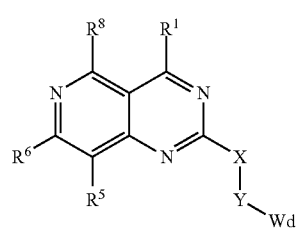

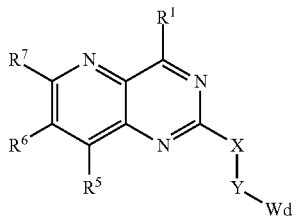

Formula VI-B


Formula VII-B

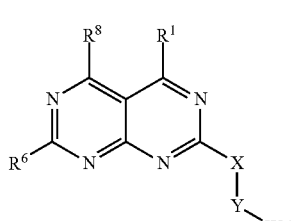

Formula VIII-B

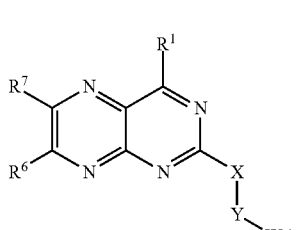

Formula IX-B

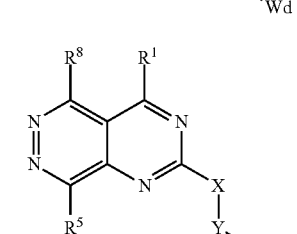

Formula X-B

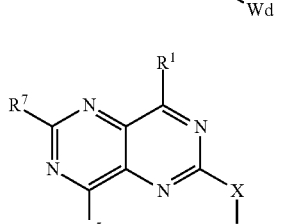

Formula XI-B

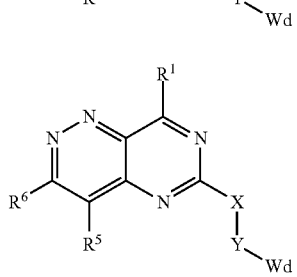

Formula XII-B

In some embodiments of the compound of Formula I, $R^1$ is $-(L)_n-R^{1'}$, wherein n is 0 or 1. In some embodiments, when $R^1$ is $-(L)_n-R^{1'}$, and n is 1, then $R^1$ is $-SR^{1'}$, $-N(R^2)R^{1'}$, $-C(R^3)_2R^{1'}$, or $-OR^{1'}$.

$R^{1'}$ can be hydrogen, or unsubstituted or substituted alkyl (including but not limited to $CH_3$, $-CH_2CH_3$, n-propyl, isopropyl, n-butyl, ten-butyl, sec-butyl, pentyl, hexyl, and heptyl). In other embodiments, $R^{1'}$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^{1'}$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, $R^{1'}$ is unsubstituted or substituted heteroaryl, including but not limited to monocyclic and bicyclic heteroaryl. Monocyclic heteroaryl $R^{1'}$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{1'}$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. The present invention also provides compounds of Formula 1 wherein $R^{1'}$ is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, $R^{1'}$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{1'}$ is unsubstituted or substituted heterocycloalkyl which includes but is not limited to pyrrolidinyl, tetrahydropyranyl, piperidinyl, tetrahydropyranyl, thiazolidinyl, imidazolidinyl, morpholinyl, and piperazinyl. In yet other embodiments of the compounds of Formula I, $R^{1'}$ is unsubstituted or substituted alkoxy including but not limited to $C_1$-$C_4$alkoxy such as methoxy, ethoxy, propoxy or butoxy. $R^{1'}$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^{1'}$ is unsubstituted or substituted amino, wherein the substituted amino includes but is not limited to dimethylamino, diethylamino, di-isopropyl amino, N-methyl N-ethyl amino, and dibutylamino. In some embodiments, $R^{1'}$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In other embodiments, $R^{1'}$ is halo, which is $-I$, $-F$, $-Cl$, or $-Br$. In some embodiments, $R^{1'}$ is selected from the group consisting of cyano, hydroxy, nitro, phosphate, urea, or carbonate. Also contemplated are $R^{1'}$ being $-CH_3$, $-CH_2CH_3$, n-propyl, isopropyl, n-butyl, tert-butyl, sec-butyl, pentyl, hexyl, heptyl, $-OCH_3$, $-OCH_2CH_3$, or $-CF_3$.

R¹' of the compounds of Formula I, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

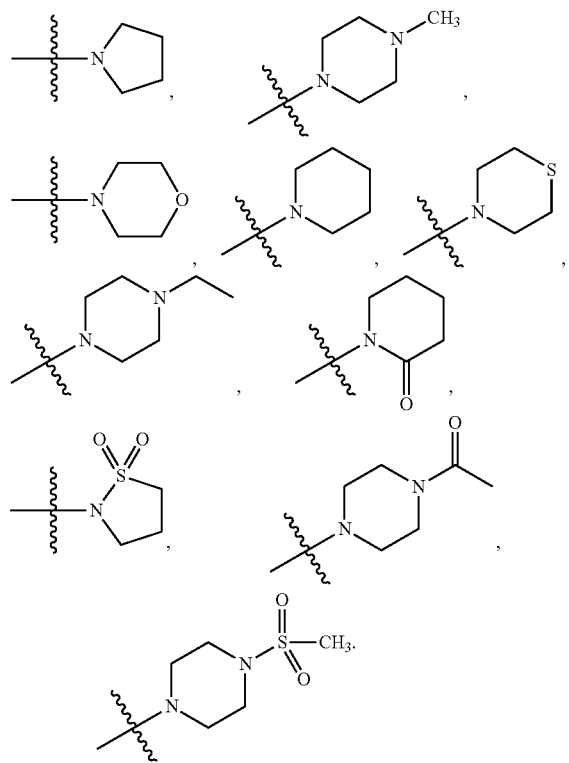

The invention also provides compounds of Formula I, wherein when R¹' is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then R¹' is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when R¹' is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, and thiomorpholinyl. In other examples of the compounds of Formula I, when R¹' is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloalkyl substituents can be unsubstituted or substituted.

In yet other examples of the compounds of Formula I, when R¹' is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1, 2-a]pyridinyl, and pyrrolo[1,2-f][1, 2, 4]triazinyl.

In some embodiments of the compound of Formula I, L is N(R²), wherein R² is hydrogen, unsubstituted or substituted C₁-C₁₀alkyl (which includes but is not limited to —CH₃, —CH₂CH₃, n-propyl, isopropyl, n-butyl, tert-butyl, sec-butyl, pentyl, hexyl, and heptyl), or unsubstituted or substituted C₃-C₇cycloalkyl (which includes but is not limited to cyclopropyl, cyclobutyl, cyclopentyl, and cyclohexyl). In other embodiments of the compound of Formula I, R² is unsubstituted or substituted heterocycloalkyl (which includes but is not limited to oxetanyl, tetrahydrofuranyl, pyrrolidinyl, tetrahydropyranyl, piperidinyl, and piperazinyl), or unsubstituted or substituted C₂-C₁₀heteroalkyl (which includes but is not limited to methoxyethoxy, methoxymethyl, and diethylaminoethyl). Alternatively, R² is unsubstituted or substituted monocyclic heteroaryl (which includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formula I, L is —C(R³)₂—, wherein R³ is hydrogen, unsubstituted or substituted C₁-C₁₀alkyl (including but not limited to —CH₃, —CH₂CH₃, n-propyl, isopropyl, n-butyl, tert-butyl, sec-butyl, pentyl, hexyl, and heptyl), or halo such as —I, —F, —Cl, or —Br. In further embodiments, R³ is unsubstituted or substituted monocyclic heteroaryl (including but not limited to pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formula I, R¹ is —C(H)₂R¹', —CH(CH₃)R¹', —CF₂R¹', —C(CH₃)₂R¹', —CH(CH₂CH₃)R¹', —CH(CH(CH₃)₂R¹', —CCl₂R¹', or —OR¹', wherein R¹' is hydrogen or alkyl. For example, R¹' is —C(H)₂-alkyl wherein the alkyl is substituted with heterocycloalkyl, amino, or NR'R" wherein heterocycloalkyl, amino, or NR'R" encompasses substitutions described above for these moieties. In another example of the compounds of the invention, R¹' is —O-alkyl, where alkyl is isopropyl.

In other embodiments of the compound of Formula I, R¹ is —NHR¹', —N(CH₃) R¹', —N(CH₂CH₃)R¹', —N(CH (CH₃)₂) R¹', or —OR¹', wherein R¹' is unsubstituted or substituted heterocycloalkyl (nonlimiting examples thereof include 4-NH piperidin-1-yl, 4-methyl piperidin-1-yl, 4-ethyl piperidin-1-yl, 4-isopropyl-piperidin-1-yl, and pyrrolidin-3-yl), unsubstituted or substituted monocyclic aryl, or unsubstituted or substituted monocyclic heteroaryl (including but not limited to pyrrolyl, thienyl, furyl, pyridinyl, pyranyl, pyrimidinyl, pyrazinyl, pyridazinyl, imidazolyl, thiazolyl, pyrazolyl, and oxazolyl). In one example, $R^1$ is —O-aryl, i.e. phenoxy. In another example, $R^1$ is —O—(4-methyl)piperidin-1-yl or —O—(4-isopropyl)piperidin-1-yl.
In some embodiments of the compound of Formula I, $R^1$ is one of the following moieties:
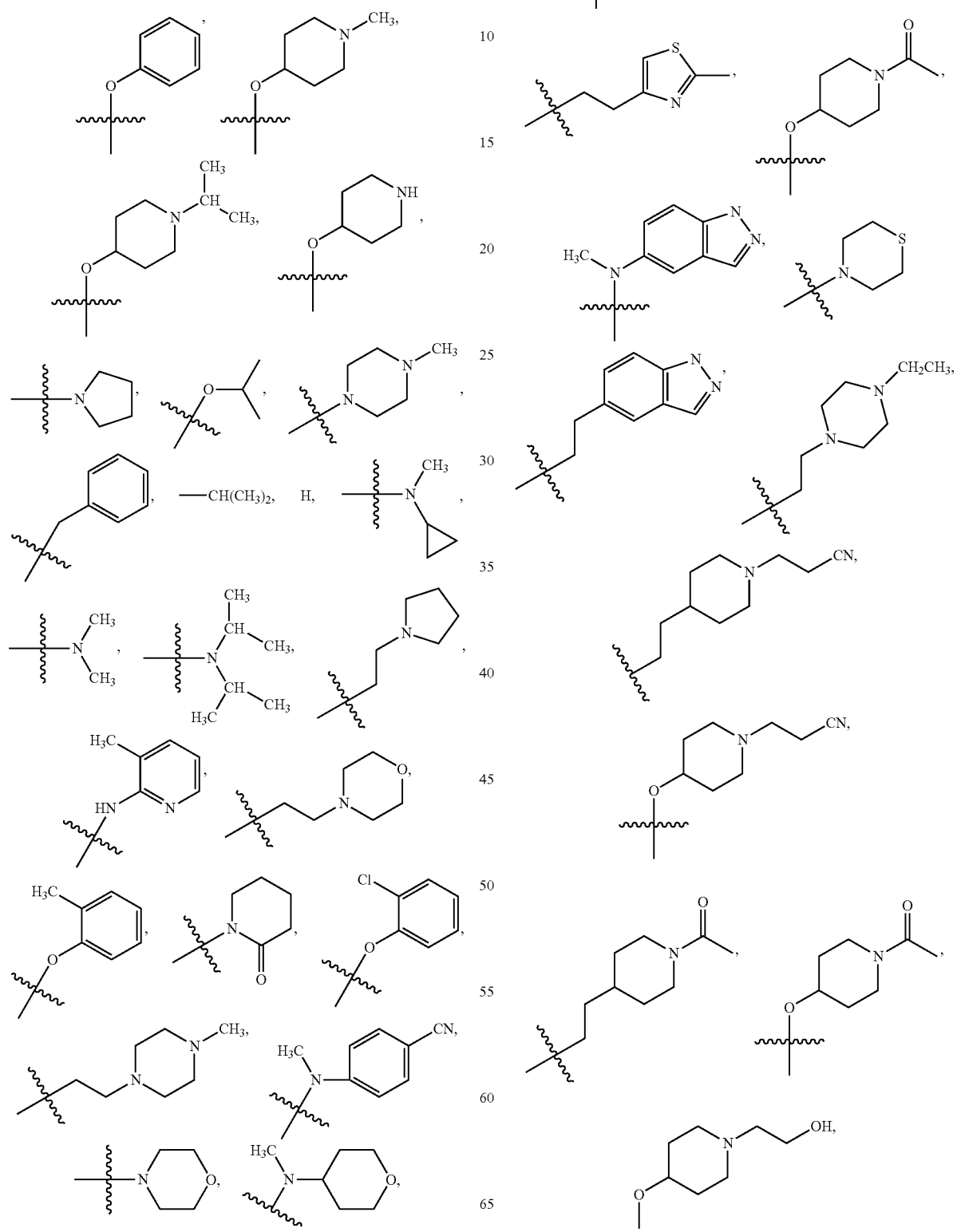

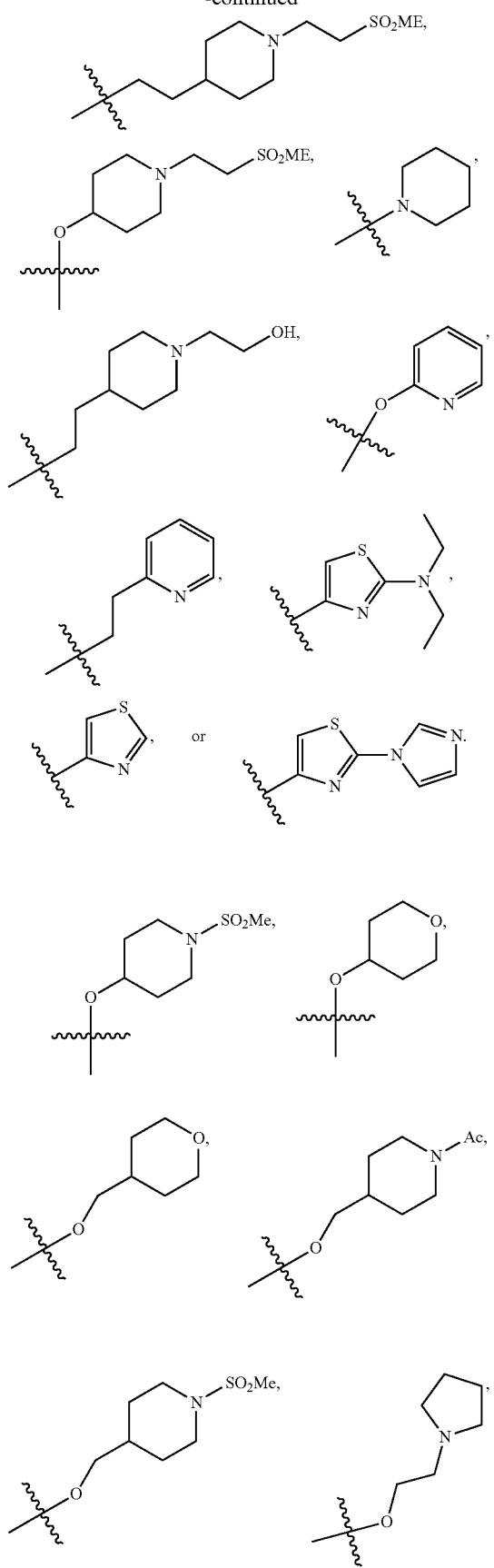
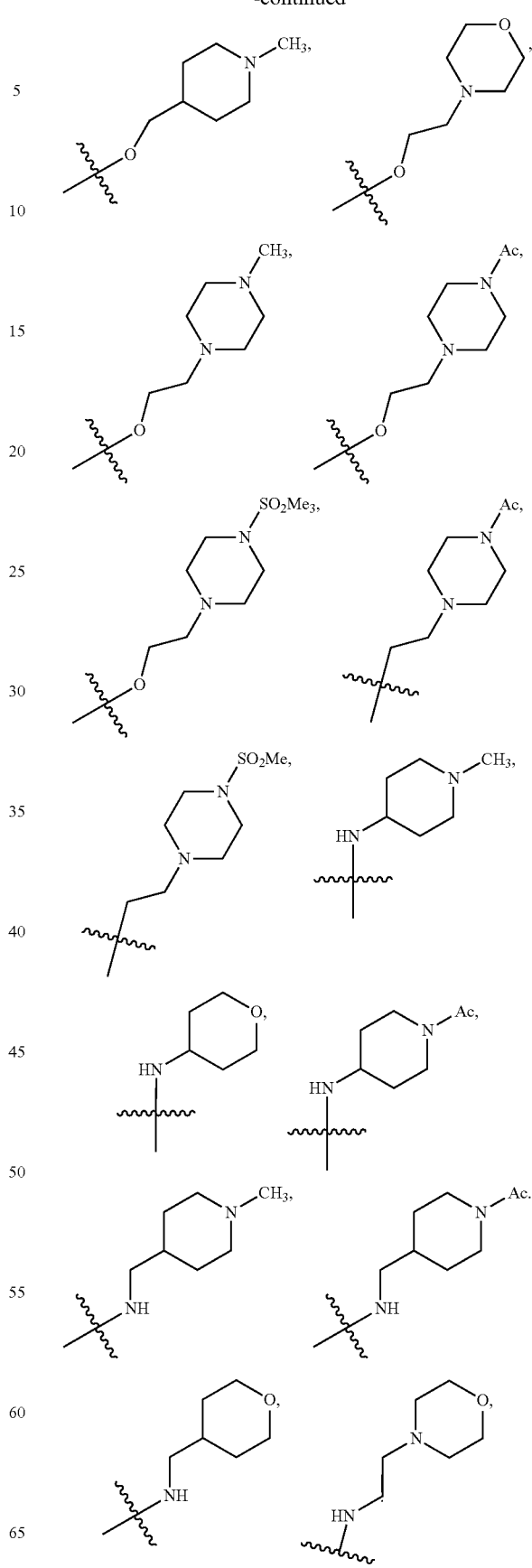

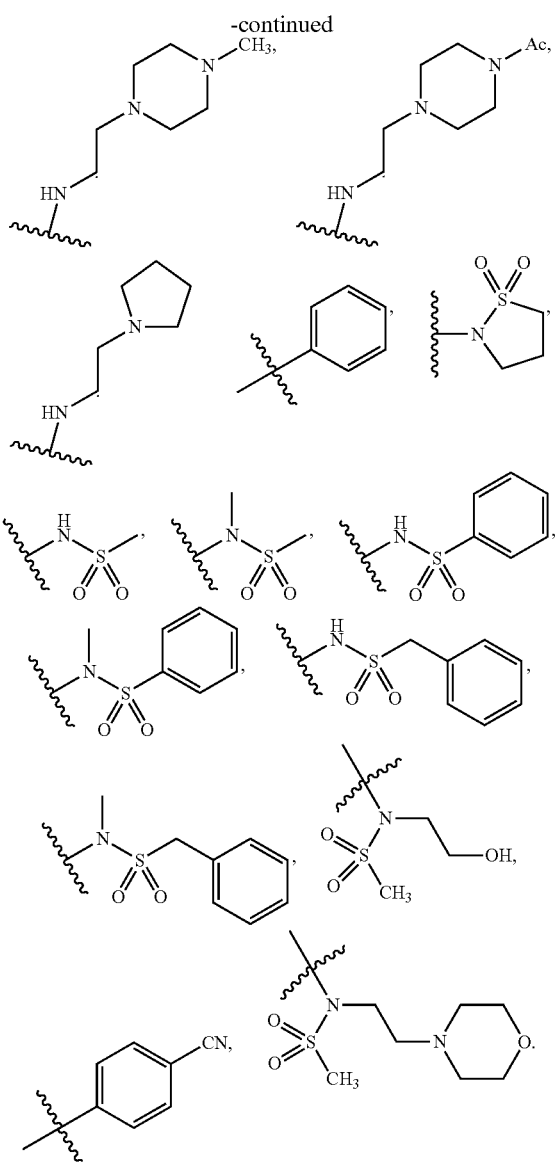

In some embodiments of the compound of Formula I, $R^4$ is a substituent attached to one of the two six membered aromatic rings of the core structure of compounds of Formula I, wherein $R^4$ can be hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^4$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^4$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^4$ is unsubstituted or substituted heteroaryl, including but not limited to monocyclic and bicyclic heteroaryl. Monocyclic heteroaryl $R^4$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^4$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

The present invention also provides compounds of Formula I wherein $R^4$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^4$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^4$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, and piperazinyl. In yet other embodiments of the compounds of Formula I, $R^4$ is unsubstituted or substituted alkoxy including but not limited to $C_1$-$C_4$alkoxy such as methoxy, ethoxy, propoxy or butoxy. $R^4$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^4$ is unsubstituted or substituted amino, wherein the substituted amino includes but is not limited to dimethylamino, diethylamino, di-isopropyl amino, N-methyl N-ethyl amino, and dibutylamino. In some embodiments, $R^4$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, $R^4$ is halo, which is —I, —F, —Cl, or —Br. In some embodiments, $R^4$ is selected from the group consisting of cyano, hydroxy, nitro, phosphate, urea, or carbonate. Also contemplated are $R^4$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

$R^4$ of the compounds of Formula I, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

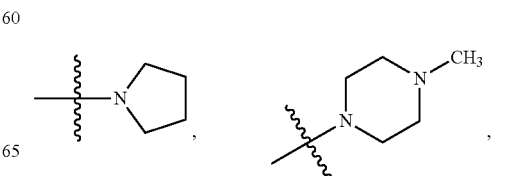

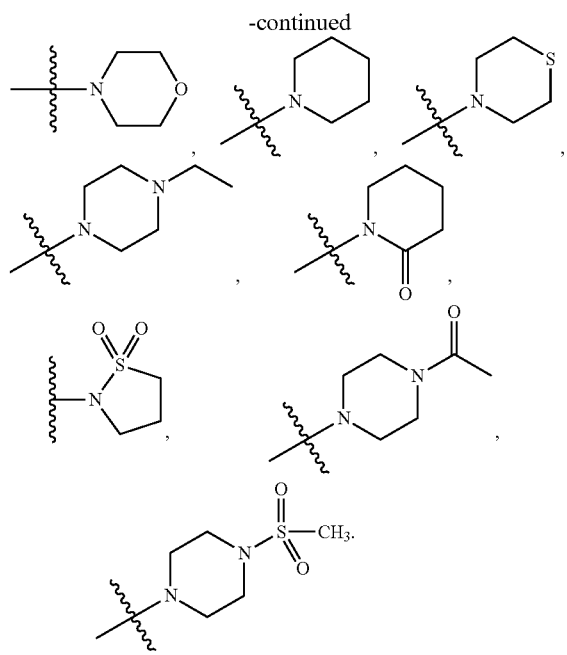

The invention also provides compounds of Formula I, wherein when $R^4$ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then $R^4$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when $R^4$ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, isothiazolidinyl 1,2, dioxide, and thiomorpholinyl. In other examples of the compounds of Formula I, when $R^4$ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloalkyl substituents can be unsubstituted or substituted.

In yet other examples of the compounds of Formula I, when $R^4$ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1, 2-a] pyridinyl, and pyrrolo[1, 2-f][1, 2, 4]triazinyl.

In some of the embodiments of the compounds of Formula I, $W^1$ is $CR^5$, $W^2$ is $CR^6$, $W^3$ is $CR^7$, and $W^4$ is $CR^8$. Each of $R^5$, $R^6$, and $R^7$ can independently be hydrogen, or unsubstituted or substituted alkyl (including but not limited to $CH_3$, $-CH_2CH_3$, n-propyl, isopropyl, n-butyl, tert-butyl, sec-butyl, pentyl, hexyl, and heptyl). In other embodiments, each of $R^5$, $R^6$, and $R^7$ independently is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, each of $R^5$, $R^6$, and $R^7$ independently is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, $-CH_2CH_3$, n-propyl, isopropyl, n-butyl, sec-butyl, and pentyl). In some other embodiments, each of $R^5$, $R^6$, and $R^7$ independently is unsubstituted or substituted heteroaryl, including but not limited to monocyclic and bicyclic heteroaryl. Monocyclic heteroaryl for each of $R^5$, $R^6$, and $R^7$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl for each of $R^5$, $R^6$, and $R^7$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a] pyridinyl, and pyrrolo[1, 2f][1, 2, 4]triazinyl. The present invention also provides compounds of Formula 1 wherein each of $R^5$, $R^6$, and $R^7$ independently is unsubstituted or substituted heteroarylalkyl, including but not limited to monocyclic and bicyclic heteroaryl as described above, that are linked to alkyl, which in turn includes but is not limited to $CH_3$, $-CH_2CH_3$, n-propyl, isopropyl, n-butyl, sec-butyl, and pentyl. In some embodiments, each of $R^5$, $R^6$, and $R^7$ independently is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, each of $R^5$, $R^6$, and $R^7$ independently is unsubstituted or substituted heterocycloalkyl which includes but is not limited to pyrrolidinyl, tetrahydropyranyl, piperidinyl, tetrahydropyranyl, thiazolidinyl, imidazolidinyl, morpholinyl, isothiazolidinyl 1,2, dioxide, and piperazinyl. In yet other embodiments of the compounds of Formula I, each of $R^5$, $R^6$, and $R^7$ independently is unsubstituted or substituted alkoxy including but not limited to $C_1$-$C_4$alkoxy such as methoxy, ethoxy, propoxy or butoxy. Each of $R^5$, $R^6$, and $R^7$ can also independently be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, each of $R^5$, $R^6$, and $R^7$ independently is unsubstituted or substituted amino, wherein the substituted amino includes but is not limited to dimethylamino, diethylamino, di-isopropyl amino, N-methyl N-ethyl amino, and dibutylamino. In some embodiments, each of $R^5$, $R^6$, and $R^7$ independently is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, each of $R^5$, $R^6$, and $R^7$ independently is halo, which is —I, —F, —Cl, or —Br. In some embodiments, each of $R^5$, $R^6$, and $R^7$ independently is selected from the group consisting of cyano, hydroxy, nitro, phosphate, urea, or carbonate. Also contemplated are each of $R^5$, $R^6$, and $R^7$ independently being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

Each of $R^5$, $R^6$, and $R^7$ of the compounds of Formula I, can also independently be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted or substituted, including but not limited to morpholinyl, azetidinyl, pyrrolidinyl, piperidinyl, piperazinyl, isothiazolidinyl 1,2, dioxide, and thiomorpholinyl. Further non-limiting exemplary cyclic moieties are the following:

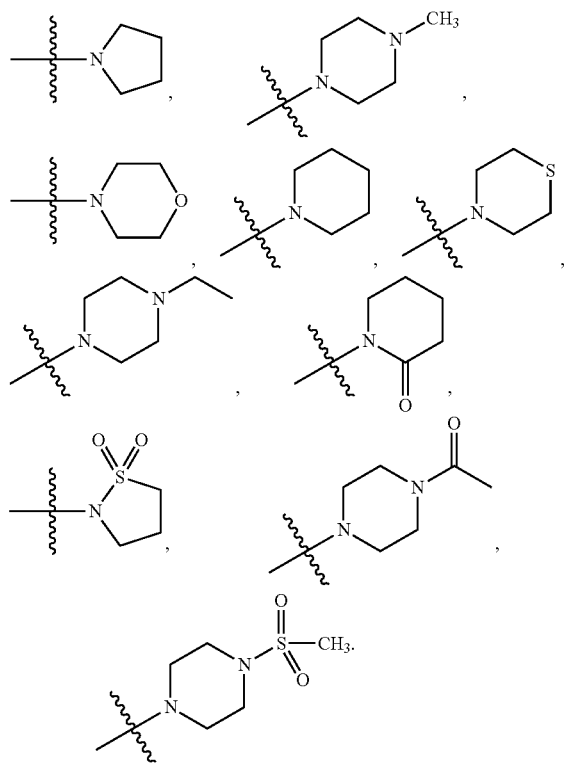

The invention also provides compounds of Formula I, wherein when each of $R^5$, $R^6$, and $R^7$ independently is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then each of $R^5$, $R^6$, and $R^7$ independently is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when each of $R^5$, $R^6$, and $R^7$ independently is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties includes but are not limited to morpholinyl, azetidinyl, pyrrolidinyl, piperidinyl, piperazinyl, isothiazolidinyl 1,2, dioxide, and thiomorpholinyl. In other examples of the compounds of Formula I, when each of $R^5$, $R^6$, and $R^7$ independently is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formula I, when each of $R^5$, $R^6$, and $R^7$ independently is alkyl, the alkyl is substituted with a 5, 6, 7, 8, 9, or 10 membered monocyclic or bicyclic heteroaryl, which is unsubstituted or substituted. The monocyclic heteroaryl for each of $R^5$, $R^6$, and $R^7$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl for each of $R^5$, $R^6$, and $R^7$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

In some embodiments of the compound of Formula I, $W^4$ is $CR^8$, wherein $R^8$ can be hydrogen, or unsubstituted or substituted alkyl (including but not limited to $CH_3$, —$CH_2CH_3$, n-propyl, isopropyl, n-butyl, tert-butyl, sec-butyl, pentyl, hexyl, and heptyl). In other embodiments, $R^8$ is unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). Alternatively, $R^8$ is unsubstituted or substituted aryl (including but not limited to monocyclic or bicyclic aryl) or unsubstituted or substituted arylalkyl (including but not limited to monocyclic or bicyclic aryl linked to alkyl wherein alkyl includes but is not limited to $CH_3$, —$CH_2CH_3$, n-propyl, isopropyl, n-butyl, sec-butyl, and pentyl). In some other embodiments, $R^8$ is unsubstituted or substituted heteroaryl, including but not limited to monocyclic and bicyclic heteroaryl. Monocyclic heteroaryl $R^8$ includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^8$ includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. The present invention also provides compounds of Formula 1 wherein $R^8$ is unsubstituted or substituted heteroarylalkyl, including but not limited to monocyclic and bicyclic heteroaryl as described above, that are linked to alkyl, which in turn includes but is not limited to $CH_3$, —$CH_2CH_3$, n-propyl, isopropyl, n-butyl, sec-butyl, and pentyl. In some embodiments, $R^8$ is unsubstituted or substituted cycloalkyl (including but not limited to cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^8$ is unsubstituted or substituted heterocycloalkyl which includes but is not limited to pyrrolidinyl, tetrahydrofuranyl, piperidinyl, tetrahydropyranyl, thiazolidinyl, imidazolidinyl, morpholinyl, isothiazolidinyl 1,2, dioxide, and piperazinyl. In yet other embodiments of the compounds of Formula I, $R^8$ is unsubstituted or substituted alkoxy including but not limited to $C_1$-$C_4$alkoxy such as methoxy, ethoxy, propoxy or butoxy. $R^8$ can also be unsubstituted or substituted heterocycloalkyloxy, including but not limited to 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, $R^8$ is unsubstituted or substituted amino, wherein the substituted amino includes but is not limited to dimethylamino, diethylamino, di-isopropyl amino, N-methyl N-ethyl amino, and dibutylamino. In some embodiments, $R^8$ is unsubstituted or substituted acyl, unsubstituted or substituted acyloxy, unsubstituted or substituted $C_1$-$C_4$acyloxy, unsubstituted or substituted alkoxycarbonyl, unsubstituted or substituted amido, or unsubstituted or substituted sulfonamido. In some embodiments, $R^8$ is halo, which is —I, —F, —Cl, or —Br. In some embodiments, $R^8$ is selected from the group consisting of cyano, hydroxy, nitro, phosphate, urea, or carbonate. Also contemplated are $R^8$ being —$C_{1-13}$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

$R^8$ of the compounds of Formula I, can also be NR'R" wherein R' and R" are taken together with the nitrogen to form a cyclic moiety having from 3 to 8 ring atoms. The cyclic moiety so formed may further include one or more heteroatoms which are selected from the group consisting of S, O, and N. The cyclic moiety so formed is unsubstituted

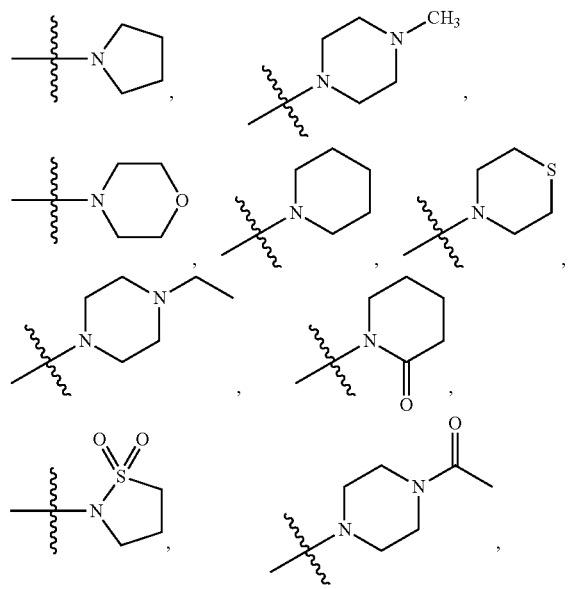

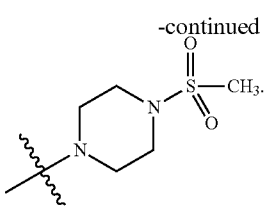

The invention also provides compounds of Formula I, wherein when $R^8$ is a member of the group consisting of alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, and NR'R" (wherein R' and R" are taken together with nitrogen to form a cyclic moiety), then $R^8$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R" wherein R' and R" are taken together with nitrogen to form a cyclic moiety. Each of the above substituents may be further substituted with one or more substituents chosen from the group consisting of alkyl, alkoxy, amido, amino, sulfonamido, acyloxy, alkoxycarbonyl, halo, cyano, hydroxy, nitro, oxo, phosphate, urea, and carbonate.

For example, the invention provides compounds wherein when $R^8$ is alkyl, the alkyl is substituted with NR'R" wherein R' and R" are taken together with the nitrogen to form a cyclic moiety. The cyclic moiety so formed can be unsubstituted or substituted. Non-limiting exemplary cyclic moieties include but are not limited to morpholinyl, azetidinyl, pyrrolidinyl, piperidinyl, piperazinyl, isothiazolidinyl 1,2, dioxide, and thiomorpholinyl. In other examples of the compounds of Formula I, when $R^8$ is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloalkyl substituents can be unsubstituted or substituted.

In yet other examples of the compounds of Formula I, when $R^8$ is alkyl, the alkyl is substituted with a 5, 6, 7, 8, 9, or 10 membered monocyclic or bicyclic heteroaryl, which is unsubstituted or substituted. The monocyclic heteroaryl includes but is not limited to pyrrolyl, thienyl, furyl, pyridinyl, pyranyl, pyrimidinyl, pyrazinyl, pyridazinyl, imidazolyl, thiazolyl, pyrazolyl, and oxazolyl. The bicyclic heteroaryl includes but is not limited to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl.

In some embodiments of the compounds of Formula I, $W^1$ is $CR^5$, $W^2$ is $CR^6$, $W^3$ is $CR^7$, $W^4$ is $CR^8$ and $R^4$, $R^5$, $R^6$, and $R^7$ are hydrogen.

In some embodiments of the compound of Formula I, at least one X or Y is present.

The invention provides compounds of Formula I wherein Y is $N(R^9)$—, —$N(R^9)(C=O)$—, —$N(R^9)(C=O)NH$—, —$N(R^9)C(R^{10})_2$—, or —$C(=O)$—$(CHR^{10})_z$— and z is an integer of 1, 2, 3, or 4. In some embodiments of the compound of Formula I, each of $R^9$ and $R^{10}$ independently is hydrogen, unsubstituted or substituted $C_1$-$C_{10}$alkyl (including but not limited to —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$cycloalkyl (non-limiting examples include cyclopropyl, cyclobutyl, cyclopentyl, and cyclohexyl). In other embodiments of the compound of Formula I, each of $R^9$ and $R^{10}$ independently is unsubstituted or substituted heterocycloalkyl (including but not limited to oxetanyl, tetrahydrofuranyl, pyrrolidinyl, tetrahydropyranyl, piperidinyl, and piperazinyl), or unsubstituted or substituted $C_2$-$C_{10}$heteroalkyl ($C_2$-$C_{10}$heteroalkyl includes but is not limited to methoxyethoxy, methoxymethyl, and diethylaminoethyl). Alternatively, each of $R^9$ and $R^{10}$ independently is unsubstituted or substituted monocyclic heteroaryl (non-limiting examples pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. For example, Y is —N(CH$_3$)CH$_2$—, N(CH(CH$_3$)$_2$)CH$_2$— or N(CH$_2$CH$_3$)CH$_2$—), —N(CH$_3$)—, —N(CH$_2$CH$_3$)—, or —N(CH(CH$_3$)$_2$)—. In some embodiments, Y is —NH—.

In other embodiments, X is —(CH($R^{10}$))$_z$, and z is an integer of 1 or 2. The invention provides compounds of Formula I wherein $R^{10}$ is hydrogen or unsubstituted or substituted $C_1$-$C_{10}$alkyl (non-limiting exemplary alkyl include —CH$_3$, —CH$_2$CH$_3$, n-propyl, isopropyl, n-butyl, tert-butyl, sec-butyl, pentyl, hexyl, and heptyl), or halo (such as —I, —F, —Cl, or —Br). In further embodiments, $R^{10}$ is unsubstituted or substituted monocyclic heteroaryl (including but not limited pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. For example, X is —CH$_2$—, —CH$_2$CH$_2$—, —CH$_2$CH$_2$CH$_2$—, —CH(CH$_3$)—, —CH(CH$_2$CH$_3$), —CH(CH$_3$)—, —CH(CH$_2$CH$_3$)-or —CH(C$_6$H$_6$)-or —CH(C$_6$H$_6$)—. In some embodiments, when X is —CH(CH$_3$)—, —CH(CH$_2$CH$_3$)-or —CH(C$_6$H$_6$)—, the asymmetric carbon center is predominately (S)— or predominately (R)-stereochemical configuration. An asymmetric carbon center is predominately (S)— or predominately (R) when the predominate stereoisomer is present in greater than about 60%, 65%, 70%, 75%, 80%, 85%, 90%, 95%, 97%, 95%, or 99% of the total proportion of the two possible stereoisomers at that asymmetric center.

In some embodiments, X—Y is —CH$_2$—, —CH$_2$—NH, —CH$_2$—N(CH$_3$),), —CH(CH$_3$)—NH—, —CH(CH$_2$CH$_3$)—NH—, —CH(C$_6$H$_6$)—NH—, (S)—CH(CH$_3$)—NH—, (R)—CH(CH$_3$)—NH—, S)—CH(CH$_2$CH$_3$)—NH—, (R)—CH(CH$_2$CH$_3$)—NH—, (S)—CH(C$_6$H$_6$)—NH—, or (R)—CH(C$_6$H$_6$)—NH—. In some embodiments, X—Y is —N(CH$_3$)—CH$_2$—, N(CH$_2$CH$_3$)CH$_2$—, —N(CH(CH$_3$)$_2$)CH$_2$—, or —NHCH$_2$—.

In some embodiments of the compounds of Formula I, $W_d$ is unsubstituted or substituted heterocycloalkyl, wherein the heterocycloalkyl includes but is not limited to morpholinyl, piperidinyl, piperazinyl, tetrahydro-2H-pyranyl, and pyrrolidinyl. The invention also provides compounds wherein $W_d$ is unsubstituted or substituted cycloalkyl wherein the cycloalkyl includes but is not limited to cyclobutyl, cyclopentyl, and cyclohexyl. Alternatively, $W_d$ is monocyclic aryl (for example, phenyl) or bicyclic aryl (for example, naphthyl), wherein the monocyclic aryl or bicyclic aryl is unsubstituted or substituted. In some embodiments, $W_d$ is unsubstituted or substituted monocyclic heteroaryl. Non-limiting exemplary monocyclic heteroaryls are pyrrolyl, thienyl, furyl, pyridinyl, pyranyl, pyrimidinyl, pyrazinyl, pyridazinyl, imidazolyl, isothiazolyl, isoxazolyl, thiazolyl, triazinyl, pyrazolyl, and oxazolyl. The invention also provides compounds of Formula I wherein $W_d$ is unsubstituted or substituted bicyclic heteroaryl, including but not limited to to benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. In some embodiments, the quinolinyl $W_d$ bicyclic heteroaryl is 4-quinolinyl. In some embodiments, the $W_d$ bicyclic heteroaryl has at least one heteroatom, including but not limited to indolyl, quinolinyl, benzothiazolyl, pyrazolopyridinyl, pyrazolopyrimidinyl, or isoquinolinyl. Additionally, the $W_d$ bicyclic heteroaryl has at least two nitrogen ring atoms, such as indazole, pyrrolopyridinyl, pyrazolopyridinyl, pyrazolopyrimidinyl, benzimidazolyl, benzothiazolyl, azaindolyl, quinazolinyl, benzoxazolyl, or pyrazolopyrimidinyl. In yet other embodiments, $W_d$ is a bicyclic heteroaryl having at least three nitrogen ring atoms, such as pyrazolopyridinyl, pyrrolopyrimidinyl, thiazolylpyrimidinyl, pyrrolo[1,2-b]pyridazinyl, or imidazo[1,2-a]pyridinyl. Alternatively, $W_d$ is a bicyclic heteroaryl having at least four nitrogen ring atoms, including but not limited to pyrazolopyrimidinyl, purinyl, or pyrrolo[1,2-f][1,2,4] triazinyl. In some embodiments, $W_d$ is a bicyclic heteroaryl having two heteroatoms in the ring which is connected to XY.

In some embodiments $W_d$ is one of the following:

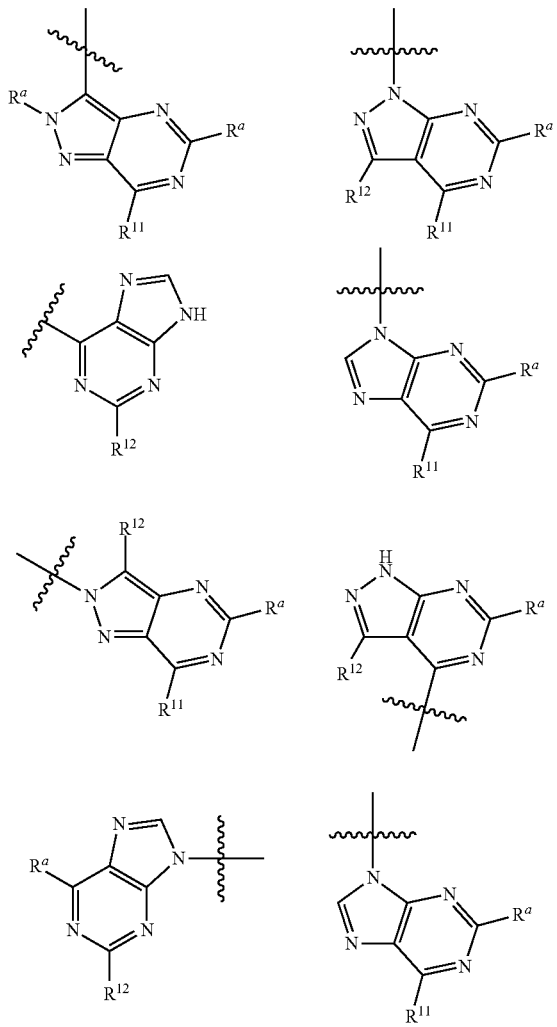

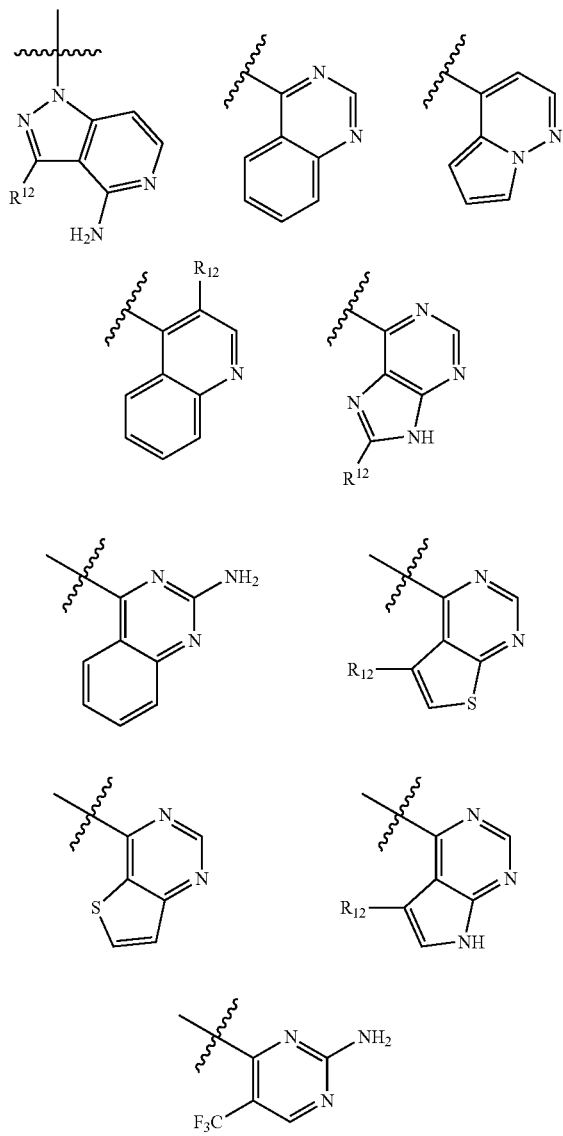
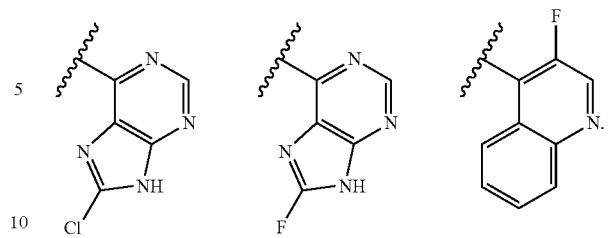

wherein $R^a$ is hydrogen, halo, phosphate, urea, carbonate, alkyl, alkenyl, alkynyl, cycloalkyl, heteroalkyl, or heterocycloalkyl;

$R^{11}$ is H, alkyl, halo, amino, amido, hydroxy, or alkoxy, and $R^{12}$ is H, alkyl, cyano, alkynyl, alkenyl, halo, aryl, heteroaryl, heterocycloalkyl, cycloalkyl, amino, carboxylic acid, alkoxycarbonyl, or amido.

In some embodiments, $W_d$ is one of the following:

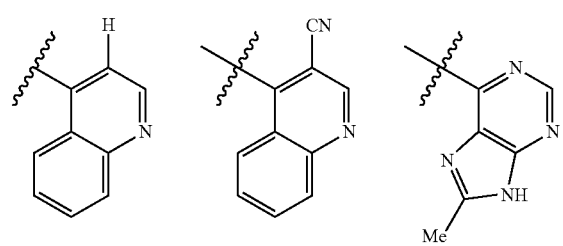

In some embodiments of $W_d$, $R^a$ is a member selected from the group consisting of hydrogen, halo, phosphate, urea, carbonate, unsubstituted or substituted alkyl, unsubstituted or substituted alkenyl, unsubstituted or substituted alkynyl, unsubstituted or substituted cycloalkyl, unsubstituted or substituted heteroalkyl, and unsubstituted or substituted heterocycloalkyl.

In some embodiments of $W_d$, when $R^a$ is alkyl, alkynyl, cycloalkyl, heteroalkyl, or heterocycloalkyl, it is substituted by phosphate, urea, carbonate, or combinations thereof.

In the compounds of Formula I, $W_d$ can be substituted by $R^{11}$ wherein $R^{11}$ is a member of the group consisting of hydrogen, unsubstituted or substituted alkyl, and halo (such as —I, —F, —Cl, and —Br). In some embodiments, $R^{11}$ is unsubstituted or substituted amino, unsubstituted or substituted amido, hydroxy, or unsubstituted or substituted alkoxy. $R^{11}$ can also be phosphate, unsubstituted or substituted urea, or carbonate.

Additionally, when $R^{11}$ is alkyl, amino, amido, hydroxy, or alkoxy, $R^{11}$ can be substituted by phosphate, urea, or carbonate.

In some embodiments of the compound of Formula I, when Wd is purinyl, X is —(CH($R^{19}$))$_z$—, wherein z is 1, and Y is —N($R^9$)—, then $R^9$ is —NH—.

In some embodiments of the compound of Formula I, —X—Y—$W_d$ is one of the following moieties:

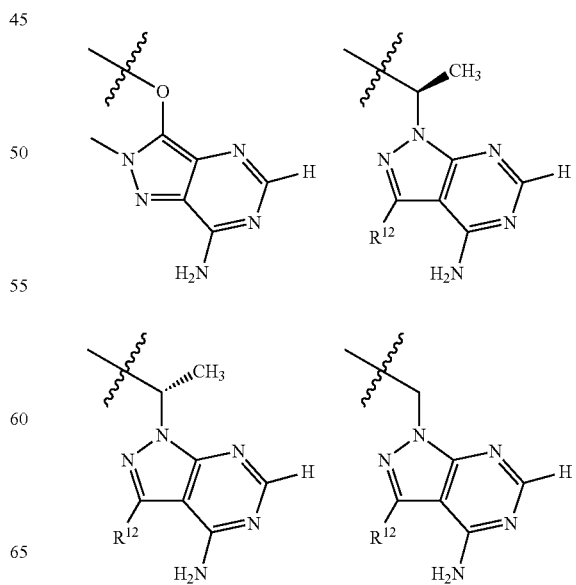

-continued
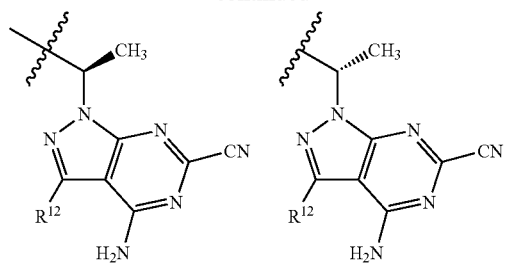
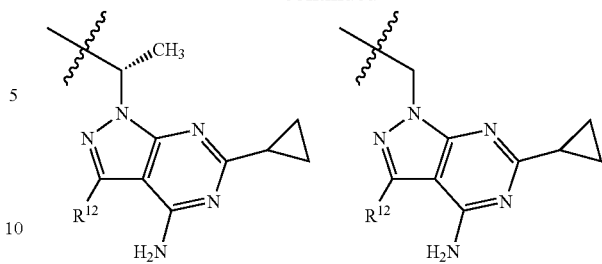
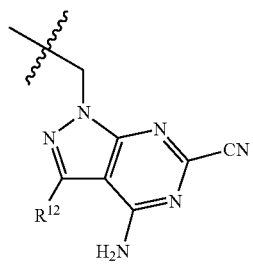
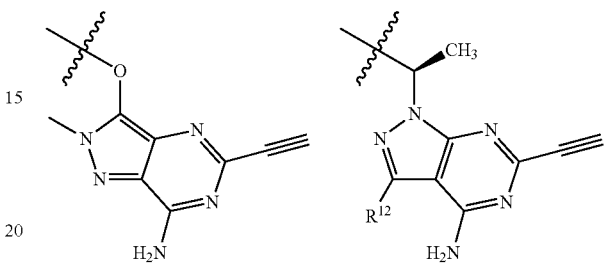
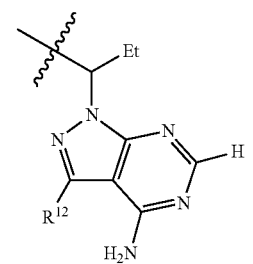
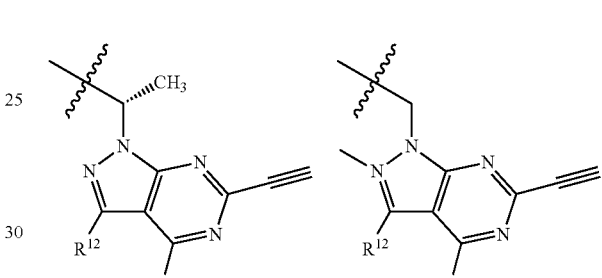
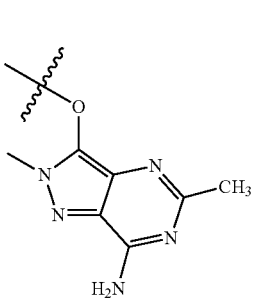
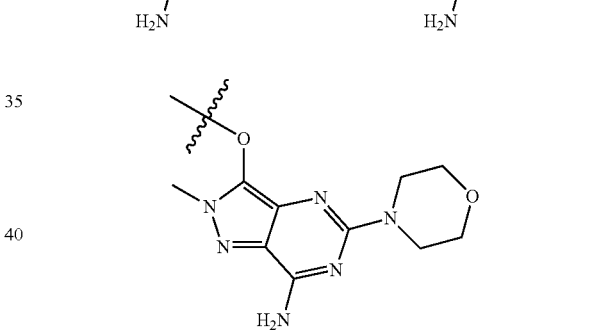
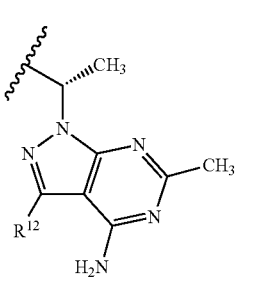
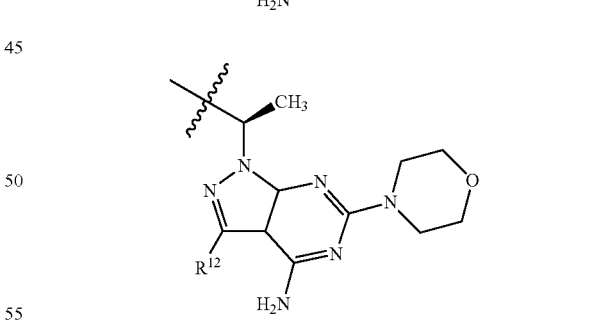
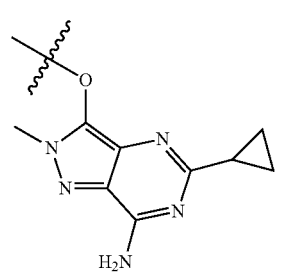
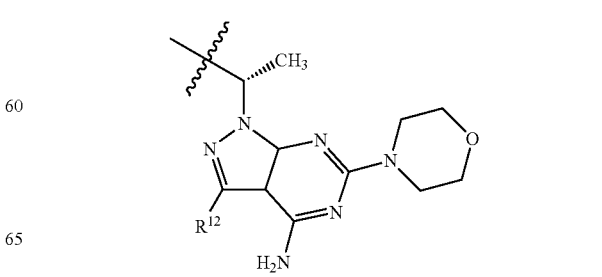

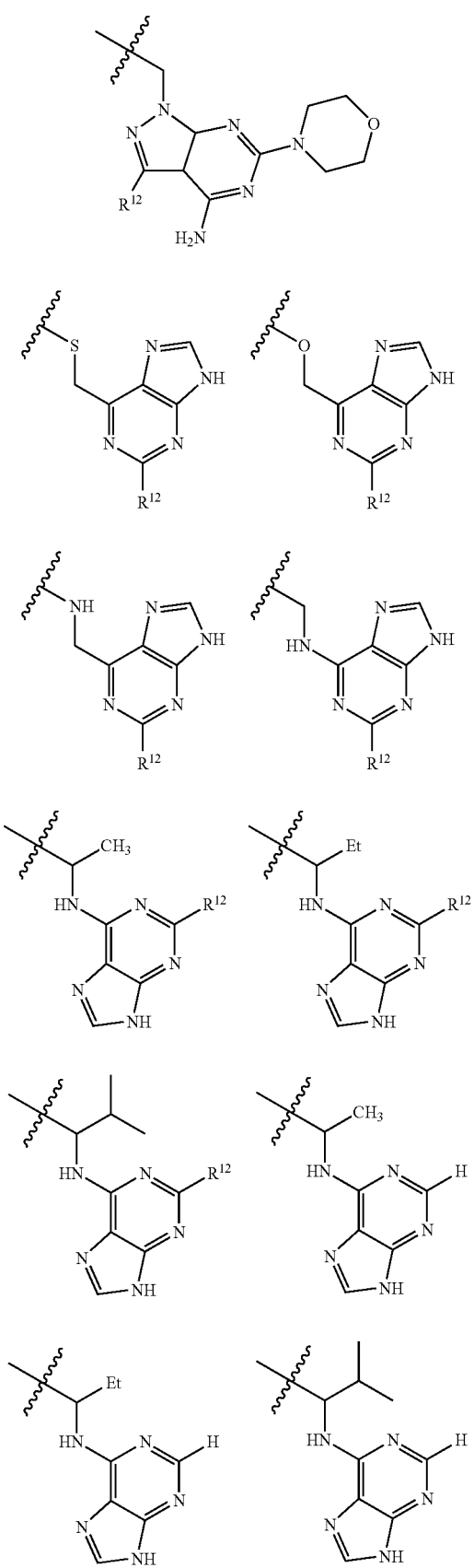
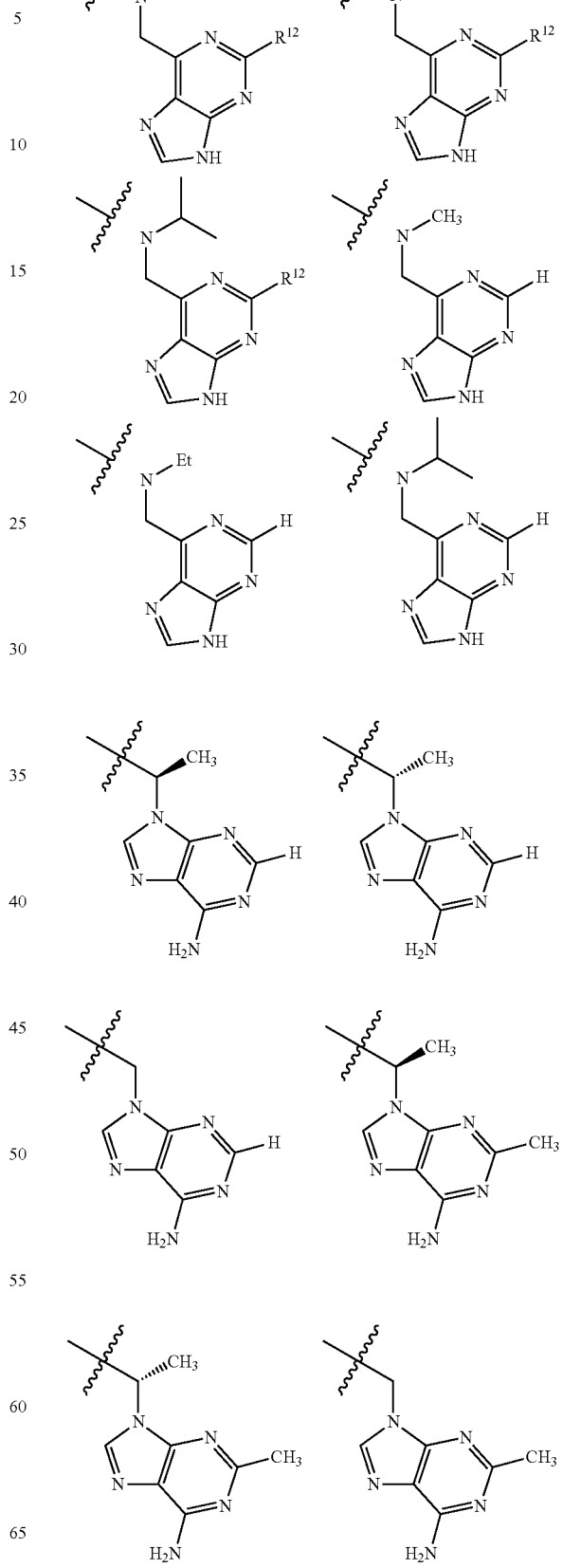

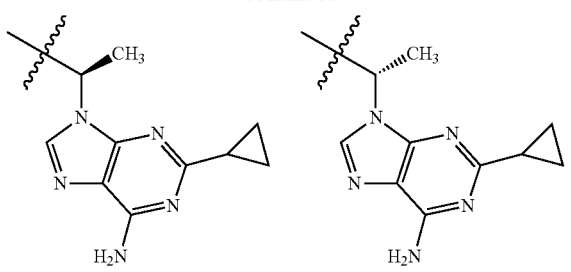
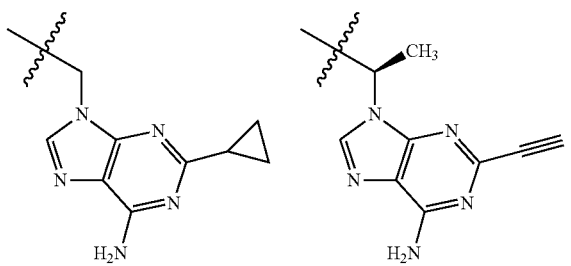
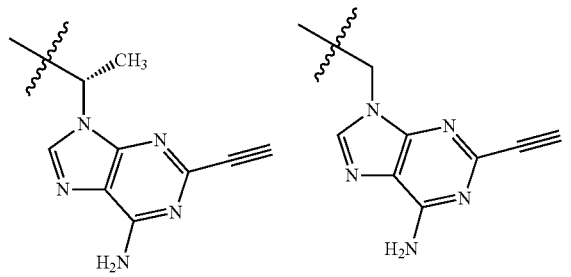
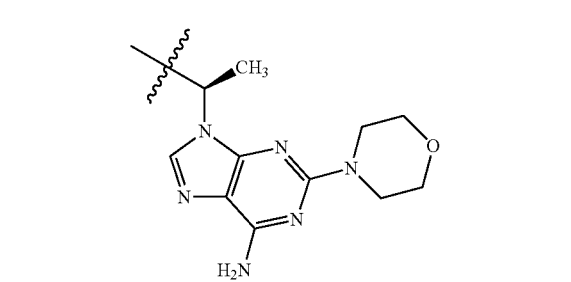
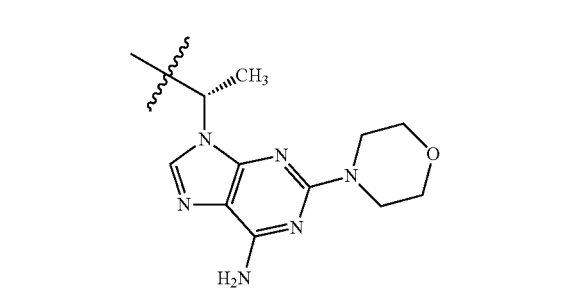
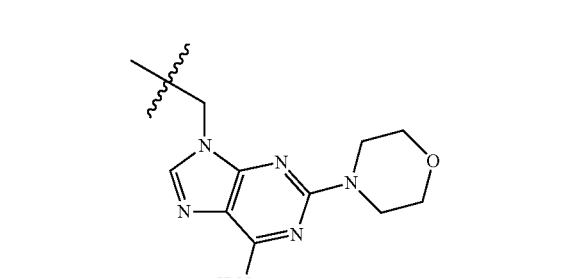
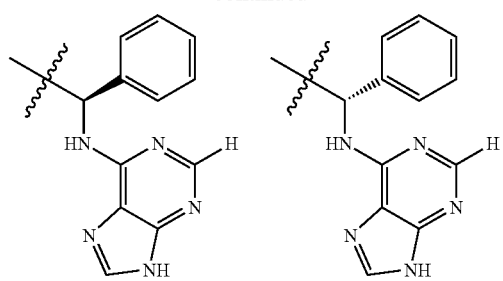
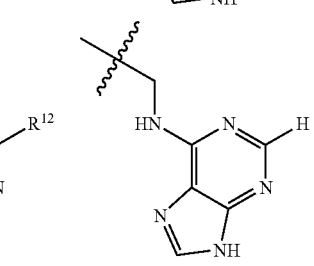
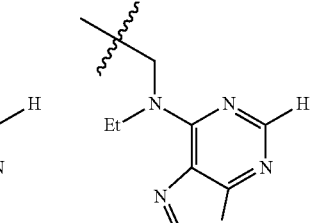
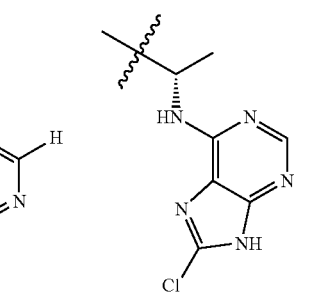
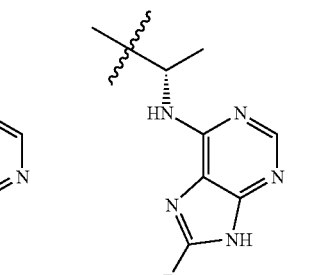
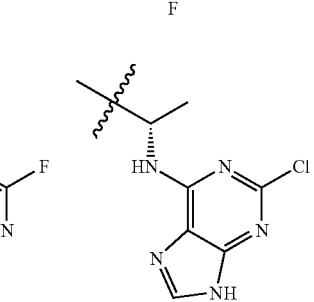

-continued

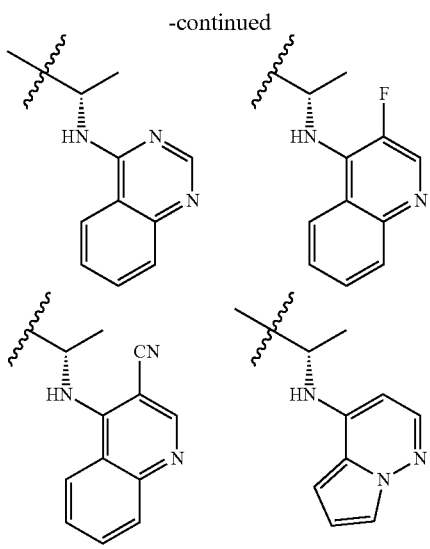

In some embodiments of the compound of Formula I, $W_d$ can be substituted by $R^{12}$ wherein $R^{12}$ is a member of the group consisting of hydrogen, cyano, halo, unsubstituted or substituted alkenyl (including but not limited to unsubstituted or substituted $C_2$-$C_5$alkenyl such as, for example, vinyl, allyl, 1-methyl propen-1-yl, butenyl, or pentenyl) or unsubstituted or substituted alkynyl (including but not limited to unsubstituted or substituted $C_2$-$C_5$alkynyl such as acetylenyl, propargyl, butynyl, or pentynyl). In other embodiments, $R^{12}$ is unsubstituted or substituted alkyl (including but not limited to —$CH_3$, —$CH_2CH_3$, n-propyl, isopropyl, n-butyl, tert-butyl, sec-butyl, pentyl, hexyl, and heptyl) Additionally, $R^{12}$ can be unsubstituted or substituted aryl (including but not limited to monocyclic or bicyclic aryl). In some embodiments, $R^{12}$ is unsubstituted or substituted heteroaryl, wherein the heteroaryl has a 5 membered ring (including but not limited to imidazolyl, furyl, thienyl, pyrrolyl, pyrazolyl, isothiazolyl, isoxazolyl, oxazolyl, and thiazolyl). The $R^{12}$ heteroaryl can be heteroaryl having a six membered ring, including pyridinyl, pyranyl, pyrazinyl, pyrimidinyl, pyridazinyl, or triazinyl The $R^{12}$ heteroaryl can be also be heteroaryl with at least one nitrogen ring atom, including but not limited to pyrrolyl, thiazolyl, pyrazolyl, imidazolyl, pyrimidinyl, pyridinyl, indolyl, benzoxazolyl, or pyrazinyl. Alternatively, the $R^{12}$ heteroaryl is heteroaryl with two nitrogen ring atoms, non-limiting exemplary heteroaryls include pyrazolyl, indazolyl, benzimidazolyl, and imidazolyl. In some embodiments, the $R^{12}$ heteroaryl can be monocyclic heteroaryl, including but not limited to imidazolyl, pyrrolyl, and thiazolyl. In further embodiments, the $R^{12}$ heteroaryl is bicyclic heteroaryl, wherein non-limiting exemplary bicyclic heteroaryls include but are not limited to benzoxazolyl, benzoisoxazolyl benzothiazolyl, benzimidazolyl, benzothiophenyl, benzofuryl, indolyl, quinolinyl, isoquinolinyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1, 2, 4]triazinyl. $R^{12}$ can also be unsubstituted or substituted heterocycloalkyl, wherein the $R^{12}$ heterocycloalkyl is heterocycloalkyl with one nitrogen ring atom, (including but not limited to pyrrolidinyl, piperidinyl, morpholinyl, isothiazolidinyl 1,2, dioxide, or caprolactam). In other embodiments, the $R^{12}$ heterocycloalkyl is heterocycloalkyl with one oxygen ring atom, including but not limited to tetrahydrofuranyl, tetrahydropyranyl, morpholinyl, or oxetanyl. Alternatively, the $R^{12}$ heterocycloalkyl is heterocycloalkyl with one sulfur ring atom, such non-limiting exemplary including thiomorpholinyl and isothiazolidinyl 1,2, dioxide. In yet other embodiments, the $R^{12}$ heterocycloalkyl is a 5 membered heterocycloalkyl, including but not limited to tetrahydrofuranyl, imidazolidinyl, isothiazolidinyl 1,2, dioxide, or pyrrolidinyl. The invention provides additionally wherein the $R^{12}$ heterocycloalkyl is a 6 membered heterocycloalkyl (non-limiting exemplary 6 membered heterocycloalkyls include tetrahydropyranyl, piperidinyl, piperazinyl, morpholinyl, or thiomorpholinyl). In some embodiments the $R^{12}$ heterocycloalkyl is saturated heterocycloalkyl, including but not limited to tetrahydrofuranyl, tetrahydropyranyl, morpholinyl, oxetanyl, pyrrolidinyl, piperidinyl, morpholinyl, piperazinyl, or azetidinyl. In other embodiments, the $R^{12}$ heterocycloalkyl is heterocycloalkyl having an unsaturated moiety connected to the heterocycloalkyl ring, including but not limited to cyano, imidazolyl, or pyrazolyl moieties connected to the heterocycloalkyl ring. Alternatively, the $R^{12}$ heterocycloalkyl is heterocycloalkyl substituted by oxo, including but not limited to one of the following:

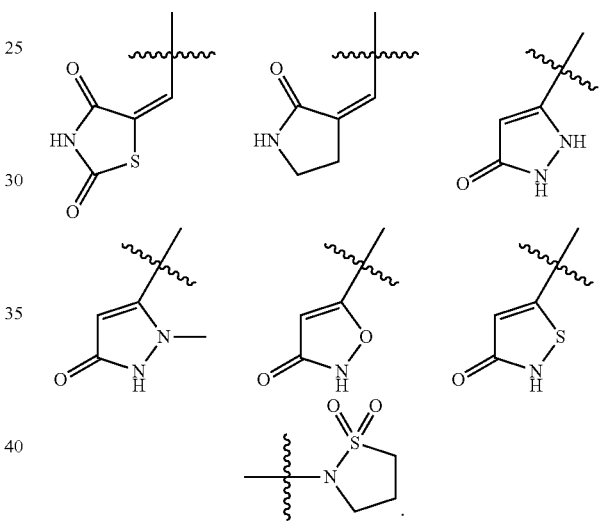

Additionally, $R^{12}$ can be unsubstituted or substituted cycloalkyl (including but not limited to cyclopropyl, cyclobutyl, cyclopentyl, or cyclohexyl). In other embodiments, $R^{12}$ is cycloalkyl substituted by one oxo (including but not limited to 2-oxo-cyclobutyl, 3-oxo-cyclopentyl, and 4-oxo-cyclohexyl). In yet other embodiments, $R^{12}$ is unsubstituted or substituted amido, carboxylic acid, unsubstituted or substituted acyloxy, or unsubstituted or substituted alkoxycarbonyl.

In some embodiments, when $R^{12}$ is alkyl, alkynyl, alkenyl, aryl, heteroaryl, heterocycloalkyl, or cycloalkyl, the $R^{12}$ moiety is substituted with phosphate. In some embodiments, when $R^{12}$ is alkyl, alkynyl, alkenyl, aryl, heteroaryl, heterocycloalkyl, or cycloalkyl, the $R^{12}$ moiety is substituted with urea. In some embodiments, when $R^{12}$ is alkyl, alkynyl, alkenyl, aryl, heteroaryl, heterocycloalkyl, or cycloalkyl, the $R^{12}$ moiety is substituted with carbonate.

In other embodiments, when $R^{12}$ is alkyl, alkynyl, alkenyl, aryl, heteroaryl, heterocycloalkyl, cycloalkyl, alkoxycarbonyl, amido, or acyloxy, the $R^{12}$ moiety is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, halo, cyano, hydroxy or nitro. Each of the substituents selected from the group consisting of alkyl, heteroalkyl, alkenyl, alkynyl, cycloalkyl, heterocycloalkyl, aryl, heteroaryl, alkoxy, amido, amino, acyl, acyloxy, aloxycarbonyl, or sulfonamido, may be further substituted by one or more of alkyl, alkoxy, amido, amino, acyl, acyloxy, alkoxycarbonyl, sulfonamido, halo, cyano, hydroxy or nitro substituents.

In some embodiments, $R^{12}$ of $W_d$ is one of the following moieties:

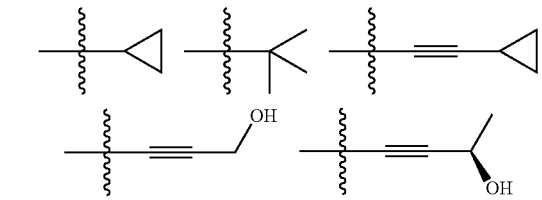
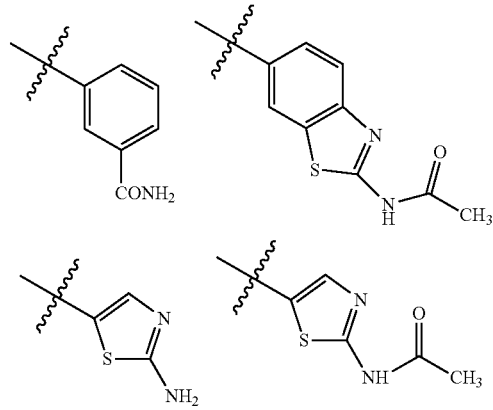
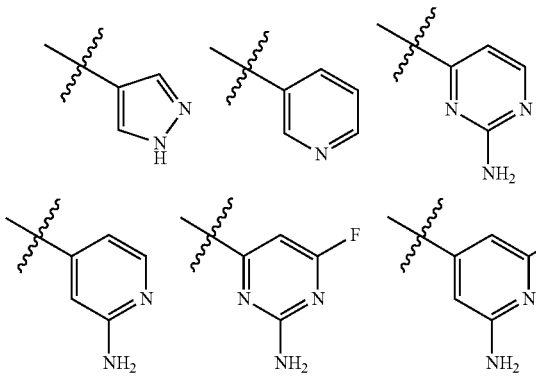
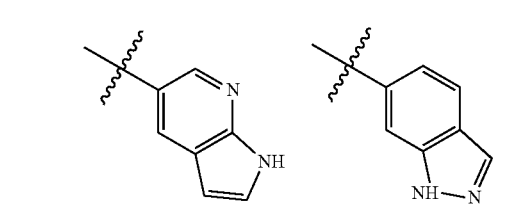
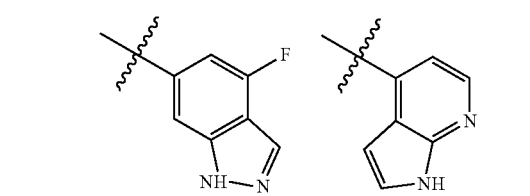

-continued

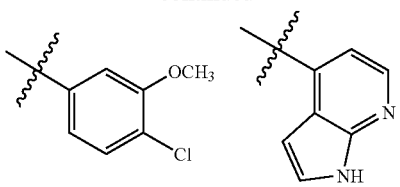
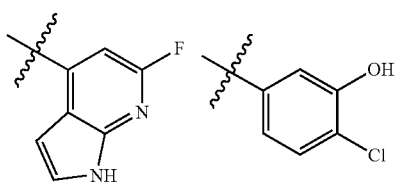
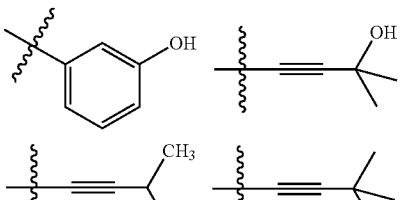
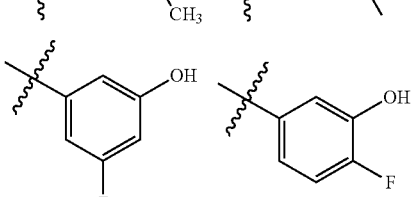
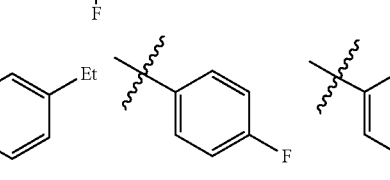
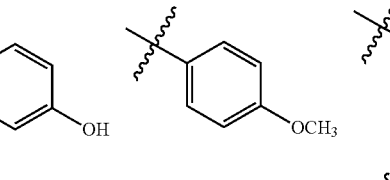
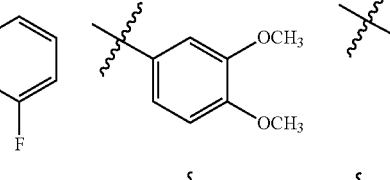
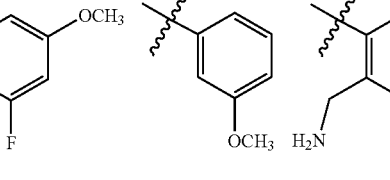
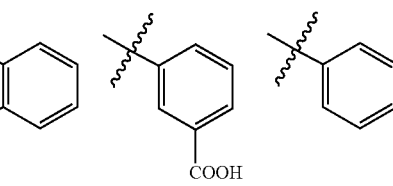

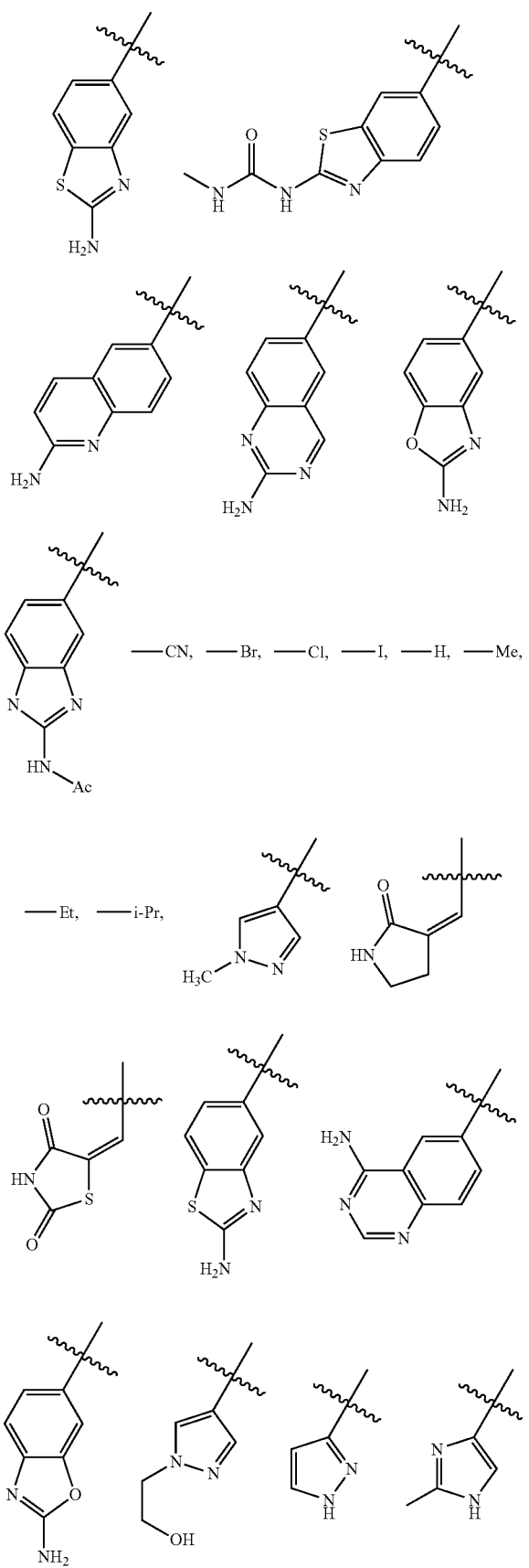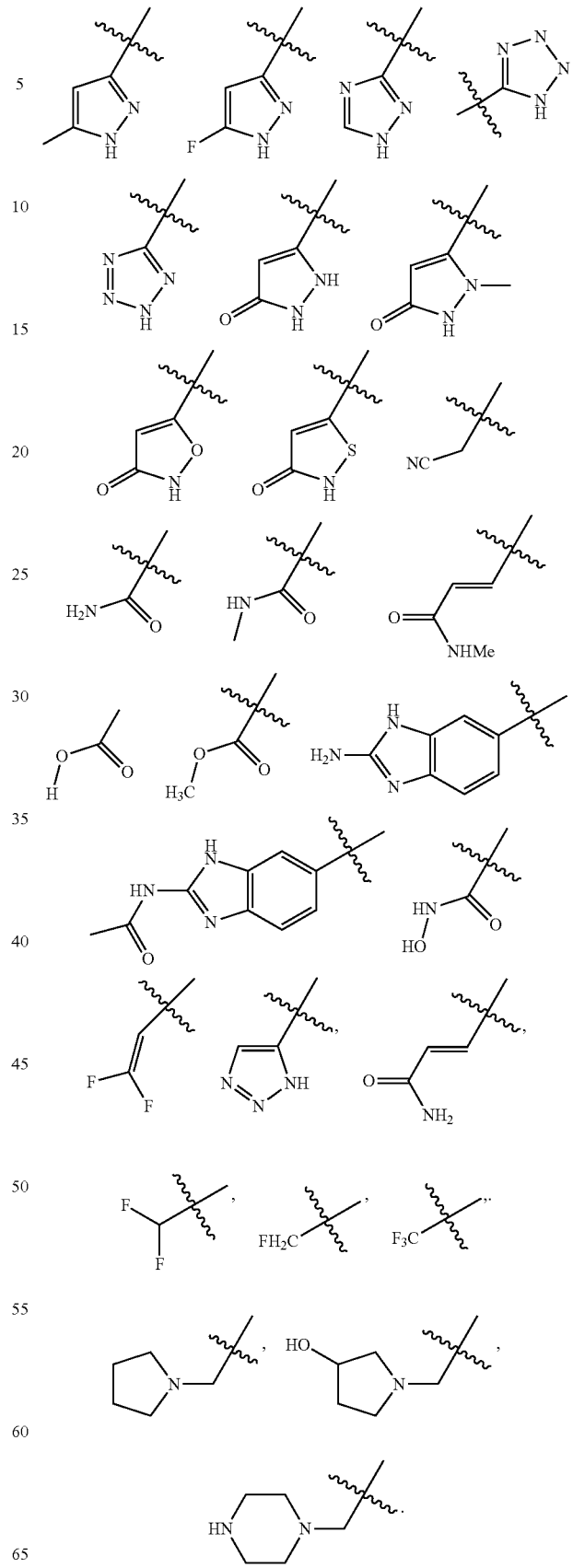

In some embodiments, $W_d$ is a pyrazolopyrimidine of Formula XIII:

Formula XIII

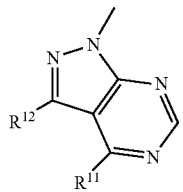

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is H, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, is amino and $R^{12}$ is bicyclic heteroaryl. In some embodiments, $R^{11}$ is amino and $R^{12}$ is cyano, amino, carboxylic acid, acyloxy, alkoxycarbonyl or amido.

In some embodiments, $W_d$ is a purine of Formula XIV:

Formula XIV

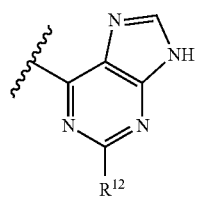

wherein $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido.

In some embodiments, the compound of Formula I is a compound of Formula XV-A or Formula XV-B:

Formula XV-A

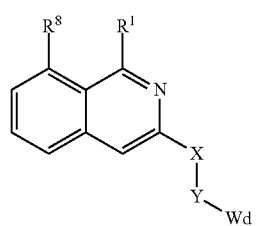

Formula XV-B

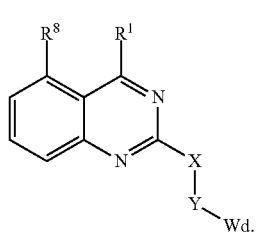

In some embodiments, the compound of Formula I is a compound of Formula XVI-A, Formula XVI-B, Formula XVII-A, Formula XVII-B, Formula XVIII-A, or Formula XVIII-B:

Formula XVI-A

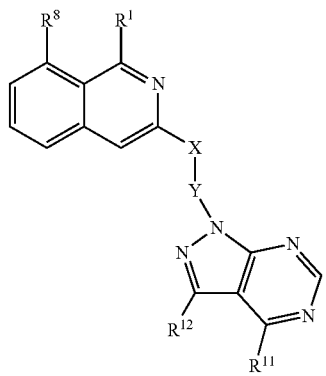

Formula XVII-A

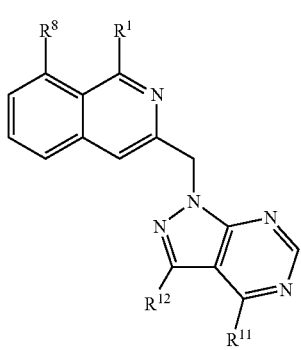

Formula XVIII-A

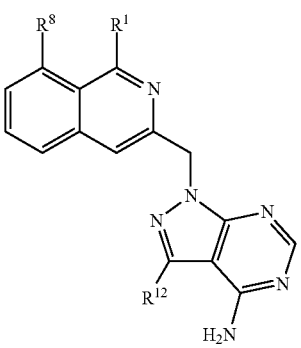

Formula XVI-B

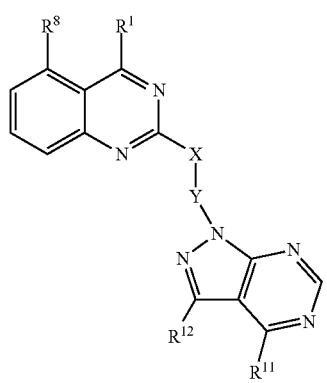

Formula XVII-B
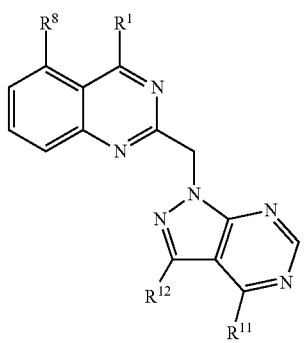
Formula XVIII-B
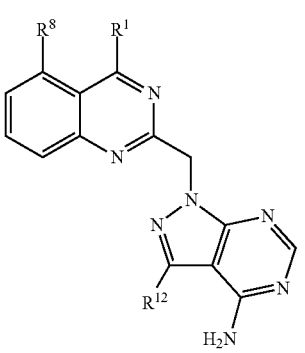
In some embodiments, the compound of Formula I is a compound of Formula XIX-A, Formula XIX-B, Formula XX-A, Formula XX-B, XXI-A, or XXI-B:
Formula XIX-A
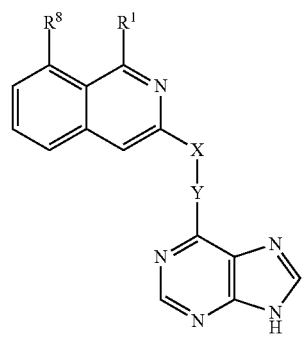
Formula XX-A
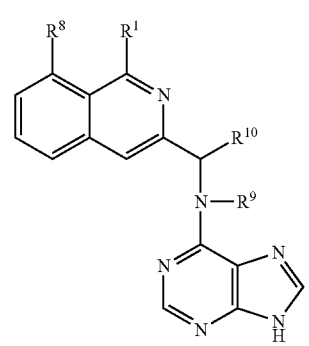
Formula XXI-A
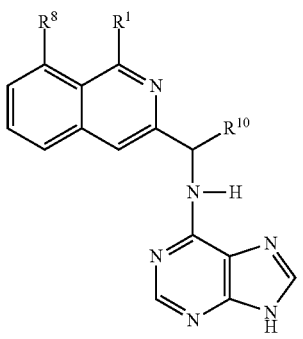
Formula XIX-B
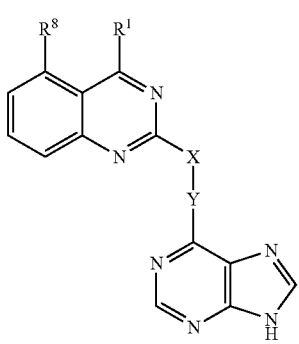
Formula XX-B
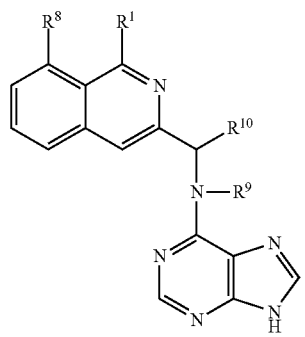
Formula XXI-B
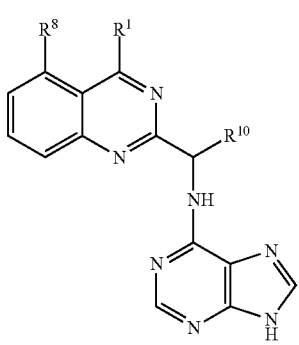
Any of the disclosed elements and their substituents for the compounds of Formula I can be used in any combination.

In one aspect, the compound of the invention is a compound of Formula II-A:

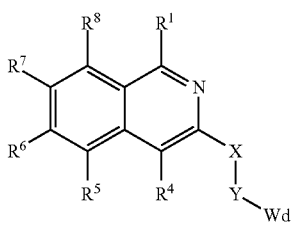

Formula II-A wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH($R^{10}$))$_z$ and z is an integer of 1, 2, 3, or 4; Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, —N($R^9$)—C(=O)NH—, —N($R^9$)C($R^{10}$)$_2$—, or —C(=O)—(CHR$^{10}$)$_z$—, each instance of $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ is independently hydrogen, alkyl, aryl, heteroaryl or halo; and W$_d$ is heterocycloalkyl, aryl, cycloalkyl, or heteroaryl. In some embodiments, Wd is purinyl, pyrazolopyrimidinyl, quinazolinyl, indazolyl, 6-quinolinyl, or H-pyrrolo[1,2-b]pyridazine, any of which is unsubstituted or substituted. In some embodiments, when Wd is purinyl, X is —(CH($R^{10}$))$_z$, z is 1, and Y is —N($R^9$)—, then $R^9$ is —NH.

In a second aspect, the compound of the invention is a compound of Formula II-A:

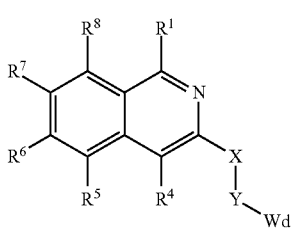

Formula II-A wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH($R^{10}$))$_z$ and z is an integer of 1, 2, 3, or 4; Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, —N($R^9$)—C(=O)NH—, —N($R^9$)C($R^{10}$)$_2$—, or —C(=O)—(CHR$^{10}$)$_z$; each instance of $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ is independently hydrogen, alkyl, aryl, heteroaryl or halo; and W$_d$ is one of the following:

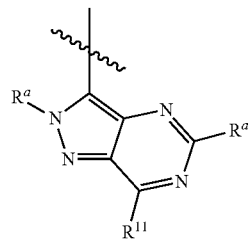 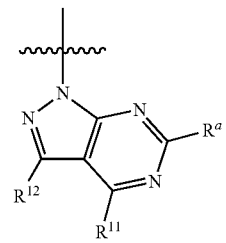

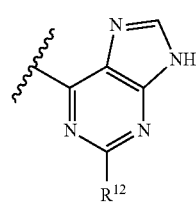 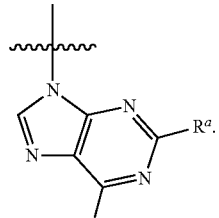

wherein $R^a$ is hydrogen, halo, phosphate, urea, carbonate, alkyl, alkenyl, alkynyl, cycloalkyl, heteroalkyl, or heterocycloalkyl;

$R^{11}$ is H, alkyl, halo, amino, amido, hydroxy, or alkoxy, and $R^{12}$ is H, alkyl, cyano, alkynyl, alkenyl, halo, aryl, heteroaryl, heterocycloalkyl, cycloalkyl, amino, carboxylic acid, alkoxycarbonyl, or amido. In some embodiments, when Wd is purinyl, X is —(CH($R^{10}$))$_z$, wherein z is 1, and Y is —N($R^9$)—, then $R^9$ is —NH—.

In a third aspect, the compound of the invention is a compound of Formula XV-A:

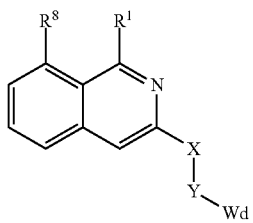

Formula XV-A wherein R¹ is -(L)$_n$-R¹'; L is —S—, —N(R²)—, —C(R³)$_2$—, or —O—; n is 0 or 1; R¹' is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; R² is independently hydrogen, C$_1$-C$_{10}$alkyl, C$_3$-C$_7$cycloalkyl, heterocycloalkyl, C$_2$-C$_{10}$heteroalkyl, aryl, or heteroaryl; and each instance of R³ is independently hydrogen, alkyl, aryl, heteroaryl or halo; R⁴, R⁵, R⁶, and R⁷ are hydrogen; R⁸ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH(R$^a$))$_z$— and z is an integer of 1, 2, 3, or 4; Y is absent, —O—, —S—, —S(=O)$_2$—, —N(R⁹)—, —C(=O)—(CHR¹⁰)$_z$—, —C(=O)—, —NR⁹)—C(=O)—, —N(R⁹)—C(=O)NH—, —N(R⁹)C(R¹⁰)$_2$—, or —C(=O)—(CHR¹⁰)$_z$—; each instance of R⁹ is independently hydrogen, C$_1$-C$_{10}$alkyl, C$_3$-C$_7$cycloalkyl, heterocycloalkyl, C$_2$-C$_{10}$heteroalkyl, aryl, or heteroaryl; each instance of R³ and R¹⁰ is independently hydrogen, alkyl, aryl, heteroaryl or halo; and W$_d$ is heterocycloalkyl, aryl, cycloalkyl, or heteroaryl. In some embodiments, Wd is purinyl, pyrazolopyrimidinyl, quinazolinyl, indazolyl, 6-quinolinyl, or H-pyrrolo[1,2-b]pyridazine, any of which is unsubstituted or substituted. In some embodiments, wherein Wd is purinyl, X is —(CH(R¹⁰))$_z$, wherein z is 1, and Y is —N(R⁹)—, then R⁹ is —NH—.

In a fourth aspect, the compound of the invention is a compound of Formula XV-A:

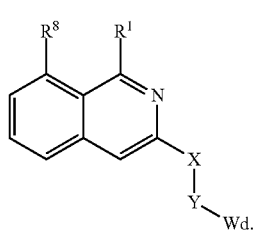

Formula XV-A wherein R¹ is -(L)-R¹'; L is —S—, —N(R²)—, —C(R³)$_2$—, or —O—; n is 0 or 1; R¹' is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; R² is independently hydrogen, C$_1$-C$_{10}$alkyl, C$_3$-C$_7$cycloalkyl, heterocycloalkyl, C$_2$-C$_{10}$heteroalkyl, aryl, or heteroaryl; and each instance of R³ is independently hydrogen, alkyl, aryl, heteroaryl or halo; R⁴, R⁵, R⁶, and R⁷ are hydrogen; R⁸ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH(R¹⁰))$_z$ and z is an integer of 1, 2, 3, or 4; Y is absent, —O—, —S—, —S(=O)—, —S(=O)$_2$—, —N(R⁹)—, —C(=O)—(CHR¹⁰)$_z$—, —C(=O)—, —N(R⁹)—C(=O)—, —N(R⁹)—C(=O)NH—, —N(R⁹)C(R¹⁰)$_2$—, or —C(=O)—(CHR¹⁰)$_z$; each instance of R⁹ is independently hydrogen, C$_1$-C$_{10}$alkyl, C$_3$-C$_7$cycloalkyl, heterocycloalkyl, C$_2$-C$_{10}$heteroalkyl, aryl, or heteroaryl; each instance of R³ and R¹⁰ is independently hydrogen, alkyl, aryl, heteroaryl or halo; and W$_d$ is one of the following:

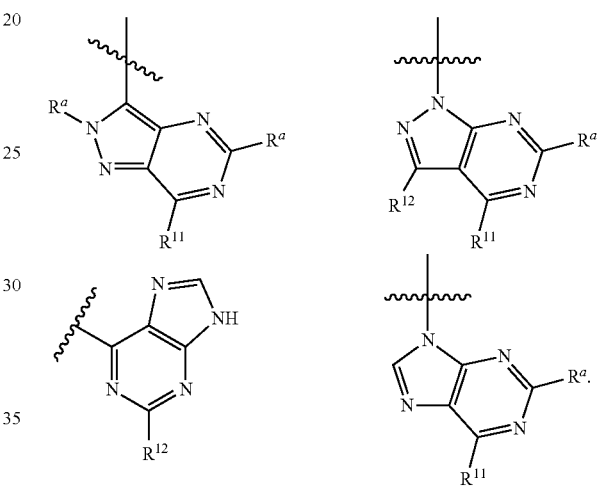

wherein R$^a$ is hydrogen, halo, phosphate, urea, carbonate, alkyl, alkenyl, alkynyl, cycloalkyl, heteroalkyl, or heterocycloalkyl;

R¹¹ is H, alkyl, halo, amino, amido, hydroxy, or alkoxy, and R¹² is H, alkyl, cyano, alkynyl, alkenyl, halo, aryl, heteroaryl, heterocycloalkyl, cycloalkyl, amino, carboxylic acid, alkoxycarbonyl, or amido. In some embodiments, when Wd is purinyl, X is —(CH(R¹⁰))$_z$, wherein z is 1 and Y is —N(R⁹)—, then R⁹ is —NH—.

In a fifth aspect, the compound of the invention is a compound of Formula XV-A:

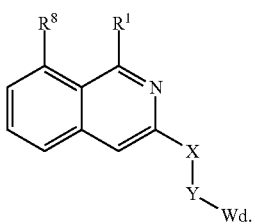

Formula XV-A wherein R¹ is -(L)$_n$-R¹'; L is —S—, —N(R²)—, —C(R³)$_2$—, or —O—; n is 0 or 1; R¹' is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^4$, $R^5$, $R^6$, and $R^7$ are hydrogen; $R^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH($R^{10}$))$_z$— and z is an integer of 1, 2, 3, or 4; Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, —N($R^9$)—C(=O)NH—, —N($R^9$)C($R^{10}$)$_2$—, or —C(=O)—(CHR$^{10}$)$_z$; each instance of $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ independently hydrogen, alkyl, aryl, heteroaryl or halo; and $W_d$ is a moiety of Formula XIII or Formula XIV:

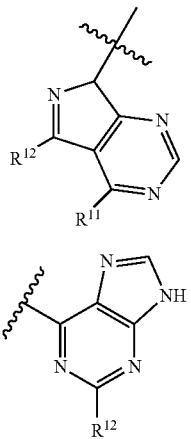

Formula XIII

Formula XIV wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido. In some embodiments, when Wd is purinyl, X is —(CH($R^{10}$))$_z$, wherein z is 1, and Y is —N($R^9$)—, then $R^9$ is —NH—

In a sixth aspect, the compound of the invention is a compound of Formula XVII-A:

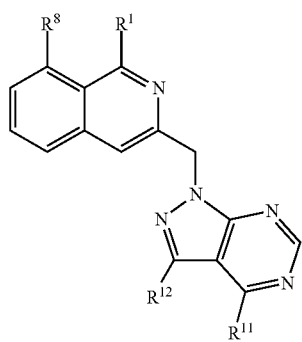

Formula XVII-A wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^4$, $R^5$, $R^6$, and $R^7$ are hydrogen; $R^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; R'1 is H, alkyl, halo, amino, amido, hydroxy, or alkoxy, and $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido. In some embodiments, $R^{11}$ is amino and $R^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety.

In a seventh aspect, the compound of the invention is a compound of Formula XIX-A:

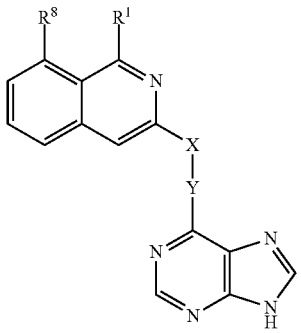

Formula XIX-A wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$allyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^4$, $R^5$, $R^6$, and $R^7$ are hydrogen; $R^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH($R^{10}$))$_z$— and z is an integer of 1, 2, 3, or 4; Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, —N($R^9$)—C(=O)NH—, —N($R^9$)C($R^{10}$)$_2$—, or —C(=O)—(CHR$^{10}$)$_z$—; each instance of $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and $R^{10}$ is hydrogen, alkyl, aryl, heteroaryl or halo. In some embodiments, when X is —(CH(R$^{10}$))$_z$, z is 1, and Y is —N(R$^9$)—, then R$^9$ is —NH—.

In an eighth aspect, the compound of the invention is a compound of Formula XX-A:

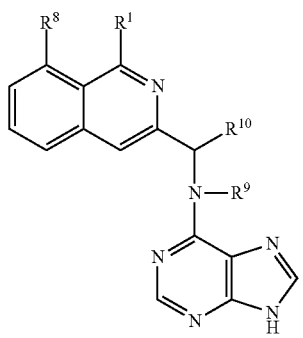

Formula XX-A wherein R$^1$ is -(L)$_n$-R$^{1'}$; L is —S—, —N(R$^2$)—, —C(R$^3$)$_2$—, or —O—; n is 0 or 1; R$^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; R$^2$ is independently hydrogen, C$_1$-C$_{10}$alkyl, C$_3$-C$_7$cycloalkyl, heterocycloalkyl, C$_2$-C$_{10}$heteroalkyl, aryl, or heteroaryl; and each instance of R$^3$ is independently hydrogen, alkyl, aryl, heteroaryl or halo; R$^4$, R$^5$, R$^6$, and R$^7$ are hydrogen; R$^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety, R$^9$ is independently hydrogen, C$_1$-C$_{10}$alkyl, C$_3$-C$_7$cycloalkyl, heterocycloalkyl, C$_2$-C$_{10}$heteroalkyl, aryl, or heteroaryl, and R$^{10}$ is hydrogen, alkyl, aryl, heteroaryl or halo. In some embodiments, R$^9$ is H.

In a ninth aspect, the compound of the invention is a compound of Formula XXI-A:

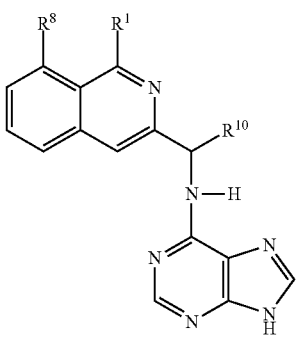

Formula XXI-A wherein R$^1$ is -(L)$_n$-R$^{1'}$; L is —S—, —N(R$^2$)—, —C(R$^3$)$_2$—, or —O—; n is 0 or 1; R$^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, or NR'R" wherein R' and R" are taken together with nitrogen to form a cyclic moiety; R$^2$ is independently hydrogen, C$_1$-C$_{10}$alkyl, C$_3$-C$_7$cycloalkyl, heterocycloalkyl, or C$_2$-C$_{10}$heteroalkyl; and each instance of R$^3$ is independently hydrogen, alkyl, or halo; R$^4$, R$^5$, R$^6$, and R$^7$ are hydrogen; R$^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety; and R$^{10}$ is hydrogen, alkyl, aryl, heteroaryl or halo.

In a tenth aspect of the invention, the compound of the invention is a compound of Formula II-B:

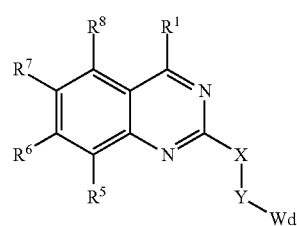

Formula II-B wherein R$^1$ is -(L)$_n$-R$^{1'}$ ; L is —S—, —N(R$^2$)—, —C(R$^3$)$_2$—, or —O—; n is 0 or 1; R$^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; R$^2$ is independently hydrogen, C$_1$-C$_{10}$alkyl, C$_3$-C$_7$cycloalkyl, heterocycloalkyl, C$_2$-C$_{10}$heteroalkyl, aryl, or heteroaryl; and each instance of R$^3$ is independently hydrogen, alkyl, aryl, heteroaryl or halo; R$^5$, R$^6$, R$^7$ and R$^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH(R$^{10}$))$_z$ and z is an integer of 1, 2, 3, or 4; Y is absent, —O—, —S—, —S(=O)—, —S(=O)$_2$—, —N(R$^9$)—, —C(=O)—(CHR$^{10}$)$_z$—, —C(=O)—, —N(R$^9$)—C(=O)—, —N(R$^9$)—C(=O)NH—, —N(R$^9$)C(R$^{10}$)$_2$—, or —C(=O)—(CHR$^{10}$)$_z$—; each instance of R$^9$ is independently hydrogen, C$_1$-C$_{10}$alkyl, C$_3$-C$_7$cycloalkyl, heterocycloalkyl, C$_2$-C$_{10}$heteroalkyl, aryl, or heteroaryl; each instance of R$^3$ and R$^{10}$ is independently hydrogen, alkyl, aryl, heteroaryl or halo; and W$_d$ is heterocycloalkyl, aryl, cycloalkyl, or heteroaryl. In some embodiments, Wd is purinyl, pyrazolopyrimidinyl, quinazolinyl, indazolyl, 6-quinolinyl, or H-pyrrolo[1,2-b]pyridazine, any of which is unsubstituted or substituted. In some embodiments, when Wd is purinyl, X is —(CH(R$^{10}$))$_z$, z is 1, and Y is —N(R$^9$)—, then R$^9$ is —NH—.

In an eleventh aspect, the compound of the invention is a compound of Formula XV-B:

Formula XV-B

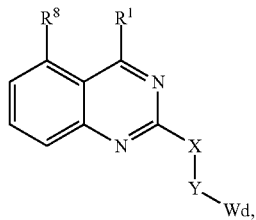

wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^5$, $R^6$, and $R^7$ are hydrogen; $R^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; X is absent or is —(CH($R^{10}$))$_z$ and z is an integer of 1, 2, 3, or 4; Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, —N($R^9$)—C(=O)NH—, —N($R^9$)C($R^{10}$)$_2$—, or —C(=O)—(CHR$^{10}$)$_z$—; each instance of $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; each instance of $R^3$ and $R^{10}$ is independently hydrogen, alkyl, aryl, heteroaryl or halo; and $W_d$ is one of the following:

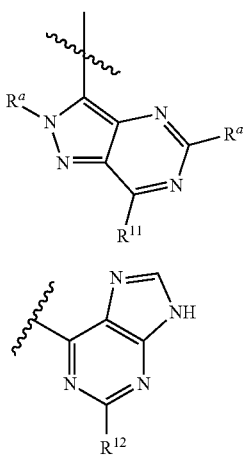

wherein $R^a$ is hydrogen, halo, phosphate, urea, carbonate, alkyl, alkenyl, alkynyl, cycloalkyl, heteroalkyl, or heterocycloalkyl;

$R^{11}$ is H, alkyl, halo, amino, amido, hydroxy, or alkoxy, and $R^{12}$ is H, alkyl, cyano, alkynyl, alkenyl, halo, aryl, heteroaryl, heterocycloalkyl, cycloalkyl, amino, carboxylic acid, alkoxycarbonyl, or amido. In some embodiments, when Wd is purinyl, X is —(CH($R^{10}$))$_z$ is 1, and Y is —N($R^9$)—, then $R^9$ is —NH—.

In a twelfth aspect, the compound of the invention is a compound of Formula XVII-B:

Formula XVII-B

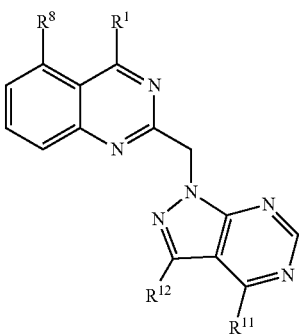

wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl; and each instance of $R^3$ is independently hydrogen, alkyl, aryl, heteroaryl or halo; $R^5$, $R^6$, and $R^7$ are hydrogen; $R^8$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety; $R^{1'}$ is H, alkyl, halo, amino, amido, hydroxy, or alkoxy, and $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido. In some embodiments, $R^{11}$ is amino and $R^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety.

In a thirteenth aspect, the compound of the invention is a compound of Formula XXI-B:

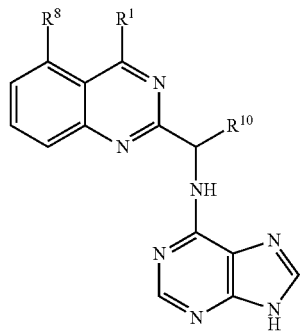

Formula XXI-B wherein $R^1$ is -(L)$_n$-$R^{1'}$; L is —S—, —N($R^2$)—, —C($R^3$)$_2$—, or —O—; n is 0 or 1; $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, or NR'R" wherein R' and R" are taken together with nitrogen to form a cyclic moiety; $R^2$ is independently hydrogen, $C_1$-$C_{10}$alkyl, $C_3$-$C_7$cycloalkyl, heterocycloalkyl, or $C_2$-$C_{10}$heteroalkyl; and each instance of $R^3$ is independently hydrogen, alkyl, or halo; $R^5$, $R^6$, and $R^7$ are hydrogen; $R^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety; and $R^{10}$ is hydrogen, alkyl, aryl, heteroaryl or halo.

Additional exemplary compounds of the present invention are disclosed having a sub-structure of Formula XVII-A or Formula XVII-B.

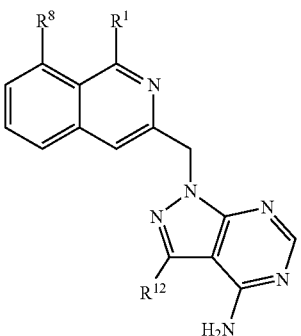

Formula XVIII-A

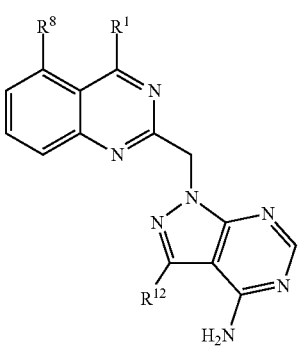

Formula XVIII-B

Some illustrative compounds of the present invention having a structure of Formula XVIII-A or Formula XVIII-B include those in which $R^8$ is —H, —$CH_3$, —$CH_2CH_3$, or —$CF_3$ in combination with any R' moiety described in Table 1, and any $R^{12}$ as described in Table 2. A compound of Formula XVIII-A or Formula XVIII-B includes any combination of $R^8$, $R^1$, and $R^{12}$. Additional exemplary compounds of Formula XVIII-A or Formula XVIII-B are illustrated in Table 4 and in paragraphs following Table 2.

TABLE 1

$R^1$ moieties of the compounds of Formula I, include but are not limited to the following:

| Subclass # | $R^1$ | Subclass # | $R^1$ | Subclass # | $R^1$ |
|---|---|---|---|---|---|
| $R^1$-1 | (phenoxy) | $R^1$-2 | (1-methylpiperidin-4-yloxy) | $R^1$-3 | (1-isopropylpiperidin-4-yloxy) |
| $R^1$-4 | (piperidin-4-yloxy) | $R^1$-5 | (pyrrolidin-1-yl) | $R^1$-6 | (isopropoxy) |

TABLE 1-continued
R¹ moieties of the compounds of Formula I, include but are not limited to the following:
| Subclass # | R¹ | Subclass # | R¹ | Subclass # | R¹ |
|---|---|---|---|---|---|
| R¹-7 | 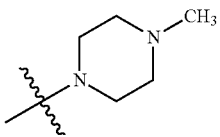 [SMILES: *N1CCN(C)CC1] | R¹-8 | 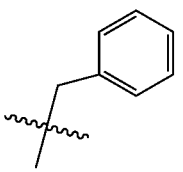 [SMILES: *Cc1ccccc1] | R¹-9 | —CH(CH₃)2 |
| R¹-10 | 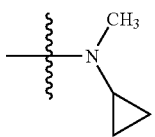 [SMILES: *N(C)C1CC1] | R¹-11 | 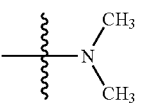 | R¹-12 | 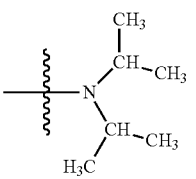 |
| R¹-13 | 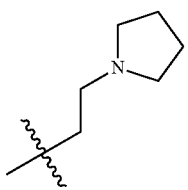 [SMILES: *CCN1CCCC1] | R¹-14 | 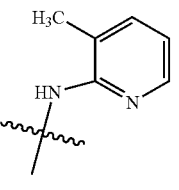 [SMILES: *Nc1ncccc1C] | R¹-15 | 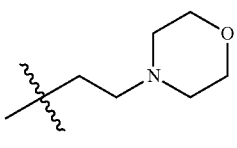 [SMILES: *CCN1CCOCC1] |
| R¹-16 | 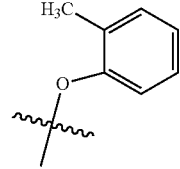 [SMILES: *Oc1ccccc1C] | R¹-17 | 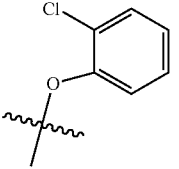 [SMILES: *Oc1ccccc1Cl] | R¹-18 | 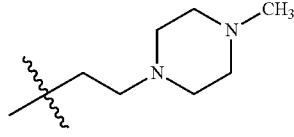 [SMILES: *CCN1CCN(C)CC1] |
| R¹-19 | 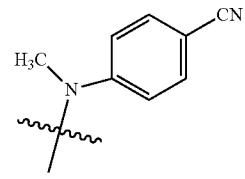 [SMILES: *N(C)c1ccc(C#N)cc1] | R¹-20 | 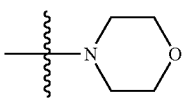 | R¹-21 | 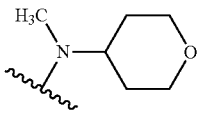 [SMILES: *N(C)C1CCOCC1] |
| R¹-22 | 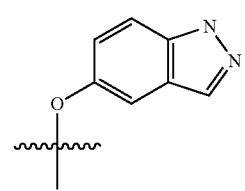 [SMILES: *Oc1ccc2[nH]ncc2c1] | R¹-23 | 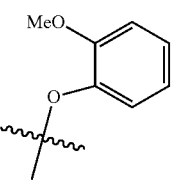 [SMILES: *Oc1ccccc1OC] | R¹-24 | 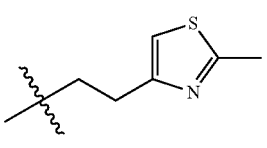 [SMILES: *CCc1csc(C)n1] |
| R¹-25 | 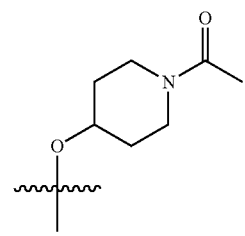 [SMILES: *OC1CCN(C(C)=O)CC1] | R¹-26 | 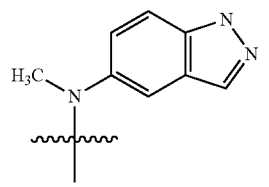 [SMILES: *N(C)c1ccc2[nH]ncc2c1] | R¹-27 | 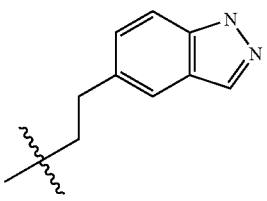 [SMILES: *CCc1ccc2[nH]ncc2c1] |

TABLE 1-continued

R¹ moieties of the compounds of Formula I, include but are not limited to the following:

| Subclass # | R¹ | Subclass # | R¹ | Subclass # | R¹ |
|---|---|---|---|---|---|
| R¹-28 | (piperazine with N-CH₂CH₃ and N-alkyl linker) | R¹-29 | (4-substituted piperidine with N-CH₂CH₂CN) | R¹-30 | (4-oxy-piperidine with N-CH₂CH₂CN) |
| R¹-31 | (4-substituted piperidine with N-acetyl) | R¹-32 | (4-oxy-piperidine with N-acetyl) | R¹-33 | (4-methoxy-piperidine with N-CH₂CH₂OH) |
| R¹-34 | (4-substituted piperidine with N-CH₂CH₂OH) | R¹-35 | (4-oxy-piperidine with N-CH₂CH₂SO₂Me) | R¹-36 | (4-substituted piperidine with N-CH₂CH₂SO₂Me) |
| R¹-37 | (2-pyridyloxy) | R¹-38 | (2-pyridyl-ethyl) | R¹-39 | (4-thiazolyl) |
| R¹-40 | H | R¹-41 | (2-diethylamino-thiazol-4-yl) | R¹-42 | (2-imidazol-1-yl-thiazol-4-yl) |
| R¹-43 | (piperidin-1-yl) | R¹-44 | (2-oxo-piperidin-1-yl) | R¹-45 | (thiomorpholin-4-yl) |
| R¹-46 | (4-ethyl-piperazin-1-yl) | R¹-47 | (4-oxy-piperidine with N-SO₂Me) | R¹-48 | (tetrahydropyran-4-yloxy) |

TABLE 1-continued
R¹ moieties of the compounds of Formula I, include but are not limited to the following:
| Subclass # | R¹ | Subclass # | R¹ | Subclass # | R¹ |
|---|---|---|---|---|---|
| R¹-49 | 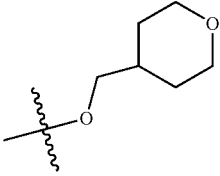 [SMILES: *OCC1CCOCC1] | R¹-50 | 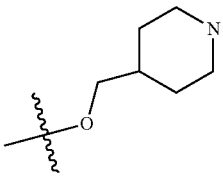 | R¹-51 | 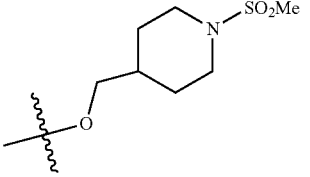 [SMILES: *OCC1CCN(S(C)(=O)=O)CC1] |
| R¹-52 | 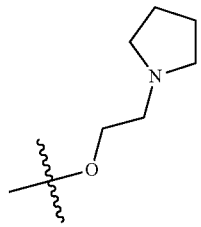 [SMILES: *OCCN1CCCC1] | R¹-53 | 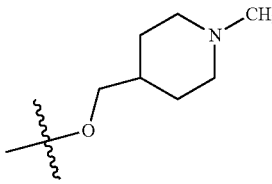 | R¹-54 | 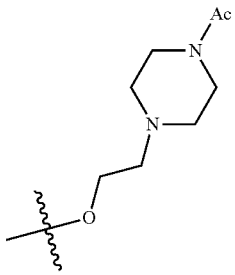 [SMILES: *OCCN1CCN(C(C)=O)CC1] |
| R¹-55 | 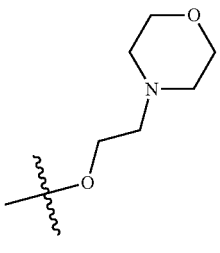 [SMILES: *OCCN1CCOCC1] | R¹-56 | 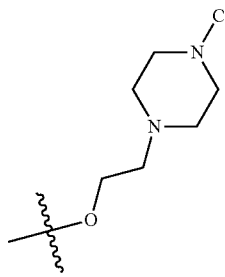 | R¹-57 | 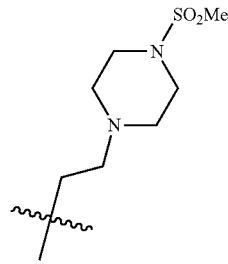 [SMILES: *CCN1CCN(S(C)(=O)=O)CC1] |
| R¹-58 | 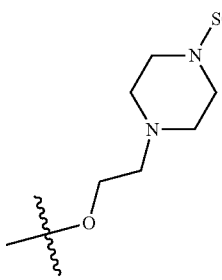 | R¹-59 | 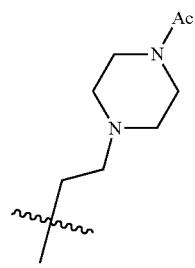 [SMILES: *CCN1CCN(C(C)=O)CC1] | R¹-60 | 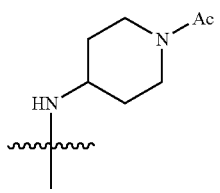 [SMILES: *NC1CCN(C(C)=O)CC1] |
| R¹-61 | 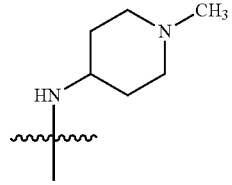 [SMILES: *NC1CCN(C)CC1] | R¹-62 | 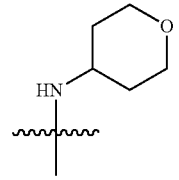 [SMILES: *NC1CCOCC1] | R¹-63 | 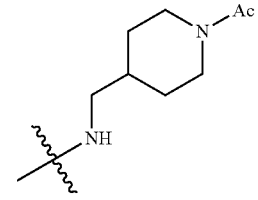 [SMILES: *NCC1CCN(C(C)=O)CC1] |
| R¹-64 | 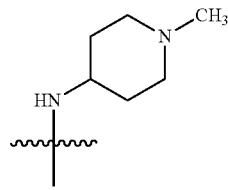 [SMILES: *NC1CCN(C)CC1] | R¹-65 | 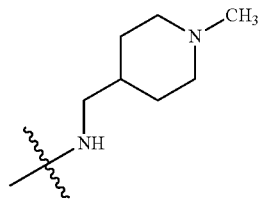 [SMILES: *NCC1CCN(C)CC1] | R¹-66 | 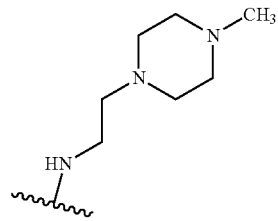 [SMILES: *NCCN1CCN(C)CC1] |

TABLE 1-continued

R¹ moieties of the compounds of Formula I, include but are not limited to the following:

| Subclass # | R¹ | Subclass # | R¹ | Subclass # | R¹ |
|---|---|---|---|---|---|
| R¹-67 | (tetrahydropyran-4-ylmethyl)amino | R¹-68 | 2-morpholinoethylamino | R¹-69 | 2-(4-acetylpiperazin-1-yl)ethylamino |
| R¹-70 | 2-(pyrrolidin-1-yl)ethylamino | R¹-71 | phenyl | R¹-72 | isothiazolidine 1,1-dioxide |
| R¹-73 | methanesulfonamido | R¹-74 | N-methyl methanesulfonamido | R¹-75 | benzenesulfonamido |
| R¹-76 | N-methyl benzenesulfonamido | R¹-77 | phenylmethanesulfonamido | R¹-78 | N-methyl phenylmethanesulfonamido |
| R¹-79 | N-(2-hydroxyethyl) methanesulfonamido | R¹-80 | 4-cyanophenyl | R¹-81 | N-(2-morpholinoethyl) methanesulfonamido |

TABLE 2

Illustrative R¹² of compounds of Formula I, include but are not limited to the following:

| Subclass # | R¹² | Subclass # | R¹² | Subclass # | R¹² |
|---|---|---|---|---|---|
| 12-1 | —CN | 12-2 | —Br | 12-3 | —Cl |
| 12-4 | —CH$_2$CH$_3$ | 12-5 | —CH$_3$ | 12-6 | —CH(CH$_3$)$_2$ |
| 12-7 | cyclopropyl | 12-8 | tert-butyl | 12-9 | pyridin-3-yl |
| 12-10 | —C≡C—CH$_2$OH | 12-11 | —C≡C—CH(OH)CH$_3$ | 12-12 | —C≡C-cyclopropyl |

US 8,785,454 B2
TABLE 2-continued
Illustrative R¹² of compounds of Formula I, include but are not limited to the following:
| Sub-class # | R¹² | Sub-class # | R¹² | Sub-class # | R¹² |
|---|---|---|---|---|---|
| 12-13 | 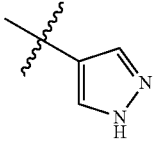 [SMILES: *c1cn[nH]c1] | 12-14 | 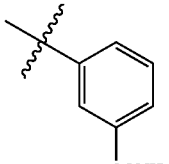 | 12-15 | 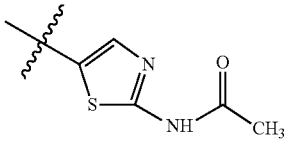 |
| 12-16 | 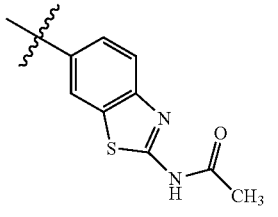 [SMILES: *c1ccc2nc(NC(C)=O)sc2c1] | 12-17 | 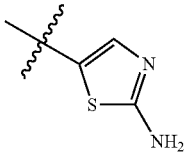 [SMILES: *c1cnc(N)s1] | 12-18 | 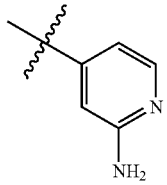 |
| 12-19 | 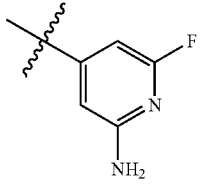 [SMILES: *c1cc(N)nc(F)c1] | 12-20 | 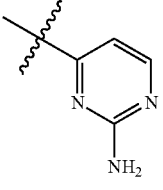 [SMILES: *c1ccnc(N)n1] | 12-21 | 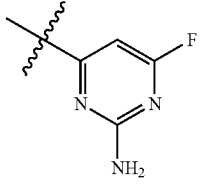 |
| 12-22 | 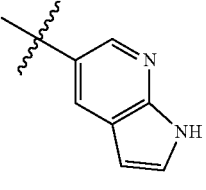 [SMILES: *c1cnc2[nH]ccc2c1] | 12-23 | 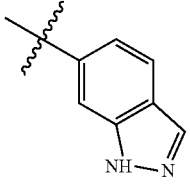 [SMILES: *c1ccc2cn[nH]c2c1] | 12-24 | 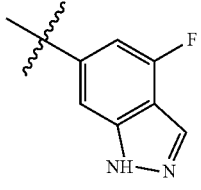 [SMILES: *c1cc(F)c2cn[nH]c2c1] |
| 12-25 | 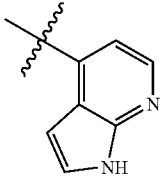 | 12-26 | 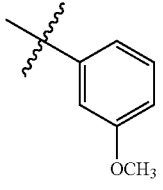 | 12-27 | 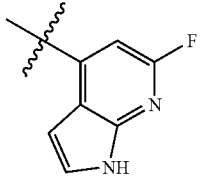 [SMILES: *c1cc(F)nc2[nH]ccc12] |
| 12-28 | 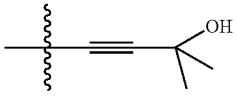 [SMILES: *C#CC(C)(C)O] | 12-29 | 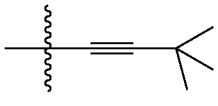 [SMILES: *C#CC(C)(C)C] | 12-30 | 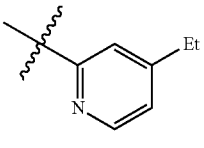 [SMILES: *c1cc(CC)ccn1] |
| 12-31 | 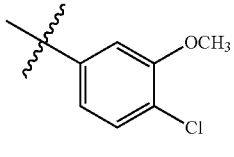 [SMILES: *c1ccc(Cl)c(OC)c1] | 12-32 | 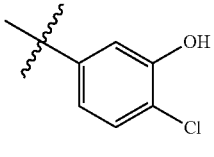 | 12-33 | 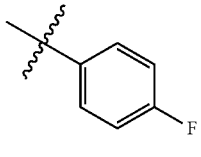 |
| 12-34 | 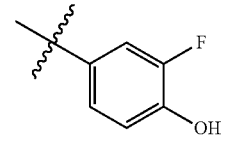 [SMILES: *c1ccc(O)c(F)c1] | 12-35 | —H | 12-36 | 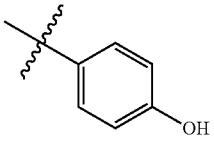 [SMILES: *c1ccc(O)cc1] |

TABLE 2-continued

Illustrative $R^{12}$ of compounds of Formula I, include but are not limited to the following:

| Subclass # | $R^{12}$ | Subclass # | $R^{12}$ | Subclass # | $R^{12}$ |
|---|---|---|---|---|---|
| 12-37 | 4-fluorophenyl | 12-38 | 3-fluoro-4-hydroxyphenyl | 12-39 | 4-hydroxyphenyl |
| 12-40 | 3-chlorophenyl | 12-41 | 3-fluorophenyl | 12-42 | 3,4-dimethoxyphenyl |
| 12-43 | 4-methoxyphenyl | 12-44 | 2-(aminomethyl)-4-fluorophenyl | 12-45 | 2-(aminomethyl)phenyl |
| 12-46 | 3-methoxyphenyl | 12-47 | 4-(aminomethyl)phenyl | 12-48 | 3-carboxyphenyl |
| 12-49 | 3-fluoro-5-methoxyphenyl | 12-50 | 2-aminobenzothiazol-6-yl | 12-51 | 2-(3-methylureido)benzothiazol-6-yl |
| 12-52 | 2-aminoquinolin-6-yl | 12-53 | 2-aminoquinazolin-6-yl | 12-54 | 2-aminobenzoxazol-5-yl |

TABLE 2-continued

Illustrative R[12] of compounds of Formula I, include but are not limited to the following:

| Sub-class # | R[12] | Sub-class # | R[12] | Sub-class # | R[12] |
|---|---|---|---|---|---|
| 12-55 | 2-aminobenzoxazol-6-yl | 12-56 | 4-aminoquinazolin-6-yl | 12-57 | 1-methyl-1H-pyrazol-4-yl |
| 12-58 | 1-(2-hydroxyethyl)-1H-pyrazol-4-yl | 12-59 | (2,4-dioxothiazolidin-5-ylidene)methyl | 12-60 | (2-oxopyrrolidin-3-ylidene)methyl |
| 12-61 | —I | 12-62 | 3-hydroxyphenyl | 12-63 | 3-fluoro-5-hydroxyphenyl |
| 12-64 | 4-fluoro-3-hydroxyphenyl | 12-65 | 4-methylpent-2-yn-1-yl | 12-66 | 4-(diethylamino)pyridin-2-yl |
| 12-67 | 2-aminobenzothiazol-6-yl | 12-68 | 1H-pyrazol-3-yl | 12-69 | 2-methyl-1H-imidazol-4-yl |
| 12-70 | 5-methyl-1H-pyrazol-3-yl | 12-71 | 5-fluoro-1H-pyrazol-3-yl | 12-72 | 1H-1,2,4-triazol-3-yl |

TABLE 2-continued

Illustrative $R^{12}$ of compounds of Formula I, include but are not limited to the following:

| Subclass # | $R^{12}$ | Subclass # | $R^{12}$ | Subclass # | $R^{12}$ |
|---|---|---|---|---|---|
| 12-73 | pyrazolone (NH, NH) | 12-74 | pyrazolone (N-Me, NH) | 12-75 | isoxazolone |
| 12-76 | isothiazolone | 12-77 | -CH₂-CN | 12-78 | -C(O)NH₂ |
| 12-79 | -C(O)NHMe | 12-80 | -C(O)CH=CH-NHMe (trans enone amide) | 12-81 | -CH₂-morpholine |
| 12-82 | -C(O)OCH₃ | 12-83 | 1H-1,2,3-triazol-5-yl | 12-84 | -C(O)NH-OH |
| 12-85 | 2-amino-1H-benzimidazol-5-yl | 12-86 | 2-acetamido-1H-benzimidazol-5-yl | 12-87 | -CH=CF₂ |
| 12-88 | 1H-pyrazol-3-yl | 12-89 | 1-methyl-1H-pyrazol-5-yl (via CH₂) | 12-90 | -CH₂CH₂C(O)NH₂ |
| 12-91 | 2-acetamido-benzoxazol-6-yl | 12-92 | morpholin-4-yl-C(O)-CH=CH- | 12-93 | morpholin-4-yl-C(O)-CH₂CH₂- |

TABLE 2-continued

Illustrative R¹² of compounds of Formula I, include but are not limited to the following:

| Sub-class # | R¹² | Sub-class # | R¹² | Sub-class # | R¹² |
|---|---|---|---|---|---|
| 12-94 | (structure) | 12-95 | (structure) | 12-96 | (structure) |
| 12-97 | (structure) | 12-98 | (structure) | 12-99 | (structure) |
| 12-100 | (structure) | 12-101 | (structure) | 12-102 | (structure) |

Other illustrative compounds of the present invention have a structure of Formula XX-A, Formula XX-B, or Formula XXI-B, in which $R^8$ is —H, —CH$_3$, —CH$_2$CH$_3$, or —CF$_3$ in combination with any R' moiety described in Table 1, any $R^{12}$ as described in Table 2, $R^9$ which is hydrogen, methyl, ethyl, or cyclopropyl, and $R^{10}$, which is —H, —CH$_3$, —CH$_2$CH$_3$, or —C$_6$H$_6$. A compound of Formula XX-A or Formula XX-B includes any combination of $R^{10}$, $R^8$, $R^9$, $R^1$, and $R^{12}$. A compound of Formula XXI-B includes any combination of $R^{10}$, $R^8$, $R^1$, and $R^{12}$.

Formula XX-A

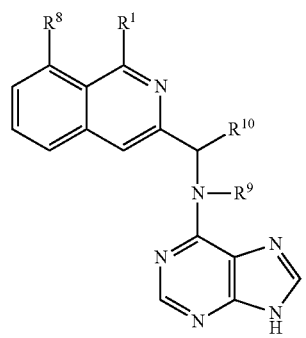

Formula XX-B

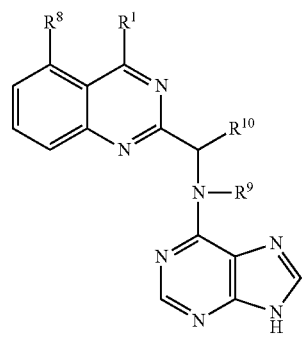

Formula XXI-B

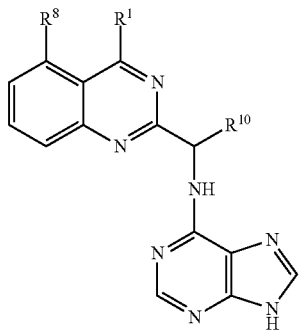

Additional exemplary compounds of Formula XIXA are illustrated in Table 4 and the following section.

Additional Exemplary Compounds of the invention include but are not limited to the following:

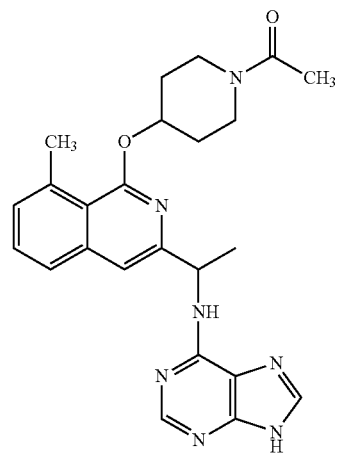

93
-continued
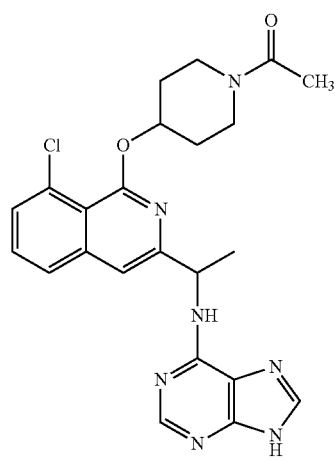
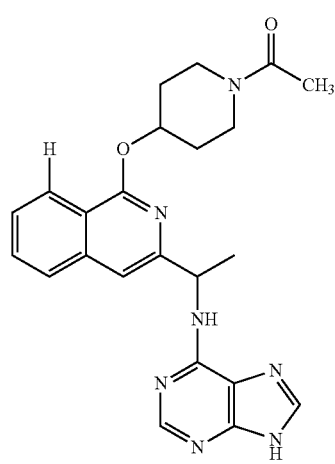
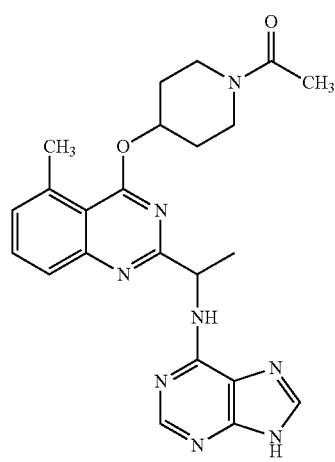
94
-continued
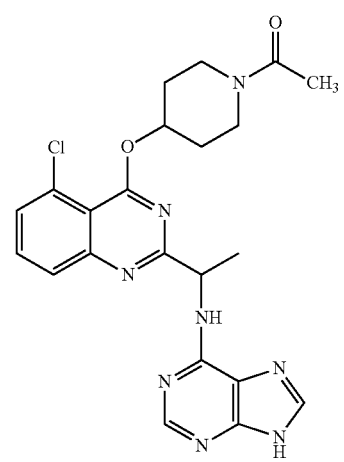
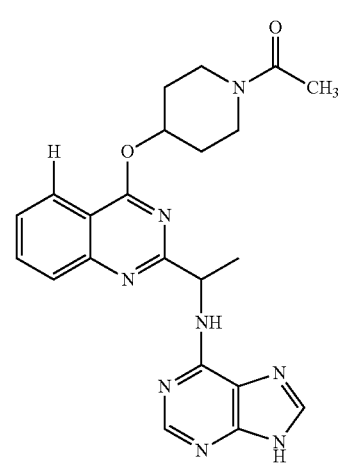
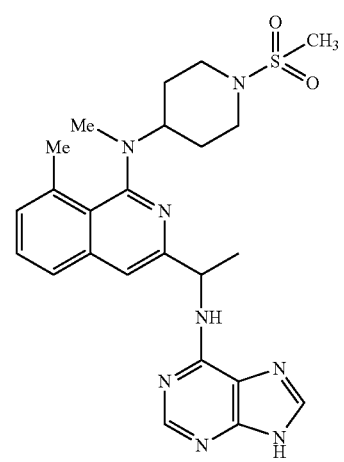

95
-continued
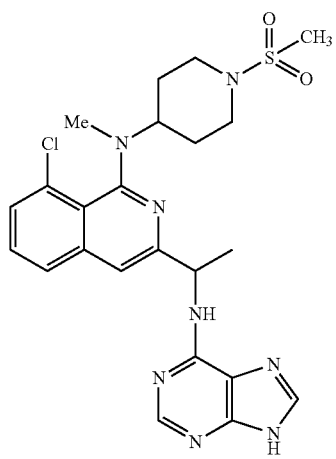
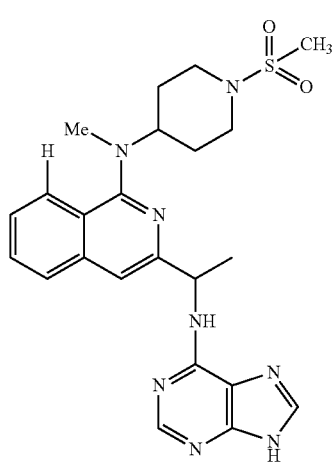
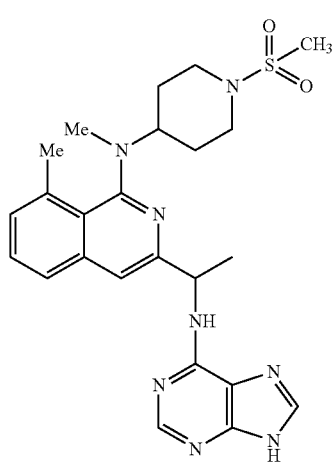
96
-continued
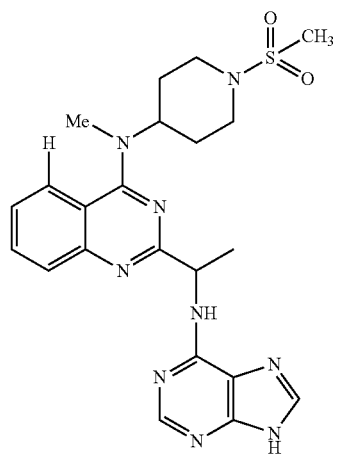
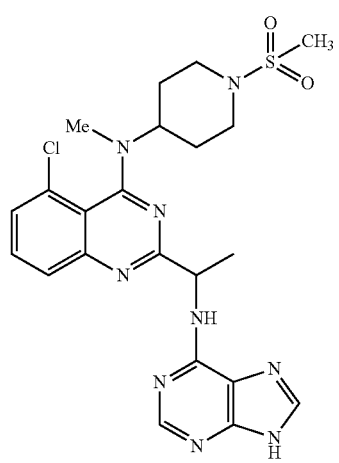
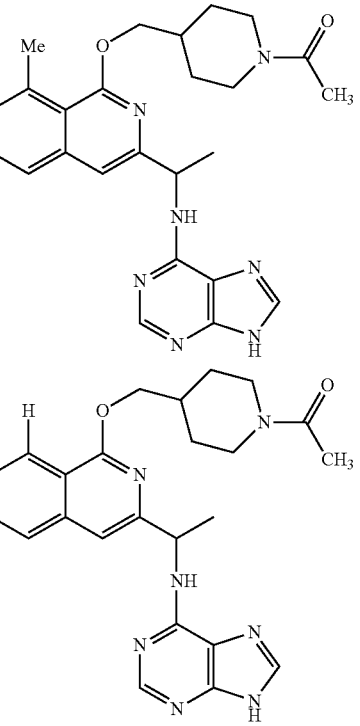

97
-continued
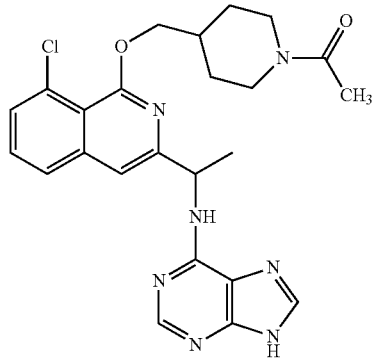
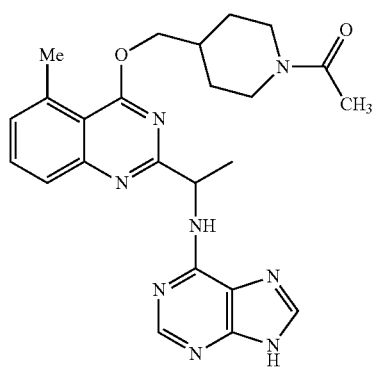
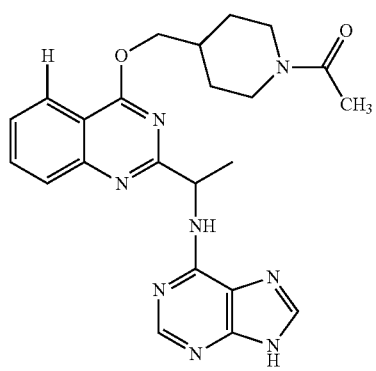
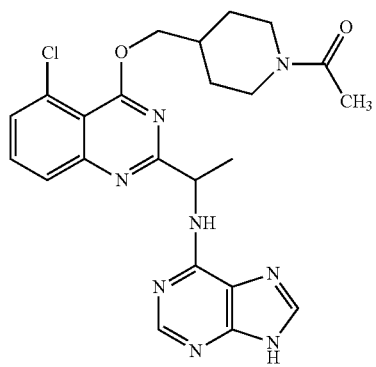
98
-continued
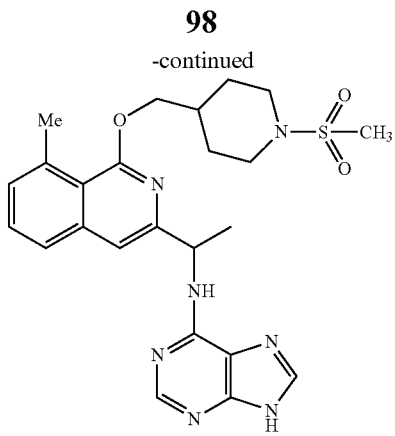
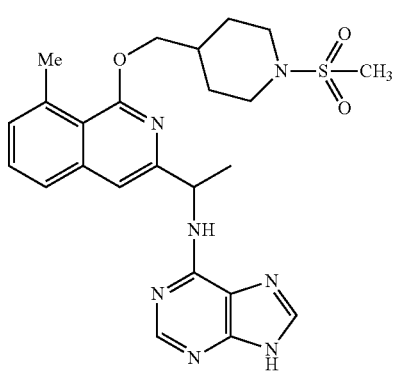
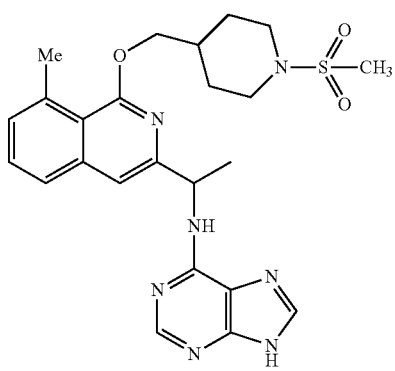
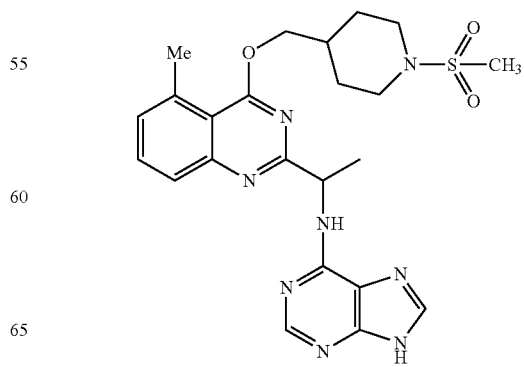

99
-continued

100
-continued

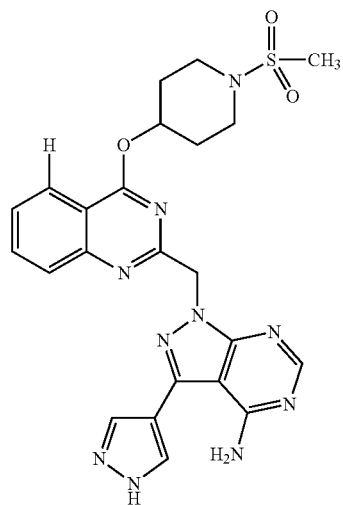
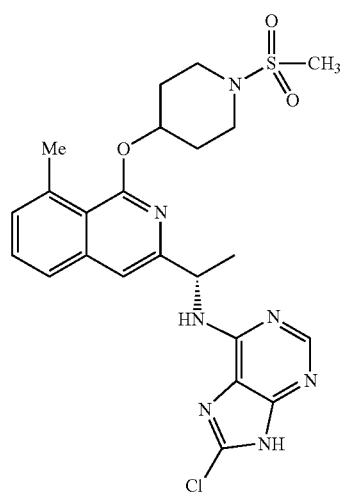
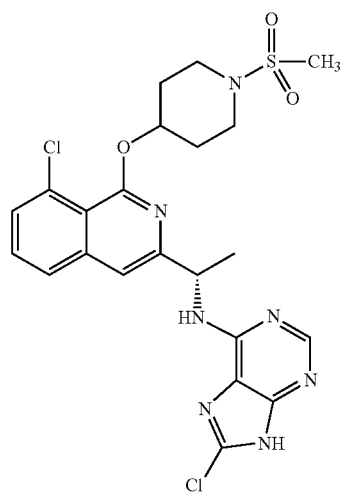
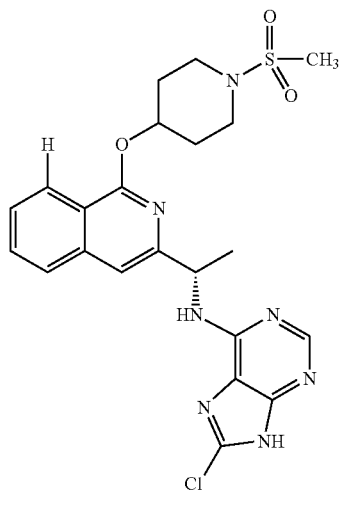
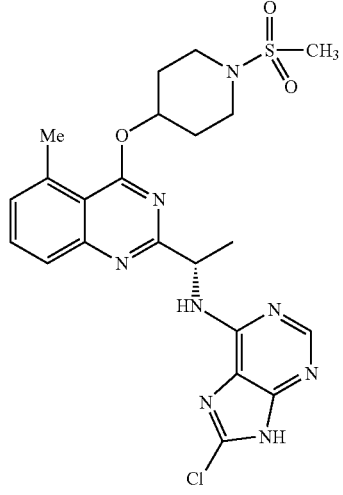
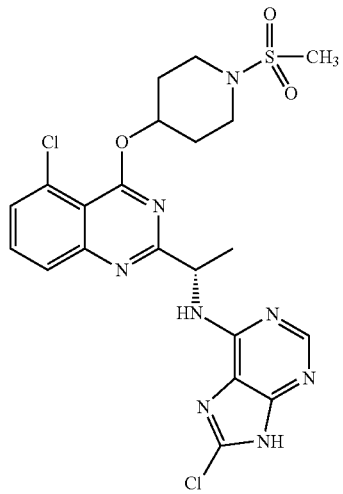

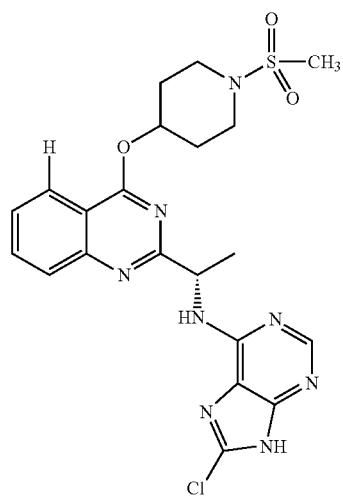
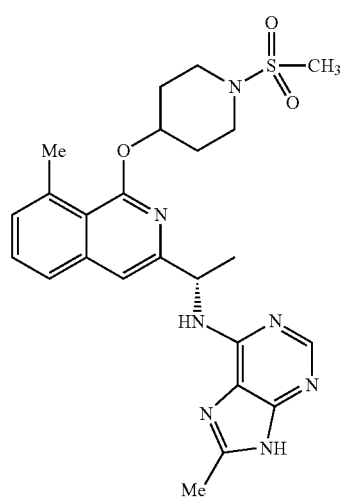
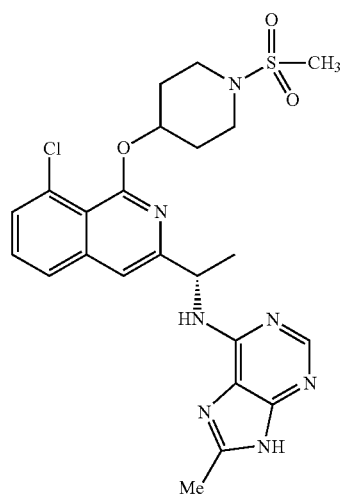
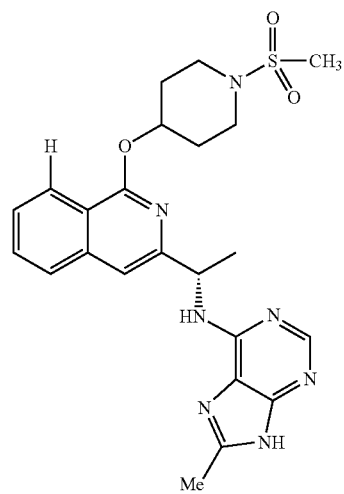
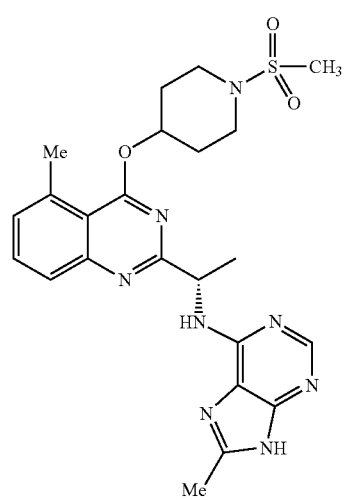
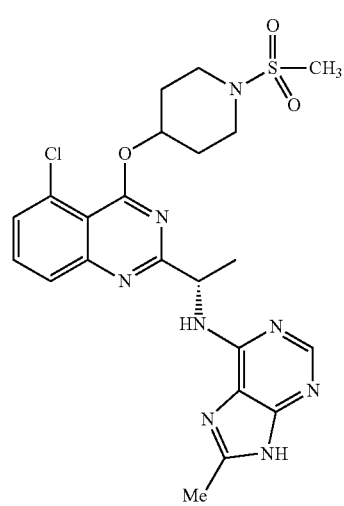

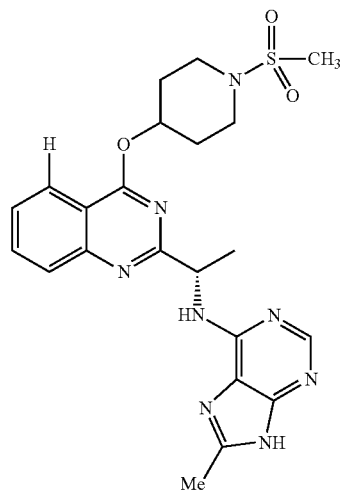
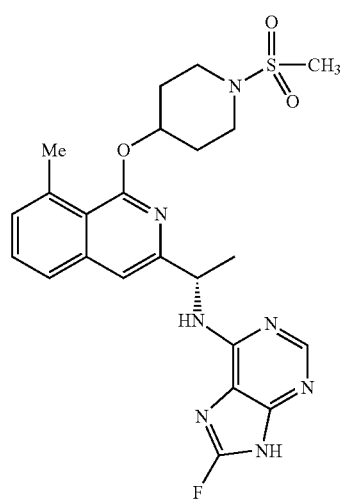
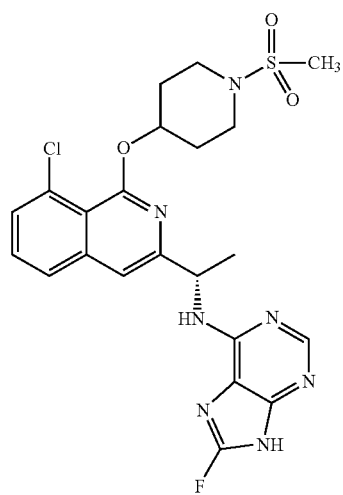
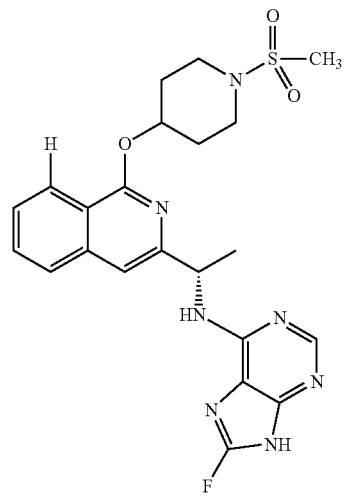
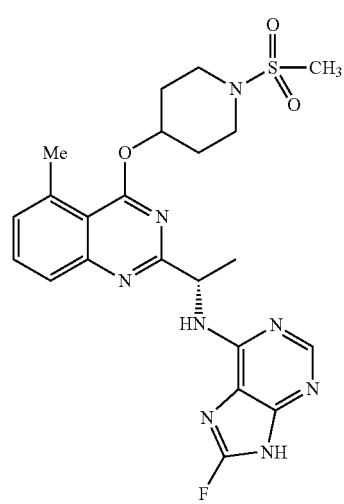
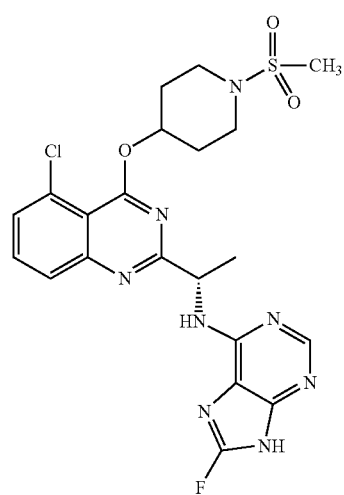

107
-continued
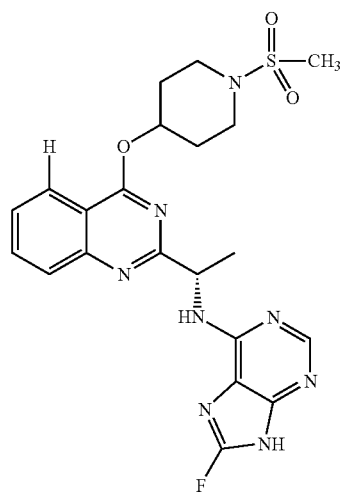
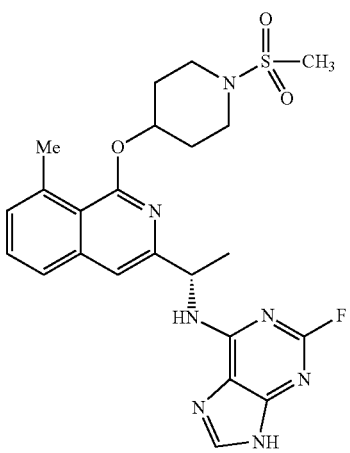
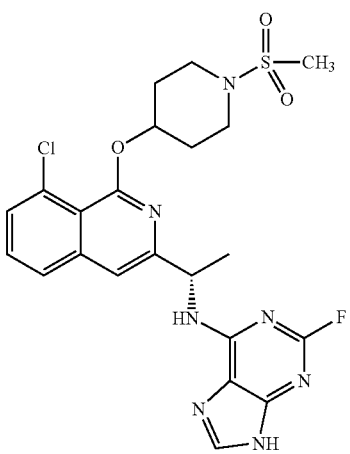
108
-continued
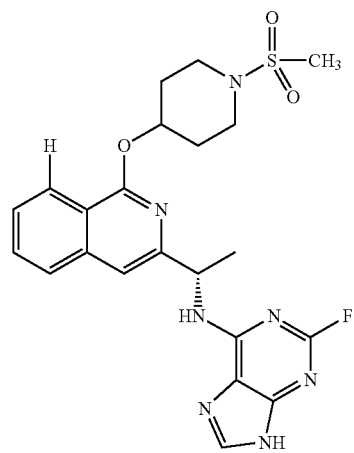
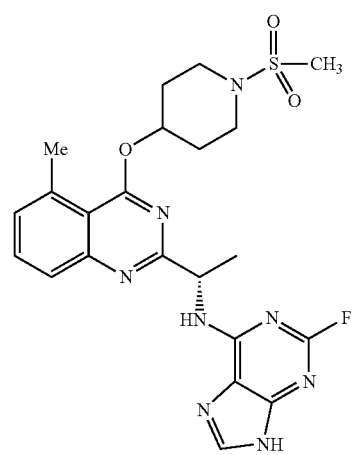
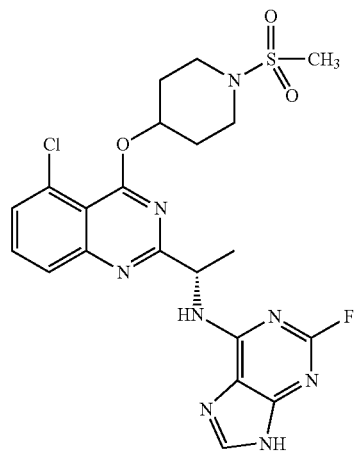

109
-continued
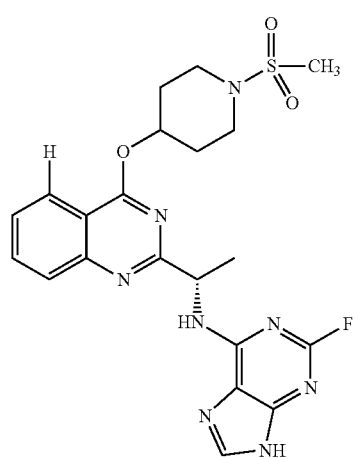
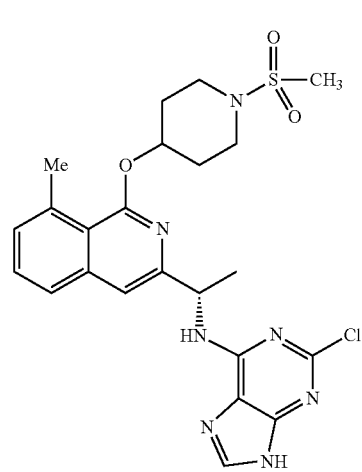
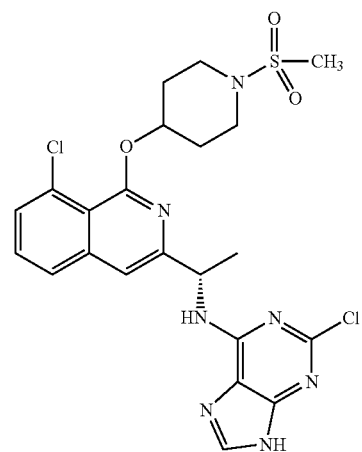
110
-continued
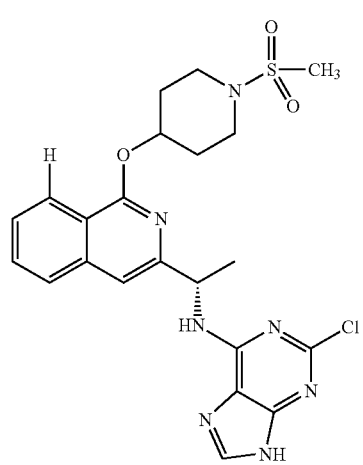
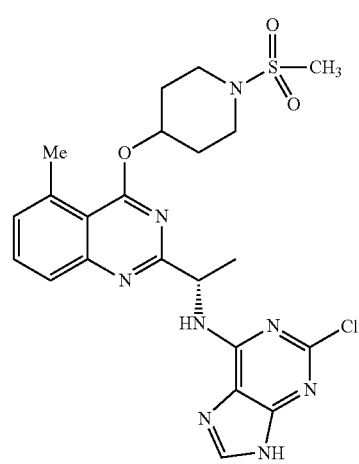
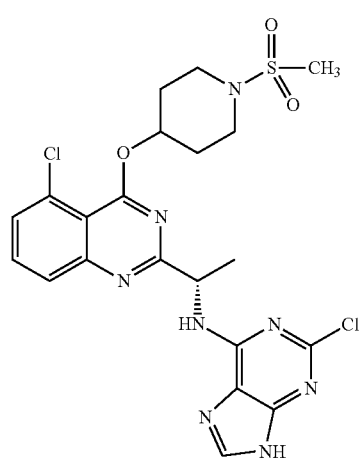

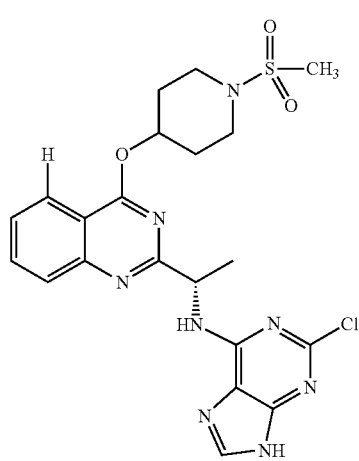
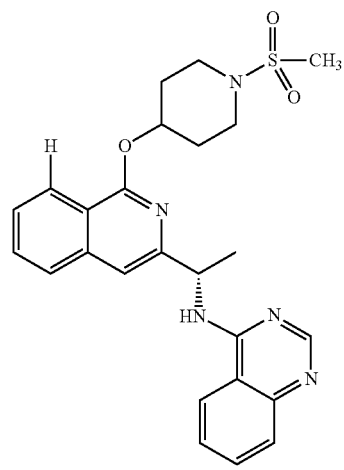
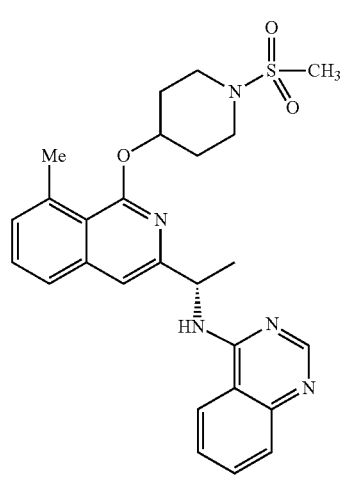
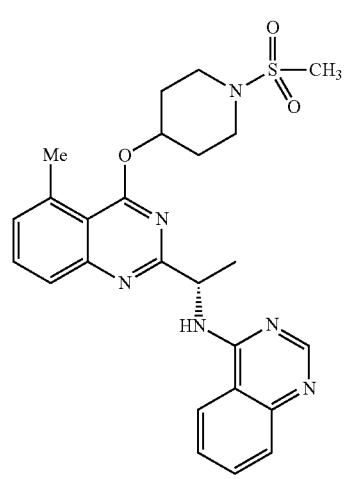
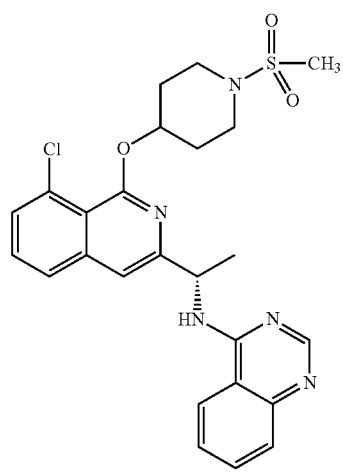
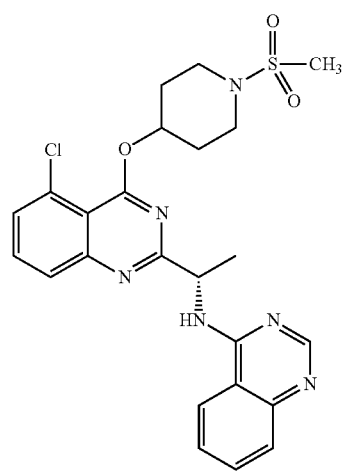

113
-continued
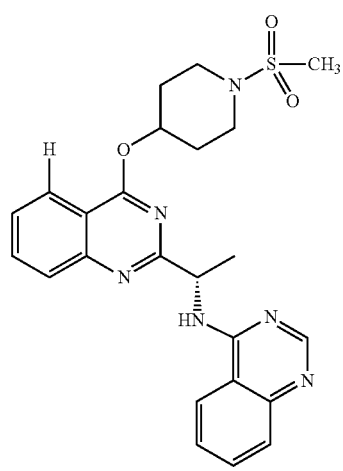
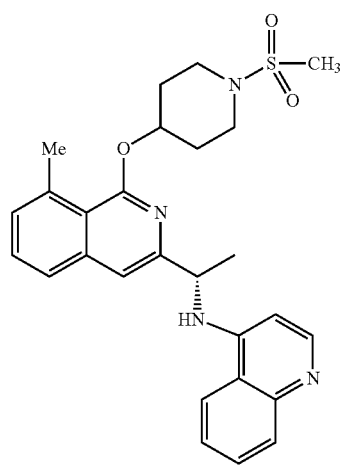
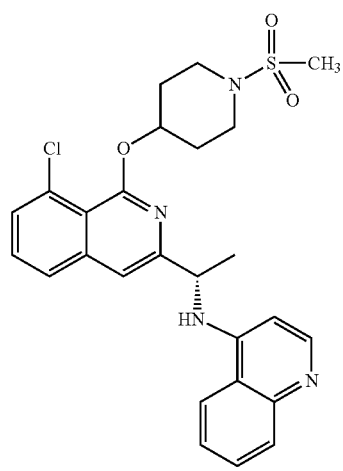
114
-continued
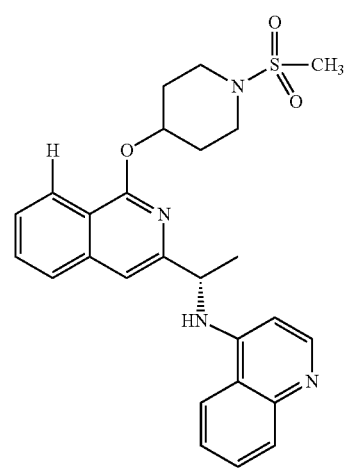
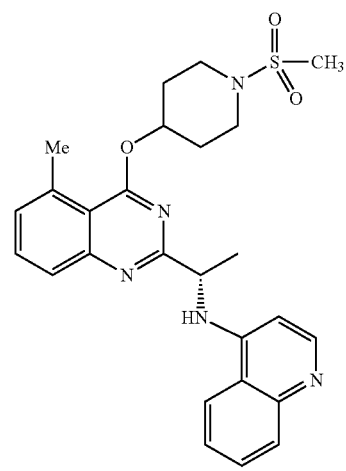
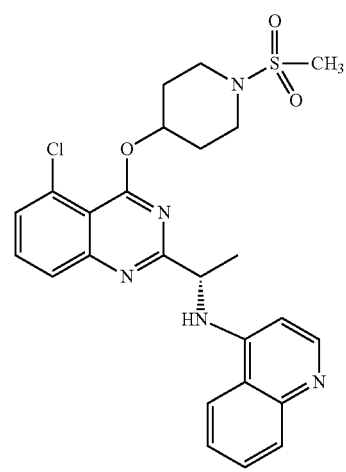

115
-continued
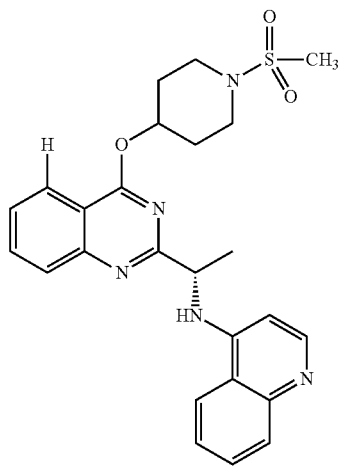
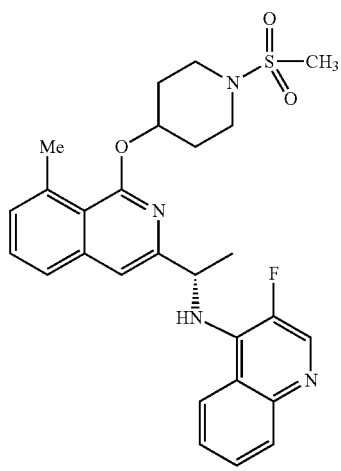
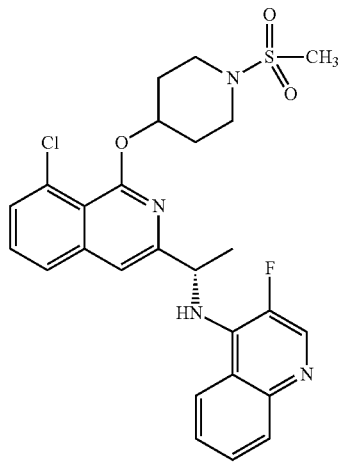
116
-continued
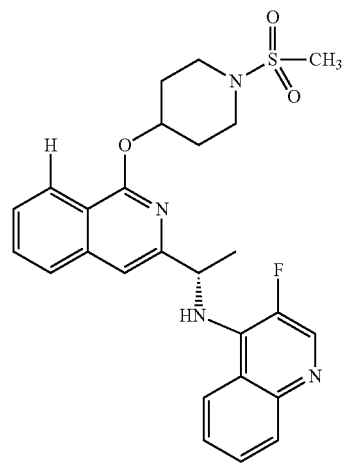
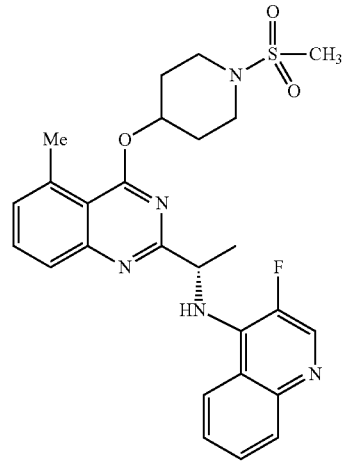
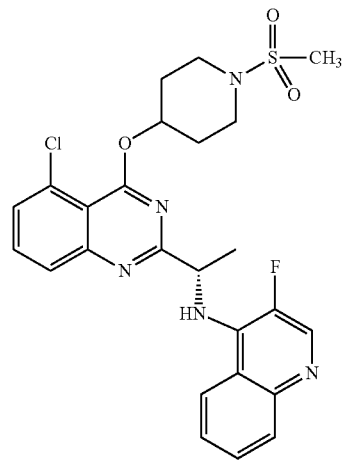

117
-continued
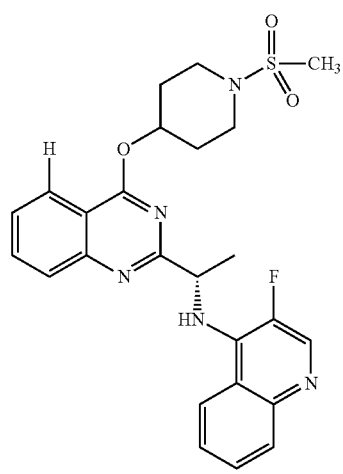
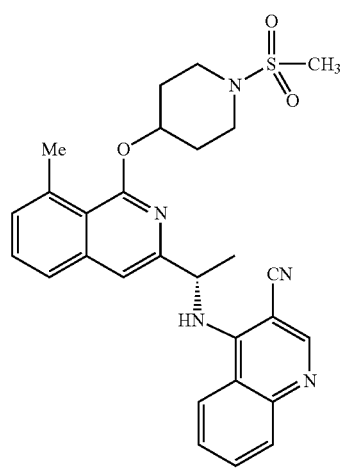
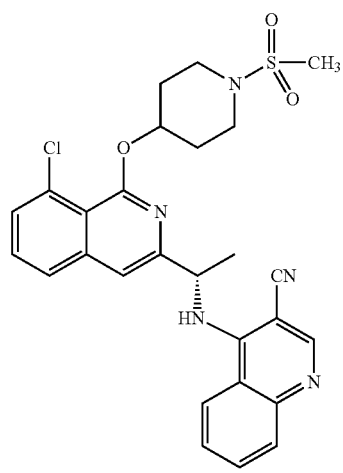
118
-continued
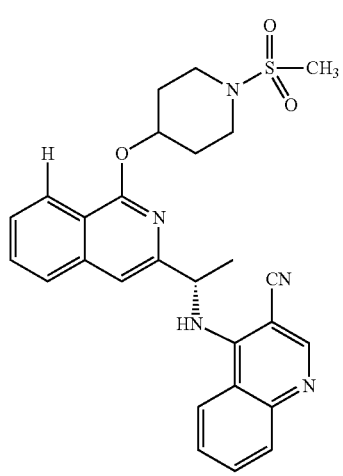
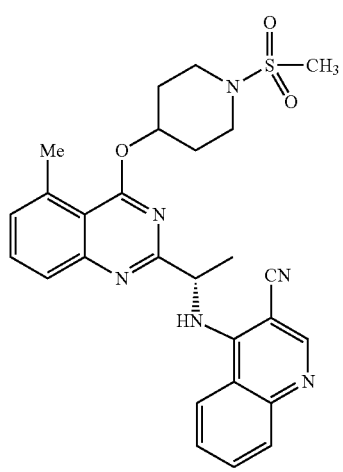
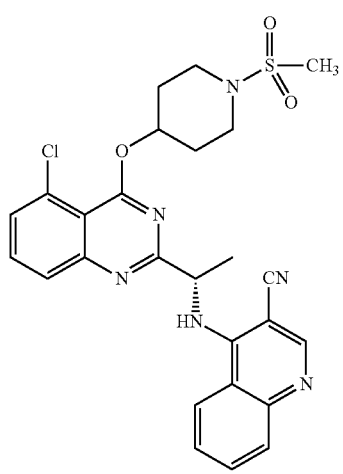

119
-continued
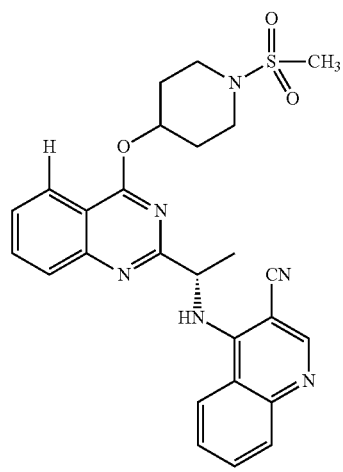
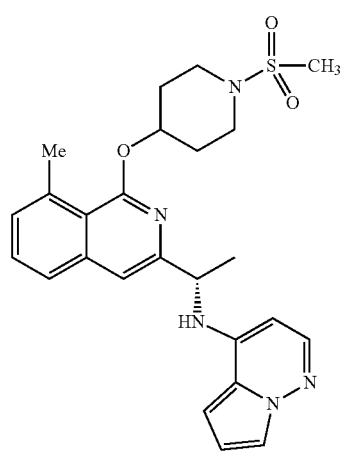
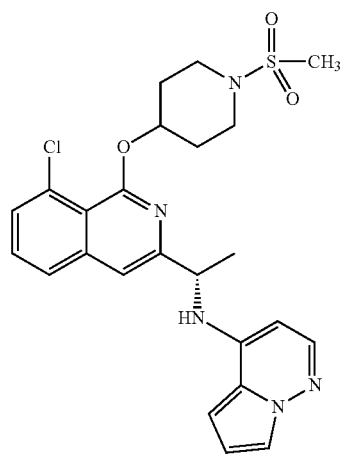
120
-continued
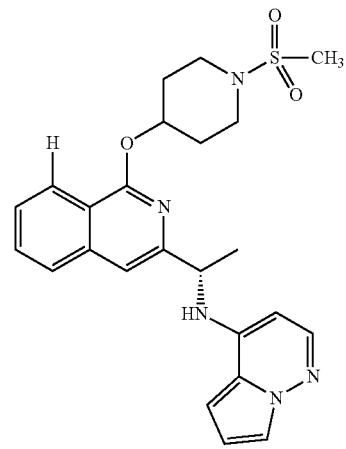
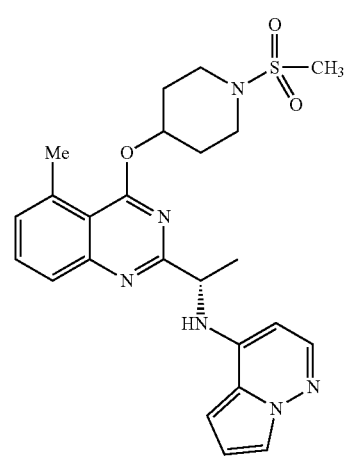
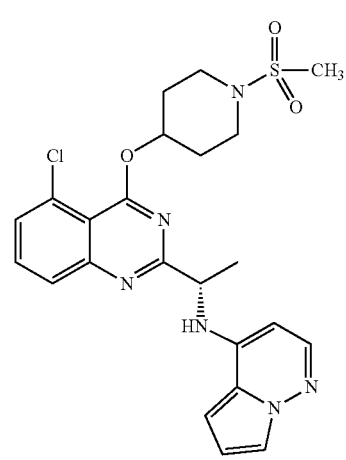

-continued

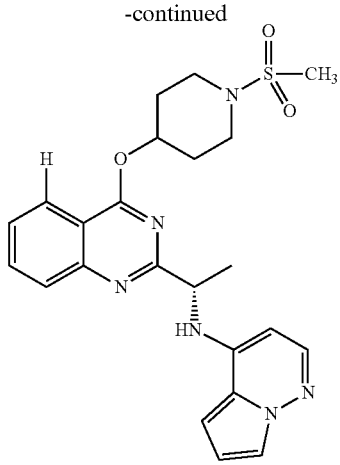

In some embodiments, the compounds of the present invention exhibits one or more functional characteristics disclosed herein. For example, one or more subject compounds bind specifically to a PI3 kinase. In some embodiments, the IC50 of a subject compound for p110α, p110β, p110γ, or p110δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compound may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, at least 10,100-fold, or lower, than the inhibitor's IC50 with respect to the rest of the other type I PI3-kinases.

The chemical entities described herein can be synthesized according to one or more illustrative schemes herein and/or techniques known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

Reaction Scheme 1:

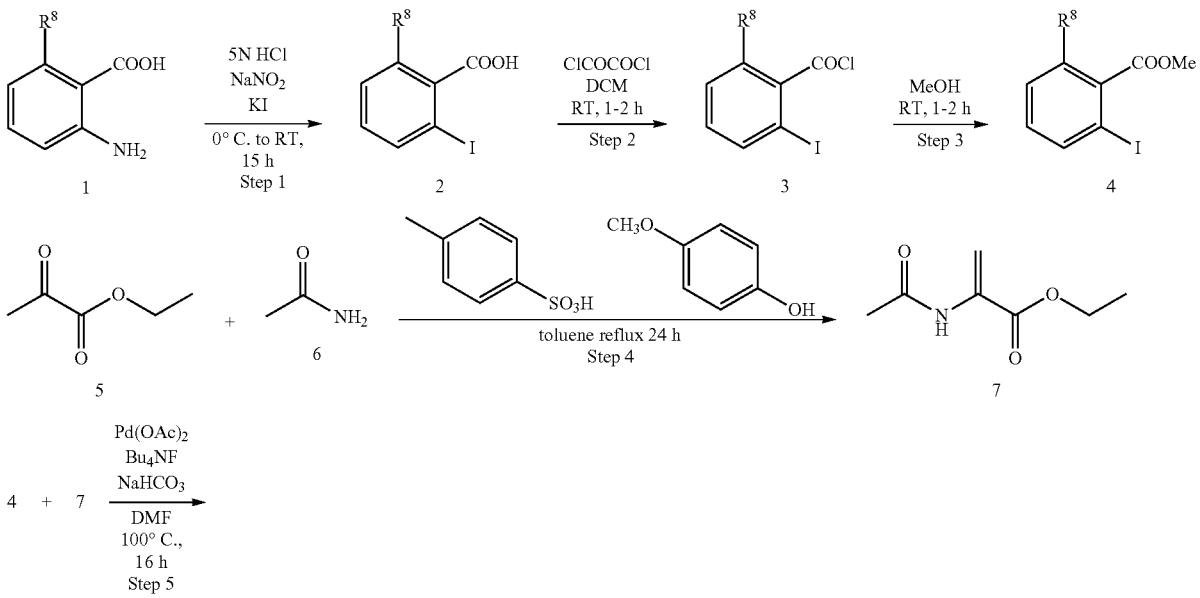

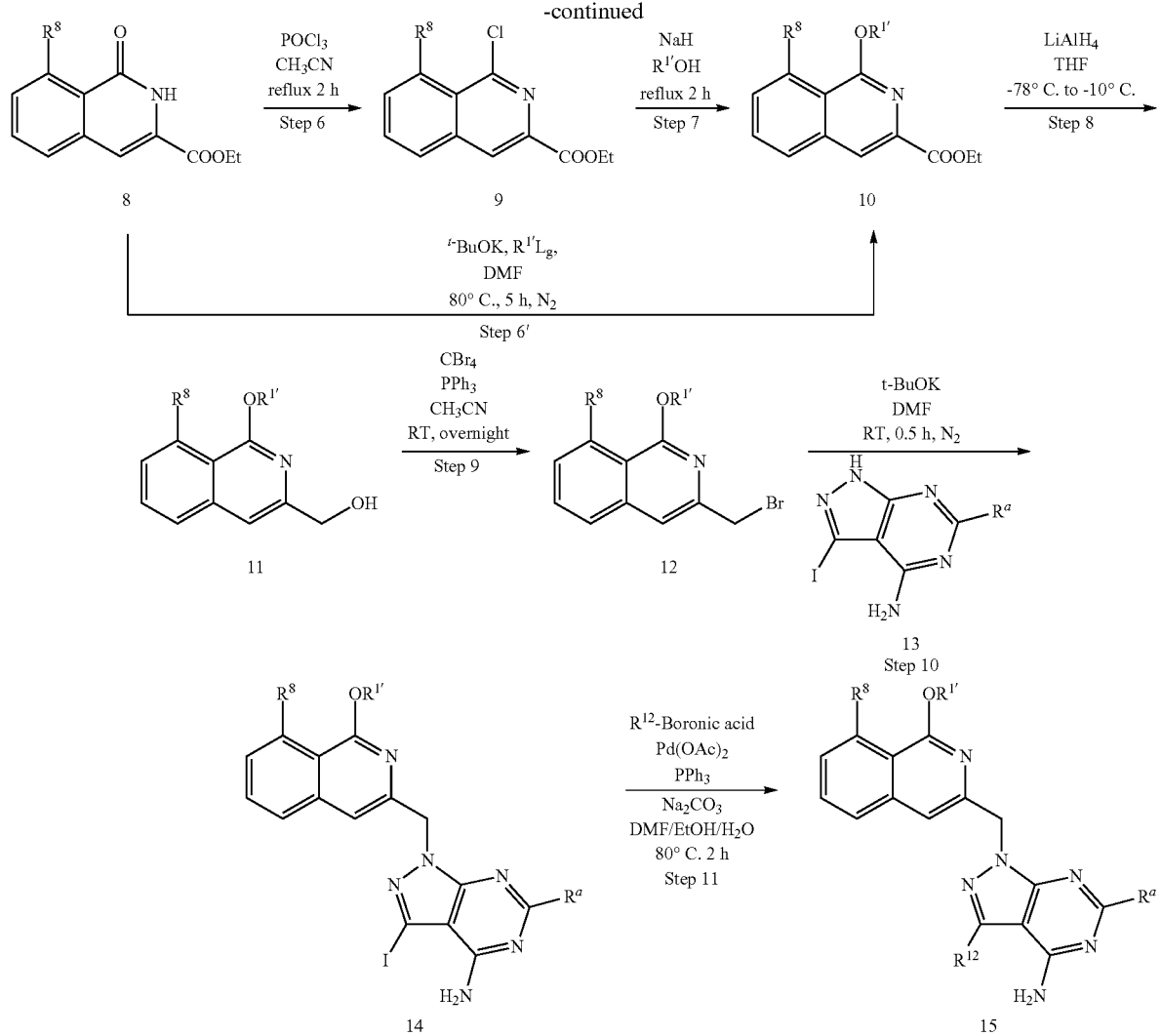

Referring to Scheme 1, Step 1, a compound of Formula 1, where $R^8$ includes but is not limited to alkyl, hydrogen or trifluoromethyl, is converted to an iodo substituted compound of Formula 2, for example by treating the compound with sodium nitrite, hydrochloric acid, and potassium iodide. The compound of Formula 2 is isolated. Referring to Scheme 1, Step 2, a compound of Formula 2 is converted to an acid chloride by reaction with a suitable reagent, i.e., oxalyl chloride to form a compound of Formula 3 which is either isolated or used directly in the next step. In Scheme 1, Step 3, the compound of Formula 3 is converted to a compound of Formula 4, by treatment with methanol. The compound of Formula 4 is isolated.

Referring to Scheme 1, Step 4, a ketoester of Formula 5 is reacted with an amide of Formula 6 in the presence of an acid, for example, toluenesulfonic acid, as well as para-methoxyphenol, in refluxing toluene to provide a compound of Formula 7, which is either isolated or used directly in the next step.

Referring to Scheme 1, Step 5, a compound of Formula 7 and a compound of Formula 4 are condensed, in the presence of, for example, palladium acetate, tetrabutylammonium fluoride, and sodium bicarbonate in dimethylformamide at 100° C., to form a compound of Formula 8, which is either isolated or used directly in the next step. In Scheme 1, Step 6, the compound of Formula 8 is converted to the compound of Formula 9 by reaction with, for example, phosphoryl chloride. The compound of Formula 9 is either isolated or used directly in the next step. In Scheme 1, Step 7, the compound of Formula 9 is converted to a compound of Formula 10 by reaction with a suitable alcohol of Formula $R^{1'}$ OH in the presence of a base, for example, sodium hydride. The compound of Formula 10 is either isolated or used directly in the next step. Alternatively, in Scheme 1, Step 6', a compound of Formula 8 is converted directly to a compound of Formula 10 by reaction with a base, for example, potassium tert-butoxide and a compound of Formula $R^{1'}$ $L_g$, where Lg is a leaving group which includes but is not limited to Cl, Br, I, OTs (toluenesulfonate), mesylate, and the like. The compound of Formula 10 is either isolated or used directly in the next step.

Referring to Scheme 1, Step 8, a compound of Formula 10 is treated with a reducing agent, such as, for example, lithium alumininum hydride to produce a compound of Formula 11, which is isolated. Referring to Scheme 1, Step 9, a compound of Formula 11 is converted to a compound of Formula 12 by treatment with, for example, carbon tetrabromide and triphenylphosphine. The compound of Formula 12 is either isolated or used directly in the next step. Referring to Scheme 1, Step 10, a compound of Formula 12 is alkylated with a pyrazolopyrimidine compound of Formula 13 in the presence of a base, such as, for example, potassium tert-butoxide to provide a compound of Formula 14, which is isolated. Referring to Scheme 1, Step 11, the pyrazolopyrimidinyl moiety of the compound of Formula 14 is coupled with an appropriate boronic acid such as an R'2-boronic acid, in the presence of palladium catalysts, such as palladium acetate; triphenylphosphine; and a base, such as sodium carbonate, to produce the compound of Formula 15, which is isolated.

Reaction Scheme 2:

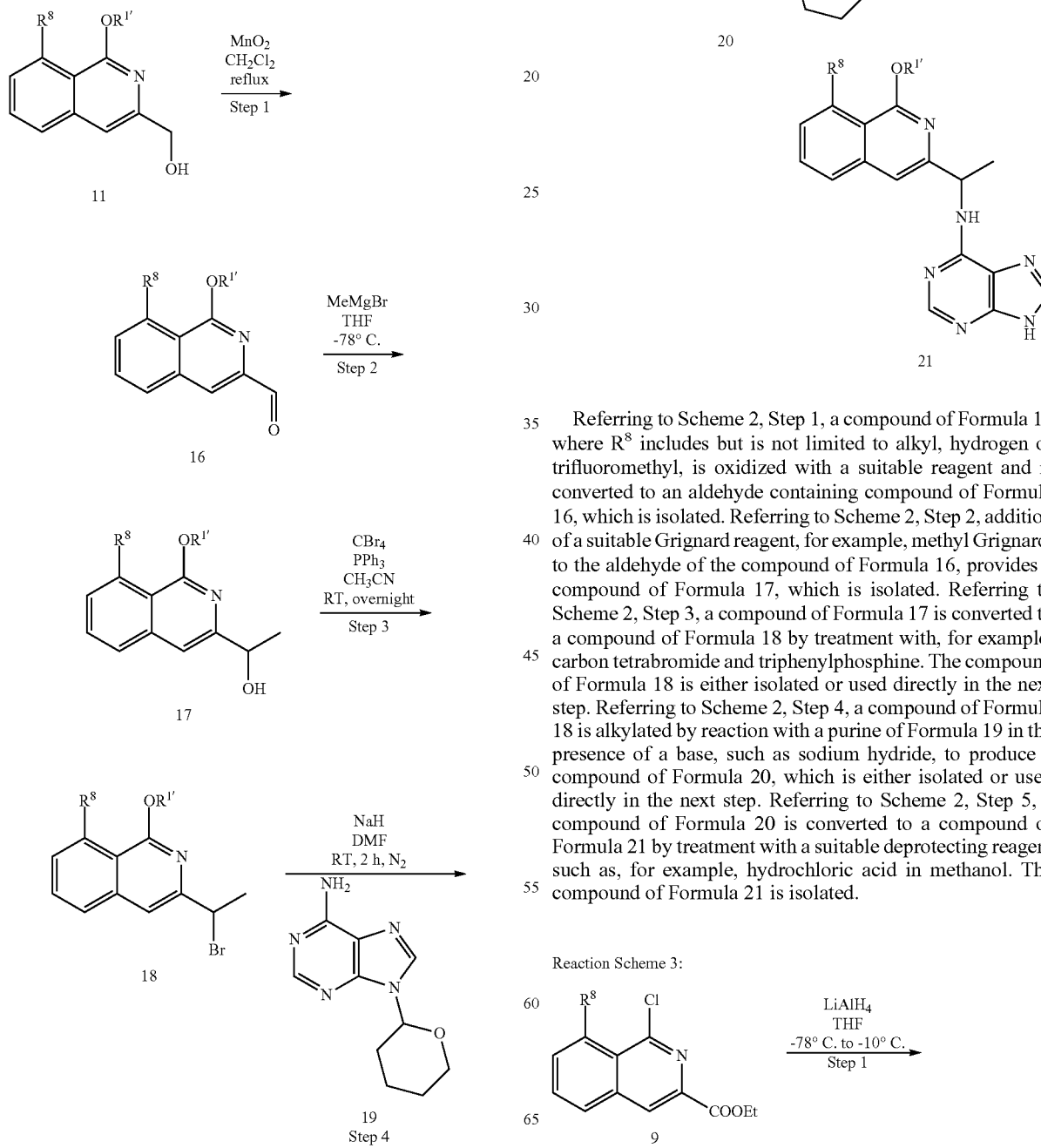

Referring to Scheme 2, Step 1, a compound of Formula 11 where $R^8$ includes but is not limited to alkyl, hydrogen or trifluoromethyl, is oxidized with a suitable reagent and is converted to an aldehyde containing compound of Formula 16, which is isolated. Referring to Scheme 2, Step 2, addition of a suitable Grignard reagent, for example, methyl Grignard, to the aldehyde of the compound of Formula 16, provides a compound of Formula 17, which is isolated. Referring to Scheme 2, Step 3, a compound of Formula 17 is converted to a compound of Formula 18 by treatment with, for example, carbon tetrabromide and triphenylphosphine. The compound of Formula 18 is either isolated or used directly in the next step. Referring to Scheme 2, Step 4, a compound of Formula 18 is alkylated by reaction with a purine of Formula 19 in the presence of a base, such as sodium hydride, to produce a compound of Formula 20, which is either isolated or used directly in the next step. Referring to Scheme 2, Step 5, a compound of Formula 20 is converted to a compound of Formula 21 by treatment with a suitable deprotecting reagent such as, for example, hydrochloric acid in methanol. The compound of Formula 21 is isolated.

Reaction Scheme 3:

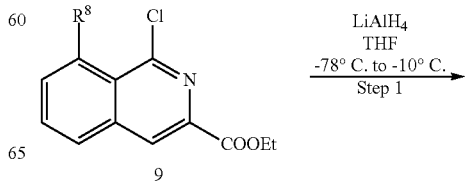

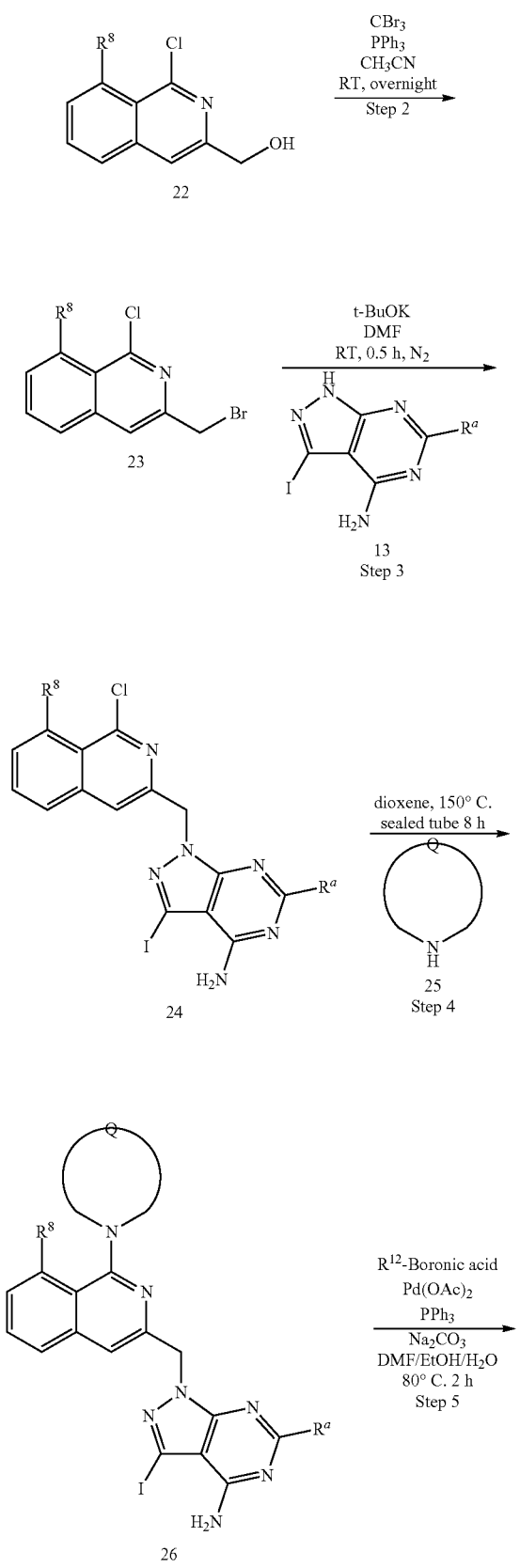

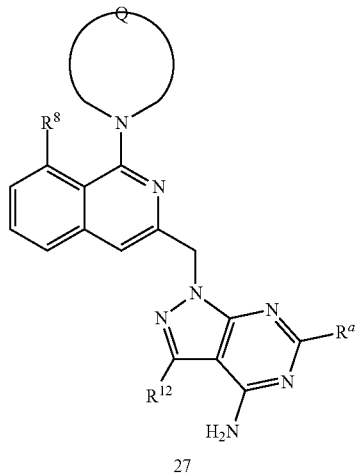

Referring to Scheme 3, Step 1, a compound of Formula 9, wherein $R^8$ includes but is not limited to alkyl, hydrogen or trifluoromethyl, is treated with lithium aluminum hydride in tetrahydrofuran at −78° C., to produce a compound of Formula 22. The compound of Formula 22 is isolated. Referring to Scheme 3, Step 2, a compound of Formula 22 is reacted with, for example, carbon tetrabromide and triphenylphosphine, to produce a compound of Formula 23, which is isolated. Referring to Scheme 3, Step 4, the compound of Formula 23 is coupled with a pyrazolopyrimidine compound of Formula 13 in the presence of a base, such as, for example, potassium tert-butoxide to provide a compound of Formula 24. The compound of Formula 24 is isolated. Referring to Scheme 3, Step 4, the compound of Formula 24 is coupled with an amine of Formula 25 by heating in at 150° C. in a sealed tube in dioxene.

An amine having a structure of:

includes the class of primary amine, secondary amines, and secondary amines which are part of a cyclic moiety. The cyclic moiety may contain additional heteroatom ring atoms and wherein the cyclic moiety may be further substituted on the ring atoms. The product of reaction step 4 is a compound of Formula 26, which is isolated or is used directly in the next step. Referring to Scheme 3, Step 5, the compound of Formula 26 is coupled with an appropriate boronic acid such as an $R^{12}$-boronic acid, in the presence of palladium catalysts, such as palladium acetate; triphenylphosphine; and a base, such as sodium carbonate, to produce a compound of Formula 15, which is isolated.

Reaction Scheme 4:

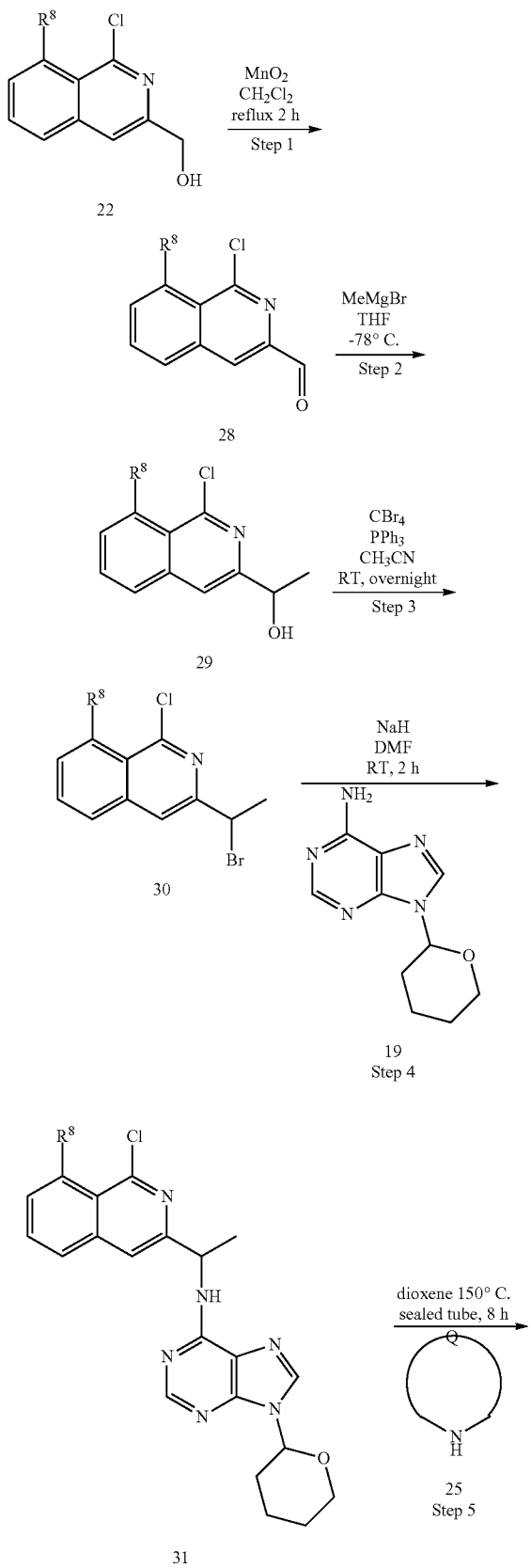

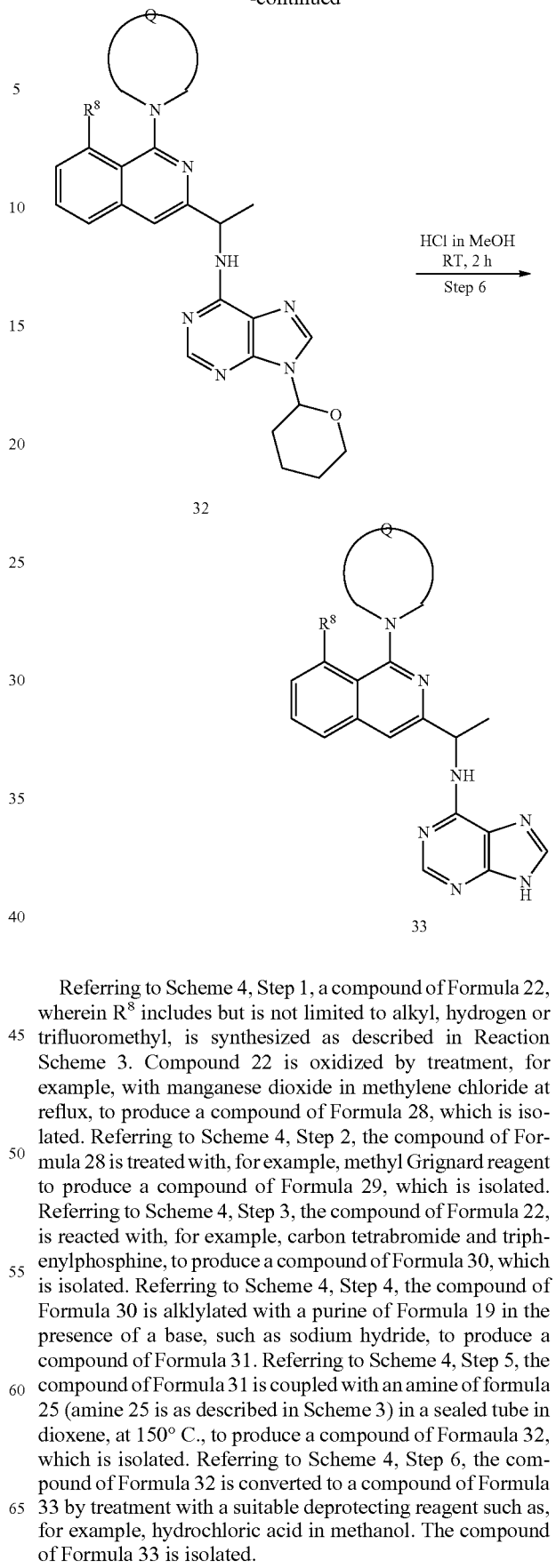

Referring to Scheme 4, Step 1, a compound of Formula 22, wherein $R^8$ includes but is not limited to alkyl, hydrogen or trifluoromethyl, is synthesized as described in Reaction Scheme 3. Compound 22 is oxidized by treatment, for example, with manganese dioxide in methylene chloride at reflux, to produce a compound of Formula 28, which is isolated. Referring to Scheme 4, Step 2, the compound of Formula 28 is treated with, for example, methyl Grignard reagent to produce a compound of Formula 29, which is isolated. Referring to Scheme 4, Step 3, the compound of Formula 22, is reacted with, for example, carbon tetrabromide and triphenylphosphine, to produce a compound of Formula 30, which is isolated. Referring to Scheme 4, Step 4, the compound of Formula 30 is alklylated with a purine of Formula 19 in the presence of a base, such as sodium hydride, to produce a compound of Formula 31. Referring to Scheme 4, Step 5, the compound of Formula 31 is coupled with an amine of formula 25 (amine 25 is as described in Scheme 3) in a sealed tube in dioxene, at 150° C., to produce a compound of Formaula 32, which is isolated. Referring to Scheme 4, Step 6, the compound of Formula 32 is converted to a compound of Formula 33 by treatment with a suitable deprotecting reagent such as, for example, hydrochloric acid in methanol. The compound of Formula 33 is isolated.

Reaction Scheme 5:

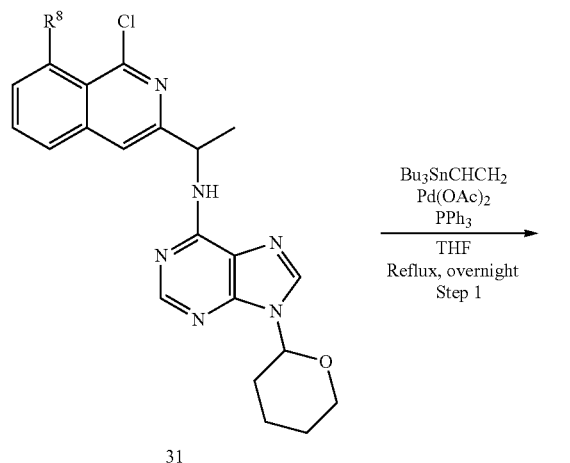

31

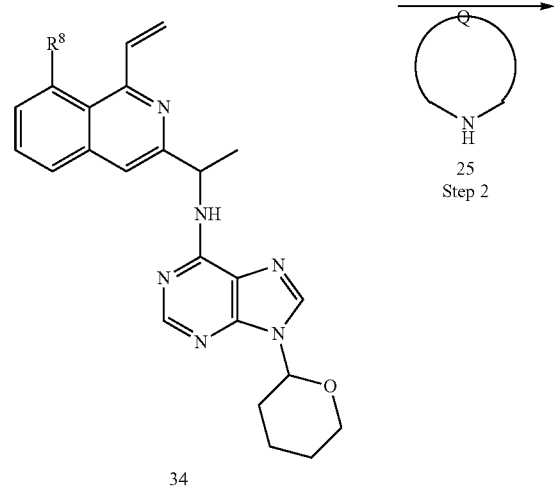

34

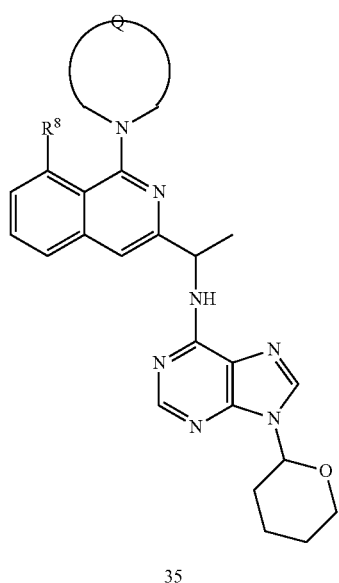

35

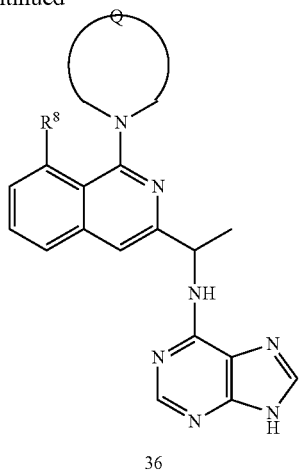

36

Referring to Scheme 5, Step 1, a compound of Formula 31, wherein $R^8$ includes but is not limited to alkyl, hydrogen or trifluoromethyl, is synthesized as described in Reaction Scheme 4. The compound of Formula 31 is converted to a compound of Formula 34 by, for example, reaction with tributyl vinyl stannane, in the presence of triphenylphosphine, and with palladium acetate catalysis. The compound of Formula 34 is isolated. Referring to Scheme 5, Step 2, the compound of Formula 34 is coupled with an amine of formula 25 (amine 25 is as described in Scheme 3) in a sealed tube in dioxene, at 150° C., to produce a compound of Formula 35, which is isolated. Referring to Scheme 5, Step 2, the compound of Formula 35 is converted to a compound of Formula 36 by treatment with a suitable deprotecting reagent such as, for example, hydrochloric acid in methanol. The compound of Formula 36 is isolated.

Reaction Scheme 6:

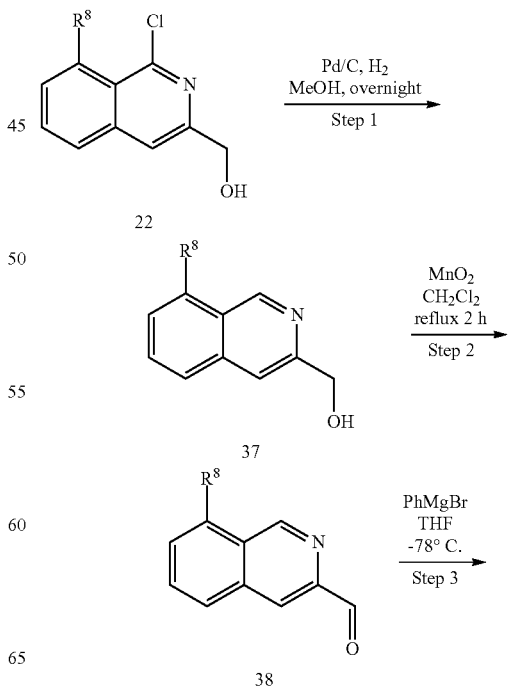

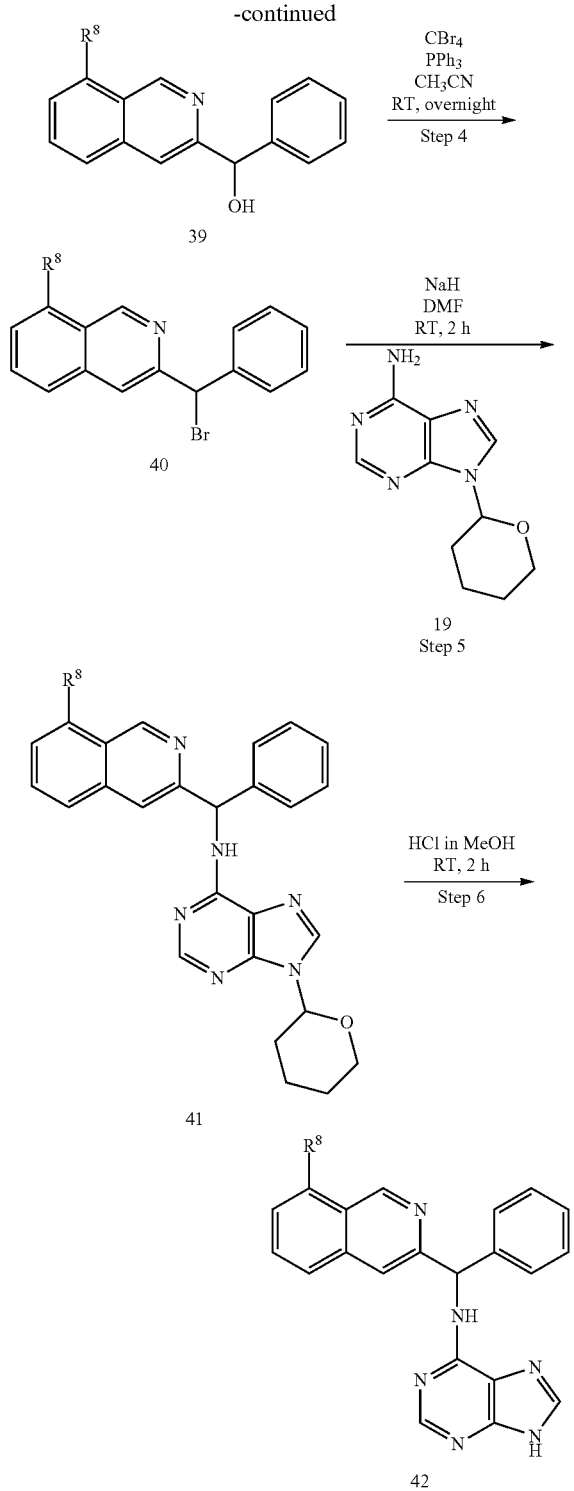

in methylene chloride, to produce a compound of Formula 38 (which is isolated). Referring to Scheme 6, Step 3, the compound of Formula 38 is reacted with, for example, phenyl Grignard reagent in tetrahydrofuran at −78° C., to produce a compound of Formula 39 (which is isolated). Referring to Scheme 6, Step 4, the compound of Formula 39 is reacted with, for example, carbon tetrabromide and triphenylphosphine, to produce a compound of Formula 40, which is isolated. Referring to Scheme 6, Step 5, the compound of Formula 40 is alklylated with a purine of Formula 19 in the presence of a base, such as sodium hydride, to produce a compound of Formula 41. The compound of Formula 41 is isolated. Referring to Scheme 6, Step 6, the compound of Formula 41 is converted to a compound of Formula 42 by treatment with a suitable deprotecting reagent such as, for example, hydrochloric acid in methanol. The compound of Formula 42 is isolated.

The invention provides pharmaceutical compositions comprising one or more compounds of the present invention.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rheumatoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The subject pharmaceutical compositions are typically formulated to provide a therapeutically effective amount of a compound of the present invention as the active ingredient, or a pharmaceutically acceptable salt, ester, prodrug, solvate, hydrate or derivative thereof. Where desired, the pharmaceu- Referring to Scheme 6, Step 1, a compound of Formula 22, wherein $R^8$ includes but is not limited to alkyl, hydrogen or trifluoromethyl, is synthesized as described in Reaction Scheme 3. The compound of Formula 22 is hydrogenolyzed, for example, by reacting with palladium on carbon under hydrogen atmosphere in methanol, to produce a compound of Formula 37. The compound of Formula 37 is isolated. Referring to Scheme 6, Step 2, the compound of Formula 37 is oxidized, for example, by treatment with manganese dioxide tical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0-003 g, 0.002 g, 0.001 g, 0.0009 g, 0.0008 g, 0.0007 g, 0.0006 g, 0.0005 g, 0.0004 g, 0.0003 g. 0.0002 g, or 0.0001 g.

In some embodiments, the amount of one or more of the compounds of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the present invention typically contains an active ingredient (e.g., a compound of the present invention or a pharmaceutically acceptable salt and/or coordination complex thereof, and one or more pharmaceutically acceptable excipients, carriers, including but not limited inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration In some embodiments, the invention provides a pharmaceutical composition for oral administration containing a compound of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, pahnitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phytosterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidine, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g., Transdermal) Delivery. In some embodiments, the invention provides a pharmaceutical composition for transdermal delivery containing a compound of the present invention and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233, 5,040,548, 5,061,273, 5,496,346, 5,292,331, 5,674,278, 3,657,744, 4,739,762, 5,195,984, 5,292,331, 5,674,278, 5,879,382, 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a compound or compounds of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The invention also provides methods of using the compounds or pharmaceutical compositions of the present invention to treat disease conditions, including but not limited to diseases associated with malfunctioning of one or more types of PI3 kinase and/or mTOR. A detailed description of conditions and disorders mediated by p110δ kinase activity is set forth in Sadu et al., WO 01/81346, which is incorporated herein by reference in its entirety for all purposes.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of PI3K-δ may further provide for a reduction in the inflammatory or undesirable immune response without a concomitant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one or more of the subject methods are effective in ameliorating symptoms assoicated with rheumatoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotrophic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptotic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, osteoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fascitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

Methods are further provided for administering the compounds of the present invention via eye drop, intraocular injection, intravitreal injection, topically, or through the use of a drug eluting device, microcapsule, implant, or microfluidic device. In some cases, the compounds of the present invention are administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltriethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltriethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

The invention further provides methods of modulating a PI3K and/or mTor kinase activity by contacting the kinase with an amount of an effective amount of compound of the invention. Modulate can be inhibiting or activating kinase activity. In some embodiments, the invention provides methods of inhibiting kinase activity by contacting the kinase with an amount of an effective amount of a compound of the invention in solution. In some embodiments, the invention provides methods of inhibiting the kinase activity by contacting a cell, tissue, organ that express the kinase of interest. In some embodiments, the invention provides methods of inhibiting kinase activity in subject including but not limited to rodents and mammal (e.g., human) by administering into the subject an effective amount of a compound of the invention. In some embodiments, the percentage of inhibiting exceeds 50%, 60%, 70%, 80%, or 90%.

In some embodiments, the kinase is selected from the group consisting of PI3 kinase including different isorforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-napthyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparinkoumadin.

In another one aspect, this invention also relates to methods and pharmaceutical compositions for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compounds describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino] methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administer with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

Administration of the compounds of the present invention can be effected by any method that enables delivery of the compounds to the site of action. An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

When a compound of the invention, is administered in a composition that comprises one or more agents, and the agent has a shorter half-life than the compound of the invention unit dose forms of the agent and the compound of the invention may be adjusted accordingly.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

Example 1

Synthesis of 1-((1-isopropoxy-8-methylisoquinolin-3-yl)methyl)-3-(1H-pyrazol-4-yl)-1H-pyrazolo[3,4-d]pyrimidin-4-amine (Compound 113)

Scheme 7: Synthesis of 1-((1-isopropoxy-8-methylisoquinolin-3-yl)methyl)-3-(1H-pyrazol-4-yl)-1H-pyrazolo[3,4-d]pyrimidin-4-amine (Compound 113) is described.

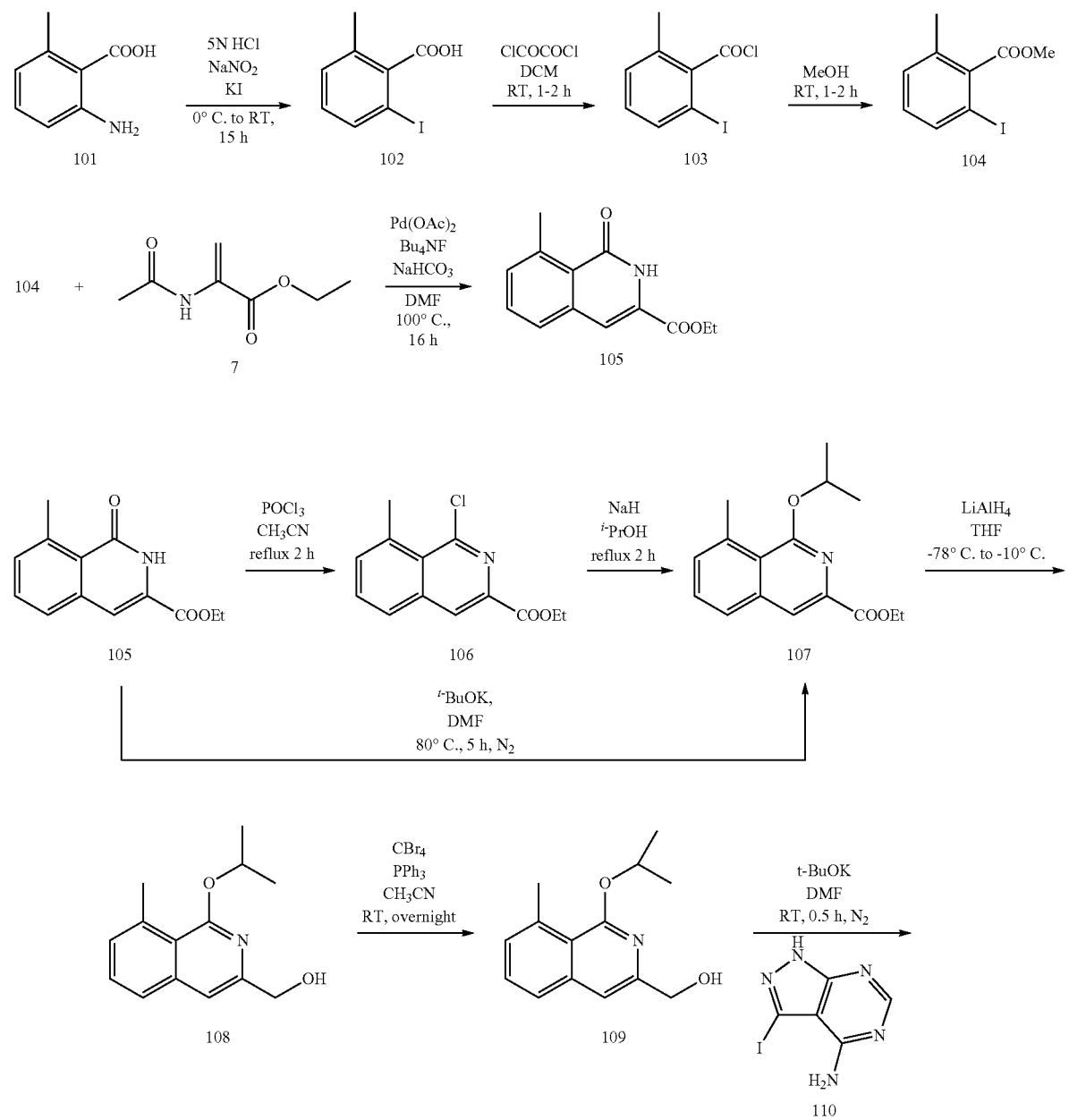

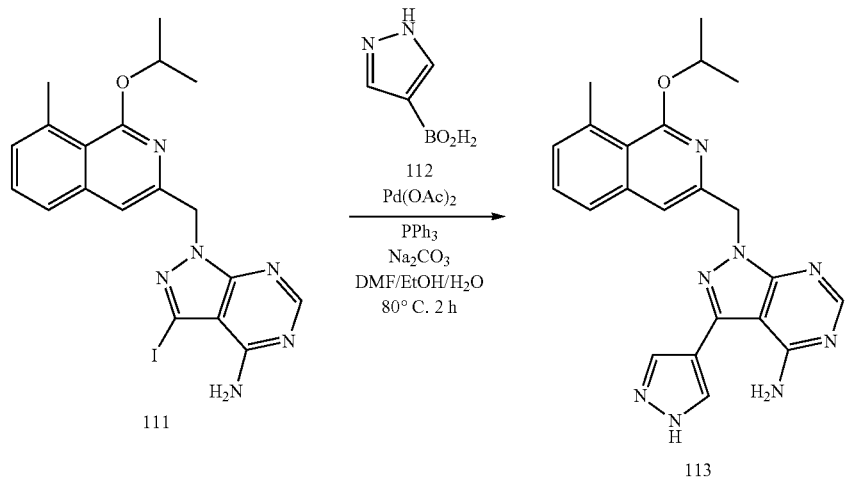

Amino acid 101 is converted to iodo acid 102 by treatment with 5 N hydrochloric acid, sodium nitrite and potassium iodide, warming the reaction mixture from 0° C. to room temperature and continuing to stir the reaction for 15 hours. Iodo acid 102 is treated with oxalyl chloride in methylene chloride at room temperature to produce the iodo acid chloride 103, which is converted to the corresponding methyl ester 104 upon reaction with methanol at room temperature.

Methyl ester 104 is coupled with compound 7, which is synthesized as described in Reaction Scheme 1, in the presence of palladium acetate coupling catalyst, tetrabutylammonium fluoride, sodium bicarbonate in dimethyl formamide at 100° C., to produce compound 105. Compound 105 is converted to isopropoxy isoquinoline compound 107 by one of two methods. In the first method, compound 105 is treated with phosphoryl chloride in refluxing acetonitrile to produce the 1-chloro isoquinoline compound 106, which is then reacted with isopropyl alcohol in the presence of sodium hydride base to product compound 107. Alternatively, compound 105 is converted directly to compound 107 by reaction with isopropyl bromide, in dimethylformamide at 80° C., in the presence of potassium tert-butoxide.

Compound 107 is treated with lithium aluminum hydride, reducing the ester, to produce compound 108. The hydroxyl moiety of compound 108 is brominated with carbon tetrabromide, in the presence of triphenyl phosphine in acetonitrile at room temperature overnight. Pyrazolopyrimidine 110 is coupled with bromide 109, using potassium tert-butoxide base in dimethylformamide at room temperature, to produce compound 111. Compound 111 is coupled with boronic acid 112 in the presence of palladium acetate, triphenylphosphine, sodium carbonate, in a mixture of dimethylformamide, ethanol and water at 80° C. to produce the product, compound 113.

Example 2

Synthesis of N-(1-(1-isopropoxy-8-methylisoquinolin-3-yl)ethyl)-9H-purin-6-amine (Compound 119)

Scheme 8: Synthesis of N-(1-isopropoxy-8-methylisoquinolin-3-yl)ethyl)-9H-purin-6-amine (Compound 119) is described.

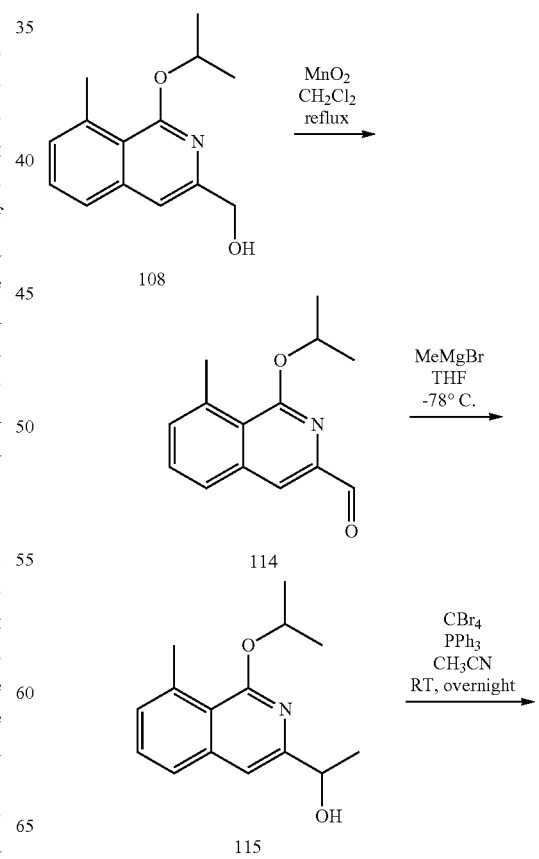

-continued

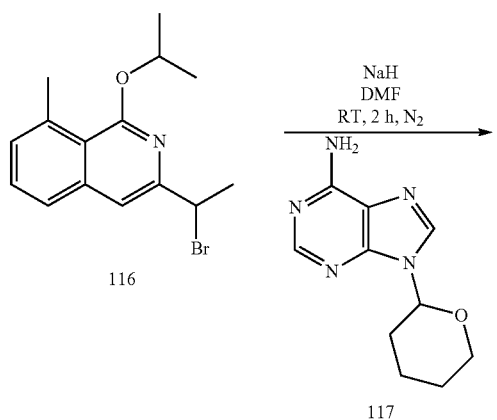

116

117

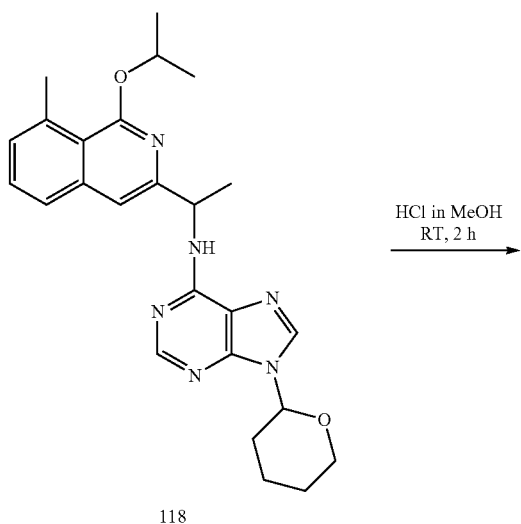

118

119

Compound 108, which is synthesized as described in Example 1, is oxidized by treatment with manganese dioxide in refluxing methylene chloride to product aldehyde 114. Compound 114 is reacted with methyl Grignard reagent in tetrahydrofuran at −78° C., to produce compound 115. Compound 115 is brominated by treatment with carbon tetrabromide and triphenylphosphine in acetonitrile at room temperature to obtain compound 116. Bromo compound 116 is alkylated with purine 117 in dimethylformamide with sodium hydride base at room temperature to produce compound 118. Compound 118 is deprotected by treatment with hydrochloric acid in methanol at room temperature to produce compound 119.

Example 3

Synthesis of 1-((8-methyl-1-(4-methylpiperazin-1-yl)isoquinolin-3-yl)methyl)-3-(1H-pyrazol-4-yl)-1H-pyrazolo[3,4-d]pyrimidin-4-amine (Compound 307)

Scheme 5.. The synthesis of 1-((8-methyl-1-(4-methylpiperazin-1-yl)isoquinolin-3-yl)methyl)-3-(1H-pyrazol-4-yl)-1H-pyrazolo[3,4-d]pyrimidin-4-amine (Compound 307) is described.

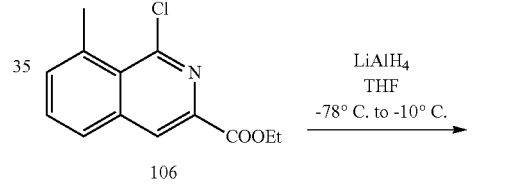

106

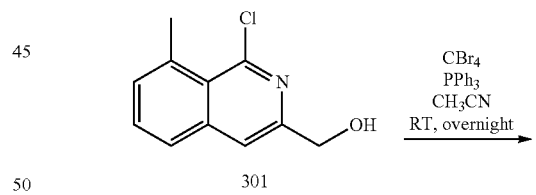

301

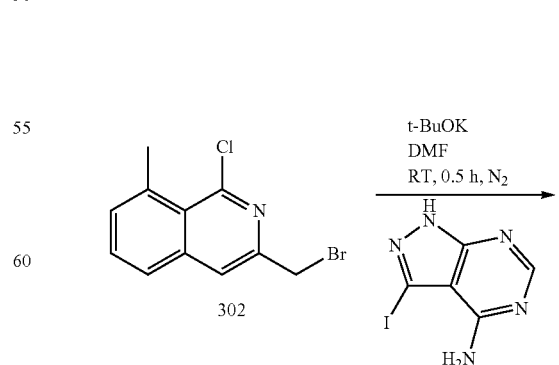

302

110

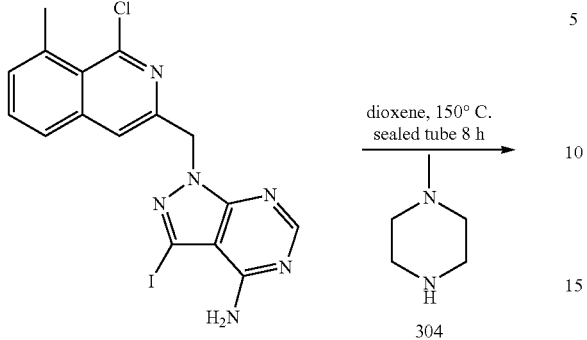

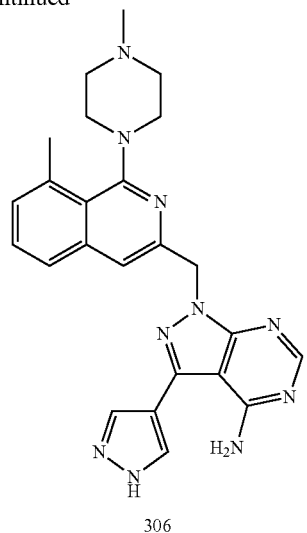

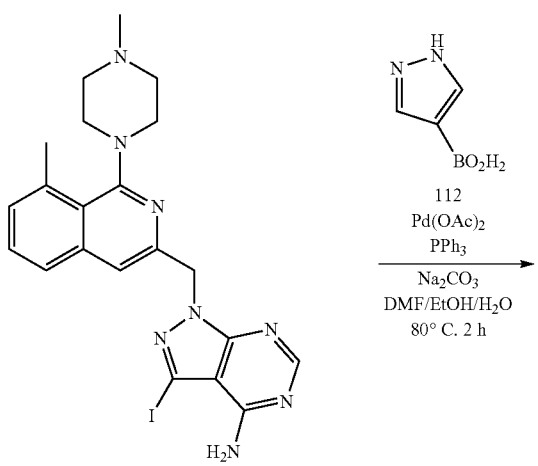

Chloro compound 106, synthesized as described in Example 1, is treated with lithium aluminum hydride in tetrahydrofuran at −78° C. to produce alcohol 301. Compound 301 is brominated by treatment with carbon tetrabromide and triphenylphosphine in acetonitrile at room temperature to obtain compound 302. Pyrazolopyrimidine 110 is coupled with bromide 302, using potassium tert-butoxide base in dimethylformamide at room temperature, to produce compound 303. Chloro compound 303 is aminated by reaction with methyl piperazine 304 in a sealed tube in dioxene at 150° C. to produce compound 305. Compound 305 is coupled with boronic acid 112 using palladium acetate catalysis, in the presence of triphenyl phosphine and sodium carbonate in a mixture of dimethylformamide, ethanol, and water at 80° C. to produce compound 306.

Example 4

IC50 Values for Selected Compounds

TABLE 3

In Vitro $IC_{50}$ data for selected compounds.

| IC50(nM) | + (greater than 10 microMolar) | ++ (less than 10 microMolar) | +++ (less than 1 microMolar | ++++ (less than 100 nM) |
|---|---|---|---|---|
| PI3K δ | Compound No. 28, 29, 83 | Compound No. 11, 22, 30, 32, 33, 34, 43, 87, 93 | Compound No. 12, 14, 23, 24, 35, 40, 41, 49, 52, 53, 54, 56, 58, 59, 60, 61, 62, 69, 76, 77, 81, 84, 86, 92, 94, 96 | Compound No. 1, 2, 3, 4, 5, 6, 7, 8, 9, 10, 13, 15, 16, 17, 18, 19, 20, 21, 25, 26, 27, 31, 36, 37, 38, 39, 42, 44, 45, 46, 47, 48, 50, 51, 55, 57, 63, 64, 65, 66, 67, 68, 70, 71, 72, 73, 74, 75, 78, 79, 80, 82, 85, 88, 89, 90, 91, 95 |
| PI3K γ | Compound No. 3, 7, 9, 10, 11, 12, 14, 15, 16, 19, 20, 21, 23, 35, 39, 40, 41, 42, 43, 45, 46, 51, 52, 53, 54, 55, 56, 57, 58, 59, 69, 75, 77, 81, 83, 84, 87, 92, 93 | Compound No. 13, 37, 38, 44, 48, 49, 50, 60, 61, 62, 63, 70, 73, 74, 76, 78, 79, 80, 88, 90, 91, 94, 95 | Compound No. 8, 25, 27, 47, 64, 65, 66, 67, 68, 71, 72, 82, 86, 89, 96 | Compound No. 1, 2, 4, 5, 6, 17, 26, 31, 36, 85 |

TABLE 3-continued

In Vitro IC$_{50}$ data for selected compounds.

| IC50(nM) | + (greater than 10 microMolar) | ++ (less than 10 microMolar) | +++ (less than 1 microMolar) | ++++ (less than 100 nM) |
|---|---|---|---|---|
| PI3K α | Compound No. 9, 10, 11, 12, 14, 15, 16, 20, 23, 35, 47, 48, 49, 52, 53, 54, 55, 56, 57, 58, 59, 60, 61, 62, 63, 69, 70, 74, 75, 76, 77, 78, 79, 80, 81, 82, 83, 84, 86, 87, 92, 93, 94, 96 | Compound No. 3, 7, 13, 18, 21, 27, 50, 51, 64, 65, 66, 67, 68, 71, 72, 73, 88, 89, 90, 91, 95 | Compound No. 1, 2, 4, 6, 8, 17, 25, 26, 85 | Compound No. 5, 31 |
| PI3K β | Compound No. 2, 10, 11, 12, 13, 14, 15, 16, 19, 20, 21 23, 35, 54, 56, 57, 59, 69, 70, 75, 76, 77, 78, 79, 80, 81, 83, 84, 87, 92, 93, 94 | Compound No. 1, 3, 4, 6, 7, 8, 9, 17, 18, 27, 47, 49, 55, 58, 60, 61, 62, 63, 64, 65, 66, 71, 72, 73, 74, 85, 86, 88, 89, 90, 91, 95, 96 | Compound No. 5, 25, 26, 48, 50, 51, 67, 68, 82 | Compound No. 31 |
| B cell proliferation EC$_{50}$ (nM) | Compound No. | Compound No. 9, 18 | Compound No. 1, 2, 8, 26, 31, 36, 42, 44, 54, 58, 59, 60, 61, 62, 63, 67, 68 | Compound No. 3, 4, 5, 6, 7, 13, 15, 16, 17, 18, 20, 25, 35, 37, 38, 39, 45, 46, 50, 55, 56, 57, 65, 66 |

TABLE 4

Structures of the Compounds for the IC50 results described in Table 3.

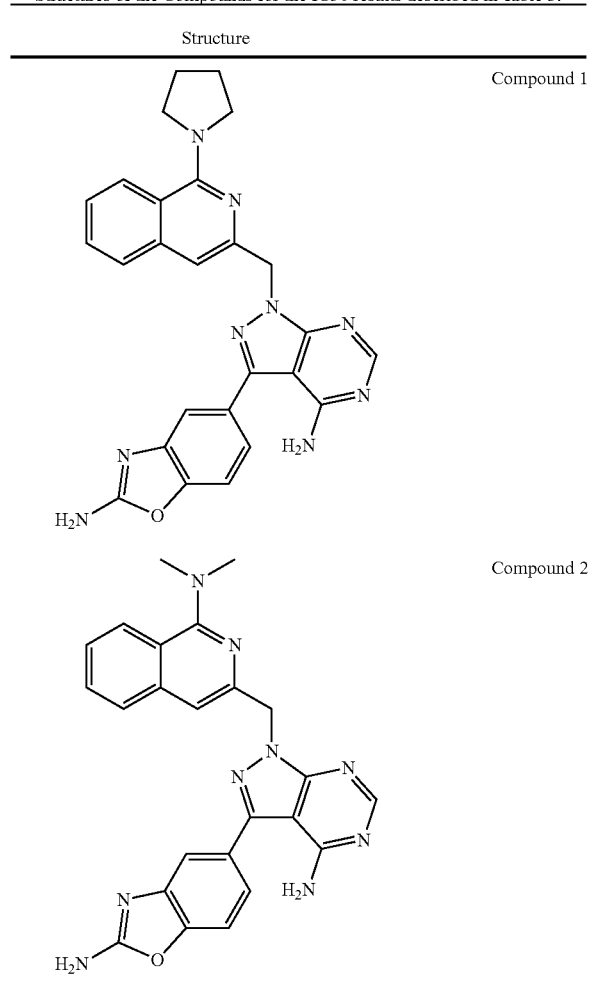

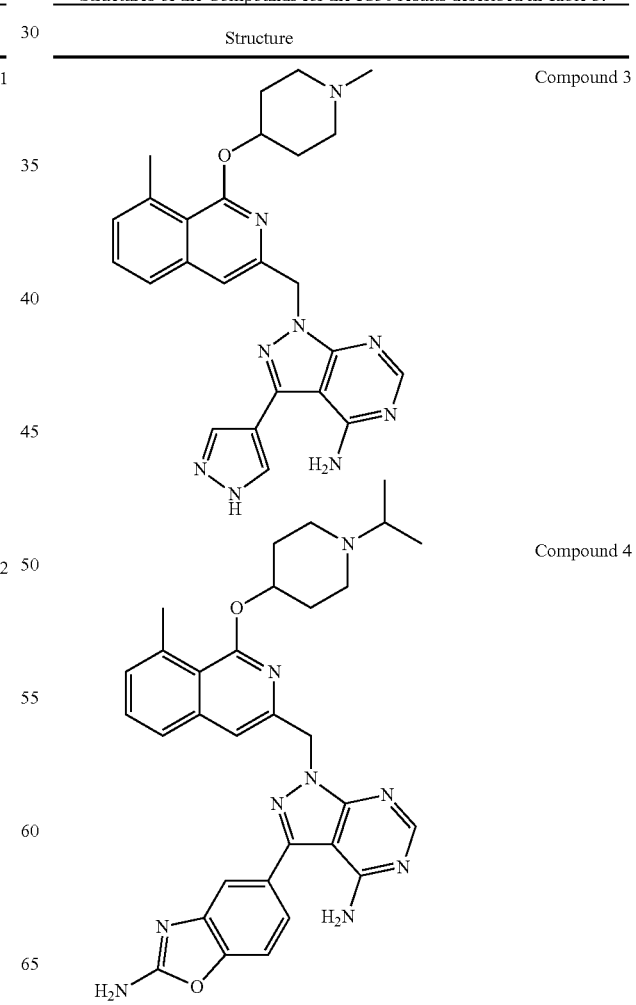

TABLE 4-continued

Structures of the Compounds for the IC50 results described in Table 3.

Structure

Compound 5

Compound 6

Compound 7

TABLE 4-continued

Structures of the Compounds for the IC50 results described in Table 3.

Structure

Compound 8

Compound 9

Compound 10

TABLE 4-continued

Structures of the Compounds for the IC50 results described in Table 3.

Structure

Compound 11

Compound 12

Compound 13

TABLE 4-continued

Structures of the Compounds for the IC50 results described in Table 3.

Structure

Compound 14

Compound 15

Compound 16

TABLE 4-continued
Structures of the Compounds for the IC50 results described in Table 3.
Structure
Compound 17
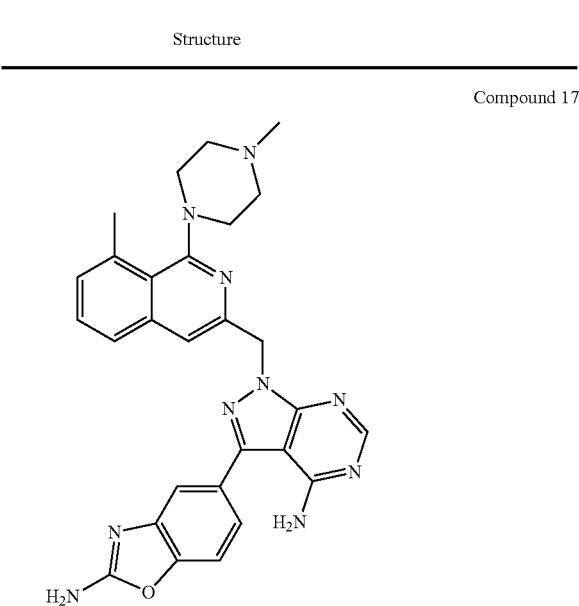
Compound 18
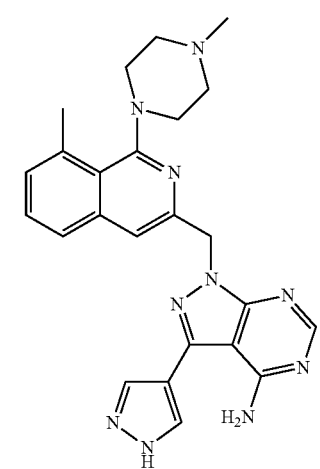 [SMILES: Cc1cccc2cc(Cn3nc(-c4cn[nH]c4)c4c(N)ncnc43)nc(N3CCN(C)CC3)c12]
Compound 19
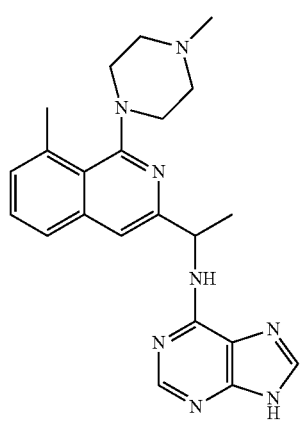 [SMILES: Cc1cccc2cc(C(C)Nc3ncnc4[nH]cnc34)nc(N3CCN(C)CC3)c12]
TABLE 4-continued
Structures of the Compounds for the IC50 results described in Table 3.
Structure
Compound 20
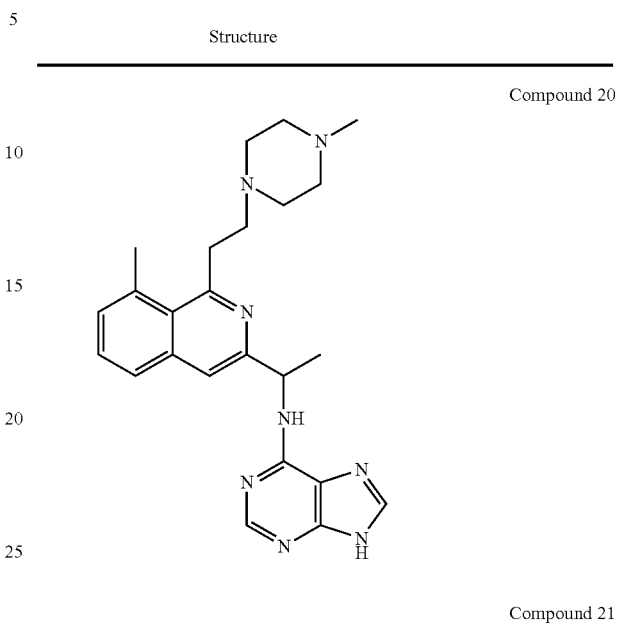
Compound 21
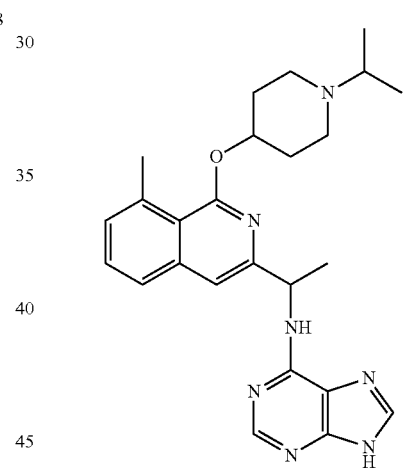
Compound 22
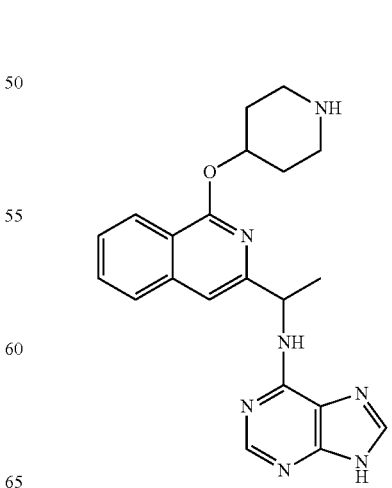

TABLE 4-continued

Structures of the Compounds for the IC50 results described in Table 3.

TABLE 4-continued
Structures of the Compounds for the IC50 results described in Table 3.
Structure
Compound 29
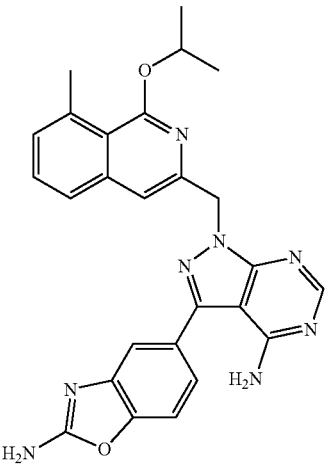 [SMILES: Cc1cccc2cc(Cn3nc(-c4ccc5oc(N)nc5c4)c4c(N)ncnc43)nc(OC(C)C)c12]
Compound 30
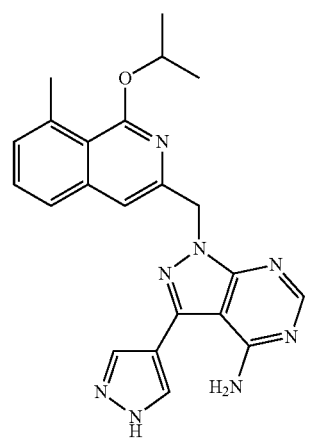 [SMILES: Cc1cccc2cc(Cn3nc(-c4cn[nH]c4)c4c(N)ncnc43)nc(OC(C)C)c12]
Compound 31
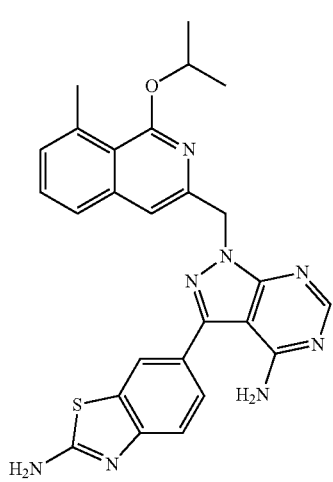 [SMILES: Cc1cccc2cc(Cn3nc(-c4ccc5nc(N)sc5c4)c4c(N)ncnc43)nc(OC(C)C)c12]
TABLE 4-continued
Structures of the Compounds for the IC50 results described in Table 3.
Structure
Compound 32
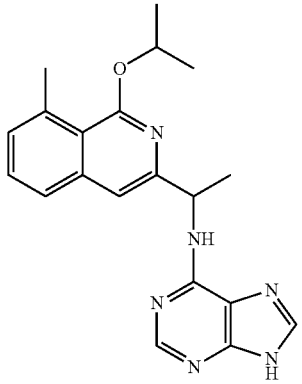 [SMILES: Cc1cccc2cc(C(C)Nc3ncnc4[nH]cnc34)nc(OC(C)C)c12]
Compound 33
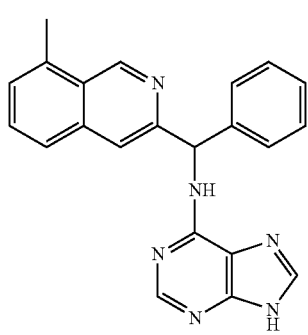 [SMILES: Cc1cccc2cc(C(Nc3ncnc4[nH]cnc34)c3ccccc3)ncc12]
Compound 34
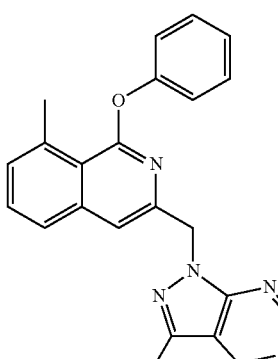

TABLE 4-continued
Structures of the Compounds for the IC50 results described in Table 3.
Structure
Compound 35
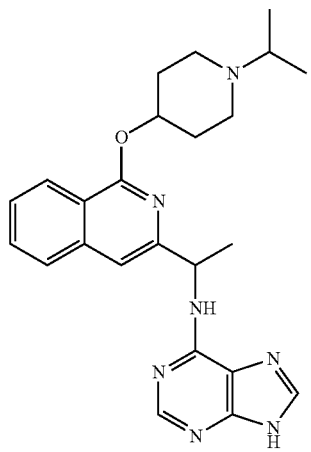 [SMILES: CC(Nc1ncnc2[nH]cnc12)c1cc2ccccc2c(OC2CCN(C(C)C)CC2)n1]
Compound 36
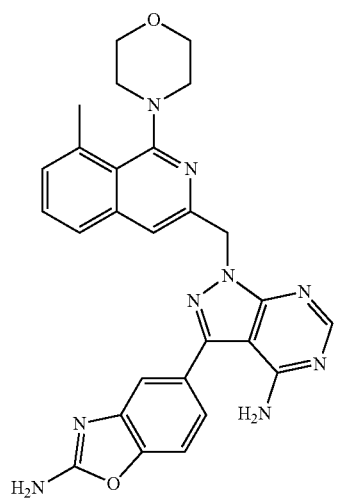 [SMILES: Cc1cccc2cc(Cn3nc(-c4ccc5oc(N)nc5c4)c4c(N)ncnc43)nc(N3CCOCC3)c12]
Compound 37
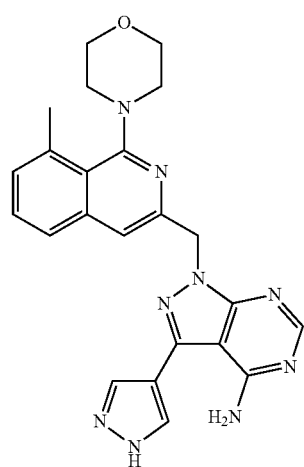 [SMILES: Cc1cccc2cc(Cn3nc(-c4cn[nH]c4)c4c(N)ncnc43)nc(N3CCOCC3)c12]
TABLE 4-continued
Structures of the Compounds for the IC50 results described in Table 3.
Structure
Compound 38
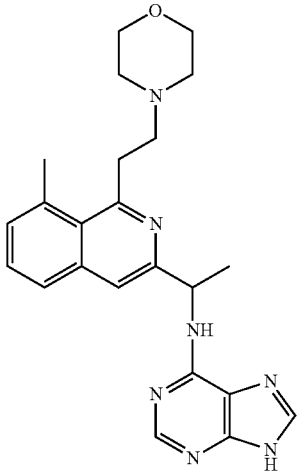 [SMILES: Cc1cccc2cc(C(C)Nc3ncnc4[nH]cnc34)nc(CCN3CCOCC3)c12]
Compound 39
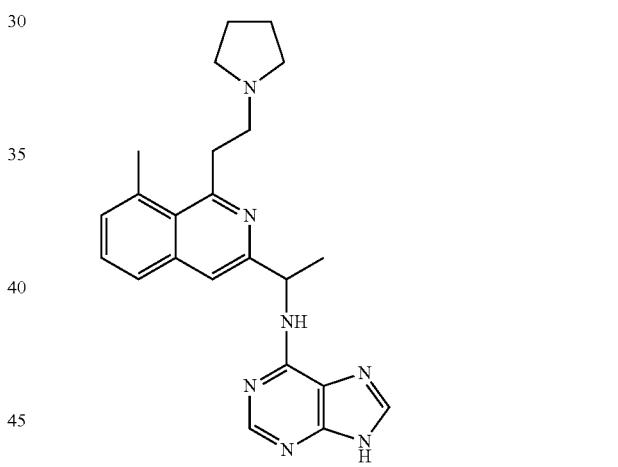
Compound 40
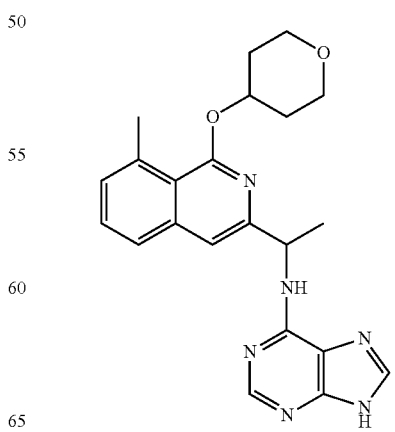

TABLE 4-continued

Structures of the Compounds for the IC50 results described in Table 3.

Structure

Compound 41

Compound 42

Compound 43

TABLE 4-continued

Structures of the Compounds for the IC50 results described in Table 3.

Structure

Compound 44

Compound 45

Compound 46

Compound 47

TABLE 4-continued
Structures of the Compounds for the IC50 results described in Table 3.
Structure
Compound 48
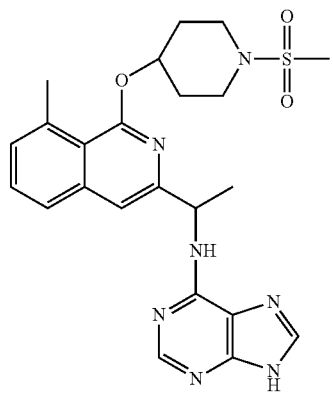 [SMILES: Cc1cccc2cc(C(C)Nc3ncnc4[nH]cnc34)nc(OC3CCN(S(C)(=O)=O)CC3)c12]
Compound 49
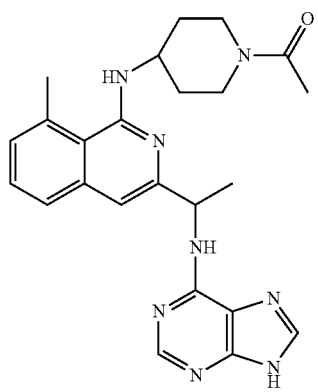 [SMILES: CC(=O)N1CCC(Nc2nc(C(C)Nc3ncnc4[nH]cnc34)cc3cccc(C)c23)CC1]
Compound 50
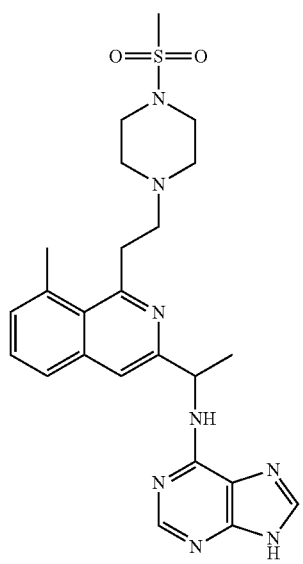 [SMILES: Cc1cccc2cc(C(C)Nc3ncnc4[nH]cnc34)nc(CCN3CCN(S(C)(=O)=O)CC3)c12]
TABLE 4-continued
Structures of the Compounds for the IC50 results described in Table 3.
Structure
Compound 51
Compound 52
Compound 53

TABLE 4-continued

Structures of the Compounds for the IC50 results described in Table 3.

| Structure | |
|---|---|
| (structure) | Compound 54 |
| (structure) | Compound 55 |
| (structure) | Compound 56 |
| (structure) | Compound 57 |
| (structure) | Compound 58 |
| (structure) | Compound 59 |

TABLE 4-continued
Structures of the Compounds for the IC50 results described in Table 3.
Structure
Compound 60
Compound 61
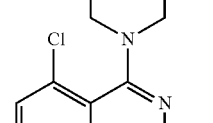
Compound 62
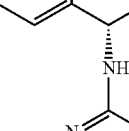
TABLE 4-continued
Structures of the Compounds for the IC50 results described in Table 3.
Structure
Compound 63
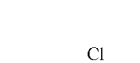
Compound 64
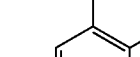
Compound 65
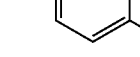

TABLE 4-continued
Structures of the Compounds for the IC50 results described in Table 3.
Structure
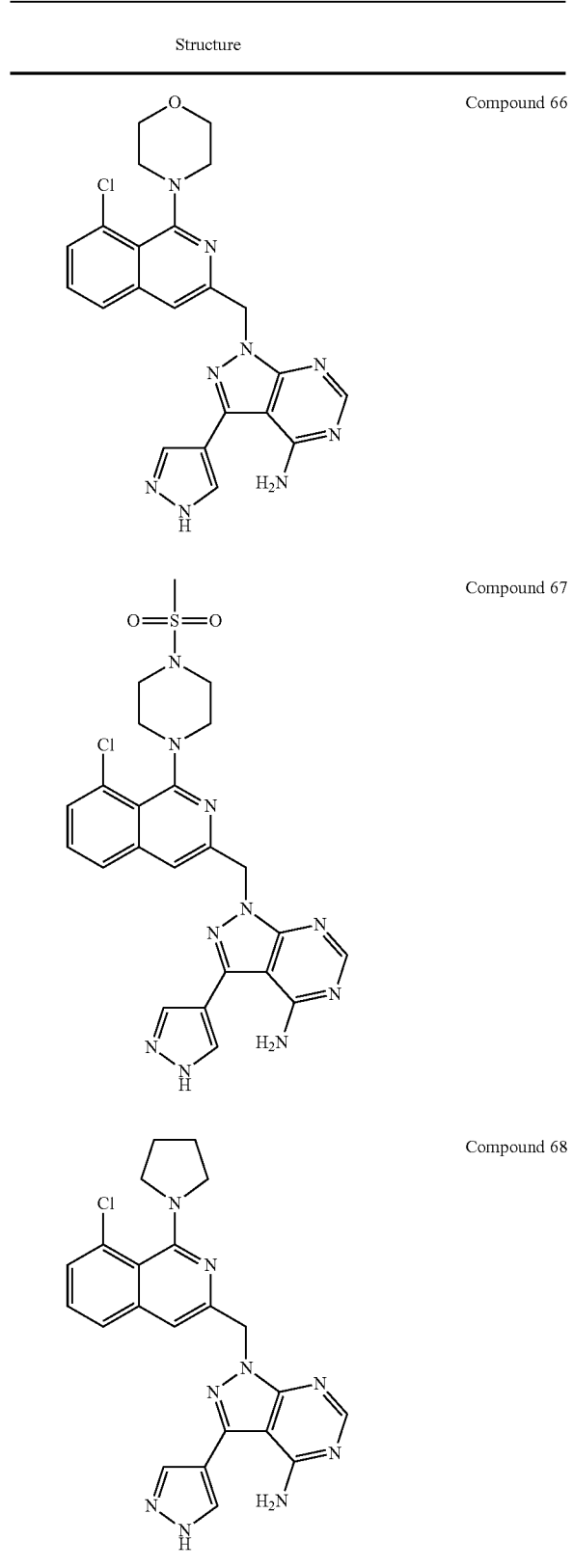
Compound 66
Compound 67
Compound 68
TABLE 4-continued
Structures of the Compounds for the IC50 results described in Table 3.
Structure
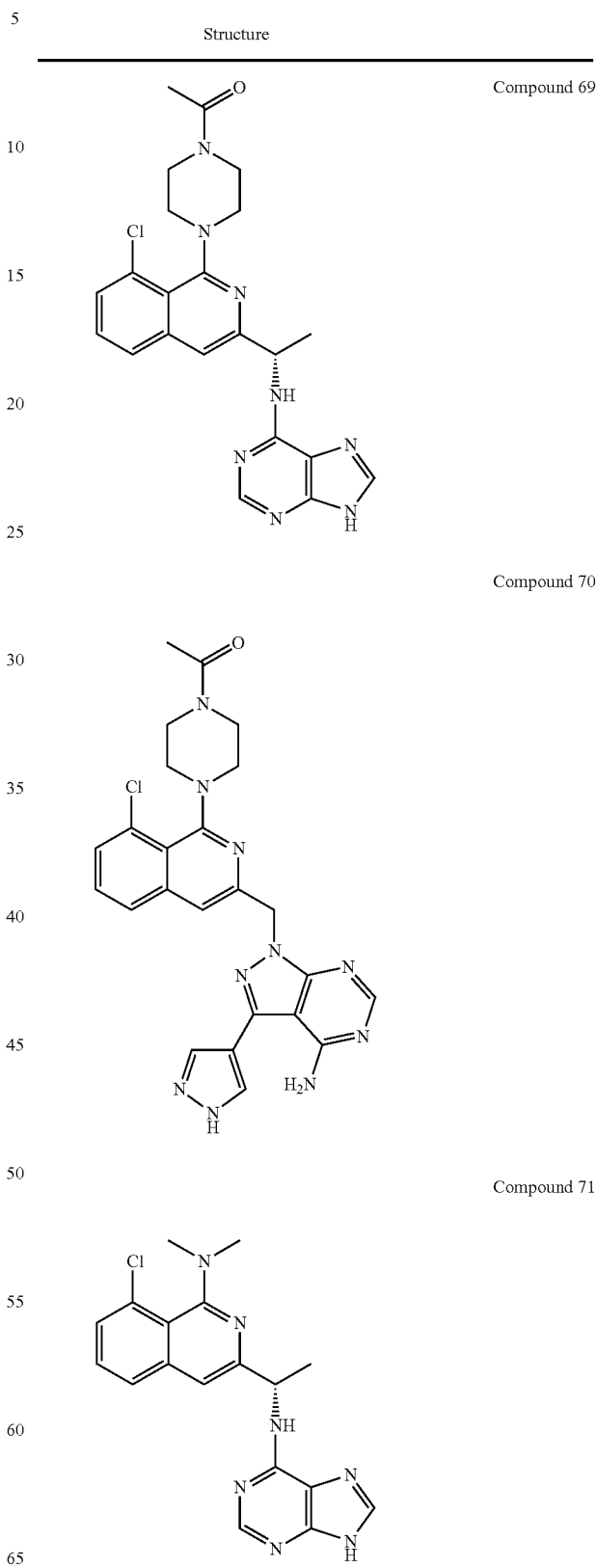
Compound 69
Compound 70
Compound 71

TABLE 4-continued
Structures of the Compounds for the IC50 results described in Table 3.
| Structure | |
|---|---|
| 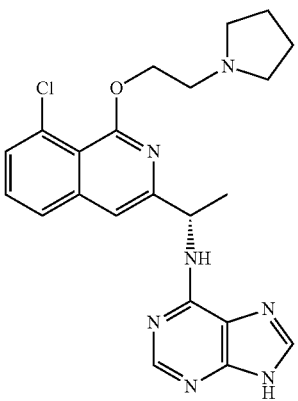 | Compound 72 |
| 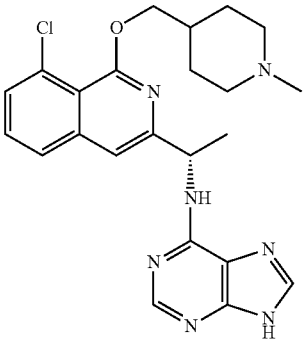 | Compound 73 |
| 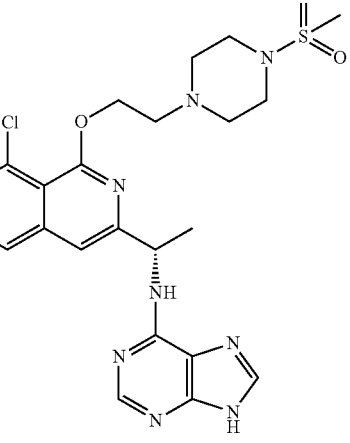 | Compound 74 |
| 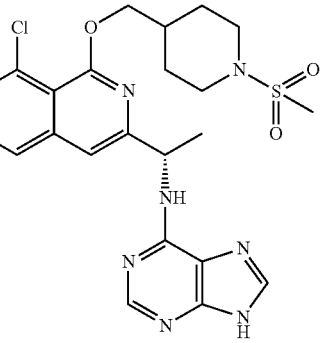 | Compound 75 |
TABLE 4-continued
Structures of the Compounds for the IC50 results described in Table 3.
| Structure | |
|---|---|
| 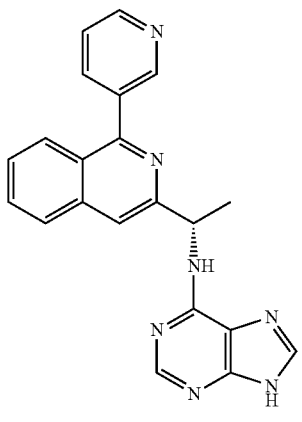 | Compound 76 |
| 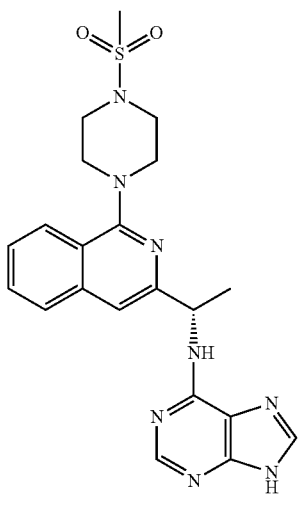 | Compound 77 |
| 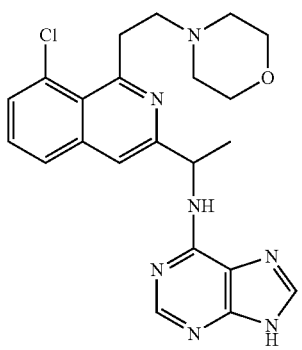 | Compound 78 |

TABLE 4-continued

Structures of the Compounds for the IC50 results described in Table 3.

| Structure | |
|---|---|
| (structure) | Compound 79 |
| (structure) | Compound 80 |
| (structure) | Compound 81 |
| (structure) | Compound 82 |
| (structure) | Compound 83 |
| (structure) | Compound 84 |
| (structure) | Compound 85 |

TABLE 4-continued

Structures of the Compounds for the IC50 results described in Table 3.

Structure

Compound 86

Compound 87

Compound 88

TABLE 4-continued

Structures of the Compounds for the IC50 results described in Table 3.

Structure

Compound 89

Compound 90

Compound 91

Compound 92

TABLE 4-continued

Structures of the Compounds for the IC50 results described in Table 3.

Structure

Compound 93, Compound 94, Compound 95, Compound 96 (structures shown).

The following MS data was obtained for the compounds listed in Table 4. 1:Calcd: 477.20; Found: 478.0 [M+H]+; 2:Calcd: 451.19; Found: 452.0 [M+H]+; 3:Calcd: 469.23; Found: 470.0 [M+H]+; 4:Calcd: 563.28; Found: 564.2[M+H]+; 5:Calcd: 535.24; Found: 536.0 [M+H]+; 6:Calcd: 549.26; Found: 550.2 [M+H]+; 7:Calcd: 483.25; Found: 484.2 [M+H]+; 8:Calcd: 521.23; Found: 522.0 [M+H]+; 9:Calcd: 455.22; Found: 456.0 [M+H]+; 10:Calcd: 431.24; Found: 432.2 [M+H]+; 11:Calcd: 459.27; Found: 460.20 [M+H]+; 12:Calcd: 445.26; Found: 446.20 [M+H]+; 13:Calcd: 497.27; Found: 498.20 [M+H]+; 14:Calcd: 403.21; Found: 404.20 [M+H]+; 15:Calcd: 417.23; Found: 418.0 [M+H]+; 16:Calcd: 431.24; Found: 432.2 [M+H]+; 17:Calcd: 520.24; Found: 521.10 [M+H]+; 18:Calcd: 454.23; Found: 455.0 [M+H]+; 19:Calcd: 402.23; Found: 403.0 [M+H]+; 20:Calcd: 430.26; Found: 431.20 [M+H]+; 21:Calcd: 445.26; Found: 446.20 [M+H]+; 22:Calcd: 389.20; Found: 390.0 [M+H]+; 23:Calcd: 403.21; Found: 404.0 [M+H]+; 24:Calcd: 39.6.17; Found: 397.0 [M+H]+; 25:Calcd: 548.28; Found: 549.20 [M+H]+; 26:Calcd: 491.22; Found: 492.20 [M+H]+; 27:Calcd: 425.21; Found: 426.20 [M+H]+; 28:Calcd: 538.19; Found: 539.0 [M+H]+; 29:Calcd: 480.20; Found: 481.20 [M+H]+; 30:Calcd: 414.19; Found: 415.20 [M+H]+; 31:Calcd: 496.18; Found: 497.0 [M+H]+; 32:Calcd: 362.43; Found: 363.20 [M+H]+; 33:Calcd: 366.16; Found: 367.0 [M+H]+; 34:Calcd: 514.19; Found: 515.0 [M+H]+; 35:Calcd: 431.24; Found: 432.20 [M+H]+; 36:Calcd: 507.21; Found: 508.0 [M+H]+; 37:Calcd: 441.20; Found: 442.20 [M+H]+; 38:Calcd: 417.23; Found: 418.20 [M+H]+; 39:Calcd: 401.23; Found: 402.20 [M+H]+; 40:Calcd: 404.20; Found: 405.20 [M+H]+; 41:Calcd: 416.24; Found: 417.20 [M+H]+; 42:Calcd: 432.24; Found: 433.20[M+H]+; 43:Calcd: 403.21; Found: 404.20 [M+H]+; 44:Calcd: 389.20; Found: 390.0 [M+H]+; 45:Calcd: 431.24; Found: 432.20 [M+H]+; 46:Calcd: 445.26; Found: 446.20 [M+H]+; 47:Calcd: 445.22; Found: 446.20 [M+H]+; 48:Calcd: 481.19; Found: 482.0 [M+H]+; 49:Calcd: 444.24; Found: 445.20 [M+H]+; 50:Calcd: 494.22; Found: 495.20 [M+H]+; 51:Calcd: 459.27; Found: 460.20 [M+H]+; 52:Calcd: 431.21; Found: 432.20 [M+H]+; 53:Calcd: 467.17; Found: 468.0 [M+H]+; 54:Calcd: 501.13; Found: 502.0 [M+H]+; 55:Calcd: 489.18; Found: 590.20

[M+H]+; 56:Calcd: 503.19; Found: 504.20 [M+H]+; 57:Calcd: 517.21; Found: 518.20 [M+H]+; 58:Calcd: 553.14; Found: 554.0 [M+H]+; 59:Calcd: 500.15; Found: 501.20 [M+H]+; 60:Calcd: 501.13; Found: 502.20 [M+H]+; 61:Calcd: 481.19; Found: 482.20 [M+H]+; 62:Calcd: 409.14; Found: 410.20 [M+H]+; 63:Calcd: 393.15; Found: 394.20 [M+H]+; 64:Calcd: 486.14; Found: 487.20 [M+H]+; 65:Calcd: 453.17; Found: 454.20 [M+H]+; 66:Calcd: 461.15; Found: 462.20 [M+H]+; 67:Calcd: 538.14; Found: 539.20 [M]+; 68:Calcd: 445.15; Found: 446.20 [M+H]+; 69:Calcd: 450.17; Found: 451.20 [M+H]+; 70:Calcd: 502.17; Found: 503.20 [M+H]+; 71:Calcd: 367.13; Found: 368.20 [M+H]+; 72:Calcd: 437.17; Found: 438.20 [M+H]+; 73:Calcd: 451.19; Found: 452.20 [M+H]+; 74:Calcd: 530.16; Found: 531.20 [M+H]+; 75:Calcd: 515.15; Found: 516.0 [M+H]+; 76:Calcd: 367.15; Found: 368.20 [M+H]+; 77:Calcd: 452.17; Found: 453.20 [M+H]+; 78:Calcd: 437.17; Found: 438.20 [M+H]+; 79:Calcd: 421.18; Found: 422.20 [M+H]+; 80: Calcd: 514.17; Found: 515.0 [M+H]+; 81: Calcd: 478.20; Found: 479.2 [M+H]+; 82: Calcd: 401.12; Found: 402.0 [M+H]+; 83: Calcd: 486.14; Found: 487.2 [M+H]+; 84: Calcd: 501.13; Found: 502.0 [M+H]+; 85: Calcd: 500.15; Found: 501.0 [M+H]+; 86: Calcd: 500.15; Found: 501.0 [M+H]+; 87: Calcd: 481.19; Found: 482.2 [M+H]+; 88: Calcd: 407.16; Found: 408.2 [M+H]+; 89: Calcd: 443.14; Found: 444.2 [M+H]+; 90: Calcd: 421.18; Found: 422.0 [M+H]+; 91: Calcd: 457.16; Found: 458.0 [M+H]+; 92: Calcd: 394.14; Found: 395.2 [M+H]+; 93: Calcd: 410.14; Found: 411.0 [M+H]+; 94: Calcd: 487.13; Found: 488.0 [M+H]+; 95: Calcd: 438.17; Found: 439.2 [M+H]+; 96: Calcd: 451.16; Found: 452.2 [M+H]+.

Example 5

Expression and Inhibition Assays of p110α/p85α, p110β/p85α, p110δ/p85α, and p110γ

Class I PI3-Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 µg/ml). Reactions are initiated by the addition of ATP containing 10 µCi of γ-32P-ATP to a final concentration 10 or 100 µM and allowed to proceed for 5 minutes at room temperature. For TLC analysis, reactions are then terminated by the addition of 105 µl 1N HCl followed by 160 µl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol:1 M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 µM). For compounds showing significant activity, IC50 determinations are repeated two to four times, and the reported value is the average of these independent measurements.

Other commercial kits or systems for assaying PI3-K activities are available. The commercially available kits or systems can be used to screen for inhibitors and/or agonists of PI3-Ks including but not limited to PI 3-Kinase α, β, δ, and γ. And exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3-K. The kinase reaction is performed in a microtitre plate (e.g., a 384 well microtitre plate). The total reaction volume is approximately 20 µl per well. In the first step, each well receives 2 ul of test compound in 20% dimethylsulphoxide resulting in a 2% DMSO final concentration. Next, approximately 14.5 ul of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 ul of ATP (diluted in 1× reaction buffer) is added per well for a final concentration of 10 uM ATP. The plate is sealed and incubated for 1 hour at room temperature. The reaction is stopped by adding 5 ul of Stop Solution per well and then 5 ul of Detection Mix is added per well. The plate is sealed, incubated for 1 hour at room temperature, and then read on an appropriate plate reader. Data is analyzed and IC50s are generated using GraphPad Prism 5.

Example 6

Expression and Inhibition Assays of Abl

The cross-activity or lack thereof of one or more compounds of the present invention against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM MgCl2, 200 µM ATP (2.5 µCi of γ-32P-ATP), and 0.5 mg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 7

Expression and Inhibition Assays of Hck

The cross-activity or lack thereof of one or more compounds of the present invention against Hck kinase can be measured according to any procedures known in the art or methods disclosed below. The compounds described herein can be assayed in triplicate against recombinant full-length Hck in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 8

Expression and Inhibition Assays of Inulsin Receptor (IR)

The cross-activity or lack thereof of one or more compounds of the present invention against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM MgCl2, 10 mM MnCl2, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 9

Expression and Inhibition Assays of Src

The cross-activity or lack thereof of one or more compounds of the present invention against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM MgCl2, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 10

Expression and Inhibition Assays of DNA-PK (DNAK)

The cross-activity or lack thereof of one or more compounds of the present invention against DNAK kinase can be measured according to any procedures known in the art. DNA-PK can be purchased from Promega and assayed using the DNA-PK Assay System (Promega) according to the manufacturer's instructions.

Example 11

Expression and Inhibition Assays of mTOR

The cross-activity or lack thereof of one or more compounds of the present invention against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM MgCl2, 2.5 mM, 0.01% Tween, 10 µM ATP (2.5 µCi of µ-32P-ATP), and 3 µg/mL BSA. Rat recombinant PHAS-¼EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 ul per well and the reaction buffer composition is 50 mM HEPES pH7.5, 0.01% Polysorbate 20, 1 mM EGTA, 10 mM MnCl2, and 2 mM DTT. In the first step, each well receives 2 ul of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 uM ATP and 0.5 uM GFP-4EBP1. The plate is sealed and incubated for 1 hour at room temperature. The reaction is stopped by adding 10 ul per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and IC50s are generated using GraphPad Prism 5.

Example 12

Expression and Inhibition Assays of Vascular Endothelial Growth Receptor

The cross-activity or lack thereof of one or more compounds of the present invention against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 13

Expression and Inhibition Assays of Ephrin Receptor B4 (EphB4)

The cross-activity or lack thereof of one or more compounds of the present invention against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM MgCl2, 0.1% BME, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 14

Expression and Inhibition Assays of Epidermal Growth Factor Receptor (EGFR)

The cross-activity or lack thereof of one or more compounds of the present invention against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM MgCl2, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 15

Expression and Inhibition Assays of KIT Assay

The cross-activity or lack thereof of one or more compounds of the present invention against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM MgCl2, 1 mM DTT, 10 mM MnCl2, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 16

Expression and Inhibition Assays of RET

The cross-activity or lack thereof of one or more compounds of the present invention against RET kinase can be measured according to any procedures known in the art or methods disclosed below. The compounds described herein can be tested against recombinant RET kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 17

Expression and Inhibition Assays of Platelet Derived Growth Factor Receptor (PDGFR)

The cross-activity or lack thereof of one or more compounds of the present invention against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 18

Expression and Inhibition Assays of FMS-Related Tyrosine Kinase 3 (FLT-3)

The cross-activity or lack thereof of one or more compounds of the present invention against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM MgCl2, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 19

Expression and Inhibition Assays of TEK Receptor Tyrosine Kinase (TIE2)

The cross-activity or lack thereof of one or more compounds of the present invention against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM MgCl2, 2 mM DTT, 10 mM MnCl2, 10 μM ATP (2.5 μCI of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 20

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 ul volume. Plates are incubated for 30 min at 37 C and 5% CO$_2$ (0.2% DMSO final concentration). A 50 ul B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% CO$_2$. A volume of 15 uL of Alamar Blue reagent is added to each well and plates are incubated for 5 hours at 37 C and 5% CO$_2$. Alamar Blue fluoresce is read at 560 Ex/590 Em, and IC50 or EC50 values are calculated using GraphPad Prism 5.

Example 21

Tumor Cell Line Proliferation Assay

The ability of one or more subject compounds to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 ul at 5,000 cells/well in Tumor Cell Media. A compound disclosed herein is diluted in Tumor Cell Media and added in a 10 μl volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560 Ex/590 Em, and IC50 values are calculated using GraphPad Prism 5. The results are expected to show that some of the compounds of the present invention are potent inhibitors of tumor cell line proliferation under the conditions tested.

Example 22

Antitumor Activity In Vivo

The compounds described herein can be evaluated in a panel of human and murine tumor models.
Paclitaxel-Refractory Tumor Models
1. Clinically-Derived Ovarian Carcinoma Model.
This tumor model is established from a tumor biopsy of an ovarian cancer patient. Tumor biopsy is taken from the patient.
The compounds described herein are administered to nude mice bearing staged tumors using an every 2 days×5 schedule.
2. A2780Tax Human Ovarian Carcinoma Xenograft (Mutated Tubulin).
A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein.
The compounds described herein can be administered to mice bearing staged tumors on an every 2 days×5 schedule.
3. HCT116/VM46 Human Colon Carcinoma Xenograft (Multi-Drug Resistant).
HCT116/VM46 is an MDR-resistant colon carcinoma developed from the sensitive HCT116 parent line. In vivo, grown in nude mice, HCT116/VM46 has consistently demonstrated high resistance to paclitaxel.
The compounds described herein can be administered to mice bearing staged tumors on an every 2 days×5 schedule.
5. M5076 Murine Sarcoma Model
M5076 is a mouse fibrosarcoma that is inherently refractory to paclitaxel in vivo.
The compounds described herein can be administered to mice bearing staged tumors on an every 2 days×5 schedule.
One or more compounds of the invention can be used in combination other therapeutic agents in vivo in the multidrug resistant human colon carcinoma xenografts HCT/VM46 or any other model known in the art including those described herein.

The results are expected to show that one or more compounds of the present invention are potent inhibitors of tumor growth in vivo under the conditions tested.

Example 23

Microsome Stability Assay

The stability of one or more subject compounds is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in 1.5 mL Eppendorf tube. Each tube contains 0.1 μL of 10.0 mg/ml NADPH; 75 μL of 20.0 mg/ml mouse, rat or human liver microsome; 0.4 μL of 0.2 M phosphate buffer, and 425 μL of dd$H_2O$, Negative control (without NADPH) tube contains 75 μL of 20.0 mg/ml mouse, rat or human liver microsome; 0.4 μL of 0.2 M phosphate buffer, and 525 μL of dd$H_2O$. The reaction is started by adding 1.0 μL of 10.0 mM tested compound. The reaction tubes are incubated at 37° C. 100 μL sample is collected into new Eppendorf tube containing 300 μL cold Methanol at 0, 5, 10, 15, 30 and 60 minutes of reaction. Samples are centrifuged at 15,000 rpm to remove protein. Supernatant of centrifuged sample is transferred to new tube. Concentration of stable compound after reaction with microsome in the supernatant is measured by Liquid Chromatography/Mass Spectrometry (LC-MS).

Example 24

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 μM stock solution to an aliquot of pre-warmed plasma to give a final assay volume of 400 μL (or 800 μl, for half-life determination), containing 5 μM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 μL of the incubation mixture to 200 μL of ice-cold acetonitrile and mixed by shaking for 5 minutes. The samples are centrifuged at 6000×g for 15 minutes at 4° C. and 120 μL of supernatant removed into clean tubes. The samples are then evaporated to dryness and submitted for analysis by HPLC-MS/MS.

Where desired, one or more control or reference compounds (5 μM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC- MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 25

Chemical Stability

The chemical stability of one or more subject compounds is determined according to standard procedures known in the art. The following details an exemplary procedure for ascertaining chemical stability of a subject compound. The default buffer used for the chemical stability assay is phosphate-buffered saline (PBS) at pH 7.4; other suitable buffers can be used. A subject compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 26

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, phylladelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt S473, phospho-Akt T308, Akt, and β-actin (Cell Signaling Technologies).

Example 27

Kinase Signaling in Blood

PI3K/Akt/mTor signaling is measured in blood cells using the phosflow method (Methods Enzymol. 2007; 434:131-54). The advantage of this method is that it is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for phosflow. Surface staining is used to distinguish T and B cells using antibodies directed to cell surface markers that are known to the art. The level of phosphorylation of kinase substrates such as Akt and S6 are then measured by incubating the fixed cells with labeled antibodies specific to the phosphorylated isoforms of these proteins. The population of cells is then analyzed by flow cytometry.

The results are expected to show that one or more of the compounds of the present invention are potent and selective inhibitors of one or more members of one or more of PI3K, mTOR, and Akt signaling in blood cells under the conditions tested.

Example 28

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+CD34+B cell progenitors. After overnight liquid culture, cells are plated in methocult GF+H4435, Stem Cell Technologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

The results are expected to show that one or more the compounds of the present invention are potent and selective inhibitors of p190 transduced cell colony formation under the conditions tested.

Example 29

In Vivo Effect of Kinase Inhibitors on Leukemic Cells

Female recipient mice are lethally irradiated from a γ source in two doses about 4 hr apart, with approximately 5 Gy each. About 1 hr after the second radiation dose, mice are injected i.v. with about $1 \times 10^6$ leukemic cells (e.g. Ph+human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about ten days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevec) alone under the conditions tested.

Example 30

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinuria within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This model established in the art can be employed to test that the kinase inhibitors disclosed herein can suppress or delay the onset of lupus symptoms in lupus disease model mice.

Example 31

Murine Bone Marrow Transplant Assay

Female recipient mice are lethally irradiated from a γ ray source. About 1 hr after the radiation dose, mice are injected with about $1 \times 10^6$ leukemic cells from early passage p190 transduced cultures (e.g. as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and post-mortem analysis is limited to enumeration of the percentage of leukemic cells in bone marrow, spleen and lymph node (LN) by flow cytometry. In the second phase, p190 cells that express a tailless form of human CD4 are used and the post-mortem analysis includes magnetic sorting of hCD4+ cells from spleen followed by immunoblot analysis of key signaling endpoints: p Akt-T308 and 5473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art may be used to test that effective therapeutic doses of the compounds disclosed herein can be used for inhibiting the proliferation of leukemic cells.

Example 32

TNP-Ficoll T-Cell Independent B-Cell Activation Assay

To test the effects of the compounds of the present invention in suppressing T cell independent antibody production, the TNP-Ficoll B-cell activation assay is used as described herein. Compounds of the present invention are dissolved in an appropriate vehicle (e.g. 5% 1-methyl-2-pyrrolidinone, 85% polyethylene glycol 400, 10% Solutor). Compounds are administered orally approximately 1 hr before TNP-Ficoll treatment to 4-10 week old mice. To study the effects of the compounds on B-cell activation, one set of mice are grouped according to the following table:

| Group# | Mice/ group treated | Comp Group | Antigen Injection at day-1 TNP-F | Route | Compound Administration from day-1 to day-7 (mg/kg) | Route | Regimen |
|---|---|---|---|---|---|---|---|
| 1 | 4 | Vehicle | Antigen only | 200 uL | 0 | Po | BID for 7 |
| 2 | 8 | — | Antigen only | (0.5 mg/ml) | 0 | | days |
| 3 | 8 | Reference compound #1 | reference | | 30 | | |
| 4 | 8 | Test | Antigen + | | 1 | | |
| 5 | 8 | compound | cmp | | 3 | | |
| 6 | 8 | | | | 10 | | |
| 7 | 8 | | | | 30 | | |
| 8 | 8 | | | | 60 | | |

Four animals in group 1, and eight animals in groups 2 to 7 are euthanized in $CO_2$ 2 hours after the last compound administration on day 7. Blood is immediately collected by cadiopuncture and kept at 37° C. for 1 hr to clot followed by overnight incubation at 4° C. to allow the clot to contract. The following day, serum is collected by decanting and centrifugation at 3000 rpm for 10 min. The collected serum is then frozen at −80° C. for future analysis.

Serum samples are analyzed for anti-TNP antibody titers by ELISA as described herein. TNP-BSA is coated onto a Nunc Maxisorb microtiter plate with 100 μl/well at a concentration of 10 μg/ml in phosphate buffered saline (PBS). The Maxisorb plate is incubated for 1.5 hours at room temperature and the solution is removed. 200 μl/well of blocking buffer (e.g. 1% BSA in PBS) is added to each well and incubated 1 hr at room temperature. The plate is washed once with 200 μl/well of PBS 0.05% Tween-20 (wash buffer). A 1:2 dilution of serum from each mouse in blocking buffer is added to each well in the first column (1) of the microtiter plate. The serum in each well of column 1 is then diluted 3-fold in blocking buffer and added to column 2. The serum in each well of column 2 is diluted 3-fold in blocking buffer and added to column 3. The procedure is repeated across the twelve columns of the microtiter plate. The microtiter plate is incubated 1 hr at room temperature. Serum is removed from the plate and the plate is washed three times with wash buffer. 100 μl/well of goat anti-mouse IgG3-HRP diluted 1:250 in blocking buffer is added to each well and incubated 1 hr at room temperature. The anti-mouse IgG3-HRP is removed from the microtiter plate and the plate is washed six times with wash buffer. HRP substrate (200 μl ABTS solution+30% $H_2O_2$+10 ml citrate buffer) is added to each well at 100 μl/well, incubated 2-20 minutes in the dark and the amount of anti-TNP IgG3 is determined spectrophotometrically at 405 nm. Similarly, anti-TNP IgM and total anti-TNP Ab are determined using anti-mouse IgM-HRP and anti-mouse Ig-HRP respectively.

Example 33

Rat Developing Type II Collagen Induced Arthritis Assay

In order to study the effects of the compounds of the present invention on the autoimmune disease arthritis, a collagen induced developing arthritis model is used. Female Lewis rats are given collagen injections at day 0. Bovine type II collagen is prepared as a 4 mg/ml solution in 0.01N acetic acid. Equal volumes of collagen and Freund's incomplete adjuvant are emulsified by hand mixing until a bead of the emulsified material holds its form in water. Each rodent receives a 300 μl injection of the mixture at each injection time spread over three subcutaneous sites on the back.

Oral compound administration begins on day 0 and continues through day 16 with vehicle (5% NMP, 85% PEG 400, 10% Solutol) or compounds of the present invention in vehicle or control (e.g. methotrexate) at 12 hour intervals daily. Rats are weighed on days 0, 3, 6, 9-17 and caliper measurements of ankles are taken on days 9-17. Final body weights are taken, and then the animals are euthanized on day 17. After euthanization, blood is drawn and hind paws and knees are removed. Blood is further processed for pharmacokinetics experiments as well as an anti-type II collagen antibody ELISA assay. Hind paws are weighed and then, with the knees, preserved in 10% formalin. The paws and knees are subsequently processed for microscopy. Livers, spleen and thymus are weighed. Sciatic nerves are prepared for histopathology.

Knee and ankle joints are fixed for 1-2 days and decalcified for 4-5 days. Ankle joints are cut in half longitudinally, and knees are cut in half along the frontal plane. Joints are processed, embedded, sectioned and stained with toluidine blue. Scoring of the joints is done according to the following criteria:

Knee and Ankle Inflammation
0=Normal
1=Minimal infiltration of inflammatory cells in synovium/ periarticular tissue
2=Mild infiltration
3=Moderate infiltration with moderate edema
4=Marked infiltration with marked edema
5=Severe infiltration with severe edema
Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)
Knee Pannus
0=Normal
1=Minimal infiltration of pannus in cartilage and subchondral bone 2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, Emphasis on Small Tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, Emphasis on Femoral Condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture
Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving >½ but <¾ of tibial or femoral surface (medial or lateral
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

% Inhibition=A−B/A×100
A=Mean Disease Control−Mean Normal
B=Mean Treated−Mean Normal The results are expected to show, relative to vehicle only control or to methotrexate control, that the compounds of the present invention exhibit a significant reduction in arthritis induced ankle diameter increase over time, and reduction of ankle histopathology in at least one or more of the categories of inflammation, pannus, cartilage damage, and bone resorption as described above. The results are expected to demonstrate a dose dependent reduction in knee histopathology. The results are expected to show that one or more compounds of the present invention may be useful for the treatment and reduction of arthritis disease symptoms.

The results further are expected to show a reduction at 10, 20, and 60 mg/kg dosage levels of serum anti-type II collagen levels for selected test compounds, suggesting that one or more compounds of the present invention may not only be useful for the treatment and reduction of arthritis disease symptoms, but may also be useful for the inhibition of the autoimmune reaction itself.

Example 34

Rat Established Type II Collagen Induced Arthritis Assay

In order to examine the dose responsive efficacy of the compounds of the present invention in inhibiting the inflammation, cartilage destruction and bone resorption of 10 day established type II collagen induced arthritis in rats, compounds are administered orally daily or twice daily for 6 days.

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats arerandomized into treatment groups. Randomization is performed after ankle joint swelling is obviously established and there is evidence of bilateral disease.

After an animal is selected for enrollment in the study, treatment is initiated by the oral route. Animals are given vehicle, control (Enbrel) or compound doses, twice daily or once daily (BID or QD respectively). Administration is performed on days 1-6 using a volume of 2.5 ml/kg (BID) or 5 ml/kg (QD) for oral solutions. Rats are weighed on days 1-7 following establishment of arthritis and caliper measurements of ankles taken every day. Final body weights are taken on day 7 and animals are euthanized.

The results are expected to show reduction in mean ankle diameter increase over time for selected test compounds with a once daily administration or twice daily administration under the conditions tested. This suggests that the compounds of the present invention may be useful for the treatment of autoimmune diseases such as arthritis.

Example 35

Adjuvant Induced Arthritis Assay

Intrathecal Catheterization of Rats

Isoflurane-anesthetized Lewis rats (200-250 g) are implanted with an intrathecal (IT) catheter. After a 6 d recovery period, all animals except those that appeared to have sensory or motor abnormalities (generally fewer than 5% of the total number) are used for experiments. For IT administration, 10 µl of drug or saline followed by 10 µl of isotonic saline is injected through the catheter.

Adjuvant Arthritis and Drug Treatment

Lewis rats are immunized at the base of the tail with 0.1 ml of complete Freund's adjuvant (CFA) on day 0 several days after catheter implantation (n=6/group). Drug (e.g. one or more compounds of the present invention or vehicle) treatment is generally started on day 8 and is continued daily until day 20. Clinical signs of arthritis generally begin on day 10, and paw swelling is determined every second day by water displacement plethysmometry.

The results are expected to show that one or more compounds of the present invention demonstrates a dose dependent reduction in the average paw volume increase as measured in this adjuvant induced arthritis model system. These results suggest that one or more of the compounds of the present invention may be useful for the treatment of one or more of the diseases or conditions described herein.

Example 36

Rodent Pharmacokinetic Assay

In order to study the pharmacokinetics of the compounds of the present invention a set of 4-10 week old mice are grouped according to the following table:

| Group# | Mice/group | Compound Administration from day-1 to day-7 | | |
|---|---|---|---|---|
| | | (mg/kg) | Route | Regimen |
| 1 | 3 | 1 | Po | BID for 7 days |
| 2 | 3 | 3 | | |
| 3 | 3 | 10 | | |
| 4 | 3 | 30 | | |
| 5 | 3 | 60 | | |

Compounds of the present invention are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results are expected to demonstrate the pharmacokinetic parameters such as absorption, distribution, metabolism, excretion, and toxicity for the compounds of the present invention.

Example 37

Basotest Assay

The basotest assay is performed using Orpegen Pharma Basotest reagent kit. Heparinized whole blood is pre-incubated with test compound or solvent at 37 C for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining red blood cells are lysed by addition of Lysing Solution. Cells are washed, and analyzed by flow cytometry. Test compounds, when evaluated in this assay inhibit allergen induced activation of basophilic granulocytes at sub micromolar range. The results are expected to demonstrate that under the conditions tested one or more compounds of the present invention are capable of inhibiting allergen induced activation of basophils.

Example 38

Combination use of PI3Kδ Inhibitors and Agents that Inhibit IgE Production or Activity The compounds of the present invention may present synergistic or additive efficacy when administered in combination with agents that inhibit IgE production or activity. Agents that inhibit IgE production include, for example, one or more of TEI-9874, 2-(4-(6-cyclohexyloxy-2-napthyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the subject compounds capable of inhibiting PI3KS are efficacious in treatment of autoimmune and inflammatory disorders (AHD) for example rheumatoid arthritis. If any of the compounds causes an undesired level of IgE production, one may choose to administer it in combination with an agent that inhibits IgE production or IgE activity. Additionally, the administration of PI3Kδ or PI3Kδ/γ inhibitors of the present invention in combination with inhibitors of mTOR may also exhibit synergy through enhanced inhibition of the PI3K pathway. Various in vivo and in vitro models may be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with PI3Kδ inhibitors of the present invention such as compound 53 with and without mTOR inhibitors such as rapamycin, rapalogs, or mTORC1/C2 inhibitors. The results are expected to show that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with PI3Kδ inhibitors alone.

(b) TNP Assay

Mice are immunized with TNP-Ficoll or TNP-KHL and treated with: vehicle, a PI3Kδ inhibitor, for example, compound 53 of the present invention, an mTOR inhibitor, for example rapamycin, or a PI3Kδ inhibitor in combination with an mTOR inhibitor such as rapamycin. Antigen-specific serum IgE is measured by ELISA using TNP-BSA coated plates and isotype specific labeled antibodies. This assay can be used to test that mice treated with an mTOR inhibitor alone exhibit little or no substantial effect on antigen specific IgG3 response and no statistically significant elevation in IgE response as compared to the vehicle control. This assay can also be used to test that mice treated with both PI3Kδ inhibitor and mTOR inhibitor exhibit a reduction in antigen specific IgG3 response as compared to the mice treated with vehicle alone. Additionally, this assay can be employed to test that the mice treated with both PI3Kδ inhibitor and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, PI3Kδ inhibitor, or PI3Kδ inhibitor in combination with rapamycin. Dosing is administered on days 1-6. Rats are weighed on days 1-7 following establishment of arthritis and caliper measurements of ankles taken every day. Final body weights are taken on day 7 and animals are euthanized.

This assay can be used to test that the combination treatment using PI3Kδ inhibitor and rapamycin provides greater efficacy than treatment with PI3Kδ inhibitor alone.

Example 39

Use of the Compounds of the Present Invention for Inhibition of Tumor Growth

Cell Lines

Cell lines of interest (A549, U87, ZR-75-1 and 786-0) are obtained from American Type Culture Collection (ATCC, Manassas, Va.). Cells are proliferated and preserved cryogenically at early passage (e.g. passage 3). One aliquot is used for further proliferation to get enough cells for one TGI study (at about passage 9).

Animals

Female a thymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model

Mice are inoculated subcutaneously in the right flank with 0.01 to 0.5 ml of tumor cells (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds of the present invention and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis

Mean tumor growth inhibition (TGI) is calculated utilizing the following formula:

$$TGI = \left[1 - \frac{(\overline{X}_{Treated(Final)} - \overline{X}_{Treated(Day\ 1)})}{(\overline{X}_{Control(Final)} - \overline{X}_{Control(Day\ 1)})}\right] \times 100\%$$

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

The model can be employed to show whether the compounds of the present invention can inhibit tumor cell growth such as renal carcinoma cell growth, breast cancer cell growth, lung cancer cell growth, or glioblastoma cell growth under the conditions tested.

$$TS = \left[1 - \frac{(Tumor\ Weight_{(Final)})}{(Tumor\ Weight_{(Day\ 1)})}\right] \times 100\%$$

What is claimed is:

1. A compound of Formula I-A:

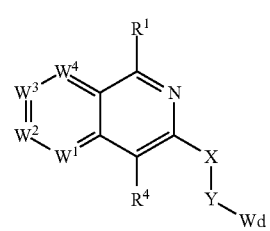

Formula I-A or a pharmaceutically acceptable salt thereof, wherein
 $W^1$ is N or $CR^5$, $W^2$ is N or $CR^6$, $W^3$ is N or $CR^7$, $W^4$ is N or $CR^8$, wherein no more than two N atoms are adjacent;

$R^1$ is $-(L)_n-R^{1'}$;

L is $-S-$, $-N(R^2)-$, $-C(R^3)_2-$, or $-O-$;

n is 0 or 1;

$R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^4$, $R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

X is absent or is $-(CH(R^{10}))_z-$ and z is an integer of 1, 2, 3, or 4;

Y is absent, $-O-$, $-S-$, $-S(=O)-$, $-S(=O)_2-$, $-N(R^9)-$, $-C(=O)-$, $-N(R^9)-C(=O)-$, $-N(R^9)-C(=O)NH-$, $-N(R^9)C(R^{10}_2-$, or $-C(=O)-(CHR^{10})_z-$;

each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;

each instance of $R^3$ and $R^{10}$ is independently hydrogen, alkyl, aryl, heteroaryl, or halo; and $W_d$ is

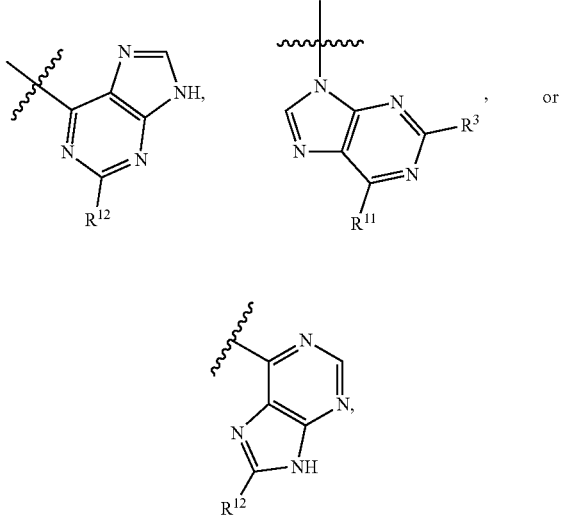

wherein each instance of $R^a$ is independently hydrogen or alkyl;

$R^{11}$ is H, alkyl, halo, amino, amido, hydroxyl, or alkoxy, and $R^{12}$ is H, alkyl, cyano, alkynyl, alkenyl, halo, aryl, heteroaryl, heterocyloalkyl, cycloalkyl, amino, carboxylic acid, acyloxy, alkoxycarbonyl, or amino.

2. A compound of Formula I-B:

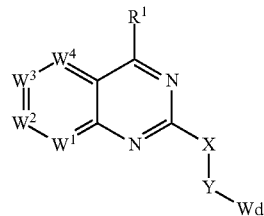

Formula I-B or a pharmaceutically acceptable salt thereof, wherein $W^1$ is N or $CR^5$, $W^2$ is N or $CR^6$, $W^3$ is N or $CR^7$, $W^4$ is N or $CR^8$, wherein no more than two N atoms are adjacent;

$R^1$ is $-(L)_n-R^{1'}$;

L is $-S-$, $-N(R^2)-$, $-C(R^3)_2-$, or $-O-$;

n is 0 or 1;

$R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

$R^5$, $R^6$, $R^7$ and $R^8$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, halo, cyano, hydroxy, nitro, phosphate, urea, carbonate, or NR'R" wherein R' and R" are taken together with nitrogen to form a cyclic moiety;

X is absent or is $-(CH(R^{10}))_z-$ and z is an integer of 1, 2, 3, or 4;

Y is absent, $-O-$, $-S-$, $-S(=O)-$, $-S(=O)_2-$, $-N(R^9)-$, $-C(=O)-$, $-N(R^9)-C(=O)-$, $-N(R^9)-C(=O)NH-$, $-N(R^9)C(R^{10}_2-$, or $-C(=O)-(CHR^{10})_z-$;

each instance of $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;

each instance of $R^3$ and $R^{10}$ is independently hydrogen, alkyl, aryl, heteroaryl or halo; and $W_d$ is

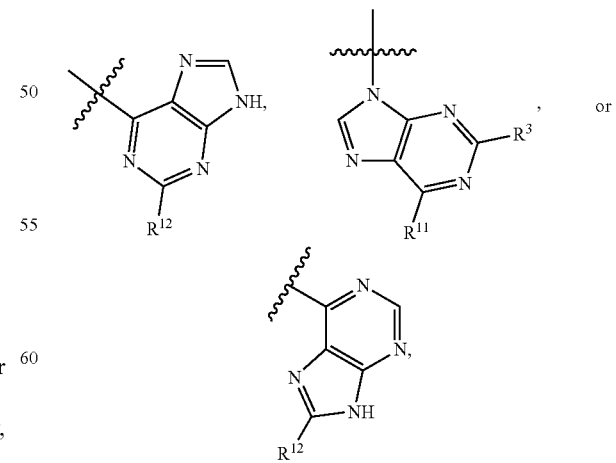

wherein each instance of $R^a$ is independently hydrogen or alkyl;

$R^{11}$ is H, alkyl, halo, amino, amido, hydroxyl, or alkoxy, and $R^{12}$ is H, alkyl, cyano, alkynyl, alkenyl, halo, aryl, heteroaryl, heterocycloalkyl, cycloalkyl, amino, carboxylic acid, acyloxy, alkoxycarbonyl, or amino.

3. The compound of claim 1 or 2 wherein
$W^1$ is N, $W^2$ is $CR^6$, $W^3$ is $CR^7$, $W^4$ is $CR^8$;
$W^1$ is $CR^5$, $W^2$ is N, $W^3$ is $CR^7$, $W^4$ is $CR^8$;
$W^1$ is $CR^5$, $W^2$ is $CR^6$, $W^3$ is N, $W^4$ is $CR^8$;
$W^1$ is N, $W^2$ is $CR^6$, $W^3$ is N, $W^4$ is $CR^8$;
$W^1$ is N, $W^2$ is N, $W^3$ is $CR^7$, $W^4$ is $CR^8$;
$W^1$ is N, $W^2$ is $CR^6$, $W^3$ is $CR^7$, $W^4$ is N;
$W^1$ is $CR^5$, $W^2$ is N, $W^3$ is N, $W^4$ is $CR^8$;
$W^1$ is $CR^5$, $W^2$ is N, $W^3$ is $CR^7$, $W^4$ is N;
$W^1$ is $CR^5$, $W^2$ is $CR^6$, $W^3$ is N, $W^4$ is N; or
$W^1$ is $CR^5$, $W^2$ is $CR^6$, $W^3$ is $CR^7$, $w^4$ is $CR^8$.

4. The compound of claim 1 wherein the compound of Formula I-A is a compound of Formula XV-A:

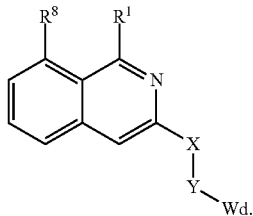

Formula XV-A

5. The compound of claim 2 wherein the compound of Formula I-B is a compound of Formula XV-B:

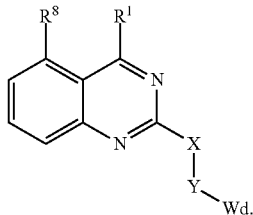

Formula XV-B

6. The compound of claim 1 or 2 wherein n is 0 and $R^{1'}$ is hydrogen, amino, alkoxy, alkyl, heterocycloalkyl, aryl, or NR'R" wherein R' and R" are taken together with nitrogen to form a cyclic moiety.

7. The compound of claim 1 or 2 wherein n is 1 and $R^{1'}$ is amino, alkoxy, alkyl, or NR'R" wherein R' and R" are taken together with nitrogen to form a cyclic moiety.

8. The compound of claim 7 wherein n is 1 and $R^{1'}$ is alkyl which is substituted with heterocycloalkyl or NR'R" wherein R' and R" are taken together with nitrogen to form a cyclic moiety.

9. The compound of claim 1 or 2 wherein $R^8$ is hydrogen, alkyl, heteroalkyl, alkenyl, alkynyl, cycloalkyl, heterocycloalkyl, alkoxy, sulfonamido, halo, cyano, hydroxy, or NR'R" wherein R' and R" are taken together with nitrogen to form a cyclic moiety.

10. The compound of claim 1 or 2 wherein $R^8$ is hydrogen or alkyl.

11. The compound of claim 10 wherein $R^8$ is alkyl substituted with one or more fluoro.

12. The compound of claim 1 or 2 wherein X is —$CH_2$—, —$CH(CH_3)$—, —$CH(C_6H_5)$—, or —$CH(CH_2CH_3)$—.

13. The compound of claim 12 wherein —$CH(CH_3)$— or —$CH(CH_2CH_3)$—has either a predominately (S) stereochemical configuration or a predominately (R) stereochemical configuration.

14. The compound of claim 1 or 2 wherein Y is absent, —O—, —$N(R^9)$—, —$N(R^9)C(R^{10})_2$—, or —$S(=O)_2$—.

15. The compound of claim 14 wherein $R^9$ and $R^{19}$ are independently hydrogen, methyl, or ethyl.

16. The compound of claim 15 wherein the compound is a compound of Formula I-A, when $R^1$ is alkyl, X is —(CH$(R^{10}))_z$—, z is 1, and Y is —$N(R^9)$—, then $R^9$ is hydrogen.

17. The compound of claim 1 or 2 wherein Y is —$N(CH_2CH_3)CH_2$—or —$N(CH_3)CH_2$—.

18. The compound of claim 1 or 2 wherein X-Y is —$CH_2$—$N(CH_3)$—, or —$CH_2$—$N(CH_2CH_3)$—.

19. The compound of claim 1 or 2 wherein $W_d$ is of Formula XIV:

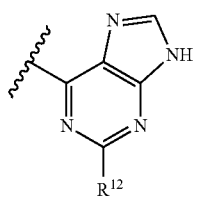

Formula XIV wherein $R^{12}$ is H, alkyl, alkynyl, alkenyl, halo, aryl, heteroaryl, heterocycloalkyl, cycloalkyl, cyano, amino, carboxylic acid, acyloxy, alkoxycarbonyl, or amido.

20. The compound of claim 1 or 2 wherein $R^{11}$ is amino.

21. The compound of claim 1 or 2 wherein $R^{12}$ is a monocyclic heteroaryl, a bicyclic heteroaryl, or a heterocycloalkyl.

22. The compound of claim 1 or 2 wherein $R^{12}$ is hydrogen.

23. The compound of claim 1, wherein the compound is a compound of Formula XIX-A:

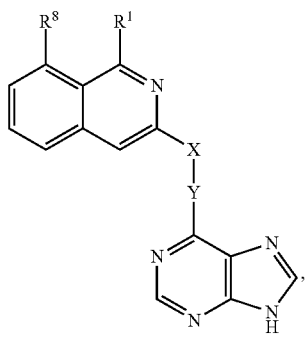

Formula XIX-A or a pharmaceutically acceptable salt thereof.

24. The compound of claim 1, wherein the compound is a compound of Formula XXI-A:

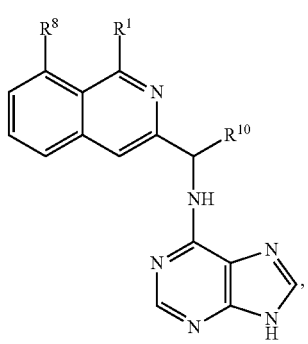

Formula XXI-A or a pharmaceutically acceptable salt thereof.

25. A composition comprising a pharmaceutically acceptable excipient and a compound of claim 1 or 2.

26. The composition of claim 25 wherein the composition is a liquid, solid, semi-solid, gel, or an aerosol form.

27. The compound of claim 2, wherein the compound is a compound of Formula XIX-B:

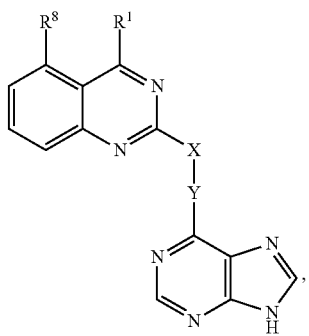

Formula XIX-B or a pharmaceutically acceptable salt thereof.

28. The compound of claim 2, wherein the compound is a compound of Formula XXI-B:

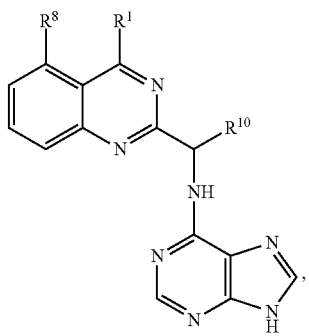

Formula XXI-B or a pharmaceutically acceptable salt thereof.

29. The compound of claim 1 wherein the compound is:

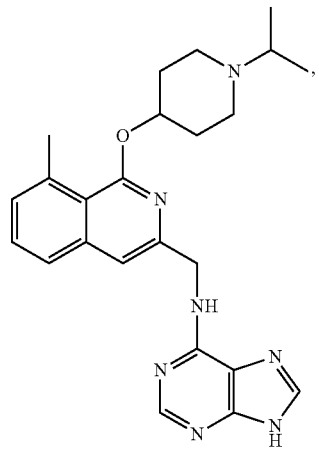

10

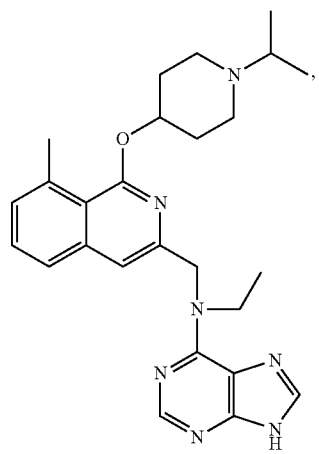

11

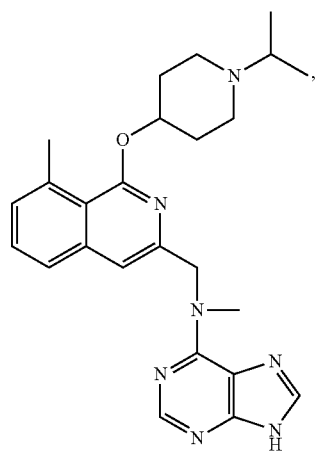

12

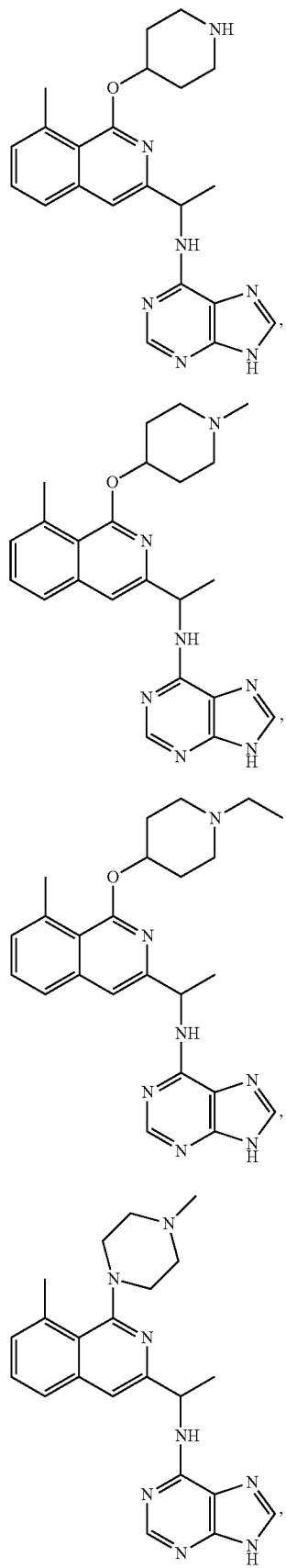
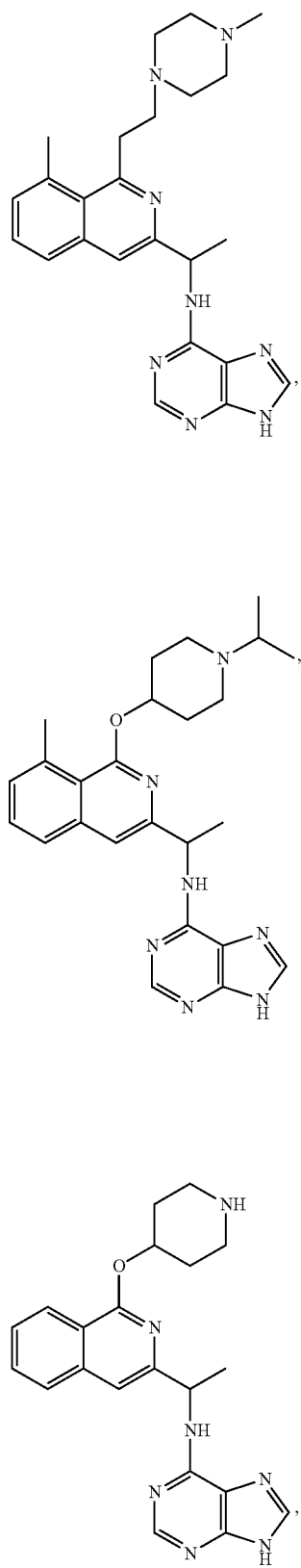

23
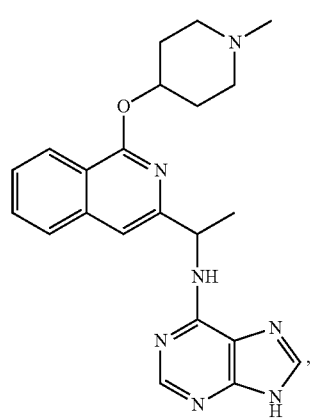
24
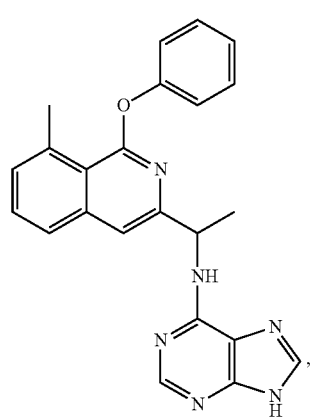
32
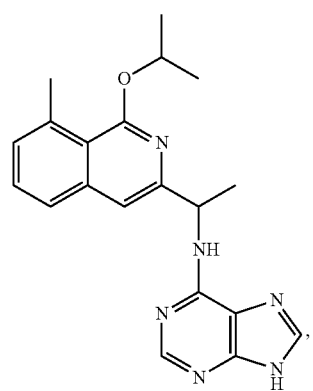
33
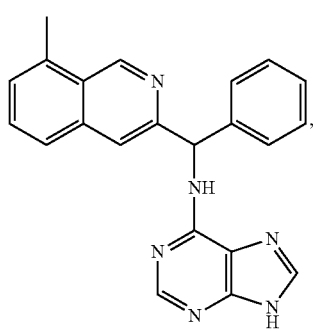
35
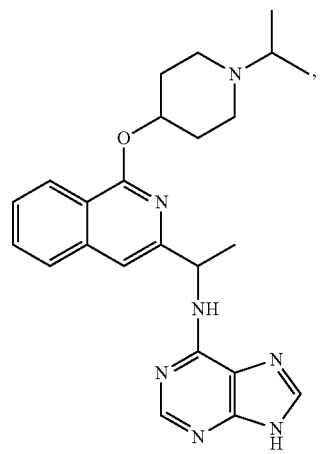
38
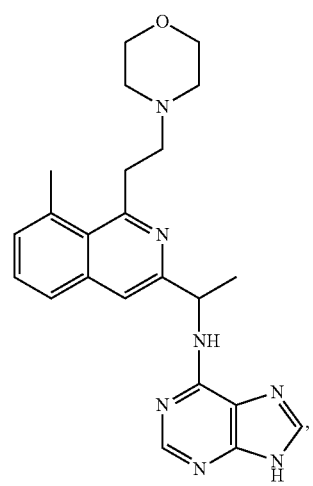
39
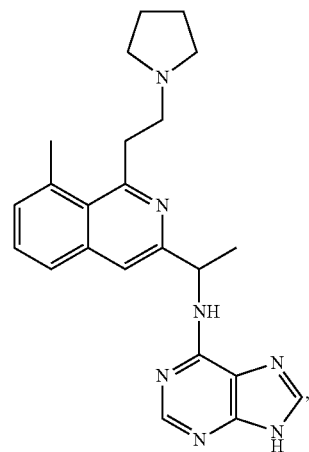

229
-continued
40 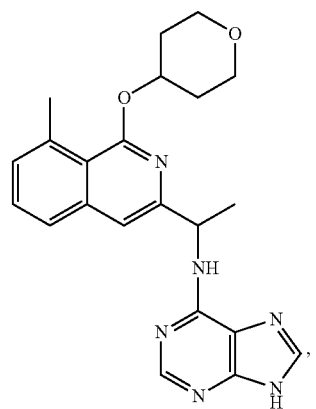
41 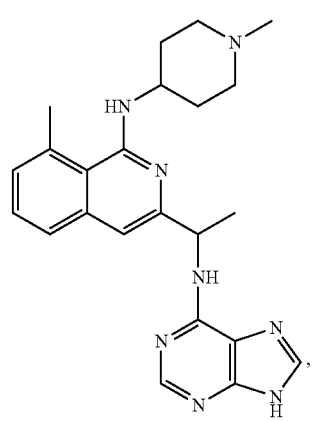
42 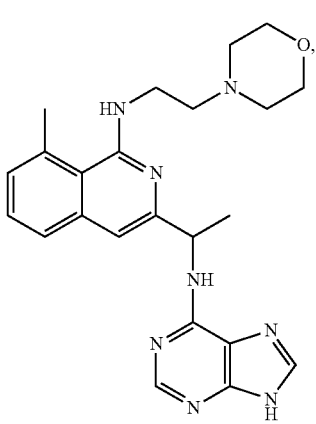
43 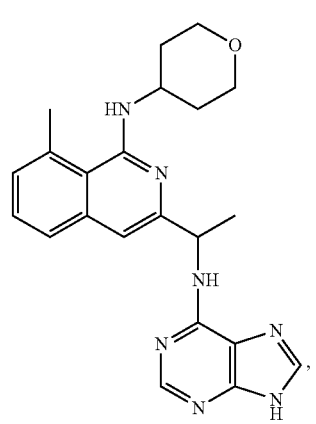
230
-continued
44 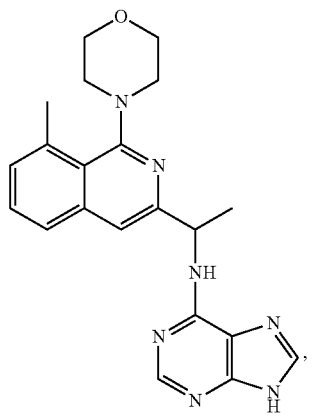
45 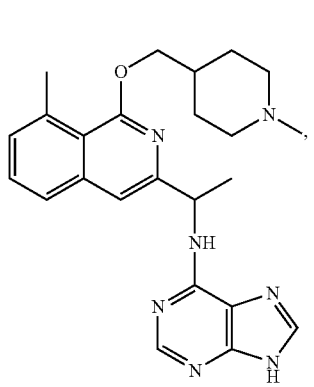
46 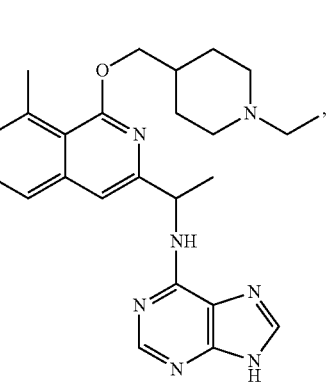
47 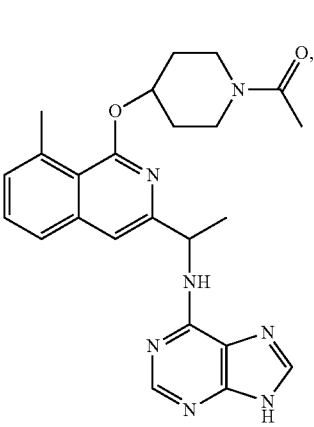

48
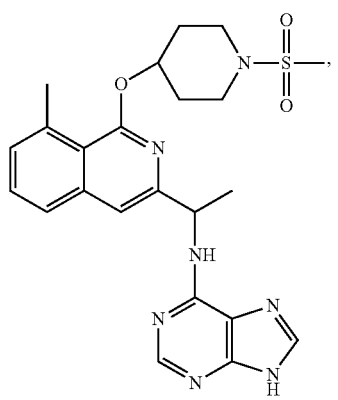
49
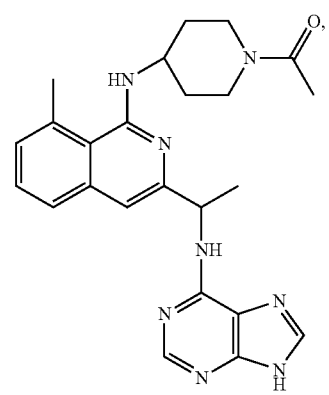
50
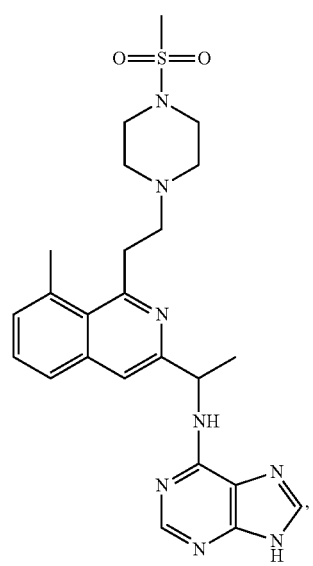
51
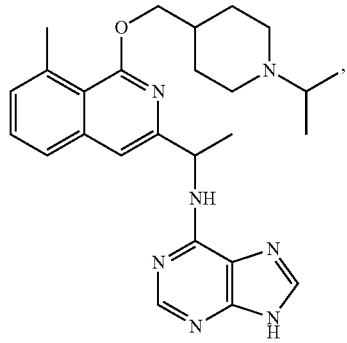
52
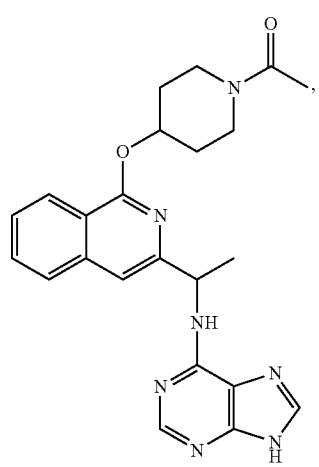
53
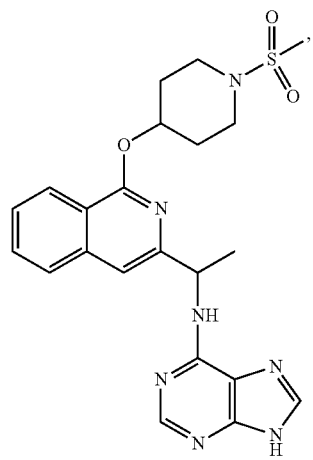 [SMILES: CC(Nc1ncnc2[nH]cnc12)c1cc2ccccc2c(OC2CCN(S(C)(=O)=O)CC2)n1]

54 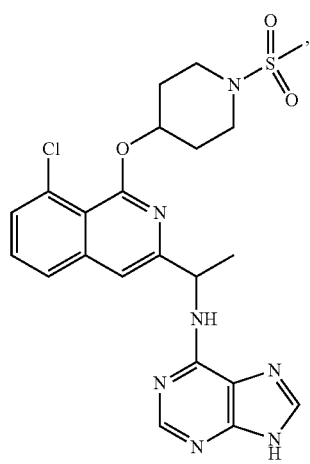 [SMILES: CC(Nc1ncnc2[nH]cnc12)c1cc2cccc(Cl)c2c(OC2CCN(S(C)(=O)=O)CC2)n1]
59 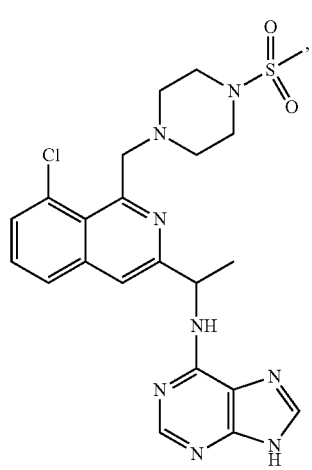 [SMILES: CC(Nc1ncnc2[nH]cnc12)c1cc2cccc(Cl)c2c(ON2CCN(S(C)(=O)=O)CC2)n1]
78 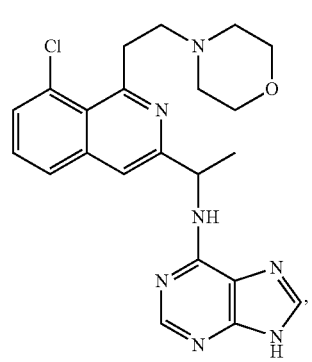
79 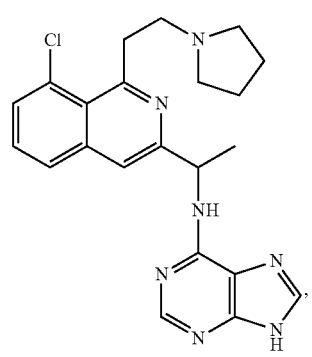
80 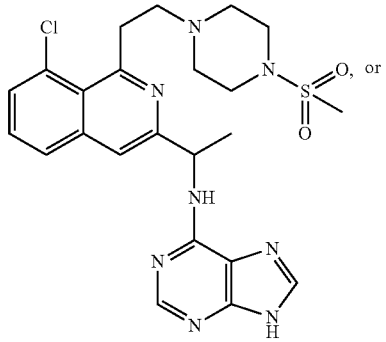
81 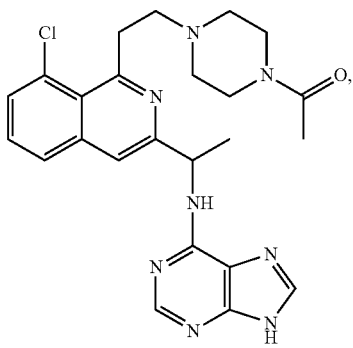
or a pharmaceutically acceptable salt thereof.
30. The compound of claim 29, wherein the compound is:
10 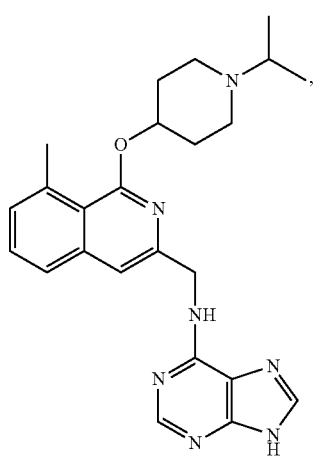

235
-continued
15
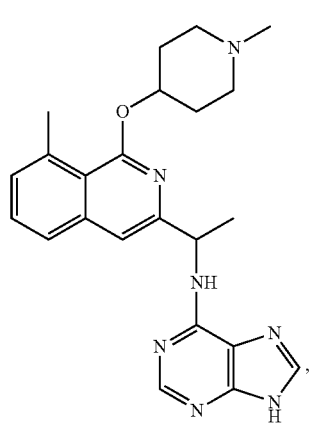
16
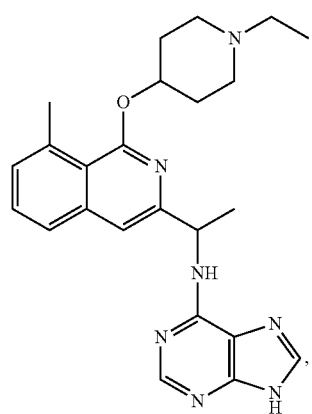
19
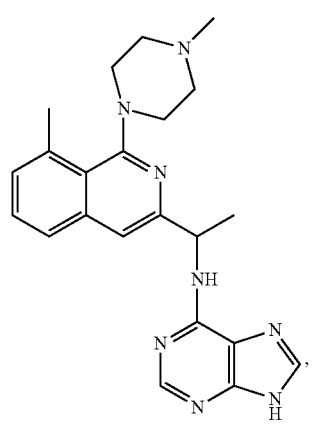
236
-continued
20
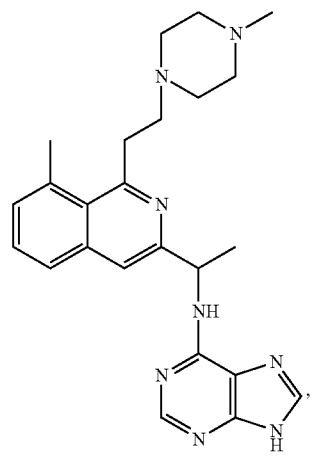
21
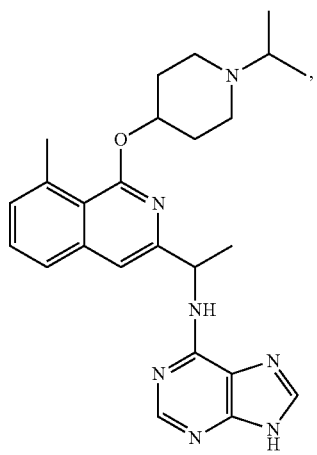
38
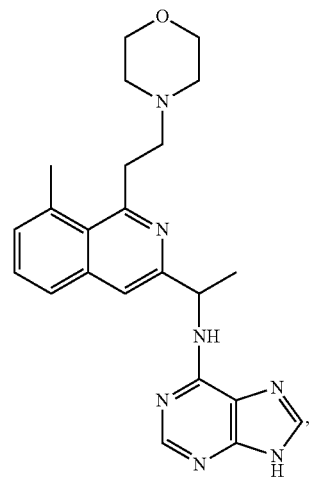

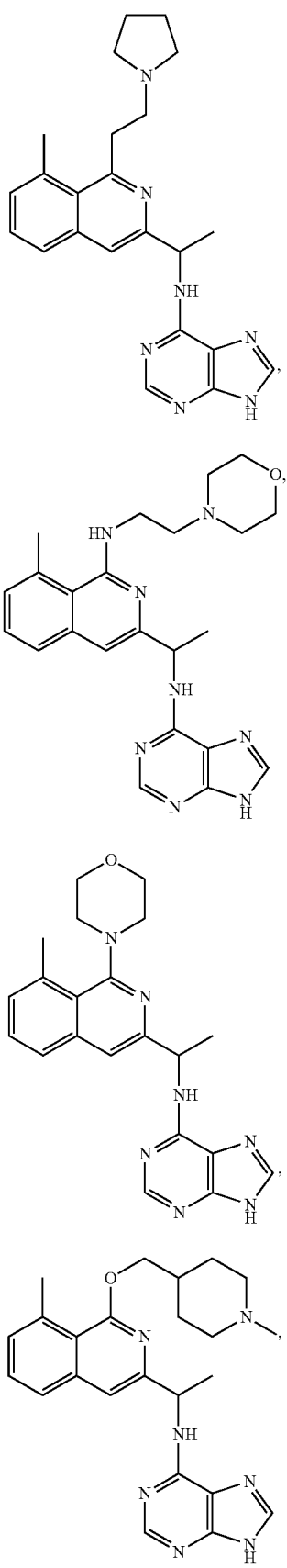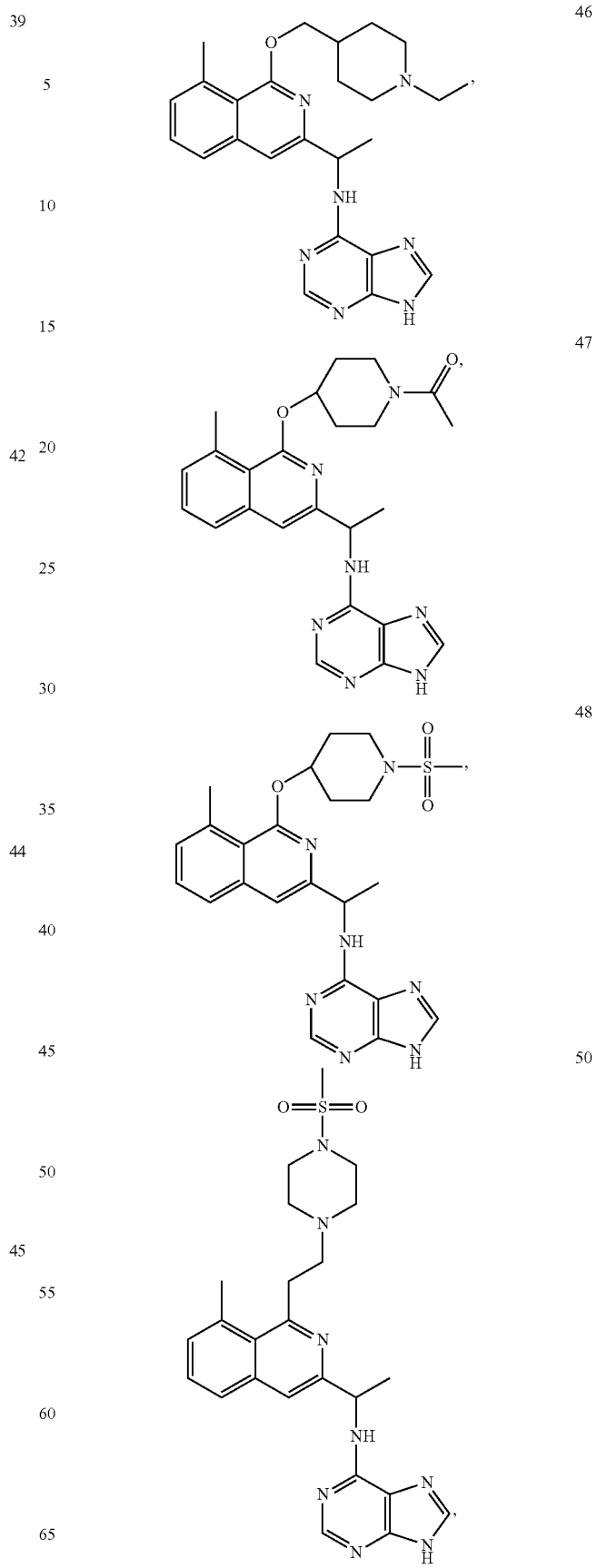

-continued
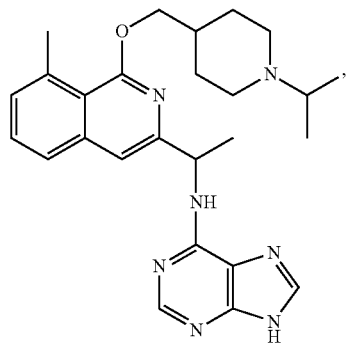
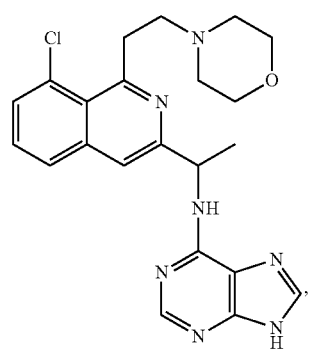
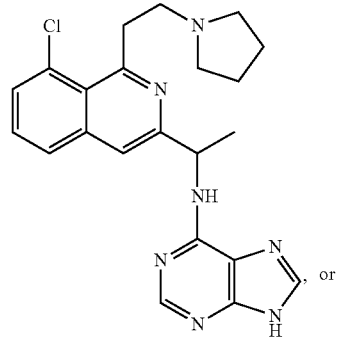
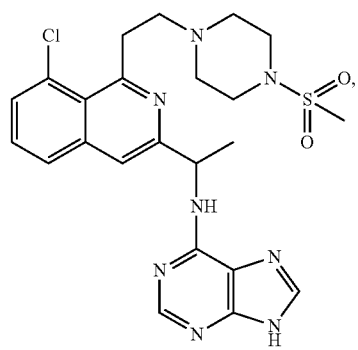
or a pharmaceutically acceptable salt thereof.
31. The compound of claim 1 wherein the compound is:
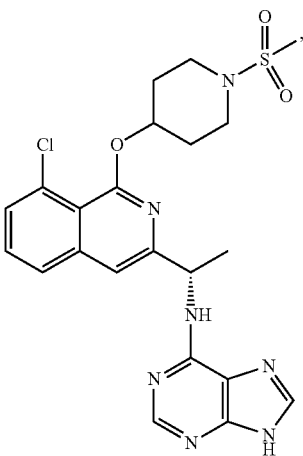 [SMILES: C[C@H](Nc1ncnc2[nH]cnc12)c1cc2cccc(Cl)c2c(OC2CCN(S(C)(=O)=O)CC2)n1]
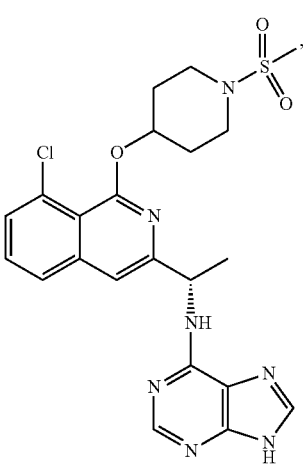
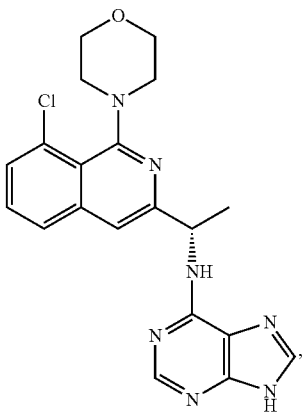

241
-continued
63
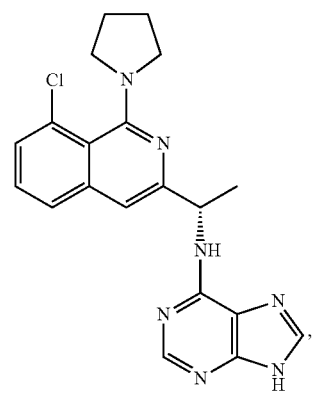
64
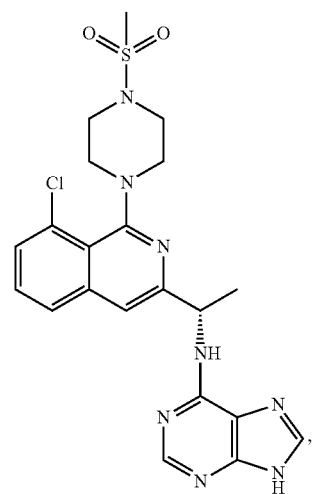
65
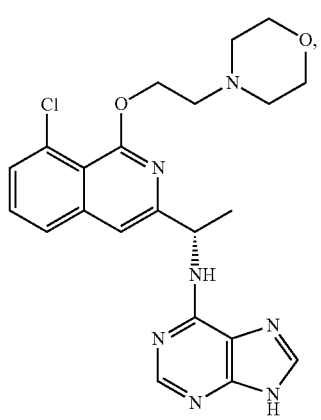
242
-continued
69
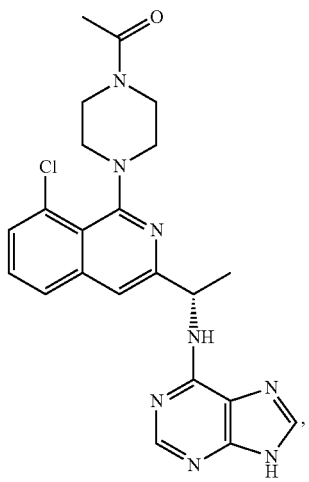
71
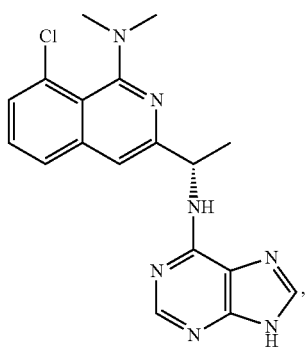
72
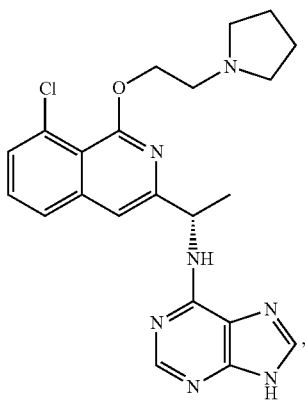
73
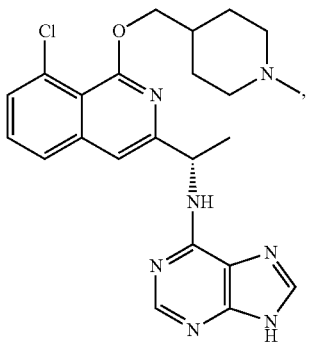 [SMILES: C[C@H](Nc1ncnc2[nH]cnc12)c1cc2cccc(Cl)c2c(OCC2CCN(C)CC2)n1]

-continued
74
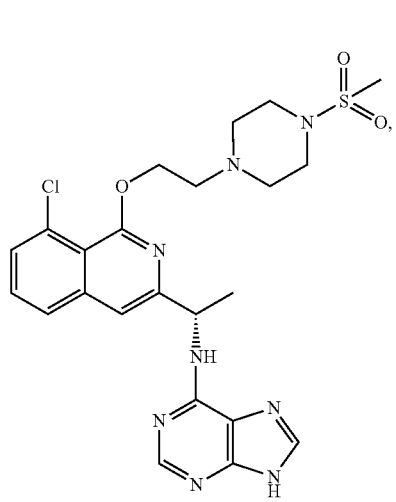
75
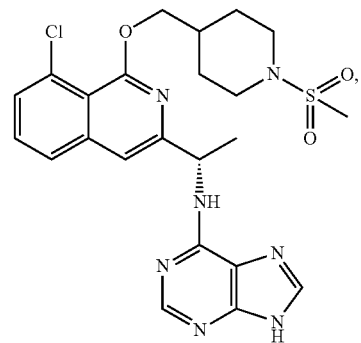
76
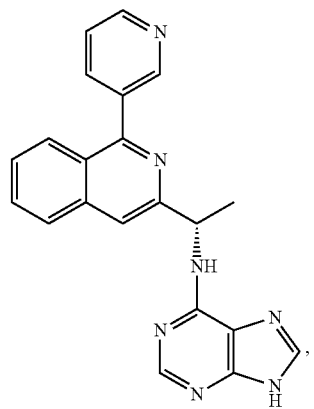
-continued
77
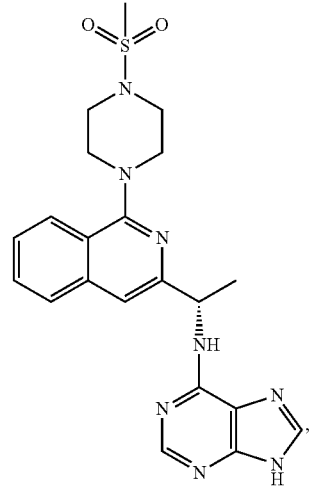
82
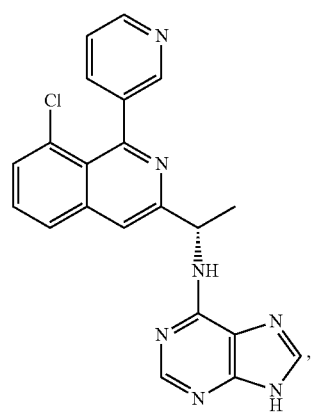
83
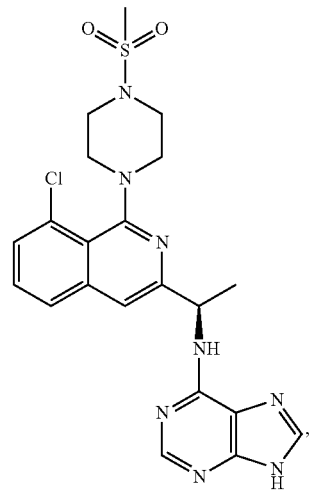

245
-continued
84
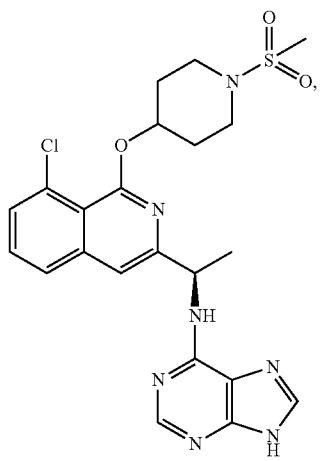
85
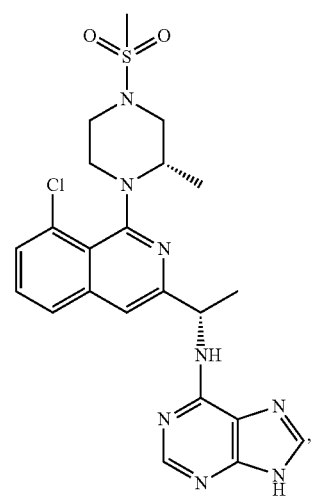
86
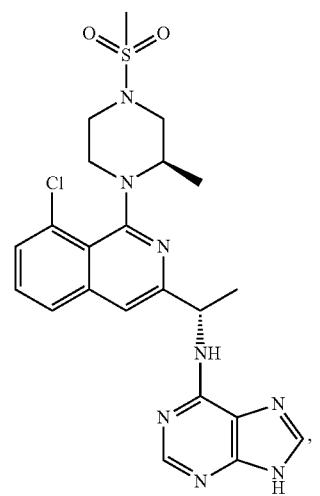
246
-continued
87
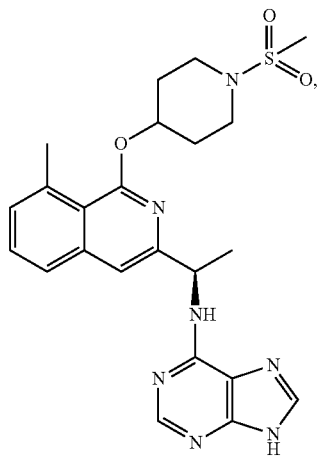
88
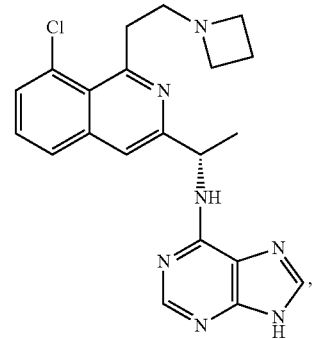
89
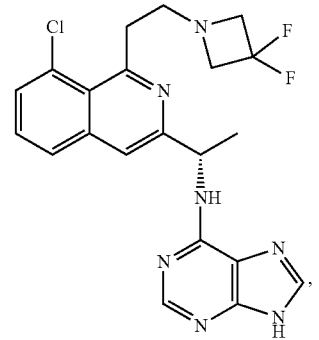
90
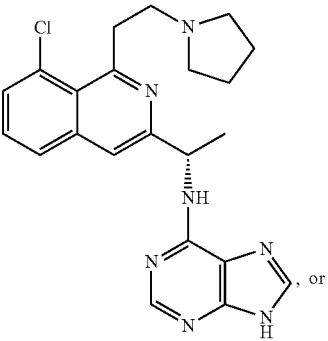
or -continued
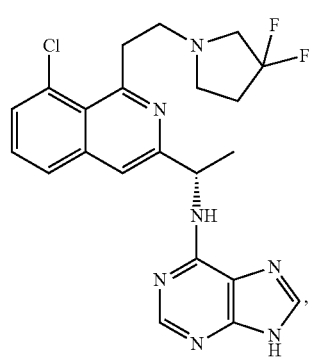
or a pharmaceutically acceptable salt thereof.
32. The compound of claim 31, wherein the compound is
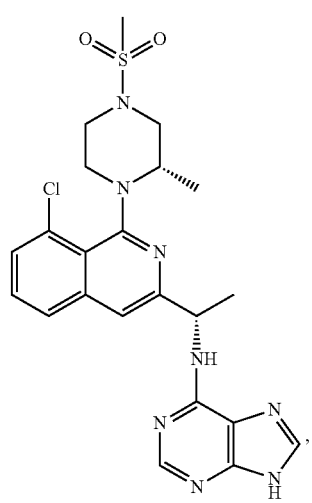
or a pharmaceutically acceptable salt thereof.
33. The compound of claim 31, wherein the compound is:
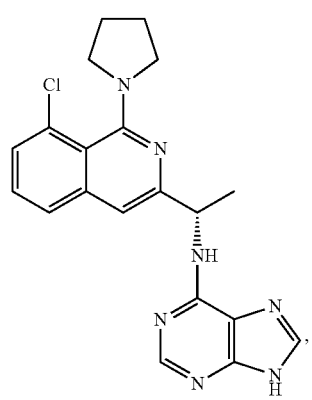
-continued
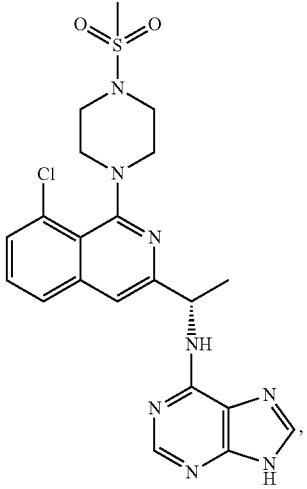
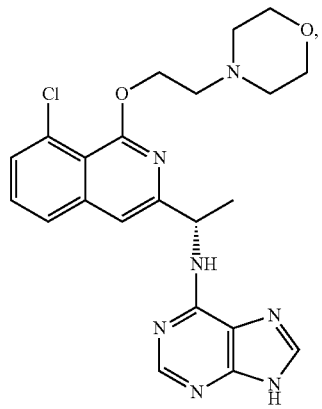
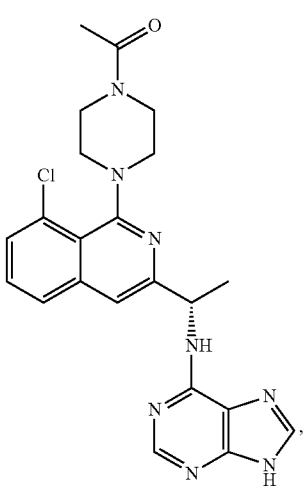

71 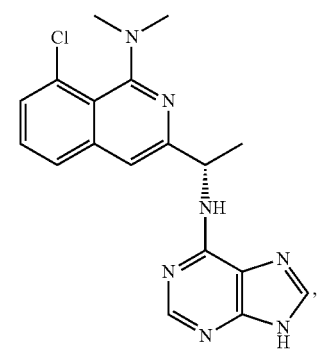
72 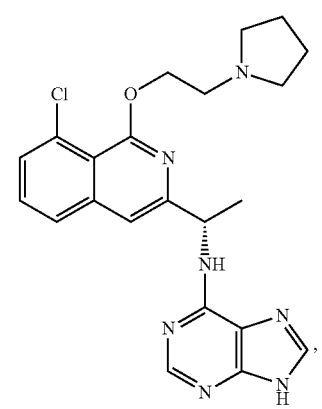
73 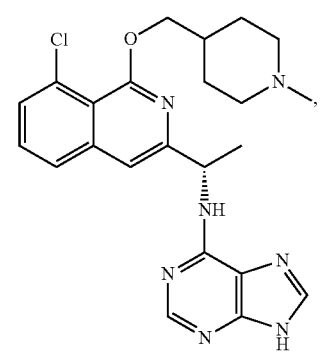
74 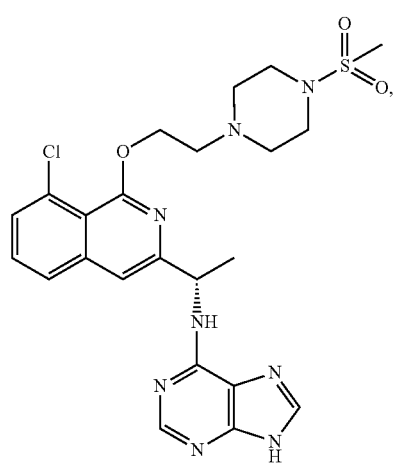
75 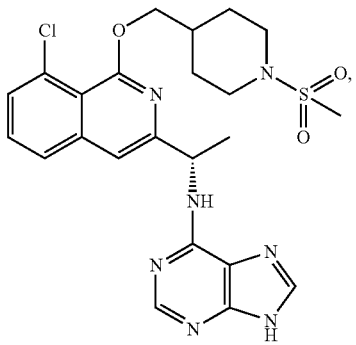
82 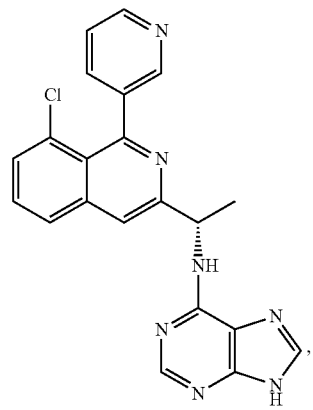
88 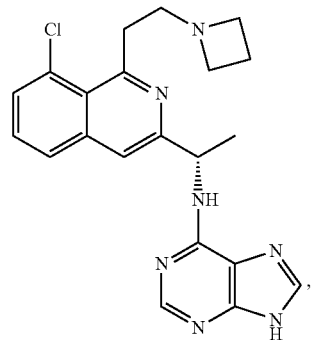
89 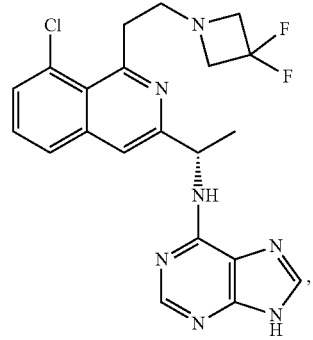

-continued
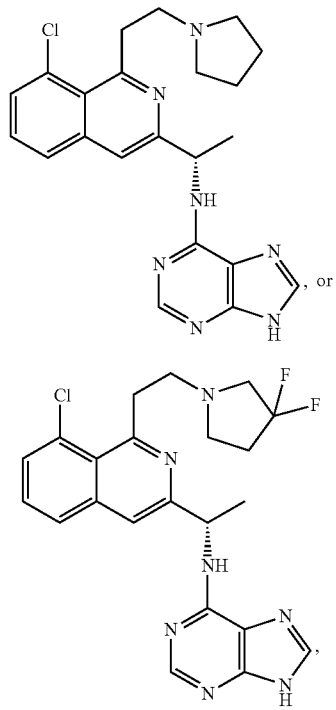
or a pharmaceutically acceptable salt thereof.
34. The compound of claim 2 wherein the compound is:
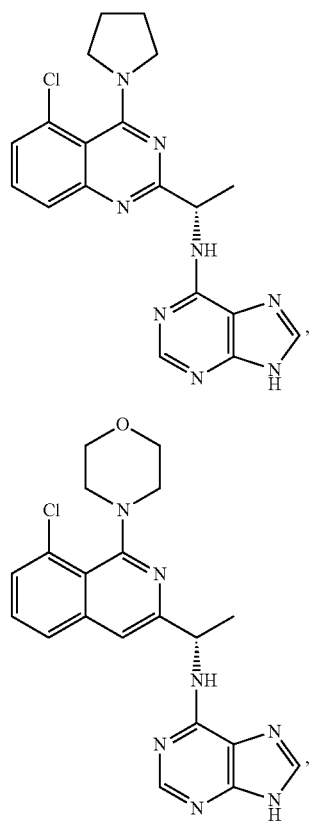
-continued
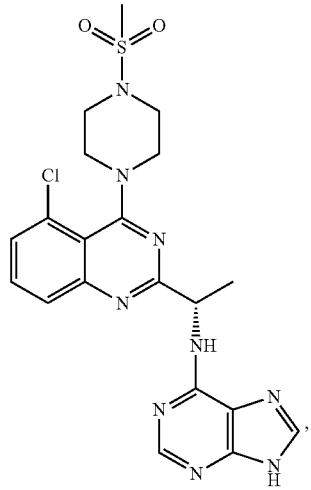
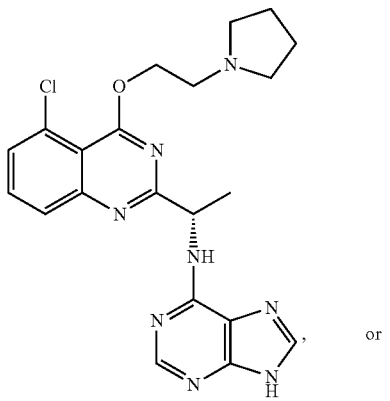
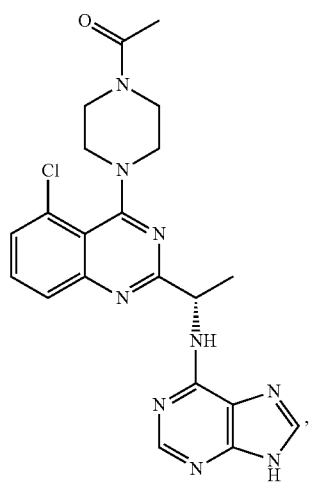
or a pharmaceutically acceptable salt thereof.

35. The compound of claim 34, wherein the compound is
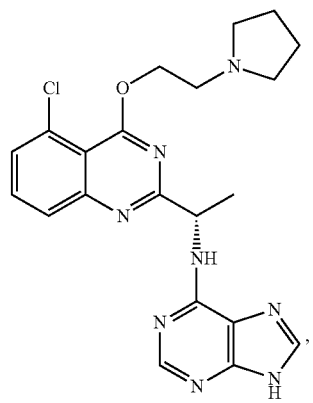
or a pharmaceutically acceptable salt thereof.
36. The compound of claim 1 wherein the compound is:
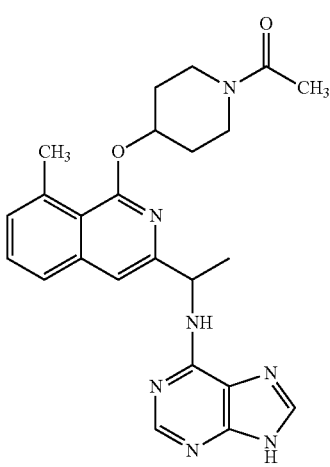
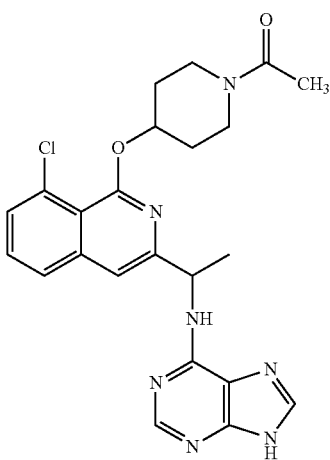
-continued
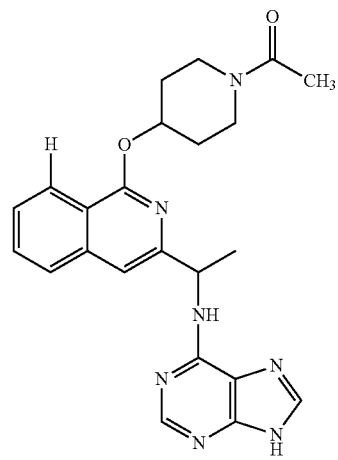
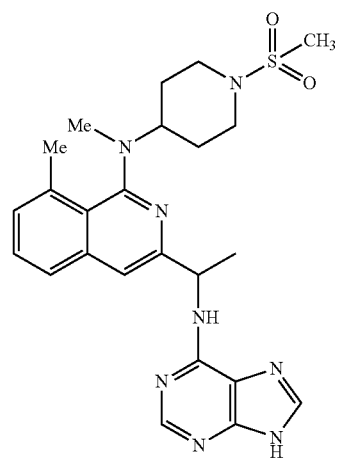
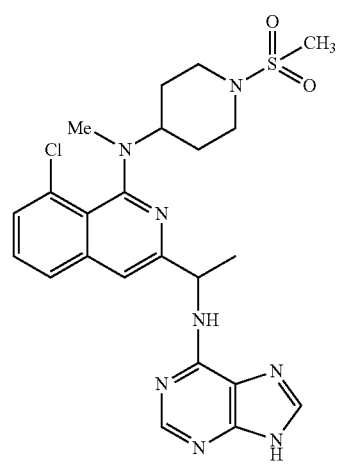

-continued
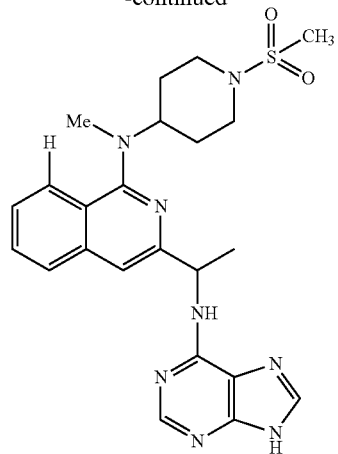
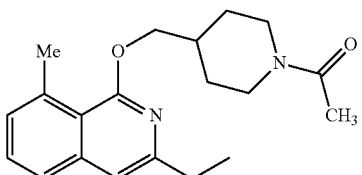
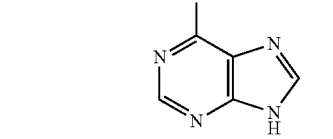
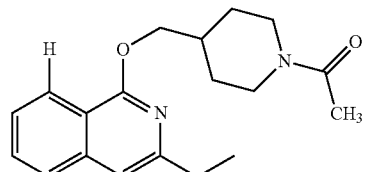
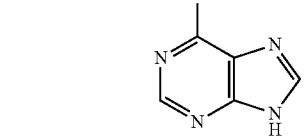
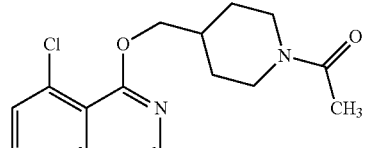
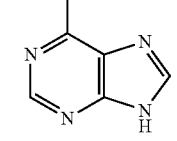
-continued
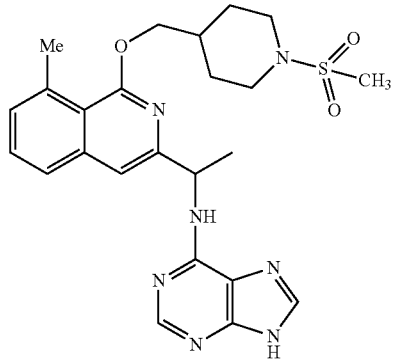
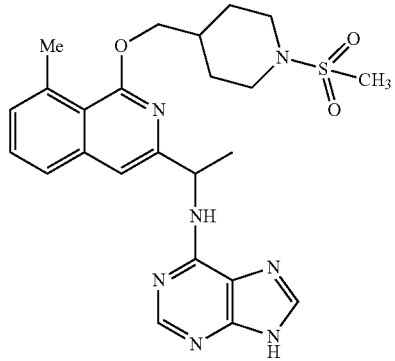
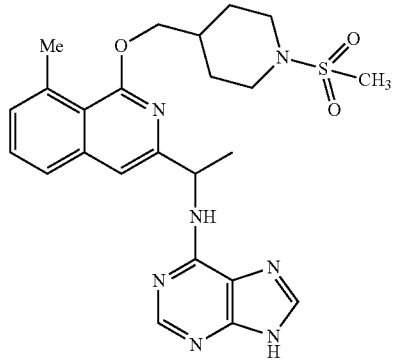
or a pharmaceutically acceptable salt thereof.
37. The compound of claim 2 wherein the compound is:
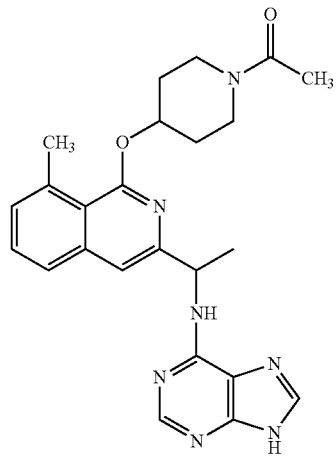

257
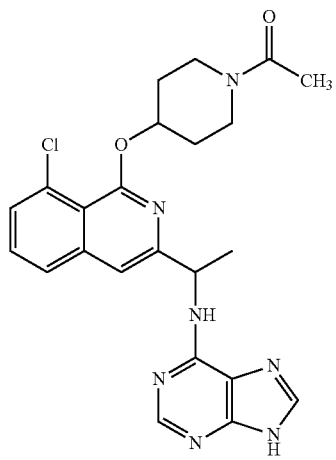
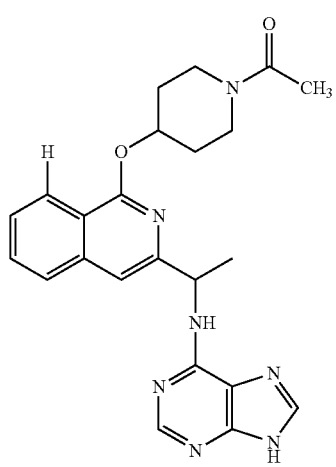
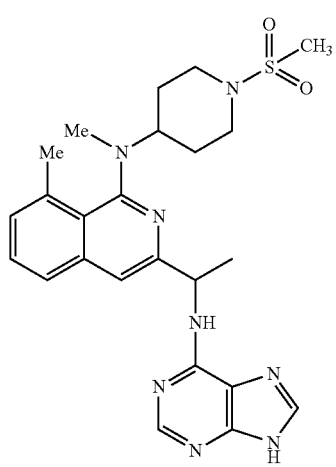
258
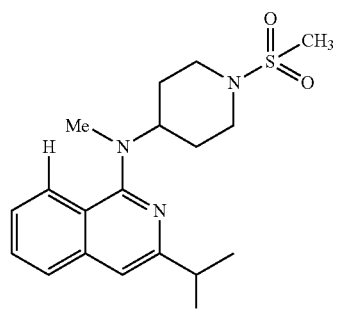
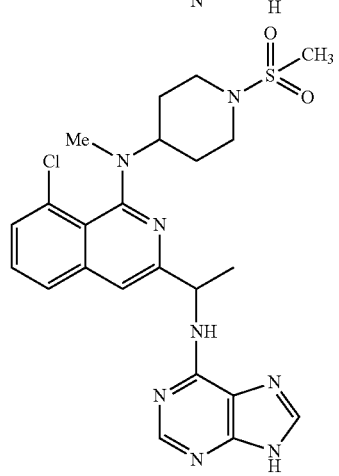
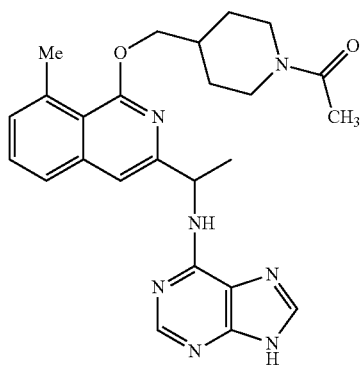
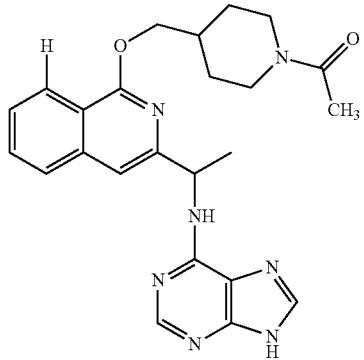

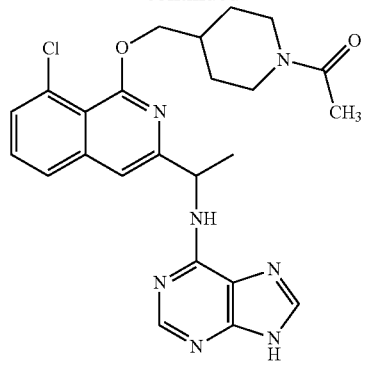
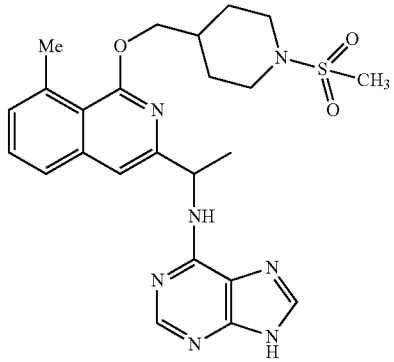
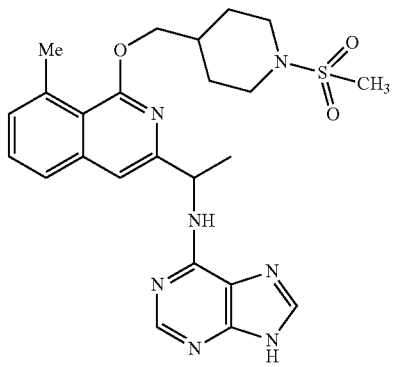
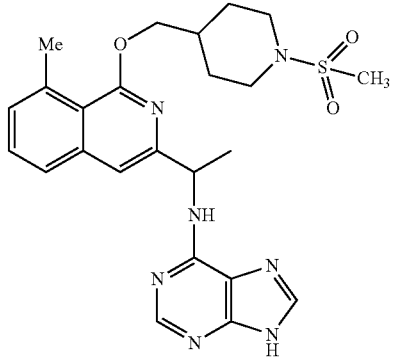
or a pharmaceutically acceptable salt thereof.
38. The compound of claim 1 wherein the compound is:
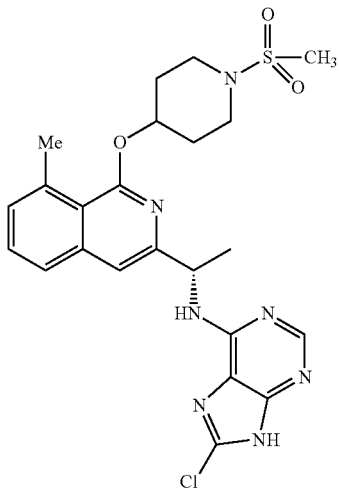
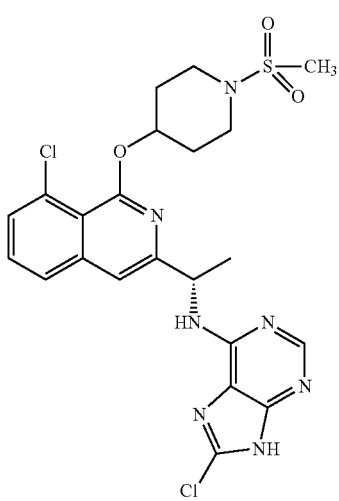
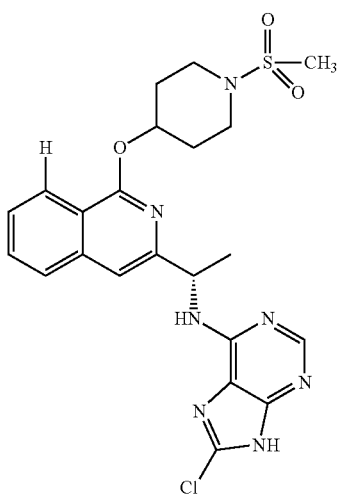

261
-continued
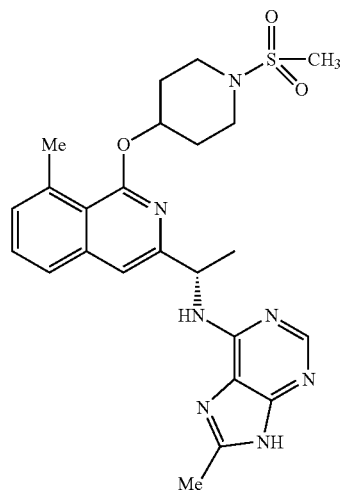
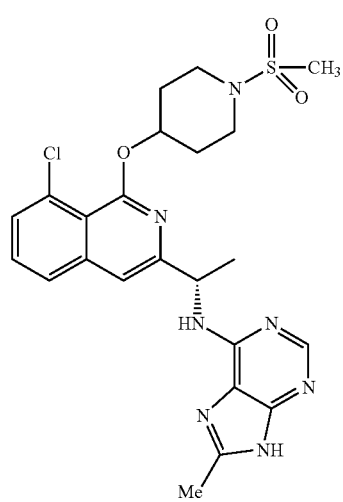
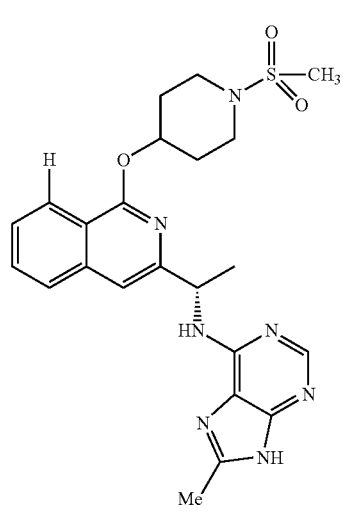
262
-continued
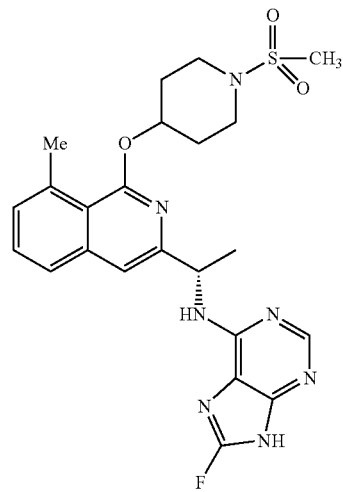
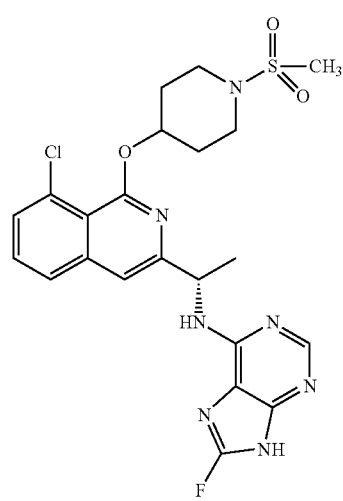
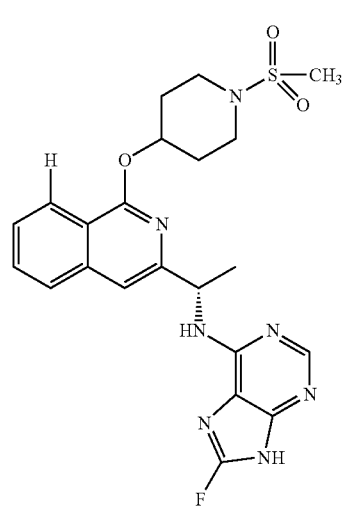

263
-continued
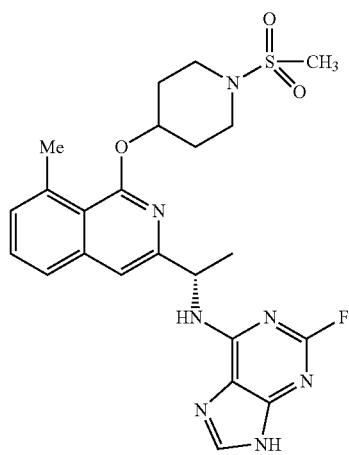
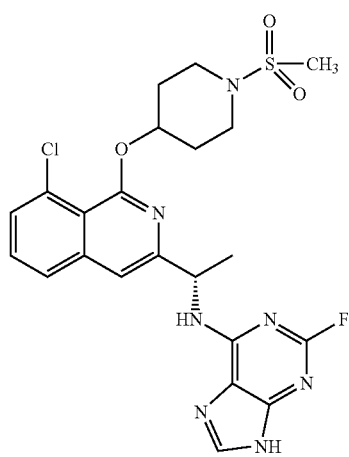
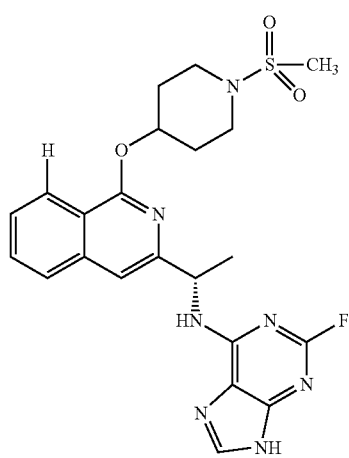
264
-continued
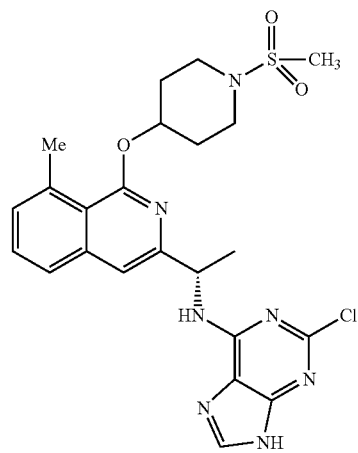
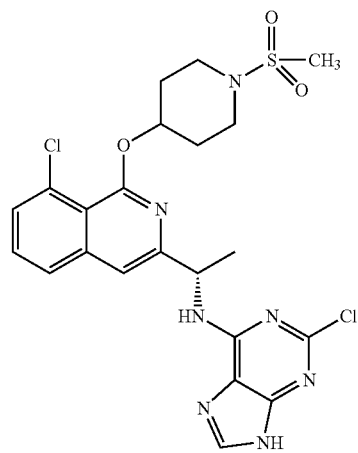
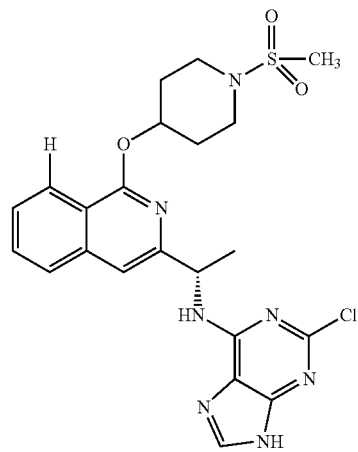
or a pharmaceutically acceptable salt thereof.

39. The compound of claim 2 wherein the compound is:
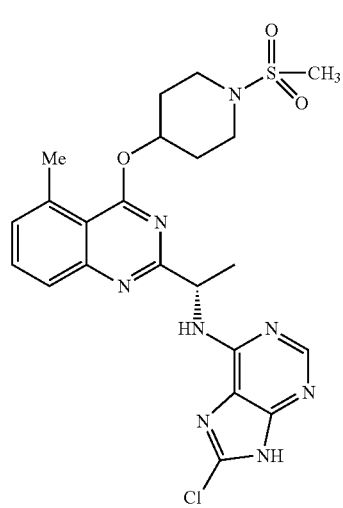
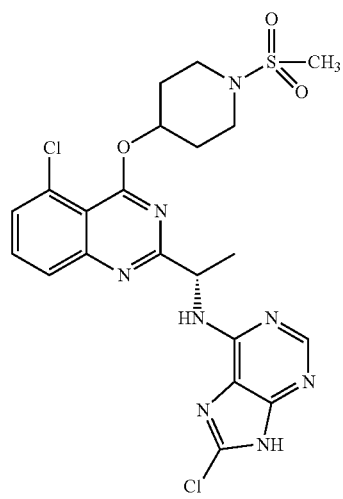
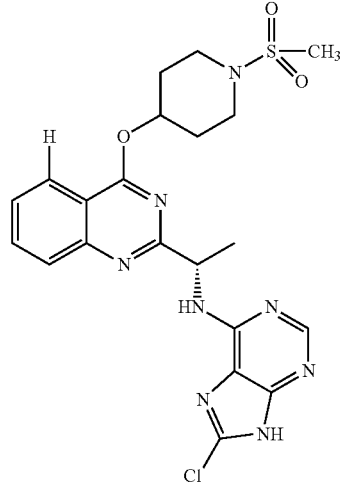
-continued
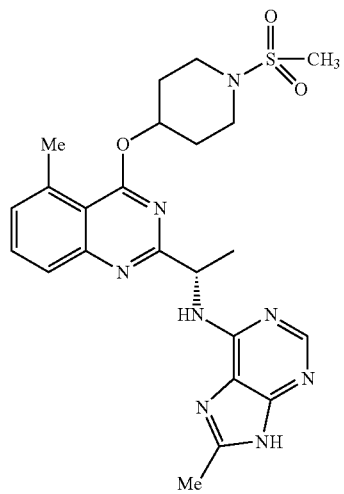
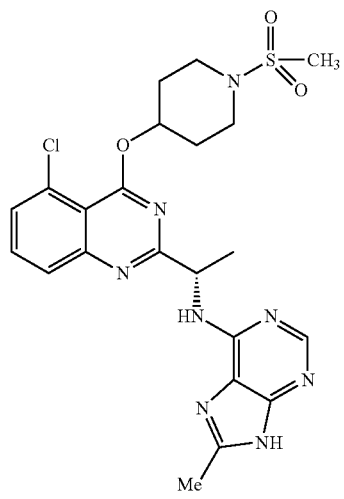
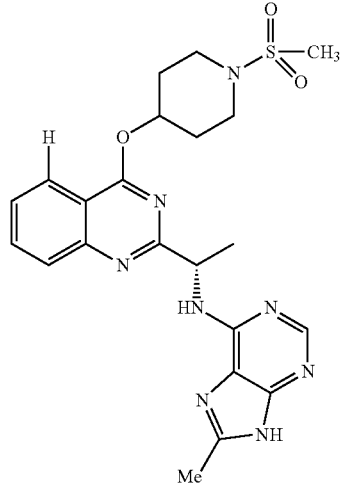

267
-continued
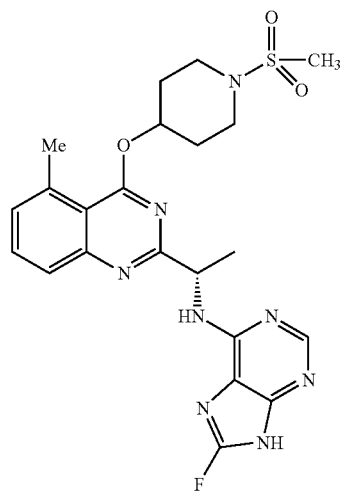
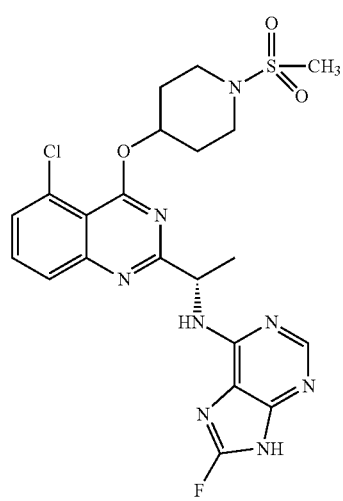
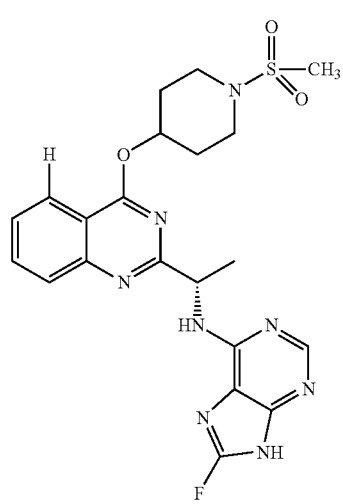
268
-continued
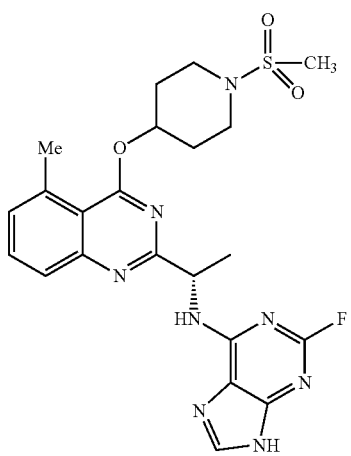
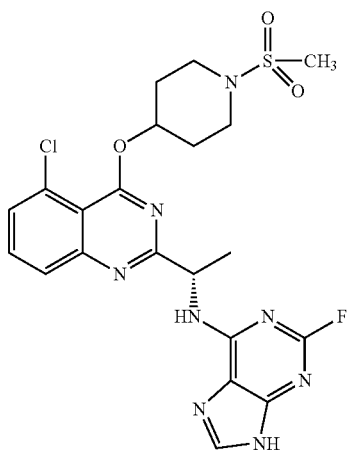
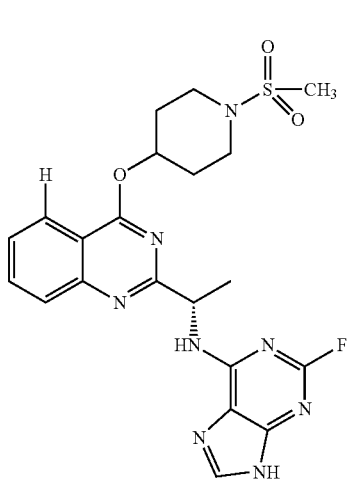

269
-continued
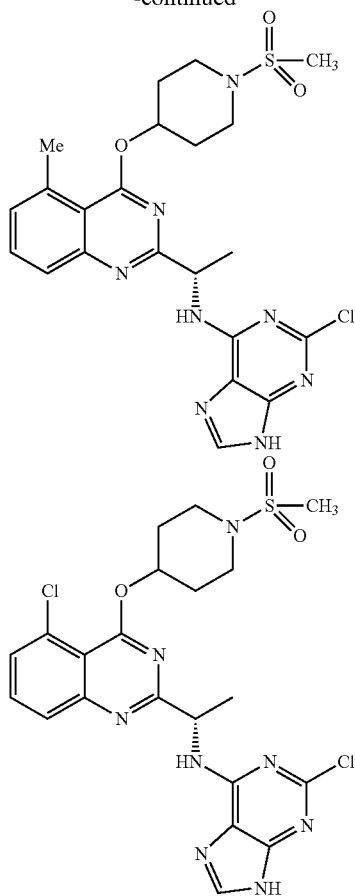
270
-continued
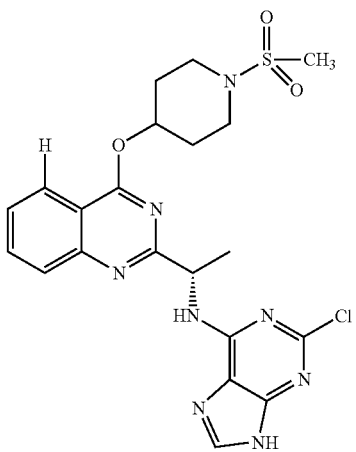
or a pharmaceutically acceptable salt thereof.
* * * * *

UNITED STATES PATENT AND TRADEMARK OFFICE
CERTIFICATE OF CORRECTION

PATENT NO. : 8,785,454 B2  
APPLICATION NO. : 13/289540  
DATED : July 22, 2014  
INVENTOR(S) : Ren et al.

Page 1 of 5

It is certified that error appears in the above-identified patent and that said Letters Patent is hereby corrected as shown below:

In the Claims

Column 219, line 1 (part of claim 1), replace the term "–(L)$_n$—R$^1$'" with "–(L)$_n$—R$^{1'}$" to read:
-- R$^1$ is –(L)$_n$—R$^{1'}$; --

Column 219, line 26 (part of claim 1), delete the extra bracket after the first comma and add a missing bracket after R$^{10}$ to read:
-- —N(R$^9$)—C(=O)NH—, —N(R$^9$)C(R$^{10}$)$_2$—, or --

Column 219, line 40 (part of claim 1), replace the second structure with

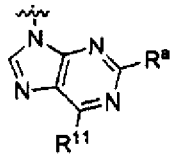

Column 220, line 19 (part of claim 2), add a space after 0 to read:
-- n is 0 or 1; --

Column 220, line 37 (part of claim 2), add a missing bracket after R$^{10}$ to read:
-- —N(R$^9$)—C(=O)NH—, —N(R$^9$)C(R$^{10}$)$_2$—, or --

Signed and Sealed this  
Twenty-fourth Day of February, 2015

Michelle K. Lee  
*Deputy Director of the United States Patent and Trademark Office*

CERTIFICATE OF CORRECTION (continued)

Column 220, line 50 (part of claim 2), replace the second structure with

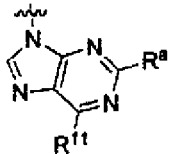

Column 221, line 17 (part of claim 3), replace the term "w$^4$" with "W$^4$" to read:

-- W$^1$ is CR$^5$, W$^2$ is CR$^6$, W$^3$ is CR$^7$, W$^4$ is CR$^8$. --

Column 222, line 10 (part of claim 15), replace the term "R$^{19}$" with "R$^{10}$" to read:

-- wherein R$^9$ and R$^{10}$ are --

Column 240 (part of claim 31), replace the structure of the second compound (compound 61) with

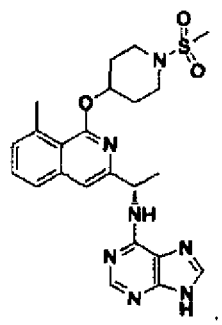

Column 251 (part of claim 34), replace the structure of the last compound (compound 93) with

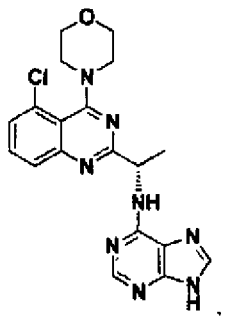

Column 256 (part of claim 36), delete the second and third structures.

Column 256 (part of claim 37), replace the structure of the fourth compound with

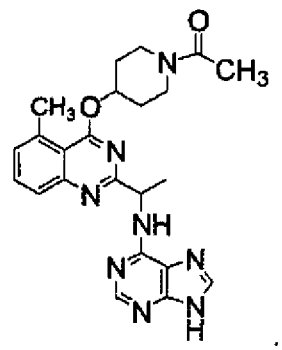
Column 257 (part of claim 37), replace the structure of the first compound with
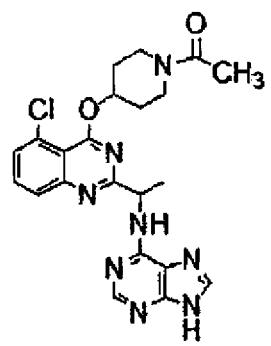
Column 257 (part of claim 37), replace the structure of the second compound with
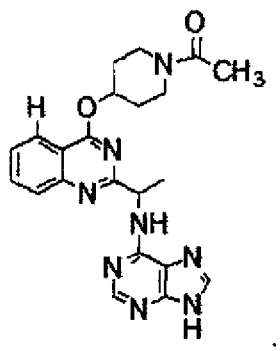
Column 257 (part of claim 37), replace the structure of the last compound with

CERTIFICATE OF CORRECTION (continued)
U.S. Pat. No. 8,785,454 B2

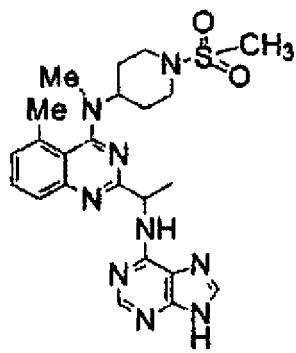

Column 258 (part of claim 37), replace the structure of the first compound with

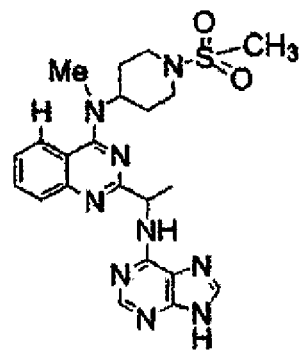

Column 258 (part of claim 37), replace the structure of the second compound with

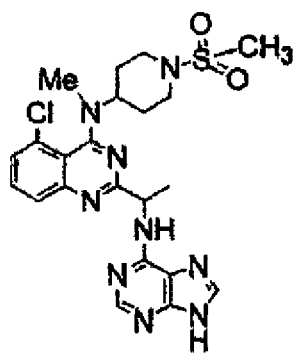

Column 258 (part of claim 37), replace the structure of the third compound with

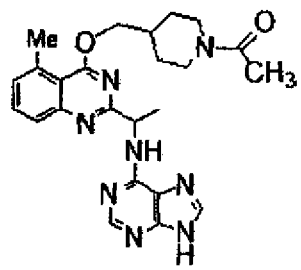
Column 258 (part of claim 37), replace the structure of the fourth compound with
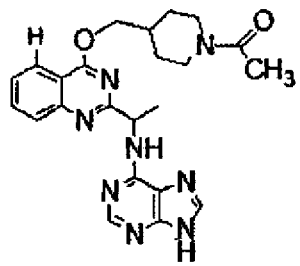
Column 259 (part of claim 37), replace the structure of the first compound with
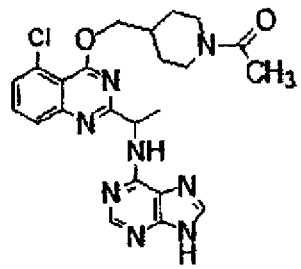
Column 259 (part of claim 37), replace the structure of the second compound with
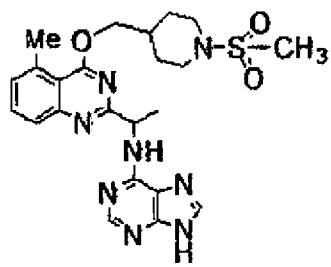
Column 259 (part of claim 37), delete the third and fourth structures.